(12) United States Patent
South et al.

(10) Patent No.: US 6,664,255 B1
(45) Date of Patent: Dec. 16, 2003

(54) SUBSTITUTED POLYCYCLIC ARYL AND HETEROARYL PYRAZINONES USEFUL FOR SELECTIVE INHIBITION OF THE COAGULATION CASCADE

(75) Inventors: Michael South, St. Louis, MO (US); John J. Parlow, Arnold, MO (US); Darin E. Jones, Ballwin, MO (US); Brenda Case, St. Louis, MO (US); Tom Dice, St. Charles, MO (US); Richard Lindmark, Kirkwood, MO (US); Michael J. Hayes, St. Louis, MO (US); Melvin L. Rueppel, St. Louis, MO (US); Horng-Chih Huang, Chesterfield, MO (US); Wei Huang, Wildwood, MO (US); Scott A. Long, Ballwin, MO (US); Matthew Mahoney, St. Peters, MO (US); William L. Neumann, St. Louis, MO (US); David Reitz, Chesterfield, MO (US); John I. Trujillo, Creve Coeur, MO (US); Ching-Cheng Wang, Wildwood, MO (US); Rhonda Wood, Maryland Heights, MO (US); Qingping Zeng, Ballwin, MO (US); Rick Fenton, Collinsville, IL (US); Gary W. Franklin, Godfrey, IL (US); Carrie Kusturin, Edwardsville, IL (US)

(73) Assignee: Pharmacia Corporation, Chicago, IL (US)

( * ) Notice: Subject to any disclaimer, the term of this patent is extended or adjusted under 35 U.S.C. 154(b) by 0 days.

(21) Appl. No.: 09/574,752

(22) Filed: May 18, 2000

Related U.S. Application Data

(60) Provisional application No. 60/134,958, filed on May 19, 1999.

(51) Int. Cl.$^7$ ............... C07D 241/20; C07D 417/12; C07D 401/12; A61K 31/495; A61P 7/02
(52) U.S. Cl. ............... 514/235.8; 544/405; 544/237; 544/295; 544/120; 514/255.05; 514/248
(58) Field of Search ............... 544/405, 237, 544/295, 120; 514/255.05, 248, 235.8

(56) References Cited

U.S. PATENT DOCUMENTS

| | | |
|---|---|---|
| 4,489,096 A | 12/1984 | Terao et al. |
| 4,851,413 A | 7/1989 | Terao et al. |
| 4,992,469 A | 2/1991 | Ozawa et al. |
| 5,008,267 A | 4/1991 | Katakami et al. |
| 5,304,658 A | 4/1994 | Terao et al. |
| 5,441,960 A | 8/1995 | Bernstein et al. |
| 5,656,645 A | 8/1997 | Tamura et al. |
| 5,658,930 A | 8/1997 | Tamura et al. |
| 5,668,289 A | 9/1997 | Sanderson et al. |
| 5,741,819 A | 4/1998 | Illig et al. |
| 5,792,779 A | 8/1998 | Sanderson et al. |
| 5,861,380 A | 1/1999 | Gyorkos et al. |
| 5,866,573 A | 2/1999 | Sanderson et al. |
| 5,869,487 A | 2/1999 | Coburn et al. |
| 5,872,138 A | 2/1999 | Naylor-Olsen et al. |
| 6,011,158 A | 1/2000 | Tamura et al. |
| 6,037,356 A | 3/2000 | Lu et al. |
| 6,180,627 B1 | 1/2001 | Blagg et al. |

FOREIGN PATENT DOCUMENTS

| | | |
|---|---|---|
| DE | 198 51 421 A1 | 5/2000 |
| EP | 0 354 495 A1 | 2/1990 |
| EP | 528 633 B1 | 2/1993 |
| EP | 826 671 A1 | 3/1998 |
| EP | 936 216 A1 | 8/1999 |
| EP | 940 400 A1 | 9/1999 |
| EP | 997 474 A1 | 5/2000 |
| WO | WO 93/21214 A1 | 10/1993 |
| WO | WO 96/18644 A1 | 6/1996 |
| WO | WO 96/33974 A1 | 10/1996 |
| WO | WO 96/39380 A1 | 12/1996 |
| WO | WO 96/40100 A1 | 12/1996 |
| WO | WO 97/01338 A1 | 1/1997 |
| WO | WO 97/30708 A1 | 8/1997 |
| WO | WO 97/40024 A1 | 10/1997 |
| WO | WO 97/46207 A2 | 12/1997 |
| WO | WO 98/08840 A1 | 3/1998 |
| WO | WO 98/09949 A1 | 3/1998 |
| WO | WO 98/09987 A1 | 3/1998 |
| WO | WO 98/10763 A1 | 3/1998 |
| WO | WO 97/17274 A1 | 4/1998 |
| WO | WO 98/16525 A1 | 4/1998 |
| WO | WO 98/16547 A1 | 4/1998 |
| WO | WO 98/31670 A1 | 7/1998 |
| WO | WO 98/42342 A1 | 10/1998 |
| WO | WO 98/47876 A1 | 10/1998 |
| WO | WO 98/50420 A1 | 11/1998 |
| WO | WO 99/00121 A1 | 1/1999 |
| WO | WO 99/00126 A1 | 1/1999 |
| WO | WO 99/00128 A1 | 1/1999 |
| WO | WO 99/11267 A1 | 3/1999 |
| WO | WO 99/26920 A1 | 6/1999 |
| WO | WO 99/26926 A1 | 6/1999 |

(List continued on next page.)

OTHER PUBLICATIONS

Tulinsky et al. Novel Asymmetric synthesis of atropisomeric 6–aryl pyrazinones, J. Org. Chem. 64:93–100, 1999.*

(List continued on next page.)

*Primary Examiner*—Mukund J. Shah
*Assistant Examiner*—Hong Liu

(57) ABSTRACT

The invention relates to substituted polycyclic aryl and heteroaryl pyrazinone compounds useful as inhibitors of serine proteases of the coagulation cascade and compounds, compositions and methods for anticoagulant therapy for the treatment and prevention of a variety of thrombotic conditions including coronary artery and cerebrovascular diseases.

27 Claims, No Drawings

FOREIGN PATENT DOCUMENTS

| | | |
|---|---|---|
| WO | WO 99/36426 A1 | 7/1999 |
| WO | WO 99/43660 A1 | 9/1999 |
| WO | WO 99/48892 A1 | 9/1999 |
| WO | WO 99/59591 A1 | 11/1999 |
| WO | WO 99/61442 A1 | 12/1999 |
| WO | WO 99/62538 A1 | 12/1999 |
| WO | WO 99/64446 A1 | 12/1999 |
| WO | WO 00/18762 A1 | 4/2000 |
| WO | WO 00/26210 A1 | 5/2000 |
| WO | WO 00/26211 A1 | 5/2000 |
| WO | WO 00/32574 A1 | 6/2000 |
| WO | WO 00/39102 A1 | 7/2000 |
| WO | WO 00/69826 A1 | 11/2000 |
| WO | WO 00/69832 A1 | 11/2000 |
| WO | WO 00/69833 A1 | 11/2000 |

OTHER PUBLICATIONS

Rauch, et al., Thrombus Formation on Atherosclerotic Plaques: Pathogenesis and Clinical Consequences, Annals of Internal Medicine, 2001, pp. 224–233, vol. 134—No. 3.

Van Aken, et al., Anticoagulation: The Present and Future, Clin. Appl. Thrombosis/Hemostasis, 2001, pp. 195–204, vol. 7—No. 3.

Coburn, C.A., "Small–molecule direct thrombine inhibitors 1997–2000." Expert Opinions on Therapeutic patents, 2001, 721–738, vol. 11, No. 5.

XP–002182132 –Darvas, et al., "Investigation of the Common Mechanism of Action of Antibacterial Compounds Containing .gamma.–pyridone–.beta.–carboxylic acid Structure by Principal Component." Arzneim.–Forshc., 1979, pp. 1334–1339, vol. 29, 9.

XP–002172033 –Kohama et al., "Preparation of Piperidinyloxyacetylaminobenzoylalanine Derivatives and Analogs as Antithrombotics." JP 07,233,148.

XP–002187583 –Moerner, Hoppe–Seyler's Z. Physiol. Chem., 69, 1910; 357.

Patel et al., "Directed Aminomethylation of 3–Hydroxy–3(1H)–pyridinones and 3–hydroxy–4(1H)–pyridinones: Synthesis of iso–Deferiprone." Tetrahedron, 1996, pp. 1835–1840, vol. 52, No. 5.

XP–002182410 –Trecourt et al., "First Synthesis of (+–)–harzianopyridone by Metalation of Polysubstituted O–pyridylcarbamates." J. Heterocycl. Chem., 1995, pp. 1117–1114, vol. 32, No. 4.

* cited by examiner

SUBSTITUTED POLYCYCLIC ARYL AND HETEROARYL PYRAZINONES USEFUL FOR SELECTIVE INHIBITION OF THE COAGULATION CASCADE

CROSS-REFERENCE TO RELATED APPLICATION

This application claims priority from Provisional Application Serial No. 60/134,958 filed on May 19, 1999, now abandoned, which is hereby incorporated by reference in its entirety.

FIELD OF THE INVENTION

This invention is in the field of anticoagulant therapy, and specifically relates to compounds, compositions and methods for preventing and treating thrombotic conditions such as coronary artery and cerebrovascular disease. More particularly, the invention relates to substituted polycyclic aryl and heteroaryl pyrazinone compounds that inhibit serine proteases of the coagulation cascade.

BACKGROUND OF THE INVENTION

Physiological systems control the fluidity of blood in mammals [Majerus, P. W. et al: Anticoagulant, Thrombolytic, and Antiplplatelet Drugs. In Hardman, J. G. and Limbird, L. E., editors: Goodman & Gilman's The Pharmacological Basis of Therapeutics. 9th edition. New York, McGraw-Hill Book Co., 1996, pp. 1341–1343]. Blood must remain fluid within the vascular systems and yet be able to undergo hemostasis, cessation of blood loss from a damaged vessel, quickly. Hemostasis or clotting begins when platelets first adhere to macromolecules in subendothelian regions of an injured and/or damaged vessels. These platelets aggregate to form the primary hemostatic plug and stimulate local activation of plasma coagulation factors leading to generation of a fibrin clot that reinforces the aggregated platelets.

Plasma coagulation factors include factors II, V, VII, VIII, IX, X, XI, and XII; these are also called protease zymogens. These coagulation factors or protease zymogens are activated by serine proteases leading to coagulation in a so called "coagulation cascade" or chain reaction [Handin, R. I.: Bleeding and Thrombosis. In Wilson, J., et al. editors: Harrison's Principles of Internal Medicine. 12th Edition, New York, McGraw-Hill Book Co., 1991,p.350]. Coagulation or clotting occurs in two ways through different pathways. An intrinsic or contact pathway leads from XII to XIIa to XIa to IXa and to the conversion of X to Xa. Xa with factor Va converts prothrombin (II) to thrombin (IIa) leading to conversion of fibrinogen to fibrin. Polymerization of fibrin leads to a fibrin clot. An extrinsic pathway is initiated by the conversion of coagulation factor VII to VIIa by Xa. The presence of Tissue Factor and VIIa accelerates formation of Xa in the presence of calcium ion and phospholipids. Formation of Xa leads to thrombin, fibrin, and a fibrin clot as described above. The presence of one or more of these many different coagulation factors and two distinct pathways of clotting could enable the efficacious, selective control and better understanding of parts of the coagulation or clotting process.

While clotting as a result of an injury to a blood vessel is a critical physiological process for mammals such as man, clotting can also lead to disease states. A pathological process called thrombosis results when platelet aggregation and/or a fibrin clot blocks (i.e., occludes) a blood vessel. Arterial thrombosis may result in ischemic necrosis of the tissue supplied by the artery. When the thrombosis occurs in a coronary artery, a myocardial infarction or heart attack can result. A thrombosis occurring in a vein may cause tissues drained by the vein to become edematous and inflamed. Thrombosis of a deep vein may be complicated by a pulmonary embolism. Preventing or treating clots in a blood vessel may be therapeutically useful by inhibiting formation of blood platelet aggregates, inhibiting formation of fibrin, inhibiting thrombus formation, inhibiting embolus formation, and for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels.

There have been several reports of non-peptidic and peptidic compounds that act as an inhibitor of a coagulation factor present in the coagulation cascade or clotting process. In PCG Patent Application WO 97/40024, Sanderson et al. describe alkyl, cycloalkyl, and trifluoromethyl substituted pyrazinones reported to inhibit thrombin activity. In PCG Patent Application WO 98/08840, Duggan et al. describe 2-heterocyclylacetyl derivatives of β-alanine esters reported to inhibit αvβ3 and αvβ5 receptors and possess utility in atheriosclerosis. In PCT Patent Application WO 98/09949, Suzuki et al. describe 2-heterocyclylacetamido derivatives of 1,2-diketones and report that they inhibit proteases, especially chymase inhibitors. In PCT Patent Application WO 98/42342, Isaacs et al. describe additional alkyl, cycloalkyl, and trifluoromethyl substituted pyrazinones reported to inhibit human thrombin. In PCG Patent Application WO 99/61442, Sanderson and Naylor-Olsen describe 1-(5-methylenecarboxamidomethyleneimidazo-[1,2-a]pyridinyl) pyrazinones without substitution in the imidazolyl portion and reported that the compounds inhibit thrombin activity. In PCT Patent Application WO 99/59591, Sanderson et al. describe 1-((N-substitutedaminopyridyl and N-substitutedphenyl)amidocarbonylmethylene)pyrazinones reported to inhibit thrombin. In PCT Patent Application WO 99/64446, Lu et al. describe 1-((N-amidinoaminooxyalkylene and N-amidinohydrazinoalkylene) amidocarbonylmethylene) pyrazinones reported to inhibit trypsin-like serine proteases and thrombin. In Japanese Patent Application 99/229491, Black et al. describe thrombin inhibiting halo and alkyl substituted pyrazinone acetamides in which the amide nitrogen is substituted by a group containing a benzimidazole or indole ring

SUMMARY OF THE INVENTION

It is an object of the present invention to provide compounds that are beneficial in anticoagulant therapy and that have a general structure:

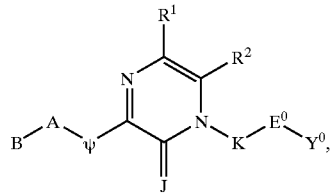

Formula (I).

It is another object of the present invention to provide methods for preventing and treating thrombotic conditions, such as coronary artery disease, cerebrovascular disease, and other coagulation related disorders. Such thrombotic conditions are prevented and treated by administering to a patient in need thereof an effective amount of compounds of Formula (I).

Various other objects and advantages of the present invention will become apparent from the following description of the invention.

DESCRIPTION OF THE INVENTION

The present invention relates to a class of compounds comprising Substituted Polycyclic Aryl and Heteroaryl Pyrazinones, which are beneficial in anticoagulant therapy for the treatment and prevention of a variety of thrombotic conditions including coronary artery and cerebrovascular disease, as given in Formula (I):

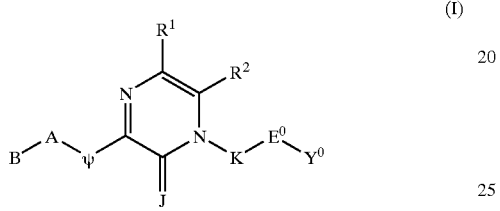

(I)

or a pharmaceutically acceptable salt thereof, wherein;

J is selected from the group consisting of O and S;

J is optionally selected from the group consisting of CH—$R^6$ and N—$R^6$ wherein $R^6$ is a linear spacer moiety having a chain length of 1 to 4 atoms linked to the point of bonding of a substituent selected from the group consisting of $R^{4a}$, $R^{4b}$, $R^{39}$, $R^{40}$, $R^5$, $R^{14}$, and $R^{15}$ to form a heterocyclyl ring having 5 through 8 contiguous members;

J is optionally selected from the group consisting of CH—$R^6$ and N—$R^6$ wherein $R^6$ is a linear spacer moiety having a chain length of 1 to 4 atoms linked to the points of bonding of both $R^{4a}$ and $R^{4b}$ to form a heterocyclyl ring having 5 through 8 contiguous members;

J is optionally selected from the group consisting of CH—$R^6$ and N—$R^6$ wherein $R^6$ is a linear spacer moiety having a chain length of 1 to 4 atoms linked to the points of bonding of both $R^{39}$ and $R^{40}$ to form a heterocyclyl ring having 5 through 8 contiguous members;

B is formula (V):

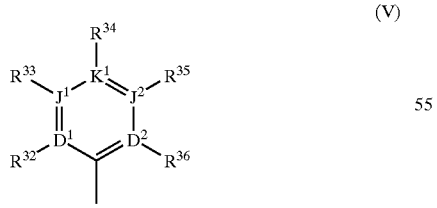

(V)

wherein
$D^1$, $D^2$, $J^1$, $J^2$ and $K^1$ are independently selected from the group consisting of C, N, O, S and a covalent bond with the provisos that no more than one can be a covalent bond, no more than one of $D^1$, $D^2$, $J^1$, $J^2$ and $K^1$ is O no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N with the proviso that $R^{32}$, $R^{33}$, $R^{34}$, $R^{35}$, and $R^{36}$ are each independently selected to maintain the tetravalent nature of carbon, trivalent nature of nitrogen, the divalent nature of sulfur, and the divalent nature of oxygen;

$R^9$, $R^{10}$, $R^{11}$, $R^{12}$, $R^{13}$, $R^{16}$, $R^{17}$, $R^{18}$, $R^{19}$, $R^{32}$, $R^{33}$, $R^{34}$, $R^{35}$, and $R^{36}$ are independently selected from the group consisting of hydrido, acetamido, haloacetamido, amidino, guanidino, dialkylsulfonium, trialkylphosphonium, dialkylsulfoniumalkyl, carboxy, heteroaralkylthio, heteroaralkoxy, cycloalkylamino, acylalkyl, acylalkoxy, aryloylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, alkoxyamino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, aryl sulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, alkylenylamino, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboxy, carboaralkoxy, carboxamido, carboxamidoalkyl, cyano, carbohaloalkoxy, phosphono, phosphonoalkyl, diaralkoxyphosphono, and diaralkoxyphosphonoalkyl;

R$^{16}$, R$^{19}$, R$^{32}$, R$^{33}$, R$^{34}$, R$^{35}$, and R$^{36}$ are independently optionally Q$^b$ with the proviso that no more than one of R$^{16}$ and R$^{19}$ is Q$^b$ at the same time and that Q$^b$ is Q$^{be}$;

R$^{32}$ and R$^{33}$, R$^{33}$ and R$^{34}$, R$^{34}$ and R$^{35}$, and R$^{35}$ and R$^{36}$ are independently optionally selected to form a spacer pair wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the proviso that no more than one of the group consisting of spacer pairs R$^{32}$ and R$^{33}$, R$^{33}$ and R$^{34}$, R$^{34}$ and R$^{35}$, and R$^{35}$ and R$^{36}$ are used at the same time;

R$^9$ and R$^{10}$, R$^{10}$ and R$^{11}$, R$^{11}$ and R$^{12}$, and R$^{12}$ and R$^{13}$ are independently optionally selected to form a spacer pair wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the proviso that no more than one of the group consisting of spacer pairs R$^9$ and R$^{10}$, R$^{10}$ and R$^{11}$, R$^{11}$ and R$^{12}$, and R$^{12}$ and R$^{13}$ are used at the same time;

B is optionally formula (VI):

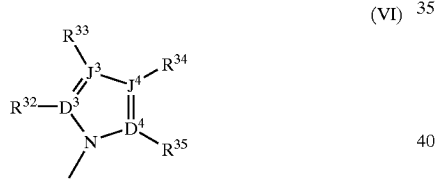

(VI)

wherein D$^3$, D$^4$, J$^3$, and J$^4$ are independently selected from the group consisting of C, N, O, and S, no more than one of D$^3$, D$^4$, J$^3$, and J$^4$ is O, no more than one of D$^3$, D$^4$, J$^3$, and J$^4$ is S, and no more than three of D$^1$, D$^2$, J$^1$, and J$^2$ are N with the proviso that R$^{32}$, R$^{33}$, R$^{34}$, and R$^{35}$ are each independently selected to maintain the tetravalent nature of carbon, trivalent nature of nitrogen, the divalent nature of sulfur, and the divalent nature of oxygen;

B is optionally selected from the group consisting of hydrido, trialkylsilyl, C2–C8 alkyl, C3–C8 alkenyl, C3–C8 alkylenyl, C3–C8 alkynyl, C2–C8 haloalkyl, and C3–C8 haloalkenyl wherein each member of group B is optionally substituted at any carbon up to and including 6 atoms from the point of attachment of B to A with one or more of the group consisting of R$_{32}$, R$_{33}$, R$_{34}$, R$_{35}$, and R$_{36}$;

B is optionally selected from the group consisting of C3–C15 cycloalkyl, C5–C10 cycloalkenyl, C4–C12 saturated heterocyclyl, and C4–C9 partially saturated heterocyclyl, wherein each ring carbon is optionally substituted with R$^{33}$, a ring carbon other than the ring carbon at the point of attachment of B to A is optionally substituted with oxo provided that no more than one ring carbon is substituted by oxo at the same time, ring carbon and nitrogen atoms adjacent to the carbon atom at the point of attachment is optionally substituted with R$^9$ or R$^{13}$, a ring carbon or nitrogen atom adjacent to the R$^9$ position and two atoms from the point of attachment is optionally substituted with R$^{10}$, a ring carbon or nitrogen atom adjacent to the R$^{13}$ position and two atoms from the point of attachment is optionally substituted with R$^{12}$, a ring carbon or nitrogen atom three atoms from the point of attachment and adjacent to the R$^{10}$ position is optionally substituted with R$^{11}$, a ring carbon or nitrogen atom three atoms from the point of attachment and adjacent to the R$^{12}$ position is optionally substituted with R$^{33}$, and a ring carbon or nitrogen atom four atoms from the point of attachment and adjacent to the R$^{11}$ and R$^{33}$ positions is optionally substituted with R$^{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 through 6, and W$^7$ is selected from the group consisting of O, S, C(O), C(S), C(O)S, C(S)O, C(O)N(R$^7$), C(S)N(R$^7$), (R$^7$)NC(O), (R$^7$)NC(S), S(O), S(O)$_2$, S(O)$_2$N(R$^7$), (R$^7$)NS(O)$_2$, Se(O), Se(O)$_2$, Se(O)$_2$N(R$^7$), (R$^7$)NSe(O)$_2$, P(O)(R$^8$), N(R$^7$)P(O)(R$^8$), P(O)(R$^8$)N(R$^7$), C(NR$^7$)N(R$^7$), (R$^7$)NC(NR$^7$), (R$^7$)NC(NR$^7$)NR$^7$, and N(R$^7$) with the proviso that no more than one of the group consisting of rr and pa is 0 at the same time;

R$^7$ and R$^8$ are independently selected from the group consisting of hydrido, hydroxy, alkyl, alkenyl, aryl, aralkyl, aryloxy, alkoxy, alkenyloxy, alkylthio, alkylamino, arylthio, arylamino, acyl, aroyl, heteroaroyl, aralkoxyalkyl, heteroaralkoxyalkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, heteroaryl, heteroaryloxy, heteroarylamino, heteroaralkyl, heteroaralkyloxy, heteroaralkylamino, and heteroaryloxyalkyl;

R$^{14}$, R$^{15}$, R$^{37}$, R$^{38}$, R$^{39}$, R$^{40}$, R$^{41}$ and R$^{42}$ are independently selected from the group consisting of amidino, hydroxyamino, hydrido, hydroxy, halo, cyano, aryloxy, amino, alkylamino, dialkylamino, hydroxyalkyl, aminoalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkylalkoxy, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, saturated heterocyclyl, partially saturated heterocyclyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, trialkylsilyl, dialkoxyphosphono, diaralkoxyphosphono, dialkoxyphosphonoalkyl, and diaralkoxyphosphonoalkyl with the proviso that $R^{37}$ and $R^{38}$ are independently selected from other than formyl and 2-oxoacyl;

$R^{14}$ and $R^{14}$, when bonded to different carbons, are optionally taken together to form a group selected from the group consisting of covalent bond, alkylene, haloalkylene, and a linear moiety spacer selected to form a ring selected from the group consisting of cycloalkyl ring having from 5 through 8 contiguous members, cycloalkenyl ring having from 5 through 8 contiguous members, and a heterocyclyl having from 5 through 8 contiguous members;

$R^{14}$ and $R^{15}$, when bonded to different carbons, are optionally taken together to form a group selected from the group consisting of covalent bond, alkylene, haloalkylene, and a linear moiety spacer selected to form a ring selected from the group consisting of a cycloalkyl ring having from 5 through 8 contiguous members, a cycloalkenyl ring having from 5 through 8 contiguous members, and a heterocyclyl having from 5 through 8 contiguous members;

$R^{15}$ and $R^{15}$, when bonded to different carbons, are optionally taken together to form a group selected from the group consisting of covalent bond, alkylene, haloalkylene, and a linear moiety spacer selected to form a ring selected from the group consisting of cycloalkyl ring having from 5 through 8 contiguous members, cycloalkenyl ring having from 5 through 8 contiguous members, and a heterocyclyl having from 5 through 8 contiguous members;

$\Psi$ is selected from the group consisting of $NR^5$, O, C(O), C(S), S, S(O), S(O)$_2$, ON($R^5$), P(O)($R^8$), and $CR^{39}R^{40}$;

$R^5$ is selected from the group consisting of hydrido, hydroxy, amino, alkyl, alkenyl, alkynyl, aryl, aralkyl, aryloxy, aralkoxy, alkoxy, alkenyloxy, alkylthio, arylthio, aralkoxyalkyl, heteroaralkoxyalkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, heteroaryl, heteroarylalkyl, monocarboalkoxyalkyl, monocarboalkoxy, dicarboalkoxyalkyl, monocarboxamido, monocyanoalkyl, dicyanoalkyl, carboalkoxycyanoalkyl, acyl, aroyl, heteroaroyl, heteroaryloxyalkyl, and dialkoxyphosphonoalkyl;

$R^{39}$ and $R^{40}$, when bonded to the same carbon, are optionally taken together to form a group selected from a group consisting of oxo, thiono, $R^5$—N, alkylene, haloalkylene, and a linear moiety spacer having from 2 through 7 contiguous atoms to form a ring selected from the group consisting of a cycloalkyl ring having from 3 through 8 contiguous members, a cycloalkenyl ring having from 3 through 8 contiguous members, and a heterocyclyl ring having from 3 through 8 contiguous members;

$R^2$ and $R^1$ are independently selected from the group consisting of $Z^0$—Q, hydrido, alkyl, alkenyl, and halo with the provisos that $R^2$ is selected from other than the group consisting of hydrido, alkyl, cycloalkyl, and trifluoromethyl and $R^1$ is selected from other than the group consisting of hydrido and halo unless $E^1$ is other than C(O)NH, or unless $E^0$ is selected from the group consisting of $E^2$ and $E^3$, or unless K is other than $(CR^{4a}R^{4b})_n$ wherein n is 1 unless one of $R^{4a}$ and $R^{4b}$ are independently selected from other than hydrido, or unless $\Psi$ is selected from other than $NR^5$, or unless $R^5$ is selected from other than hydrido, or unless $Y^0$ is selected from other than wherein $Q^s$ is $C_{1-4}$ alkyl, $C_{3-4}$ alkenyl or $C_{3-4}$ alkynyl where the $C_{1-4}$ alkyl, $C_{3-4}$ alkenyl or $C_{3-4}$ alkynyl group is bonded concurrently to $E^1$ wherein $E^1$ is C(O)NH and to the 4-position of an imidazole, the 4-position of a thiazole or the 5-position of a thiazole, or unless a spacer pair is present selected from the group of spacer pairs consisting of $R^2$ and $R^{4a}$, $R^2$ and $R^{4b}$, $R^2$ together with both $R^{4a}$ and $R^{4b}$, $R^2$ and $R^{14}$, $R^2$ and $R^{15}$, and $R^6$ with another group selected from the group consisting of $R^{4a}$, $R^{4b}$, $R^{4a}$ and $R^{4b}$ together, $R^{39}$, $R^{40}$, $R^{39}$ and $R^{40}$ together, $R^{14}$, $R^{15}$, and $R^5$, that $R^2$ is selected from other than the group consisting of alkyl, aryl, and heteroaryl and $R^1$ is selected from other than the group consisting of hydrido unless $E^1$ is other than C(O)NH, or unless $E^0$ is selected from the group consisting of $E^2$ and $E^3$, or unless K is other than $(CR^{4a}R^{4b})_n$ wherein n is 1 unless one of $R^{4a}$ and $R^{4b}$ are independently selected from other than hydrido, or unless $\Psi$ is selected from other than $NR^5$, or unless $R^5$ is selected from other than hydrido, or unless $R^{37}$ and $R^{38}$ are independently selected from other than formyl and 2-oxoacyl, that $R^2$ is selected from other than the group consisting of hydroxymethyl, methyl, methoxymethyl, methylthiomethyl, phenylthiomethyl, methylsulfinyl, methylthio, alkoxy, cycloalkoxy, alkylthio, alkylsulfinyl, alkysulfonyl, cycloalkylthio, cycloalkylsulfinyl, and cycloalkysulfonyl, when $Y^o$ is other than phenyl, mono-substituted phenyl, di-substituted phenyl, 5(2-amino)pyridindyl, or 4-(2-amino)pyridindyl, and that $R^2$ is selected from other than the group consisting of hydrido, halo, alkyl, cycloalkyl when $Y^o$ is methyleneimidazo(1,2-a)pyridinyl, 4,5-benzimidazol-5-yl, or indol-5-yl unless $R^1$ is selected from other than the group consisting of hydrido or halo, or unless $E^1$ is other than C(O)NH, or unless $E^0$ is selected from the group consisting of $E^2$ and $E^3$, or unless K is other than $(CR^{4a}R^{4b})_n$ wherein n is 1 unless one of $R^{4a}$ and $R^{4b}$ are independently selected from other than hydrido, or unless $\Psi$ is selected from other than $NR^5$ wherein $R^5$ is hydrido;

$R^1$ is optionally selected from the group consisting of amino. aminoalkyl, alkylamino, amidino, guanidino, hydroxy, hydroxyamino, alkoxy, hydroxyalkyl, alkoxyamino. thiol, alkylthio, dialkylsulfonium, trialkylphosphonium, dialkylsulfoniumalkyl, heteroarylamino, nitro, arylamino, aralkylamino, alkanoyl, alkenoyl, aroyl, heteroaroyl, aralkanoyl, heteroaralkanoyl, haloalkanoyl, hydroxyhaloalkyl, cyano, and phosphono;

$R^2$ is optionally selected from the group consisting of amidino, guanidino, dialkylsulfonium, trialkylphosphonium, dialkylsulfoniumalkyl, heteroarylamino, amino, nitro, alkylamino, arylamino, aralkylamino, alkanoyl, alkenoyl, aroyl, heteroaroyl, aralkanoyl, heteroaralkanoyl, haloalkanoyl, hydroxyhaloalkyl, cyano, and phosphono;

$R^2$ and $R^1$ are optionally taken together to form a spacer pair wherein the spacer pair forms a linear moiety having from 3 through 6 contiguous atoms connecting the points of bonding of said spacer pair members to form a ring selected from the group consisting of a cycloalkenyl ring having from 5 through 8 contiguous members and a partially saturated heterocyclyl ring having from 5 through 8 contiguous members;

$R^2$ and $R^1$ spacer pairs are optionally selected to be —W=X—Y=Z— forming a ring selected from the group consisting of a heteroaryl ring having from 5 through 6 contiguous members and an aryl, wherein W, X, Y, and Z are independently selected from the group consisting of $C(R^9)$, N, $N(R^{10})$, O, S and a covalent bond with the provisos that one of W, X, Y, and Z is independently selected to be a covalent bond when one of W, X, Y, and Z is selected from the group consisting of O and S, no more than one of W, X, Y, and Z is selected from the group consisting of O and S, no more than three of W, X, Y, and Z are selected from the group consisting of N and $N(R^{10})$, and $C(R^9)$, N, $N(R^{10})$, O, and S are independently selected to maintain the tetravalent nature of carbon, trivalent nature of nitrogen, the divalent nature of sulfur, the divalent nature of oxygen, and the aromaticity of the ring;

$R^2$ and $R^{4a}$, $R^2$ and $R^{4b}$, $R^2$ and $R^{14}$, and $R^2$ and $R^{15}$ are optionally independently selected to form spacer pairs wherein a spacer pair is taken together to form a linear moiety having from 2 through 5 contiguous atoms connecting the points of bonding of said spacer pair members to form a heterocyclyl ring having from 5 through 8 contiguous members with the proviso that no more than one of the group of spacer pairs consisting of $R^2$ and $R^{4a}$, $R^2$ and $R^{4b}$, $R^2$ and $R^{14}$, and $R^2$ and $R^{15}$ is used at the same time;

$R^2$ is optionally independently selected to form a linear moiety having from 2 through 5 contiguous atoms linked to the points of bonding of both $R^{4a}$ and $R^{4b}$ to form a heterocyclyl ring having from 5 through 8 contiguous members;

$Z^0$ is selected from the group consisting of covalent single bond, $(CR^{41}R^{42})_q$ wherein q is an integer selected from 1 through 6, $(CH(R^{41}))_g$—$W^0$—$(CH(R^{42}))_p$ wherein g and p are integers independently selected from 0 through 3 and $W^0$ is selected from the group consisting of O, S, C(O), C(S), C(O)O, C(S)O, C(O)S, C(S)S, $C(O)N(R^{41})$, $(R^{41})NC(O)$, $C(S)N(R^{41})$, $(R^{41})NC(S)$, $OC(O)N(R^{41})$, $(R^{41})NC(O)O$, $SC(S)N(R^{41})$, $(R^{41})NC(S)S$, $SC(O)N(R^{41})$, $(R^{41})NC(O)S$, $OC(S)N(R^{41})$, $(R^{41})NC(S)O$, $N(R^{42})C(O)N(R^{41})$ $(R^{41})NC(O)N(R^{42})$, $N(R^{42})C(S)N(R^{41})$, $(R^{41})NC(S)N(R^{42})$, S(O), $S(O)_2$, $S(O)_2N(R^{41})$, $N(R^{41})S(O)_2$, Se, Se(O), $Se(O)_2$, $Se(O)_2N(R^{41})$, $N(R^{41})Se(O)_2$, $P(O)(R^8)$, $N(R^7)P(O)(R^8)$, $P(O)(R^8)N(R^7)$, $N(R^{41})$, $ON(R^{41})$, and $SiR^{28}R^{29}$, and $(CH(R^{41}))_e$—$W^{22}$—$(CH(R^{42}))_h$ wherein e and h are integers independently selected from 0 through 2 and $W^{22}$ is selected from the group consisting of $CR^{41}=CR^{42}$, $CR^{41}R^{42}=C$; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4pyrrolidinyl, 2,3-tetrahydrofuranyl, 2,4-tetrahydrofuranyl, 2,5-tetrahydrofuranyl, and 3,4-tetrahydrofuranyl, with the provisos that $R^{41}$ and $R^{42}$ are selected from other than halo and cyano when directly bonded to N and $Z^0$ is directly bonded to the pyrazinone ring;

$R^{28}$ and $R^{29}$ are independently selected from the group consisting of hydrido, hydroxyalkyl, alkyl, alkenyl, alkynyl, aryl, aralkyl, aryloxyalkyl, acyl, aroyl, aralkanoyl, heteroaroyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroaralkyl, heteroarylthioalkyl, heteroaralkylthioalkyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, arylsulfinylalkyl, arylsulfonylalkyl, aralkylsulfinyl, cycloalkylsulfinylalkyl, cycloalkylsufonylalkyl, heteroarylsulfonylalkyl, heteroarylsulfinylalkyl, aralkylsulfinylalkyl, aralkylsulfonylalkyl, carboxy, dialkoxyphosphono, diaralkoxyphosphono, dialkoxyphosphonoalkyl and diaralkoxyphosphonoalkyl;

$R^{28}$ and $R^{29}$ are optionally taken together to form a linear moiety spacer having from 2 through 7 contiguous atoms and forming a ring selected from the group consisting of a cycloalkyl ring having from 3 through 8 contiguous members, a cycloalkenyl ring having from 3 through 8 contiguous members and a heterocyclyl ring having from 3 through 8 contiguous members;

Q is formula (II):

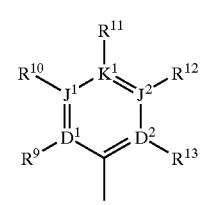

(II)

wherein $D^1$, $D^2$, $J^1$, $J^2$ and $K^1$ are independently selected from the group consisting of C, N, O, S and a covalent bond with the provisos that no more than one can be a covalent bond, no more than one of $D^1$, $D^2$, $J^1$, $J^2$ and $K^1$ can be O, no more than one of $D^1$, $D^2$, $J^1$, $J^2$ and $K^1$ can be S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ can be N, with the proviso that $R^9$, $R^{10}$, $R^{11}$, $R^{12}$, and $R^{13}$ are each independently selected to maintain the tetravalent nature of carbon, trivalent nature of nitrogen, the divalent nature of sulfur, and the divalent nature of oxygen;

Q is optionally selected from formula (III):

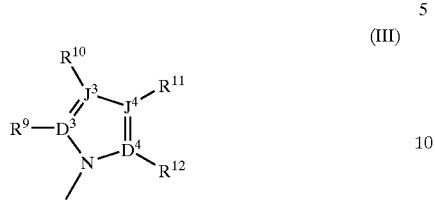

(III)

wherein $D^3$, $D^4$, $J^3$, and $J^4$ are independently selected from the group consisting of C, N, O, and S, no more than one of $D^3$, $D^4$, $J^3$, and $J^4$ is O, no more than one of $D^3$, $D^4$, $J^3$, and $J^4$ is S, and no more than three of $D^1$, $D^2$, $J^1$, and $J^2$ are N with the proviso that $R^9$, $R^{10}$, $R^{11}$, and $R^{12}$ are each independently selected to maintain the tetravalent nature of carbon, trivalent nature of nitrogen, the divalent nature of sulfur, and the divalent nature of oxygen;

Q is optionally selected from the group consisting of hydrido, alkyl, alkoxy, alkylamino, alkylthio, haloalkylthio, alkenyl, alkynyl, saturated heterocyclyl, partially saturated heterocyclyl, acyl, aroyl, heteroaroyl, cycloalkyl, cycloalkylalkyl, cycloalkenyl, cycloalkenylalkyl, cycloalkylalkenyl, haloalkyl, haloalkoxy, haloalkenyl, halocycloalkyl, halocycloalkenyl, haloalkoxyalkyl, haloalkenyloxyalkyl, halocycloalkoxyalkyl, and halocycloalkenyloxyalkyl with the proviso that $Z^0$ is selected from other than a single covalent bond when Q is hydrido;

K is $(CR^{4a}R^{4b})_n$ wherein n is an integer selected from 1 through 4;

$R^{4a}$ and $R^{4b}$ are independently selected from the group consisting of halo, hydrido, hydroxy, cyano, hydroxyalkyl, alkyl, alkenyl, aryl, aralkyl, aralkoxyalkyl, aryloxyalkyl, alkoxyalkyl, heteroaryloxyalkyl, alkenyloxyalkyl, alkylthioalkyl, aralkylthioalkyl, arylthioalkyl, cycloalkyl, cycloalkylalkyl, haloalkyl, haloalkenyl, heteroaryl, heteroarylalkyl, heteroarylthioalkyl, heteroaralkylthioalkyl, cyanoalkyl, alkylsulfinylalkyl, alkylsulfonylalkyl, haloalkylsulfinyl, arylsulfinylalkyl, arylsulfonylalkyl, heteroarylsulfonylalkyl, heteroarylsulfinylalkyl, aralkylsulfinylalkyl, and aralkylsulfonylalkyl with the provisos that halo, hydroxy, and cyano are bonded to different carbons when simultaneously present and that $R^{4a}$ and $R_{4b}$ are other than hydroxy or cyano when bonded to the carbon directly bonded to the pyrazinone nitrogen;

$R^{4a}$ and $R^{4b}$, when bonded to the same carbon, are optionally taken together to form a group selected from the group consisting of oxo, thiono, and a linear spacer moiety having from 2 through 7 contiguous atoms connected to form a ring selected from the group consisting of a cycloalkyl ring having 3 through 8 contiguous members, a cycloalkenyl ring having 5 through 8 contiguous members, and a heterocyclyl ring having 5 through 8 contiguous members with the proviso that $R^{4a}$ and $R^{4b}$ taken together is other than oxo or thiono when the common carbon is directly bonded to the pyrazinone nitrogen;

$E^0$ is $E^1$, when K is $(CR^{4a}R^{4b})_n$, wherein $E^1$ is selected from the group consisting of a covalent single bond, O, S, C(O), C(S), C(O)O, C(S)O, C(O)S, C(S)S, C(O)N($R^7$), ($R^7$)NC(O), C(S)N($R^7$), ($R^7$)NC(S), OC(O)N($R^7$), ($R^7$)NC(O)O, SC(S)N($R^7$), ($R^7$)NC(S)S, SC(O)N($R^7$), ($R^7$)NC(O)S, OC(S)N($R^7$), ($R^7$)NC(S)O, N($R^8$)C(O)N($R^7$), ($R^7$)NC(O)N($R^8$), N($R^8$)C(S)N($R^7$), ($R^7$)NC(S)N($R^8$), S(O), S(O)$_2$, S(O)$_2$N($R^7$), N($R^7$)S(O)$_2$, S(O)$_2$N($R^7$)C(O), C(O)N($R^7$)S(O)$_2$, Se, Se(O), Se(O)$_2$, Se(O)$_2$N($R^7$), N($R^7$)Se(O)$_2$, P(O)($R^8$), N($R^7$)P(O)($R^8$), P(O)($R^8$)N($R^7$), N($R^7$), ON($R^7$), Si$R^{28}R^{29}$, $CR^{4a}$=$CR^{4b}$, ethynylidene (C≡C; 1,2-ethynyl), and C=$CR^{4a}R^{4b}$;

K is optionally selected to be $(CH(R^{14}))_j$—T wherein j is selected from a integer from 0 through 3 and T is selected from the group consisting of single covalent bond, O, S, and N($R^7$) with the provisos that $R^{14}$ is other than hydroxy, cyano, halo, amino, alkylamino, dialkylamino, and sulfhydryl when j is 1 and that $(CH(R^{14}))_j$ is bonded to the pyrazinone ring;

$E^0$ is optionally $E^2$, when K is $(CH(R^{14}))_j$—T, wherein $E^2$ is selected from the group consisting of a covalent single bond, C(O), C(S), C(O)O, C(S)O, C(O)S, C(S)S, C(O)N($R^7$), ($R^7$)NC(O), C(S)N($R^7$), ($R^7$)NC(S), ($R^7$)NC(O)O, ($R^7$)NC(S)S, ($R^7$)NC(O)S, ($R^7$)NC(S)O, N($R^8$)C(O)N($R^7$), ($R^7$)NC(O)N($R^8$), N($R^8$)C(S)N($R^7$), ($R^7$)NC(S)N($R^8$), S(O), S(O)$_2$, S(O)$_2$N($R^7$), N($R^7$)S(O)$_2$, S(O)$_2$N(H)C(O), C(O)N(H)S(O)$_2$, Se(O), Se(O)$_2$, Se(O)$_2$N($R^7$), N($R^7$)Se(O)$_2$, P(O)($R^8$), N($R^7$)P(O)($R^8$), P(O)($R^8$)N($R^7$), and N($R^7$);

K is optionally selected to be G—$(CH(R^{15}))_k$ wherein k is selected from an integer from 1 through 3 and G is selected from the group consisting of O, S, and N($R^7$) with the proviso that $R^{15}$ is other than hydroxy, cyano, halo, amino, alkylamino, dialkylamino, and sulfhydryl when k is 1;

$E^0$ is optionally $E^3$ when K is G—$(CH(R^{15}))_k$ wherein $E^3$ is selected from the group consisting of a covalent single bond, O, S, C(O), C(S), C(O)O, C(S)O, C(O)S, C(S)S, C(O)N($R^7$), ($R^7$)NC(O), C(S)N($R^7$), ($R^7$)NC(S), OC(O)N($R^7$), ($R^7$)NC(O)O, SC(S)N($R^7$), ($R^7$)NC(S)S, SC(O)N($R^7$), ($R^7$)NC(O)S, OC(S)N($R^7$), ($R^7$)NC(S)O, N($R^8$)C(O)N($R^7$), ($R^7$)NC(O)N($R^8$), N($R^8$)C(S)N($R^7$), ($R^7$)NC(S)N($R^8$), S(O), S(O)$_2$, S(O)$_2$N($R^7$), N($R^7$)S(O)$_2$, Se, Se(O), Se(O)$_2$, Se(O)$_2$N($R^7$), N($R^7$)Se(O)$_2$, P(O)($R^8$), N($R^7$)P(O)($R^8$) P(O)($R^8$)N($R^7$), N($R^7$), ON($R^7$), Si$R^{28}R^{29}$, $CR^{4a}$=$CR^{4b}$, ethynylidene (C≡C; 1,2-ethynyl), and C=$CR^{4a}R^{4b}$;

$Y^0$ is formula (IV):

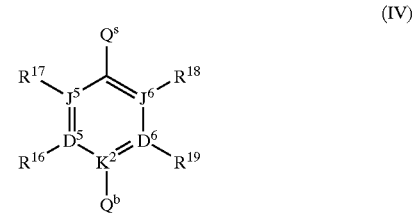

(IV)

wherein $D^5$, $D^6$, $J^5$, and $J^6$ are independently selected from the group consisting of C, N, O, S and a covalent bond with the provisos that no more than one is a covalent bond, $K^2$ is independently selected from the group consisting of C and $N^+$, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, no more than three of $D^5$, $D^6$, $J^5$, and $J^6$ are N when $K^2$ is $N^+$, and no more than four of $D^5$, $D^6$, $J^5$, and $J^6$ are N when $K^2$ is carbon with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$ and $R^{17}$ are independently optionally taken together to form a linear moiety spacer having from 3 through 6 contiguous atoms connected to form a ring selected from the group consisting of a cycloalkenyl ring having from 5 through 8 contiguous members, a partially saturated heterocyclyl ring having from 5 through 8 contiguous members, a heteroaryl having from 5 through 6 contiguous members, and an aryl;

$R^{18}$ and $R^{19}$ are independently optionally taken together to form a linear moiety spacer having from 3 through 6 contiguous atoms connected to form a ring selected from the group consisting of a cycloalkenyl ring having from 5 through 8 contiguous members, a partially saturated heterocyclyl ring having from 5 through 8 contiguous members, a heteroaryl having from 5 through 6 contiguous members, and an aryl;

$Q^b$ is selected from the group consisting of $NR^{20}R^{21}$, $^+NR^{20}R^{21}R^{22}$, oxy, alkyl, aminoalkylenyl, alkylamino, dialkylamino, dialkylsulfoniumalkyl, acylamino and $Q^{be}$ wherein $Q^{be}$ is hydrido and $R^{20}$, $R^{21}$, and $R^{22}$ are independently selected from the group consisting of hydrido, amino, alkyl, hydroxy, alkoxy, aminoalkylenyl, alkylamino, dialkylamino, and hydroxyalkyl with the provisos that no more than one of $R^{20}$, $R^{21}$, and $R^{22}$ is hydroxy, alkoxy, alkylamino, amino, and dialkylamino at the same time and that $R^{20}$, $R^{21}$, and $R^{22}$ must be other than be hydroxy, alkoxy, alkylamino, amino, and dialkylamnino when $K^2$ is $N^+$;

$R^{20}$ and $R^{21}$, $R^{20}$ and $R^{22}$, and $R^{21}$ and $R^{22}$ are independently optionally selected to form a spacer pair wherein a spacer pair is taken together to form a linear moiety having from 4 through 7 contiguous atoms connecting the points of bonding of said spacer pair members to form a heterocyclyl ring having 5 through 8 contiguous members with the proviso that no more than one of the group consisting of spacer pairs $R^{20}$ and $R^{21}$, $R^{20}$ and $R^{22}$, and $R^{21}$ and $R^{22}$ is used at the same time;

$Q^b$ is optionally selected from the group consisting of $N(R^{26})SO_2N(R^{23})(R^{24})$, $N(R^{26})C(O)OR^5$, $N(R^{26})C(O)SR^5$, $N(R^{26})C(S)OR^5$ and $N(R^{26})C(S)SR^5$ with the proviso that no more than one of $R^{23}$, $R^{24}$, and $R^{26}$ can be hydroxy, alkoxy, alkyleneamino, alkylamino, amino, or dialkylamino when two of the group consisting of $R^{23}$, $R^{24}$, and $R^{26}$ are bonded to the same atom;

$Q^b$ is optionally selected from the group consisting of dialkylsulfonium, trialkylphosphonium, $C(NR^{25})NR^{23}R^{24}$, $N(R^{26})C(NR^{25})N(R^{23})(R^{24})$, $N(R^{26})C(O)N(R^{23})(R^{24})$, $N(R^{26})C(S)N(R^{23})(R^{24})$, $C(NR^{25})OR^5$, $C(O)N(R^{26})C(NR^{25})N(R^{23})(R^{24})$, $C(S)N(R^{26})C(NR^{25})N(R^{23})(R^{24})$, $N(R^{26})N(R^{26})C(NR^{25})N(R^{23})(R^{24})$, $ON(R^{26})C(NR^{25})N(R^{23})(R^{24})$, $N(R^{26})N(R^{26})SO_2N(R^{23})(R^{24})$, $C(NR^{25})SR^5$, $C(O)NR^{23}R^{24}$, and $C(O)NR^{23}R^{24}$ with the provisos that no more than one of $R^{23}$, $R^{24}$, and $R^{26}$ can be hydroxy, alkoxy, alkylamino, amino, or dialkylamino when any two of the group consisting of $R^{23}$, $R^{24}$, and $R^{26}$ are bonded to the same atom and that said $Q^b$ group is bonded directly to a carbon atom;

$R^{23}$, $R^{24}$, $R^{25}$, and $R^{26}$ are independently selected from the group consisting of hydrido, alkyl, hydroxy, alkoxy, alkylenylamino, amino, alkylamino, dialkylamino, and hydroxyalkyl;

$R^{23}$ and $R^{24}$ are optionally taken together to form a linear spacer moiety having from 4 through 7 contiguous atoms connecting the points of bonding to form a heterocyclyl ring having 5 through 8 contiguous members;

$R^{23}$ and $R^{25}$, $R^{24}$ and $R^{25}$, $R^{25}$ and $R^{26}$, $R^{24}$ and $R^{26}$, and $R^{23}$ and $R^{26}$ are independently optionally selected to form a spacer pair wherein a spacer pair is taken together from the points of bonding of selected spacer pair members to form the group L—U—V wherein L, U, and V are independently selected from the group consisting of O, S, C(O), C(S), $C(J_H)_2S(O)$, $SO_2$, $OP(OR^{31})R^{30}$, $P(O)R^{30}$, $P(S)R^{30}$, $C(R^{30})R^{31}$, $C=C(R^{30})R^{31}$, $(O)_2POP(O)_2$, $R^{30}(O)POP(O)R^{30}$, $Si(R^{29})R^{28}$, $Si(R^{29})R^{28}Si(R^{29})R^{28}$, $Si(R^{29})R^{28}OSi(R^{29})R^{28}$, $(R^{28})R^{29}COC(R^{28})R^{29}$, $(R^{28})R^{29}CSC(R^{28})R^{29}$, $C(O)C(R^{30})=C(R^{31})$, $C(S)C(R^{30})=C(R^{31})$, $S(O)C(R^{30})=C(R^{31})$, $SO_2C(R^{30})=C(R^{31})$, $PR^{30}C(R^{30})=C(R^{31})$, $P(O)R^{30}C(R^{30})=C(R^{31})$, $P(S)R^{30}C(R^{30})=C(R^{31})$, $DC(R^{30})(R^{31})D$, $OP(OR^{31})R^{30}$, $P(O)R^{30}$, $P(S)R^{30}$, $Si(R^{28})R^{29}$ and $N(R^{30})$, and a covalent bond with the proviso that no more than any two of L, U and V are simultaneously covalent bonds and the heterocyclyl comprised of by L, U, and V has from 5 through 10 contiguous member;

D is selected from the group consisting of oxygen, C=O, C=S, $S(O)_m$ wherein m is an integer selected from 0 through 2;

$J_H$ is independently selected from the group consisting of $OR^{27}$, $SR^{27}$ and $N(R^{20})R^{21}$;

$R^{27}$ is selected from the group consisting of hydrido, alkyl, alkenyl, alkynyl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryloxyalkyl, heteroaryl, heteroarylalkyl, heteroarylthioalkyl, heteroaralkylthioalkyl, arylsulfinylalkyl, arylsulfonylalkyl, cycloalkylsulfinylalkyl, cycloalkylsufonylalkyl, heteroarylsulfonylalkyl, heteroarylsulfinylalkyl, aralkylsulfinylalkyl and aralkylsulfonylalkyl;

$R^{30}$ and $R^{31}$ are independently selected from the group consisting of hydrido, hydroxy, thiol, aryloxy, amino, alkylamino, dialkylamino, hydroxyalkyl, heteroaryloxyalkyl, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, haloaralkylsulfinylalkyl, aralkylsulfonylalkyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, sulfonylalkyl, alkoxysulfonylalkyl, aralkoxysulfonylalkyl, alkoxysulfonylalkoxy, aralkoxysulfonylalkoxy, sulfonylalkoxy, alkoxysulfonylalkylamino, aralkoxysulfonylalkylamino, and sulfonylalkylamino;

$R^{30}$ and $R^{31}$ are optionally taken to form a linear moiety spacer group having from 2 through 7 contiguous atoms to form a ring selected from the group consisting of a cycloalkyl ring having from 3 through 8 contiguous members, a cycloalkenyl ring having from 3 through 8 contiguous members, and a heterocyclyl ring having from 3 through 8 contiguous members;

$R^{23}$ and $R^{25}$, $R^{24}$ and $R^{25}$, $R^{25}$ and $R^{26}$, $R^{24}$ and $R^{26}$, and $R^{23}$ and $R^{26}$ are independently optionally selected to form a spacer pair wherein a spacer pair is taken together from the points of bonding of selected spacer pair members to form the group L—U—V wherein L, U, and V are independently selected from the group of 1,2-disubstituted radicals consisting of a cycloalkyl radical, a cycloalkenyl radical wherein cycloalkyl and cycloalkenyl radicals are substituted with one or more groups selected from $R^{30}$ and $R^{31}$, an aryl radical, an heteroaryl radical, a saturated heterocyclic radical and a partially saturated heterocyclic radical wherein said 1,2-substitutents are independently selected from C=O, C=S, C($R^{28}$)$R^{32}$, S(O), S(O)$_2$, OP(O$R^{31}$)$R^{30}$, P(O)$R^{30}$, P(S)$R^{30}$ and Si($R^{28}$)$R^{29}$;

$R^{23}$ and $R^{25}$, $R^{24}$ and $R^{25}$, $R^{25}$ and $R^{26}$, $R^{24}$ and $R^{26}$, and $R^{23}$ and $R^{26}$ are independently optionally selected to form a spacer pair wherein a spacer pair is taken together from the points of bonding of selected spacer pair members to form the group L—U—V wherein L, U, and V are independently selected from the group of radicals consisting of 1,2-disubstituted alkylene radicals and 1,2-disubstituted alkenylene radical wherein said 1,2-substitutents are independently selected from C=O, C=S, C($R^{28}$)$R^{29}$, S(O), S(O)$_2$, OP(O$R^{31}$)$R^{30}$, P(O)$R^{30}$, P(S)$R^{30}$, and Si($R^{28}$)$R^{29}$ and said alkylene and alkenylene radical are substituted with one or more $R^{30}$ or $R^{31}$ substituents;

$Q^s$ is selected from the group consisting of a single covalent bond, $(CR^{37}R^{38})_b$—$(W^0)_{az}$ wherein az is an integer selected from 0 through 1, b is an integer selected from 1 through 4, and $W^0$ is selected from the group consisting of O, S, C(O), C(S), C(O)O, C(S)O, C(O)S, C(S)S, C(O)N($R^{14}$), ($R^{14}$)NC(O), C(S)N($R^{14}$), ($R^{14}$)NC(S), OC(O)N($R^{14}$), SC(S)N ($R^{14}$), SC(O)N($R^{14}$), OC(S)N($R^{14}$), N($R^{15}$)C(O)N ($R^{14}$), ($R^{14}$)NC(O)N($R^{15}$), N($R^{15}$)C(S)N($R^{14}$), ($R^{14}$) NC(S)N($R^{15}$), S(O), S(O)$_2$, S(O)$_2$N($R^{14}$), N($R^{14}$)S (O)$_2$, Se, Se(O), Se(O)$_2$, Se(O)$_2$N($R^{17}$), N($R^{14}$)Se (O)$_2$, P(O)($R^8$), N($R^7$)P(O)($R^8$), P(O)($R^8$)N($R^7$), N($R^{14}$), ON($R^{14}$), and Si$R^{28}R^{29}$, $(CH(R^{14}))_c$—$W^1$—$(CH(R^{15}))_d$ wherein c and d are integers independently selected from 1 through 4, and $W^1$ is selected from the group consisting of O, S, C(O), C(S), C(O)O, C(S)O, C(O)S, C(S)S, C(O)N($R^{14}$), ($R^{14}$) NC(O), C(S)N($R^{14}$), ($R^{14}$)NC(S), OC(O)N($R^{14}$), ($R^{14}$)NC(O)O, SC(S)N($R^{14}$), ($R^{14}$)NC(S)S, SC(O)N ($R^{14}$), ($R^{14}$)NC(O)S, OC(S)N($R^{14}$), ($R^{14}$)NC(S)O, N($R^{15}$)C(O)N($R^{14}$), ($R^{14}$)NC(O)N($R^{14}$), N($R^{15}$)C (S)N($R^{14}$), ($R^{14}$)NC(S)N($R^{15}$), S(O), S(O)$_2$, S(O)$_2$N ($R^{14}$), N($R^{14}$)S(O)$_2$, Se, Se(O), Se(O)$_2$, Se(O)$_2$N ($R^{14}$), N($R^{14}$)Se(O)$_2$, P(O)($R^8$), N($R^7$)P(O)($R^8$), P(O)($R^8$)N($R^7$), N($R^{14}$), ON($R^{14}$), Si$R^{28}R^{29}$, and $(CH(R^{14}))_e$—$W^{22}$—$(CH(R^{15}))_h$ wherein e and h are integers independently selected from 0 through 2 and $W^{22}$ is selected from the group consisting of $CR^{41}$=$CR^{42}$, $CR^{41}R^{42}$=C; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that $R^{14}$ and $R^{15}$ are selected from other than halo and cyano when directly bonded to N and that $(CR^{37}R^{38})_b$, $(CH(R^{14}))_c$, $(CH(R^{14}))_e$ and are bonded to $E^0$;

$R^{37}$ and $R^{37}$, when bonded to different carbons, are optionally taken together to form a linear moiety spacer having from 1 through 7 contiguous atoms to form a ring selected from the group consisting of a cycloalkyl ring having from 3 through 8 contiguous members, a cycloalkenyl ring having from 3 through 8 contiguous members, and a heterocyclyl ring having from 3 through 8 contiguous members;

$R^{37}$ and $R^{38}$, when bonded to different carbons, are taken together to form a linear moiety spacer having from 1 through 7 contiguous atoms to form a ring selected from the group consisting of a cycloalkyl ring having from 3 through 8 contiguous members, a cycloalkenyl ring having from 3 through 8 contiguous members, and a heterocyclyl ring having from 3 through 8 contiguous members;

$R^{38}$ and $R^{38}$, when bonded to different carbons, are taken together to form a linear moiety spacer having from 1 through 7 contiguous atoms to form a ring selected from the group consisting of a cycloalkyl ring having from 3 through 8 contiguous members, a cycloalkenyl ring having from 3 through 8 contiguous members, and a heterocyclyl ring having from 3 through 8 contiguous members;

$R^{37}$ and $R^{38}$, when bonded to the same carbon, are taken together to form a group selected from a group consisting of oxo, thiono, alkylene, haloalkylene, and a linear moiety spacer having from 2 through 7 contiguous atoms to form a ring selected from the group consisting of a cycloalkyl ring having from 3 through 8 contiguous members, a cycloalkenyl ring having from 3 through 8 contiguous members, and a heterocyclyl ring having from 3 through 8 contiguous members;

$Y^0$ is optionally $Q^b$—$Q^{ss}$ wherein $Q^{ss}$ is selected from the group consisting of $(CR^{37}R^{38})_f$ wherein f is an integer selected from 1 through 6, $(CH(R^{14}))_c$—$W^1$—$(CH(R^{15}))_d$ wherein c and d are integers independently selected from 1 through 4, and $W^1$ is selected from the group consisting of $W^1$ is selected from the group consisting of O, S, C(O), C(S), C(O)O, C(S)O, C(O)S, C(S)S, C(O)N($R^{14}$), ($R^{14}$)NC(O), C(S)N($R^{14}$), ($R^{14}$)NC(S), OC(O)N($R^{14}$), ($R^{14}$)NC(O)O, SC(S)N($R^{14}$), ($R^{14}$)NC(S)S, SC(O)N($R^{14}$), ($R^{14}$)NC(O)S, OC(S)N($R^{14}$), ($R^{14}$)NC(S)O, N($R^{15}$)C(O)N($R^{14}$), ($R^{14}$)NC(O)N($R^{15}$), N($R^{15}$)C(S)N($R^{14}$), ($R^{14}$)NC(S)N($R^{15}$), S(O), S(O)$_2$, S(O)$_2$N($R^{14}$), N($R^{14}$)S(O)$_2$, Se, Se(O), Se(O)$_2$, Se(O)$_2$N($R^{14}$), N($R^{14}$)Se(O)$_2$, P(O)($R^8$), N($R^7$)P(O)($R^8$), P(O)($R^8$)N($R^7$), N($R^{14}$), ON($R^{14}$) SiR$^{28}$R$^{29}$, and $(CH(R^{14}))_e$—$W^2$—$(CH(R^{15}))_h$ wherein e and h are integers independently selected from 0 through 2 and $W^2$ is selected from the group consisting of $CR^{4a}$=$CR^{4b}$, ethynylidene (C≡C; 1,2-ethynyl), and C=$CR^{4a}R^{4b}$ with the provisos that $R^{14}$ and $R^{15}$ are selected from other than halo and cyano when directly bonded to N, that $(CR^{37}R^{38})_f$, $(CH(R^{15}))_c$, and $(CH(R^{15}))_e$ are bonded to $E^0$, and $Q^b$ is selected from other than N($R^{26}$)N($R^{26}$)C(NR$^{25}$)N($R^{23}$)($R^{24}$) or ON($R^{26}$)C(NR$^{25}$)N($R^{23}$)($R^{24}$) when $Q^{ss}$ is $(CR^{37}R^{38})_f$ wherein f is other than the integer 1;

$Y^0$ is optionally $Q^b$—$Q^{sss}$ wherein $Q^{sss}$ is $(CH(R^{38}))_r$—$W^3$, r is an integer selected from 1 through 3, $W^3$ is selected from the group consisting of 1,1-cyclopropyl, 1,2-cyclopropyl, 1,1-cyclobutyl, 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hyrido containing nitrogen member of the ring of the $W^3$ other than the points of attachment is optionally substituted with one or more of the group consisting of $R^9$, $R^{10}$, $R^{11}$, and $R^{12}$, with the proviso that $(CH(R^{38}))_r$ is bonded to $E^0$ and $Q^b$ is bonded to lowest numbered substituent position of each $W^3$;

$Y^0$ is optionally $Q^b$—$Q^{sssr}$ wherein $Q^{sssr}$ is $(CH(R^{38}))_r$—$W^4$, is an integer selected from 1 through 3, $W^4$ is selected from the group consisting of 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hydrido containing nitrogen member of the ring of the $W^4$ other than the points of attachment is optionally substituted with one or more of the group consisting of $R^9$, $R^{10}$, $R^{11}$, and $R^{12}$, with the provisos that $(CH(R^{38}))_r$ is bonded to $E^0$ and $Q^b$ is bonded to highest number substituent position of each $W^4$;

$Y^0$ is optionally $Q^b$—$Q^{ssss}$ wherein $Q^{ssss}$ is $(CH(R^{38}))_r$—$W^5$, r is an integer selected from 1 through 3, $W^5$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4benzothiophenyl, 2,5-benzothiophenyl, 2,6-benzothiophenyl, 2,7-benzothiophenyl, 3,5-benzothiophenyl, 3,5-benzothiophenyl, 3,6-benzothiophenyl, 3,7-benzothiophenyl, 2,4-imidazo(1,2-a)pyridinyl, 2,5-imidazo(1,2-a)pyridinyl, 2,6-imidazo(1,2-a)pyridinyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hydrido containing nitrogen member of the ring of the $W^5$ other than the points of attachment is optionally substituted with one or more of the group consisting of $R^9$, $R^{10}$, $R^{11}$, and $R^{12}$, with the proviso that $Q^b$ is bonded to lowest number substituent position of each $W^5$ and that $(CH(R^{38}))_r$ is bonded to $E^0$;

$Y^0$ is optionally $Q^b$—$Q^{ssssr}$ wherein $Q^{ssssr}$ is $(CH(R^{38}))_r$—$W^6$, r is an integer selected from 1 through 3, $W^6$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,4-imidazo(1,2-a)pyridinyl, 2,5-imidazo(1,2-a)pyridinyl, 2,6-imidazo(1,2-a)pyridinyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1 3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hydrido containing nitrogen member of the ring of the $W^6$ other than the points of attachment is optionally substituted with one or more of the group consisting of $R^9$, $R^{10}$, $R^{11}$, and $R^{12}$, with the proviso that $Q^b$ is bonded to highest number substituent position of each $W^6$ and that $(CH(R^{38}))_r$ is bonded to $E^0$.

In an embodiment of compounds of Formula I or a pharmaceutically acceptable salt thereof, J is selected from the group consisting of O and S;

J is optionally selected from the group consisting of CH—$R^6$ and N—$R^6$ wherein $R^6$ is a linear spacer moiety having a chain length of 1 to 4 atoms linked to the point of bonding of a substituent selected from the group consisting of $R^{4a}$, $R^{4b}$, $R^{39}$, $R^{40}$, $R^5$, $R^{14}$, and $R^{15}$ to form a heterocyclyl ring having 5 through 8 contiguous members;

B is formula (V):

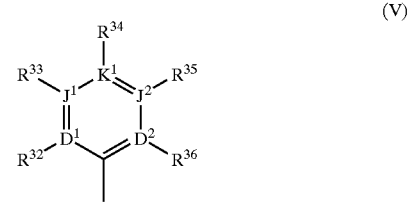

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N with the proviso that $R^{32}$, $R^{33}$, $R^{34}$, $R^{35}$, and $R^{36}$ are each independently selected to maintain the tetravalent nature of carbon, trivalent nature of nitrogen, the divalent nature of sulfur, and the divalent nature of oxygen;

$R^9$, $R^{10}$, $R^{11}$, $R^{12}$, $R^{13}$, $R^{16}$, $R^{17}$, $R^{18}$, $R^{19, R32}$, $R^{33}$, $R^{34}$, $R^{35}$, and $R^{36}$ are independently selected from the group consisting of hydrido. acetamido, haloacetamido, amidino, guanidino, dialkylsulfonium, trialkylphosphonium, dialkylsulfoniumalkyl, carboxy, heteroaralkylthio, heteroaralkoxy, cycloalkylamino, acylalkyl, acylalkoxy, aryloylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylaamino, heteroarylaminoalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, alkoxyamino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, aryl sulfonyl alkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, alkylenylamino, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboxy, carboaralkoxy, carboxamido, carboxamidoalkyl, cyano, carbohaloalkoxy, phosphono, phosphonoalkyl, diaralkoxyphosphono, and diaralkoxyphosphonoalkyl;

$R^{16}$, $R^{19}$, $R^{32}$, $R^{33}$, $R^{34}$, $R^{35}$, and $R^{36}$ are independently optionally $Q^b$ with the proviso that no more than one of $R^{16}$ and $R^{19}$ is $Q^b$ at the same time and that $Q^b$ is $Q^{be}$;

$R^{32}$ and $R^{33}$, $R^{33}$ and $R^{34}$, $R^{34}$ and $R^{35}$, and $R^{35}$ and $R^{36}$ are independently optionally selected to form a spacer pair wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the proviso that no more than one of the group consisting of spacer pairs $R^{32}$ and $R^{33}$, $R^{33}$ and $R^{34}$, $R^{34}$ and $R^{35}$, and $R^{35}$ and $R^{36}$ can be used at the same time;

$R^9$ and $R^{10}$, $R^{10}$ and $R^{11}$, $R^{11}$ and $R^{12}$, and $R^{12}$ and $R^{13}$ are independently optionally selected to form a spacer pair wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the proviso that no more than one of the group consisting of spacer pairs $R^9$ and $R^{10}$, $R^{10}$ and $R^{11}$, $R^{11}$ and $R^{12}$, and $R^{12}$ and $R^{13}$ can be used at the same time;

B is optionally selected from the group consisting of hydrido, trialkylsilyl, C2–C8 alkyl, C3–C8 alkylenyl, C3–C8 alkenyl, C3–C8 alkynyl, C2–C8 haloalkyl, and C3–C8 haloalkenyl wherein each member of group B may be optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally selected from the group consisting of C3–C15 cycloalkyl, C5–C10 cycloalkenyl, C4–C12 saturated heterocyclyl, and C4–C9 partially saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, a ring carbon or nitrogen atom adjacent to the $R^{13}$ position and two atoms from the point of attachment is optionally substituted with $R^{12}$, a ring carbon or nitrogen atom three atoms from the point of attachment and adjacent to the $R^{10}$ position is optionally substituted with $R^{11}$, a ring carbon or nitrogen atom three atoms from the point of attachment and adjacent to the $R^{12}$ position is optionally substituted with $R^{33}$, and a ring carbon or nitrogen atom four atoms from the point of attachment and adjacent to the $R^{11}$ and $R^{33}$ positions is optionally substituted with $R^{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 through 6, and $W^7$ is selected from the group consisting of O, S, C(O), C(S), C(O)S, C(S)O, C(O)N($R^7$), C(S)N($R^7$), ($R^7$)NC(O), ($R^7$)NC(S), S(O), S(O)$_2$, S(O)$_2$N($R^7$), ($R^7$)NS(O)$_2$, P(O)($R^8$), N($R^7$)P(O)($R^8$), P(O)($R^8$)N($R^7$), C(N$R^7$)N ($R^7$), ($R^7$)NC(N$R^7$), ($R^7$)NC(N$R^7$)N$R^7$, and N($R^7$) with the proviso that no more than one of the group consisting of rr and pa can be 0 at the same time;

$R^7$ and $R^8$ are independently selected from the group consisting of hydrido, hydroxy, alkyl, acyl, aroyl, heteroaroyl, and alkoxyalkyl;

$R^{14}$, $R^{15}$, $R^{37}$, and $R^{38}$ are independently selected from the group consisting of hydrido, hydroxy, halo, cyano, hydroxyalkyl, alkoxy, alkyl, alkoxyalkyl, cycloalkyl, cycloalkylalkyl, cycloalkenyl, cycloalkenylalkyl, haloalkyl, haloalkenyl, haloalkoxy, haloalkoxyalkyl, haloalkenyloxyalkyl, halocycloalkoxy, halocycloalkoxyalkyl, halocycloalkenyloxyalkyl, carboxy, carboxyalkyl, carboalkoxy, carboxamide, and carboxamidoalkyl;

$R^{14}$ and $R^{38}$ can be independently selected from the group consisting of acyl, aroyl, and heteroaroyl with the proviso that acyl is selected from other than formyl and 2-oxoacyl;

Ψ is selected from the group consisting of $NR^5$, O, C(O), C(S), S, S(O), S(O)$_2$, ON($R^5$), P(O)($R^8$), and $CR^{39}R^{40}$;

$R^5$ is selected from the group consisting of hydrido, hydroxy, amino, alkyl, alkoxy, alkoxyalkyl, haloalkyl, acyl, aroyl, and heteroaroyl;

$R^{39}$ and $R^{40}$ are independently selected from the group consisting of hydrido, hydroxy, halo, cyano, hydroxyalkyl, acyl, aroyl, heteroaroyl, acylamido, alkoxy, alkyl, alkoxyalkyl, haloalkyl, haloalkoxy, haloalkoxyalkyl, alkylsulfonyl, haloalkylsulfonyl, carboxy, carboxyalkyl, carboalkoxy, carboxamide, and carboxamidoalkyl;

$R^2$ and $R^1$ are independently selected from the group consisting of $Z^0$—Q, hydrido, alkyl, alkenyl, and halo with the provisos that $R^2$ is selected from other than the group consisting of hydrido, alkyl, cycloalkyl, and trifluoromethyl and $R^1$ is selected from other than the group consisting of hydrido and halo unless $E^1$ is other than C(O)NH, or unless $E^0$ is selected from the group consisting of $E^2$ and $E^3$, or unless K is other than $(CR^{4a}R^{4b})_n$ wherein n is 1 unless one of $R^{4a}$ and $R^{4b}$ are independently selected from other than hydrido, or unless Ψ is selected from other than $NR^5$, or unless $R^5$ is selected from other than hydrido, or unless $Y^o$ is selected from other than wherein $Q^s$ is $C_{1-4}$ alkyl, $C_{3-4}$ alkenyl or $C_{3-4}$ alkynyl where the $C_{1-4}$ alkyl, $C_{3-4}$ alkenyl or $C_{3-4}$ alkynyl group is bonded concurrently to $E^1$ wherein $E^1$ is C(O)NH and to the 4-position of an imidazole, the 4-position of a thiazole or the 5-position of a thiazole, or unless a spacer pair is present selected from the group of spacer pairs consisting of $R^2$ and $R^{4a}$, $R^2$ and $R^{4b}$, $R^2$ together with both $R^{4a}$ and $R^{4b}$, $R^2$ and $R^{14}$, $R^2$ and $R^{15}$, and $R^6$ with another group selected from the group consisting of $R^{4a}$, $R^{4b}$, $R^{4a}$ and $R^{4b}$ together, $R^{39}$ $R^{40}$, $R^{39}$ and $R^{40}$ together, $R^{14}$, $R^{15}$, and $R^5$, that $R^2$ is selected from other than the group consisting of hydroxymethyl, methyl, methoxymethyl, methylthiomethyl, phenylthiomethyl, methylsulfinyl, methylthio, alkoxy, cycloalkoxy, alkylthio, alkylsulfinyl, alkysulfonyl, cycloalkylthio, cycloalkylsulfinyl, and cycloalkysulfonyl, when $Y^o$ is other than phenyl, mono-substituted phenyl, and di-substituted phenyl 5-(2-amino)pyridindyl, or 4-(2-amino)pyridindyl, and that $R^2$ is selected from other than the group consisting of hydrido, halo, alkyl, cycloalkyl when $Y^o$ is methyleneimidazo(1,2-a)pyridinyl, 4,5-benzimidazol-5-yl, or indol-5-yl unless $R^1$ is selected from other than the group consisting of hydrido or halo, or unless $E^1$ is other than C(O)NH, or unless $E^0$ is selected from the group consisting of $E^2$ and $E^3$, or unless K is other than $(CR^{4a}R^{4b})_n$ wherein n is 1 unless one of $R^{4a}$ and $R^{4b}$ are independently selected from other than hydrido, or unless $\Psi$ is selected from other than $NR^5$ wherein $R^5$ is hydrido;

$R^1$ is optionally selected from the group consisting of amino, aminoalkyl, alkylamino, amidino, guanidino, hydroxy, hydroxyamino, alkoxy, hydroxyalkyl, alkoxyamino, thiol, alkylthio, dialkylsulfonium, trialkylphosphonium, dialkylsulfoniumalkyl, heteroarylamino, nitro, arylamino, aralkylamino, alkanoyl, alkenoyl, aroyl, heteroaroyl, aralkanoyl, heteroaralkanoyl, haloalkanoyl, hydroxyhaloalkyl, cyano, and phosphono;

$Z^0$ is selected from the group consisting of covalent single bond, $(CR^{41}R^{42})_q$ wherein q is an integer selected from 1 through 6, $(CH(R^{41}))_g$—$W^0$—$(CH(R^{42}))_p$ wherein g and p are integers independently selected from 0 through 3 and $W^0$ is selected from the group consisting of O, S, C(O), C(S), C(O)O, C(S)O, C(O)S, C(S)S, C(O)N($R^{41}$), ($R^{41}$)NC(O), C(S)N($R^{41}$), ($R^{41}$)NC(S), OC(O)N($R^{41}$), ($R^{41}$)NC(O)O, SC(S)N($R^{41}$), ($R^{41}$)NC(S)S, SC(O)N($R^{41}$), ($R^{41}$)NC(O)S, OC(S)N($R^{41}$), ($R^{41}$)NC(S)O, N($R^{42}$)C(O)N($R^{41}$), ($R^{41}$)NC(O)N($R^{41}$), N($R^{42}$)C(S)N($R^{41}$), ($R^{41}$)NC(S)N($R^{42}$), S(O), S(O)$_2$, S(O)$_2$N($R^{41}$), N($R^{41}$)S(O)$_2$, Se, Se(O), Se(O)$_2$, Se(O)$_2$N($R^{41}$), N($R^{41}$)Se(O)$_2$, P(O)($R^8$), N($R^7$)P(O)($R^8$), P(O)($R^8$)N($R^7$), N($R^{41}$), ON($R^{41}$), and SiR$^{28}$R$^{29}$, and (CH($R^{41}$))$_e$—$W^{22}$—(CH($R^{42}$))$_h$ wherein e and h are integers independently selected from 0 through 2 and $W^{22}$ is selected from the group consisting of CR$^{41}$=CR$^{42}$, CR$^{41}$R$^{42}$=C; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that $R^{41}$ and $R^{42}$ are selected from other than halo and cyano when directly bonded to N and $Z^0$ is directly bonded to the pyrazinone ring;

$R^{41}$ and $R^{42}$ are independently selected from the group consisting of amidino, hydroxyamino, hydrido, hydroxy, amino, halo, cyano, aryloxy, hydroxyalkyl, acyl, aroyl, heteroaroyl, heteroaryloxyalkyl, alkoxy, alkyl, aryl, aralkyl, aryloxyalkyl, aralkoxyalkylalkoxy, alkoxyalkyl, heteroaryloxyalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, saturated heterocyclyl, partially saturated heterocyclyl, heteroaryl, heteroaralkyl, heteroarylthioalkyl, heteroaralkylthioalkyl, alkylsulfonyl, haloalkylsulfonyl, arylsulfonyl, arylsulfonylalkyl, aralkylsulfonyl, cycloalkylsulfonyl, cycloalkylsufonylalkyl, heteroarylsulfonylalkyl, heteroaryl sulfonyl, and aralkylsulfonylalkyl;

$Q^b$ is formula (II):

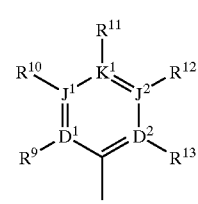

(II)

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N, with the proviso that $R^9$, $R^{10}$, $R^{11}$, $R^{12}$, and $R^{13}$ are each independently selected to maintain the tetravalent nature of carbon, trivalent nature of nitrogen, the divalent nature of sulfur, and the divalent nature of oxygen;

Q is optionally selected from formula (III):

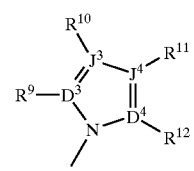

(III)

wherein $D^3$, $D^4$, $J^3$, and $J^4$ are independently selected from the group consisting of C, N, O and S, no more than one of $D^3$, $D^4$, $J^3$, and $J^4$ is O, no more than one of $D^3$, $D^4$, $J^3$, and $J^4$ is S, and no more than three of $D^1$, $D^2$, $J^1$, and $J^2$ are N with the proviso that $R^9$, $R^{10}$, $R^{11}$, and $R^{12}$ are each independently selected to maintain the tetravalent nature of carbon, trivalent nature of nitrogen, the divalent nature of sulfur, and the divalent nature of oxygen;

25

Q is optionally selected from the group consisting of hydrido, alkyl, alkoxy, alkylamino, alkylthio, haloalkylthio, alkenyl, alkynyl, saturated heterocyclyl, partially saturated heterocyclyl, acyl, aroyl, heteroaroyl, cycloalkyl, cycloalkylalkyl, cycloalkenyl, cycloalkenylalkyl, cycloalkylalkenyl, haloalkyl, haloalkoxy, haloalkenyl, halocycloalkyl, halocycloalkenyl, haloalkoxyalkyl, haloalkenyloxyalkyl, halocycloalkoxyalkyl, and halocycloalkenyloxyalkyl with the proviso that $Z^0$ is selected from other than a single covalent bond when Q is hydrido;

K is $(CR^{4a}R^{4b})_n$ wherein n is an integer selected from 1 through 2;

$R^{4a}$ and $R^{4b}$ are independently selected from the group consisting of halo, hydrido, hydroxy, cyano, hydroxyalkyl, alkyl, alkenyl, alkoxyalkyl, aralkyl, heteroaralkyl, alkylthioalkyl, haloalkyl, haloalkenyl, and cyanoalkyl;

$E^0$ is $E^1$, when K is $(CR^{4a}R^{4b})_n$ wherein $E^1$ is selected from the group consisting of a covalent single bond, O, S, C(O), C(S), C(O)O, C(S)O, C(O)S, C(S)S, C(O)N(R$^7$), (R$^7$)NC(O), C(S)N(R$^7$), (R$^7$)NC(S), OC(O)N(R$^7$), (R$^7$)NC(O)O, SC(S)N(R$^7$), (R$^7$)NC(S)S, SC(O)N(R$^7$), (R$^7$)NC(O)S, OC(S)N(R$^7$), (R$^7$)NC(S)O, N(R$^8$)C(O)N(R$^7$), (R$^7$)NC(O)N(R$^8$), N(R$^8$)C(S)N(R$^7$), (R$^7$)NC(S)N(R$^8$), S(O), S(O)$_2$, S(O)$_2$N(R$^7$), N(R$^7$)S(O)$_2$, S(O)$_2$N(R$^7$)C(O), C(O)N(R$^7$)S(O)$_2$, P(O)(R$^8$), N(R$^7$)P(O)(R$^8$), P(O)(R$^8$)N(R$^7$), N(R$^7$), ON(R$^7$), $CR^{4a}$=$CR^{4b}$, ethynylidene (C≡C; 1,2-ethynyl), and C=$CR^{4a}R^{4b}$;

K is optionally $(CH(R^{14}))_j$—T wherein j is selected from a integer from 0 through 2 and T is selected from the group consisting of single covalent bond, O, S, and N(R$^7$) with the proviso that $(CH(R^{14}))_j$ is bonded to the pyrazinone ring;

$E^0$ is optionally $E^2$, when K is $(CH(R^{14}))_j$—T, wherein $E^2$ is selected from the group consisting of a covalent single bond, C(O), C(S), C(O)O, C(S)O, C(O)S, C(S)S, C(O)N(R$^7$), (R$^7$)NC(O), C(S)N(R$^7$), (R$^7$)NC(S), (R$^7$)NC(O)O, (R$^7$)NC(S)S, (R$^7$)NC(O)S, (R$^7$)NC(S)O, N(R$^8$)C(O)N(R$^7$), (R$^7$)NC(O)N(R$^8$), N(R$^8$)C(S)N(R$^7$), (R$^7$)NC(S)N(R$^8$), S(O), S(O)$_2$, S(O)$_2$N(R$^7$), N(R$^7$)S(O)$_2$, S(O)$_2$N(H)C(O), C(O)N(H)S(O)$_2$, P(O)(R$^8$), N(R$^7$)P(O)(R$^8$), P(O)(R$^8$)N(R$^7$), and N(R$^7$);

K is optionally G—$(CH(R^{15}))_k$ wherein k is selected from an integer from 1 through 2 and G is selected from the group consisting of O, S, and N(R$^7$) with the proviso that $R^{15}$ is other than hydroxy, cyano, halo, amino, alkylamino, dialkylamino, and sulfhydryl when k is 1;

$E^0$ is optionally $E^3$ when K is G—$(CH(R^{15}))_k$, wherein $E^3$ is selected from the group consisting of a covalent single bond, O, S, C(O), C(S), C(O)O, C(S)O, C(O)S, C(S)S, C(O)N(R$^7$), (R$^7$)NC(O), C(S)N(R$^7$), (R$^7$)NC(S), OC(O)N(R$^7$), (R$^7$)NC(O)O, SC(S)N(R$^7$), (R$^7$)NC(S)S, SC(O)N(R$^7$), (R$^7$)NC(O)S, OC(S)N(R$^7$), (R$^7$)NC(S)O, N(R$^8$)C(O)N(R$^7$), (R$^7$)NC(O)N(R$^8$), N(R$^8$)C(S)N(R$^7$), (R$^7$)NC(S)N(R$^8$), S(O), S(O)$_2$, S(O)$_2$N(R$^7$), N(R$^7$)S(O)$_2$, P(O)(R$^8$), N(R$^7$)P(O)(R$^8$), P(O)(R$^8$)N(R$^7$), N(R$^7$), ON(R$^7$), $CR^{4a}$=$CR^{4b}$, ethynylidene (C≡C; 1,2-ethynyl), and C=$CR^{4a}R^{4b}$;

26

$Y^0$ is formula (IV):

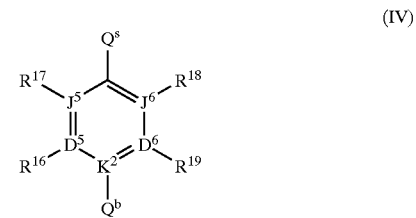

(IV)

wherein $D^5$, $D^6$, $J^5$, and $J^6$ are independently selected from the group consisting of C, N, O, S and a covalent bond with the provisos that no more than one is a covalent bond, $K^2$ is independently selected from the group consisting of C and N$^+$, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, no more than three of $D^5$, $D^6$, $J^5$, and $J^6$ is N when $K^2$ is N$^+$, and no more than four of $D^5$, $D^6$, $J^5$, and $J^6$ are N when $K^2$ is carbon with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$ and $R^{17}$ are optionally independently taken together to form a linear moiety spacer having from 3 through 6 contiguous atoms connected to form a ring selected from the group consisting of a cycloalkenyl ring having from 5 through 8 contiguous members, a partially saturated heterocyclyl ring having from 5 through 8 contiguous members, a heteroaryl having from 5 through 6 contiguous members, and an aryl;

$Q^b$ is selected from the group consisting of NR$^{20}$R$^{21}$, $^+$NR$^{20}$R$^{21}$R$^{22}$, oxy, alkyl, aminoalkylenyl, alkylamino, dialkylamino, dialkylsulfoniumalkyl, acylamino and $Q^{be}$, wherein $Q^{be}$ is hydrido and R$^{20}$, R$^{21}$, and R$^{22}$ are independently selected from the group consisting of hydrido, amino, alkyl, hydroxy, alkoxy, aminoalkylenyl, alkylamino, dialkylamino, and hydroxyalkyl with the provisos that no more than one of R$^{20}$, R$^{21}$, and R$^{22}$ is hydroxy, alkoxy, alkylamino, amino, and dialkylamino at the same time and that R$^{20}$, R$^{21}$, and R$^{22}$ must be other than be hydroxy, alkoxy, alkylamino, amino, and dialkylamino when $K^2$ is N$^+$;

R$^{20}$ and R$^{21}$, R$^{20}$ and R$^{22}$, and R$^{21}$ and R$^{22}$ are independently optionally selected to form a spacer pair wherein a spacer pair is taken together to form a linear moiety having from 4 through 7 contiguous atoms connecting the points of bonding of said spacer pair members to form a heterocyclyl ring having 5 through 8 contiguous members with the proviso that no more than one of the group consisting of spacer pairs R$^{20}$ and R$^{21}$, R$^{20}$ and R$^{22}$, and R$^{21}$ and R$^{22}$ is used at the same time;

$Q^b$ is optionally selected from the group consisting of N(R$^{26}$)SO$_2$N(R$^{23}$)(R$^{24}$), N(R$^{26}$)C(O)OR$^5$, N(R$^{26}$)C(O)SR$^5$, N(R$^{26}$)C(S)OR$^5$ and N(R$^{26}$)C(S)SR$^5$ with the proviso that no more than one of R$^{23}$, R$^{24}$, and R$^{26}$ is hydroxy, alkoxy, alkylamino, amino, and dialkylamino when two of the group consisting of R$^{23}$, R$^{24}$, and R$^{26}$ are bonded to the same atom;

$Q^b$ is optionally selected from the group consisting of dialkylsulfonium, trialkylphosphonium, C(NR$^{25}$)

NR²³R²⁴, N(R²⁶)C(NR²⁵)N(R²³)(R²⁴), N(R²⁶)C(O)N(R²³)(R²⁴), N(R²⁶)C(S)N(R²³)(R²⁴), C(NR²⁵)OR⁵, C(O)N(R²⁶)C(NR²⁵)N(R²³)(R²⁴), C(S)N(R²⁶)C(NR²⁵)N(R²³)(R²⁴), N(R²⁶)N(R²⁶)C(NR²⁵)N(R²³)(R²⁴), ON(R²⁶)C(NR²⁵)N(R²³)(R²⁴), N(R²⁶)N(R²⁶)SO₂N(R²³)(R²⁴), C(NR²⁵)SR⁵, C(O)NR²³R²⁴, and C(O)NR²³R²⁴ with the provisos that no more than one of R²³, R²⁴, and R²⁶ can be hydroxy, alkoxy, alkylaminol, amino, or dialkylamino when two of the group consisting of R²³, R²⁴, and R²⁶ are bonded to the same atom and that said $Q^b$ group is bonded directly to a carbon atom;

R²³, R²⁴, R²⁵, and R²⁶ are independently selected from the group consisting of hydrido, alkyl, hydroxy, alkoxy, aminoalkylenyl, alkylamino, dialkylamino, amino, and hydroxyalkyl;

R²³ and R²⁴ are optionally taken together to form a linear spacer moiety having from 4 through 7 contiguous atoms connecting the points of bonding to form a heterocyclyl ring having 5 through 8 contiguous members;

$Q^s$ is selected from the group consisting of a single covalent bond, $(CR^{37}R^{38})_b$—$(W^0)_{az}$ wherein az is an integer selected from 0 through 1, b is an integer selected from 1 through 4, and $W^0$ is selected from the group consisting of O, S, C(O), C(S), C(O)O, C(S)O, C(O)S, C(S)S, C(O)N(R¹⁴), (R¹⁴)NC(O), C(S)N(R¹⁴), (R¹⁴)NC(S), OC(O)N(R¹⁴), SC(S)N(R¹⁴), SC(O)N(R¹⁴), OC(S)N(R¹⁴) N(R¹⁵)C(O)N(R¹⁴) (R¹⁴)NC(O)N(R¹⁵), N(R¹⁵)C(S)N(R¹⁴), (R¹⁴)NC(S)N(R¹⁵) S(O), S(O)₂, S(O)₂N(R¹⁴), N(R¹⁴)S(O)₂, P(O)(R⁸), N(R⁷)P(O)(R⁸), P(O)(R⁸)N(R⁷), N(R¹⁴), ON(R¹⁴), (CH(R¹⁴))_c W¹—(CH(R¹⁵))_d wherein c and d are integers independently selected from 1 through 4, and W¹ is selected from the group consisting of O, S, C(O), C(S), C(O)O, C(S)O, C(O)S, C(S)S, C(O)N(R¹⁴), (R¹⁴)NC(O), C(S)N(R¹⁴), (R¹⁴)NC(S), OC(O)N(R¹⁴), (R¹⁴)NC(O)O, SC(S)N(R¹⁴), (R¹⁴)NC(S)S, SC(O)N(R¹⁴), (R¹⁴)NC(O)S, OC(S)N(R¹⁴), (R¹⁴)NC(S)O, N(R¹⁵)C(O)N(R¹⁴), (R¹⁴)NC(O)N(R¹⁵), N(R¹⁵)C(S)N(R¹⁴), (R¹⁴)NC(S)N(R¹⁵), S(O), S(O)₂, S(O)₂N(R¹⁴), N(R¹⁴)S(O)₂, P(O)(R⁸), N(R⁷)P(O)(R⁸), P(O)(R⁸)N(R⁷), N(R¹⁴), ON(R¹⁴), and (CH(R¹⁴))_e—W²²—(CH(R¹⁵))_h wherein e and h are integers independently selected from 0 through 2 and W²² is selected from the group consisting of CR⁴¹=CR⁴², CR⁴¹R⁴²=C; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1 3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that R¹⁴ and R¹⁵ are selected from other than halo and cyano when directly bonded to N and that $(CR^{37}R^{38})_b$, $(CH(R^{14}))_c$, $(CH(R^{14}))_e$ and are bonded to E⁰;

$Y^0$ is optionally $Q^b$—$Q^{ss}$ wherein $Q^{ss}$ is selected from the group consisting of $(CR^{37}R^{38})_f$ wherein f is an integer selected from 1 through 6, $(CH(R^{14}))_c$—W¹—(CH(R¹⁵))_d wherein c and d are integers independently selected from 1 through 4, and W¹ is selected from the group consisting of W¹ is selected from the group consisting of O, S, C(O), C(S), C(O)O, C(S)O, C(O)S, C(S)S, C(O)N(R¹⁴), (R¹⁴)NC(O), C(S)N(R¹⁴), (R¹⁴)NC(S), OC(O)N(R¹⁴), (R¹⁴)NC(O)O, SC(S)N(R¹⁴), (R¹⁴)NC(S)S, SC(O)N(R¹⁴), (R¹⁴)NC(O)S, OC(S)N(R¹⁴), (R¹⁴)NC(S)O, N(R¹⁵)C(O)N(R¹⁴), (R¹⁴)NC()N(R¹⁵) N(R¹⁵)C(S)N(R¹⁴), (R¹⁴)NC(S)N(R¹⁵), S(O), S(O)₂, S(O)₂N(R¹⁴), N(R¹⁴)S(O)₂, P(O)(R⁸), N(R⁷)P(O)(R⁸), P(O)(R⁸)N(R⁷), N(R¹⁴), ON(R¹⁴), and (CH(R¹⁴))_e—W²—(CH(R¹⁵))_h wherein e and h are integers independently selected from 0 through 2 and W² is selected from the group consisting of $CR^{4a}$=$CR^{4b}$, ethynylidene (C≡C; 1,2-ethynyl), and C=$CR^{4a}R^{4b}$ with the provisos that R¹⁴ and R¹⁵ are selected from other than halo and cyano when directly bonded to N and that $(CR^{37}R^{38})_f$, $(CH(R^{14}))_c$, and $(CH(R^{14}))_e$ are bonded to E⁰;

$Y^0$ is optionally $Q^b$—$Q^{sss}$ wherein $Q^{sss}$ is $(CH(R^{38}))_r$—W³, r is an integer selected from 1 through 3, W³ is selected from the group consisting of 1,1-cyclopropyl, 1,2-cyclopropyl, 1,1-cyclobutyl, 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hyrido containing nitrogen member of the ring of the W³ other than the points of attachment is optionally substituted with one or more of the group consisting of R⁹, R¹⁰, R¹¹, and R¹², with the proviso that $(CH(R^{38}))_r$ is bonded to E⁰ and $Q^b$ is bonded to lowest numbered substituent position of each W³;

$Y^0$ is optionally $Q^b$—$Q^{sssr}$ wherein $Q^{sssr}$ is $(CH(R^{38}))_r$—W⁴, r is an integer selected from 1 through 3, W⁴ is selected from the group consisting of 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5- tetrahydropyranyl, 2,6-tetrahydropyranyl, 3,4-tetrahydropyranyl, and 3,5-tetrahydropyranyl, and each carbon and hydrido containing nitrogen member of the ring of the $W^4$ other than the points of attachment is optionally substituted with one or more of the group consisting of $R^9$, $R^{10}$, $R^{11}$, and $R^{12}$, with the provisos that $(CH(R^{38}))_r$ is bonded to $E^0$ and $Q^b$ is bonded to highest number substituent position of each $W^4$;

$Y^0$ is optionally $Q^b$—$Q^{ssss}$ wherein $Q^{ssss}$ is $(CH(R^{38}))_r$—$W^5$, r is an integer selected from 1 through 3, $W^5$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5isoquinolinyl, 4,6-isoquinolinyl, 4,7-isoquinolinyl, 4,8-isoquinolinyl, 3,4cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hydrido containing nitrogen member of the ring of the $W^5$ other than the points of attachment is optionally substituted with one or more of the group consisting of $R^9$, $R^{10}$, $R^{11}$, and $R^{12}$, with the proviso that $Q^b$ is bonded to lowest number substituent position of each $W^5$ and that $(CH(R^{38}))_r$ is bonded to $E^0$;

$Y^0$ is optionally $Q^b$—$Q^{sssr}$ wherein, $Q^{sssr}$ is $(CH(R^{38}))_r$—$W^6$, r is an integer selected from 1 through 3, $W^6$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hydrido containing nitrogen member of the ring of the $W^6$ other than the points of attachment is optionally substituted with one or more of the group consisting of $R^9$, $R^{10}$, $R^{11}$, and $R^{12}$, with the proviso that $Q^b$ is bonded to highest number substituent position of each $W^6$ and that $(CH(R^{38}))_r$ is bonded to $E^0$.

In another embodiment of compounds of Formula I or a pharmaceutically acceptable salt thereof, J is selected from the group consisting of O and S;

B is formula (V):

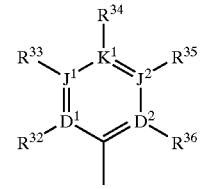

(V)

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N;

$R^9$, $R^{10}$, $R^{11}$, $R^{12}$, $R^{13}$, $R^{16}$, $R^{17}$, $R^{18}$, $R^{19}$, $R^{32}$, $R^{33}$, $R^{34}$, $R^{35}$, and $R^{36}$ are independently selected from the group consisting of hydrido, acetamido, haloacetamido, amidino, guanidino, dialkylsulfonium, trialkylphosphonium, dialkylsulfoniumalkyl, carboxy, heteroaralkylthio, heteroaralkoxy, cycloalkylamino, acylalkyl, acylalkoxy, aryloylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, alkoxyamino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, alkylenylamino, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboxy, carboaralkoxy, carboxamido, carboxamidoalkyl, cyano, carbohaloalkoxy, phosphono, phosphonoalkyl, diaralkoxyphosphono, and diaralkoxyphosphonoalkyl;

$R^{16}$, $R^{19}$, $R^{32}$, $R^{33}$, $R^{34}$, $R^{35}$, and $R^{36}$ are independently optionally $Q^b$ with the proviso that no more than one of $R^{16}$ and $R^{19}$ is $Q^b$ at the same time and that $Q^b$ is $Q^{be}$;

B is optionally selected from the group consisting of hydrido, trialkylsilyl, C2–C8 alkyl, C3–C8 alkylenyl, C3–C8 alkenyl, C3–C8 alkynyl, C2–C8 haloalkyl, and C3–C8 haloalkenyl wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally selected from the group consisting of C3–C12 cycloalkyl, C5–C10 cycloalkenyl, and C4–C9 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, a ring carbon or nitrogen atom adjacent to the $R^{13}$ position and two atoms from the point of attachment is optionally substituted with $R^{12}$, a ring carbon or nitrogen atom three atoms from the point of attachment and adjacent to the $R^{10}$ position is optionally substituted with $R^{11}$, a ring carbon or nitrogen atom three atoms from the point of attachment and adjacent to the $R^{12}$ position is optionally substituted with $R^{33}$, and a ring carbon or nitrogen atom four atoms from the point of attachment and adjacent to the $R^{11}$ and $R^{33}$ positions is optionally substituted with $R^{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 through 6, and $W^7$ is selected from the group consisting of O, S, C(O), C(O)N($R^7$), C(S)N($R^7$), ($R^7$)NC(O), ($R^7$)NC(S), and N($R^7$) with the proviso that no more than one of the group consisting of rr and pa can be 0 at the same time;

$R^7$ and $R^8$ are independently selected from the group consisting of hydrido, hydroxy, alkyl, and alkoxyalkyl;

$R^{14}$, $R^{15}$, $R^{37}$, and $R^{38}$ are independently selected from the group consisting of hydrido, hydroxy, halo, alkyl, alkoxyalkyl, haloalkyl, haloalkoxy, and haloalkoxyalkyl;

$R^{14}$ and $R^{38}$ can be independently selected from the group consisting of aroyl and heteroaroyl;

$\Psi$ is selected from the group consisting of $NR^5$, C(O), and $S(O)_2$;

$R^5$ is selected from the group consisting of hydrido, hydroxy, alkyl, and alkoxy;

$R^{39}$ and $R^{40}$ are independently selected from the group consisting of hydrido, hydroxy, halo, hydroxyalkyl, alkyl, alkoxyalkyl, haloalkyl, haloalkoxy, and haloalkoxyalkyl;

$R^1$ is selected from the group consisting of hydrido, alkyl, alkenyl, cyano, halo, haloalkyl, haloalkoxy, haloalkylthio, amino, aminoalkyl, alkylamino, amidino, guanidino, hydroxy, hydroxyamino, alkoxy, hydroxyalkyl, alkoxyamino, thiol, alkylthio, and phosphono;

$R^2$ is $Z^0$—Q;

$Z^0$ is selected from the group consisting of covalent single bond, $(CR^{R41}R^{42})_q$ wherein q is an integer selected from 1 through 3, $(CH(R^{41}))_g$—$W^0$—$(CH(R^{42}))_p$ wherein g and p are integers independently selected from 0 through 3 and $W^0$ is selected from the group consisting of O, S, C(O), S(O), $S(O)_2$, N($R^{41}$), and ON($R^{41}$), and $(CH(R^{41}))_e$—$W^{22}$—$(CH(R^{42}))_h$ wherein e and h are integers independently selected from 0 through 2 and $W^{22}$ is selected from the group consisting of $CR^{41}$=$CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4- piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the proviso that Z is directly bonded to the pyrazinone ring;

$R^{41}$ and $R^{42}$ are independently selected from the group consisting of amidino, hydroxyamino, hydrido, hydroxy, amino, and alkyl;

$Q^b$ is selected from the group consisting of hydrido, with the proviso that $Z^0$ is other than a covalent single bond, the formula (II):

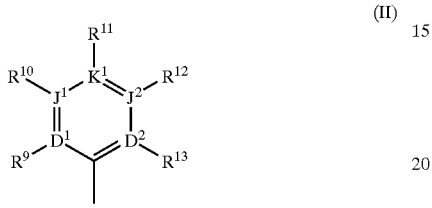

(II)

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ is N, with the proviso that $R^9$, $R^{10}$, $R^{11}$, $R^{12}$, and $R^{13}$ are each independently selected to maintain the tetravalent nature of carbon, trivalent nature of nitrogen, the divalent nature of sulfur, and the divalent nature of oxygen;

K is $(CR^{4a}R^{4b})_n$ wherein n is an integer selected from 1 through 2;

$R^{4a}$ and $R^{4b}$ are independently selected from the group consisting of halo, hydrido, hydroxyalkyl, alkyl, alkoxyalkyl, alkylthioalkyl, and haloalkyl;

$E^0$ is selected from the group consisting of a covalent single bond, C(O), C(S), C(O)N($R^7$), ($R^7$)NC(O), S(O)$_2$, ($R^7$)NS(O)$_2$, and S(O)$_2$N($R^7$);

$Y^0$ is formula (IV):

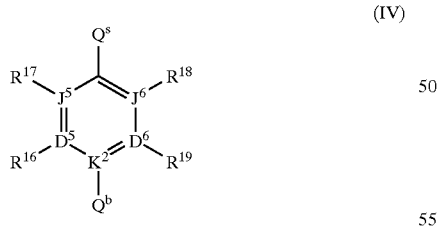

(IV)

wherein
$D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of, $D^5$, $D^6$, $J^5$, and $J^6$ is S one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N when $K^2$ is carbon with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$Q^b$ is selected from the group consisting of $NR^{20}R^{21}$, $^+NR^{20}R^{21}R^{22}$, aminoalkylenyl, and $Q^{be}$, wherein $Q^{be}$ is hydrid and $R^{20}$, $R^{21}$, and $R^{22}$ are independently selected from the group consisting of hydrido, alkyl, hydroxy, amino, aminoalkylenyl, dialkylamino, alkylamino, and hydroxyalkyl with the proviso that no more than one of $R^{20}$ and $R^{21}$ is hydroxy, amino, alkylamino, or dialkylamino at the same time;

$Q^b$ is optionally selected from the group consisting of $C(NR^{25})NR^{23}R^{24}$, $N(R^{26})C(NR^{25})N(R^{23})(R^{24})$, $C(O)N(R^{26})C(NR^{25})N(R^{23})(R^{24})$, $N(R^{26})N(R^{26})C(NR^{25})N(R^{23})(R^{24})$, and $ON(R^{26})C(NR^{25})N(R^{23})(R^{24})$ with the provisos that no more than one of $R^{23}$, $R^{24}$, and $R^{26}$ is hydroxy, alkylamino, amino, or dialkylamino when two of the group consisting of $R^{23}$, $R^{24}$, and $R^{26}$ are bonded to the same atom;

$R^{23}$, $R^{24}$, $R^{25}$, and $R^{26}$ are independently selected from the group consisting of hydrido, alkyl, hydroxy, amino, alkylenylamino, dialkylamino, alkylamino, and hydroxyalkyl;

$Q^s$ is selected from the group consisting of a single covalent bond, $(CR^{37}R^{38})_b$—$(W^0)_{az}$ wherein az is an integer selected from 0 through 1, b is an integer selected from 1 through 5, and $W^0$ is selected from the group consisting of O, C(O), S(O), S(O)$_2$, S(O)$_2$N($R^{14}$), N($R^{14}$)S(O)$_2$, and N($R^{14}$), (CH($R^{14}$))$_c$—$W^1$—(CH($R^{15}$)) wherein c and d are integers independently selected from 1 through 4 and $W^1$ is selected from the group consisting of O, S, C(O), C(S), C(O)O, C(S)O, C(O)S, C(S)S, C(O)N($R^{14}$), ($R^{14}$)NC(O), C(S)N($R^{14}$), ($R^{14}$)NC(S), OC(O)N ($R^{14}$), ($R^{14}$)NC(O)O, SC(S)N($R^{14}$), ($R^{14}$)NC(S)S, SC(O)N($R^{14}$), ($R^{14}$)NC(O)S, OC(S)N($R^{14}$), ($R^{14}$)NC(S)O, N($R^{15}$)C(O)N($R^{14}$), ($R^{14}$)NC(O)N($R^{15}$). N($R^{15}$)C(S)N($R^{14}$), ($R^{14}$)NC(S)N($R^{15}$), S(O), S(O)$_2$, S(O)$_2$N($R^{14}$), N($R^{14}$)S(O)$_2$, P(O)($R^8$), N($R^7$)P(O) ($R^8$), P(O)($R^8$)N($R^7$), N($R^{14}$), ON($R^{14}$), and (CH ($R^{14}$))$_e$—$W^{22}$—(CH($R^{15}$))$_h$ wherein e and h are integers independently selected from 0 through 2 and $W^{22}$ is selected from the group consisting of $CR^{41}$=$CR^{42}$, $CR^{41}$=$R^{42}$=C; vinylidene), ethynylidene (C≡C; 1,2-ethynyl), 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the provisos that $R^{14}$ and $R^{15}$ are selected from other than halo and cyano when directly bonded to N and that $(CR^{37}R^{38})_b$, $(CH(R^{14}))_c$, and $(CH(R^{14}))_e$ are bonded to $E^0$;

Y is optionally $Q^b$—$Q^{ss}$ wherein $Q^{ss}$ is selected from the group consisting of $(CR^{37}R^{38})_f$ wherein f is an integer selected from 1 through 4, $(CH(R^{14}))_c$—$W^1$—CH ($R^{15}$))$_d$ wherein c and d are integers independently selected from 1 through 2, and $W^1$ is selected from the group consisting of $W^1$ is selected from the group consisting of O, S, C(O), C(O)N($R^{14}$), ($R^{14}$)NC(O), N(R$^{15}$)C(O)N(R$^{14}$) (R$^{14}$)NC(O)N(R$^{15}$), N(R$^{14}$), ON(R$^{14}$), and (CH(R$^{14}$))$_e$—W$^2$—(CH(R$^{15}$))$_h$ wherein e and h are integers independently selected from 0 through 2 and W$^2$ is selected from the group consisting of CR$^{4a}$=CR$^{4b}$, ethynylidene (C≡C; 1,2-ethynyl), and C=CR$^{4a}$R$^{4b}$ with the provisos that R$^{14}$ and R$^{15}$ are selected from other than halo when directly bonded to N and that (CR$^{37}$R$^{38}$)$_p$, (CH(R$^{14}$))$_c$, and (CH(R$^{14}$))$_e$ are bonded to E$^0$;

Y$^0$ is optionally Q$^b$—Q$^{sss}$ wherein Q$^{sss}$ is (CH(R$^{38}$))$_r$—W$^3$, r is an integer selected from 1 through 2, W$^3$ is selected from the group consisting of 1,1-cyclopropyl, 1,2-cyclopropyl, 1,1-cyclobutyl, 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hyrido containing nitrogen member of the ring of the W$^3$ other than the points of attachment is optionally substituted with one or more of the group consisting of R$^9$, R$^{10}$, R$^{11}$, and R$^{12}$, with the proviso that (CH(R$^{38}$))$_r$ is bonded to E$^0$ and Q$^b$ is bonded to lowest numbered substituent position of each W$^3$;

Y$^0$ is optionally Q$^b$—Q$^{sssr}$ wherein Q$^{sssr}$ is (CH(R$^{38}$))$_r$—W$^4$, r is integer selected from 1 through 2, W$^4$ is selected from the group consisting of 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl, and each carbon and hyrido containing nitrogen member of the ring of the W$^4$ other than the points of attachment is optionally substituted with one or more of the group consisting of R$^9$, R$^{10}$, R$^{11}$, and R$^{12}$, with the provisos that (CH(R$^{38}$))$_r$ is bonded to E$^0$ and Q$^b$ is bonded to highest number substituent position of each W$^4$;

Y$^0$ is optionally Q$^b$—Q$^{ssss}$ wherein Q$^{ssss}$ (CH(R$^{38}$))$_r$—W$^5$, r is an integer selected from 1 through 2, W$^5$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hyrido containing nitrogen member of the ring of the W$^5$ other than the points of attachment is optionally substituted with one or more of the group consisting of R$^9$, R$^{10}$, R$^{11}$, and R$^{12}$, with the proviso that Q$^b$ is bonded to lowest number substituent position of each W$^5$ and that (CH(R$^{38}$))$_r$ is bonded to E$^0$;

Y$^0$ is Q$^b$—Q$^{ssssr}$ wherein Q$^{ssssr}$ is (CH(R$^{38}$))$_r$—W$^6$, r is an integer selected from 1 through 2, W$^6$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a)pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5- naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hyrido containing nitrogen member of the ring of the $W^6$ other than the points of attachment is optionally substituted with one or more of the group consisting of $R^9$, $R^{10}$, $R^{11}$, and $R^{12}$, with the proviso that $Q^b$ is bonded to highest number substituent position of each $W^6$ and that $(CH(R^{38}))_r$ is bonded to $E^0$.

In a preferred embodiment of compounds of Formula I or a pharmaceutically acceptable salt thereof, J is O;

B is formula (V):

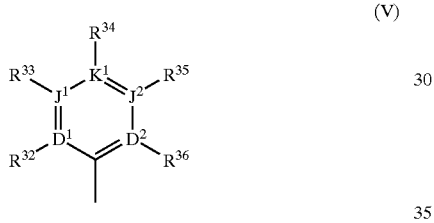

(V)

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N;

$R^9$, $R^{10}$, $R^{11}$, $R^{12}$, $R^{13}$, $R^{32}$, $R^{33}$, $R^{34}$, $R^{35}$, and $R^{36}$ are independently selected from the group consisting of hydrido, acetamido, haloacetamido, amidino, guanidino, alkylenedioxy, haloalkylthio, alkanoyloxy, alkoxy, alkoxyalkyl, haloalkoxylalkyl, hydroxy, amino, alkoxyamino, nitro, lower alkylamino, alkylthio, alkylthioalkyl, alkylsulfinyl, alkylsulfonyl, alkylsulfonylalkyl, aryl, aralkyl, cycloalkyl, cycloalkylalkyl, heteroaryl, heterocyclyl, alkylsulfonamido, alkylaminosulfonyl, amidosulfonyl, monoalkyl amidosulfonyl, dialkyl amidosulfonyl, alkanoyl, haloalkanoyl, alkyl, alkenyl, halo, haloalkyl, haloalkenyl, haloalkoxy, hydroxyhaloalkyl, hydroxyalkyl, aminoalkyl, haloalkoxyalkyl, carboxyalkyl, carboalkoxy, carboxy, carboxamido, carboxamidoalkyl, and cyano;

$R^{16}$, $R^{19}$, $R^{32}$, $R^{33}$, $R^{34}$, $R^{35}$, and $R^{36}$ are independently optionally $Q^b$ with the proviso that no more than one of $R^{16}$ and $R^{19}$ is $Q^b$ at the same time and that $Q^b$ is $Q^{be}$;

B is optionally selected from the group consisting of hydrido, trialkylsilyl, C2–C8 alkyl, C3–C8 alkylenyl, C3–C8 alkenyl, C3–C8 alkynyl, and C2–C8 haloalkyl, wherein each member of group B may be optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally selected from the group consisting of C3–C12 cycloalkyl and C4–C9 saturated heterocyclyl, wherein each ring carbon may be optionally substituted with $R^{33}$, a ring carbon other than the ring carbon at the point of attachment of B to A may be optionally substituted with oxo provided that no more than one ring carbon is substituted by oxo at the same time, ring carbon and nitrogen atoms adjacent to the carbon atom at the point of attachment may be optionally substituted with $R^9$ or $R^{13}$, a ring carbon or nitrogen atom adjacent to the $R^9$ position and two atoms from the point of attachment may be substituted with $R^{10}$, a ring carbon or nitrogen atom adjacent to the $R^{13}$ position and two atoms from the point of attachment may be substituted with $R^{12}$, a ring carbon or nitrogen atom three atoms from the point of attachment and adjacent to the $R^{10}$ position may be substituted with $R^{11}$, a ring carbon or nitrogen atom three atoms from the point of attachment and adjacent to the $R^{12}$ position may be substituted with $R^{33}$, and a ring carbon or nitrogen atom four atoms from the point of attachment and adjacent to the $R^{11}$ and $R^{33}$ positions may be substituted with $R^{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 through 6, and $W^7$ is selected from the group consisting of O, S, C(O), $(R^7)NC(O)$, $(R^7)NC(S)$, and $N(R^7)$ with the proviso that no more than one of the group consisting of rr and pa is 0 at the same time;

$R^7$ is selected from the group consisting of hydrido, hydroxy, and alkyl;

$R^{15}$ is selected from the group consisting of hydrido, hydroxy, halo, alkyl, and haloalkyl;

Ψ is selected from the group consisting of NH and NOH;

$R^1$ is selected from the group consisting of hydrido, alkyl, alkenyl, cyano, halo, haloalkyl, haloalkoxy, haloalkylthio, amino, aminoalkyl, alkylamino, amidino, hydroxy, hydroxyamino, alkoxy, hydroxyalkyl, alkoxyamino, thiol, and alkylthio;

$R^2$ is $Z^0$—Q;

$Z^0$ is selected from the group consisting of covalent single bond, $(CR^{41}R^{42})_q$ wherein q is an integer selected from 1 through 3, $(CH(R^{41}))_g$—$W^0$—$(CH(R^{42}))_p$ wherein g and p are integers independently selected from 0 through 3 and $W^0$ is selected from the group consisting of O, S, C(O), S(O), $N(R^{41})$, and $ON(R^{41})$, and $(CH(R^{41}))_e$—$W^{22}$—$(CH(R^{42}))_h$ wherein e and h are integers independently selected from 0 through 1 and $W^{22}$ is selected from the group consisting of $CR^{41}$=$CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3- tetrahydrofuranyl, 2,4-tetrahydrofuranyl, 2,5-tetrahydrofuranyl, and 3,4-tetrahydrofuranyl, with the proviso that Z is directly bonded to the pyrazinone ring;

$R^{41}$ and $R^{42}$ are independently selected from the group consisting of amidino, hydroxyamino, hydrido, hydroxy, amino, and alkyl;

$Q^b$ is selected from the group consisting of hydrido, with the proviso that $Z^0$ is other than a covalent single bond, and the formula (II):

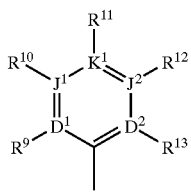

(II)

wherein $D^1$, $D^2$, $J^1$, $J^2$ and $K^1$ are independently selected from the group consisting of C, N, O, S and a covalent bond with the provisos that no more than one is a covalent bond, no more than one of $D^1$, $D^2$, $J^1$, $J^2$ and $K^1$ is O, no more than one of $D^1$, $D^2$, $J^1$, $J^2$ and $K^1$ is S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ are N, with the proviso that $R^9$, $R^{10}$, $R^{11}$, $R^{12}$, and $R^{13}$ are each independently selected to maintain the tetravalent nature of carbon, trivalent nature of nitrogen, the divalent nature of sulfur, and the divalent nature of oxygen;

K is $(CR^{4a}R^{4b})_n$ wherein n is an integer selected from 1 through 2;

$R^{4a}$ and $R^{4b}$ are independently selected from the group consisting of halo, hydrido, hydroxyalkyl, alkyl, alkoxyalkyl, alkylthioalkyl, and haloalkyl;

$E^0$ is $E^1$, when K is $(CR^{4a}R^{4b})_n$, wherein $E^1$ is selected from the group consisting of a covalent single bond, C(O), C(S), C(O)N($R^7$), ($R^7$)NC(O), S(O)$_2$, ($R^7$)NS(O)$_2$, and S(O)$_2$N($R^7$);

$Y^0$ is formula (IV):

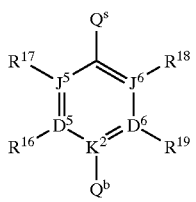

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^5$, $J^5$, and $J^6$ is O, no more than one of $D^5$, $D^6$, $J^5$, and $J^6$ is S, one of $D^5$, $D^6$, $J^5$, and $J^6$ must be a covalenthbond when two of $D^5$, $D^6$, and $J^6$ are O and S, and no more than four of $D^5$, $D^6$, $J^5$, and $J^6$ are N with the proviso that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$, $R^{17}$, $R^{18}$, and $R^{19}$ are independently selected from the group consisting of hydrido, amidino, guanidino, carboxy, haloalkylthio, alkoxy, hydroxy, amino, nitro, alkoxyamino, lower alkylamino, alkylthio, alkylsulfinyl, alkylsulfonyl, alkanoyl, haloalkanoyl, alkyl, alkenyl, halo, haloalkyl, haloalkoxy, hydroxyalkyl, alkylenylamino, haloalkoxyalkyl, carboalkoxy, and cyano;

$Q^b$ is selected from the group consisting of $NR^{20}R^{21}$, aminoalkylenyl, $Q^{be}$ wherein $Q^{be}$ is hydrido, $N(R^{26})$ $C(NR^{25})N(R^{23})(R^{24})$, and $C(NR^{25})NR^{23}R^{24}$, with the provisos that no more than one of $R^{20}$ and $R^{21}$ is hydroxy, amino, alkylamino, or dialkylamino at the same time and that no more than one of $R^{23}$ and $R^{24}$ is hydroxy, amino, alkylamino, or dialkylamino at the same time;

$R^{20}$, $R^{21}$, $R^{23}$, $R^{24}$, $R^{25}$, and $R^{26}$ are independently selected from the group consisting of hydrido, alkyl, hydroxy, aminoalkylenyl, amino, dialkylamino, alkylamino, and hydroxyalkyl;

$Q^s$ is selected from the group consisting of a single covalent bond, $(CR^{37}R^{38})_b$, wherein b is an integer selected from 1 through 4, and $(CH(R^{14}))_c$—$W^1$—$(CH(R^{15}))_d$ wherein c and d are integers independently selected from 1 through 3 and $W^1$ is selected from the group consisting of C(O)N($R^{14}$), ($R^{14}$)NC(O), S(O), S(O)$_2$, S(O)$_2$N($R^{14}$), N($R^{14}$)S(O)$_2$, and N($R^{14}$), with the provisos that $R^{14}$ is selected from other than halo when directly bonded to N and that $(CR^{37}R^{38})_b$, and $(CH(R^{14}))_c$ are bonded to $E^0$;

$R^{14}$ is selected from the group consisting of hydrido, halo, alkyl, and haloalkyl;

$R^{37}$ and $R^{38}$ are independently selected from the group consisting of hydrido, alkyl, and haloalkyl;

$R^{38}$ is optionally selected from the group consisting of aroyl and heteroaroyl;

$Y^0$ is optionally $Q^b$—$Q^{ss}$ wherein $Q^{ss}$ is $(CH(R^{14}))_e$—$W^2$—$(CH(R^{15}))_h$, wherein e and h are integers independently selected from 1 through 2 and $W^2$ is $CR^{4a}$=$CR^{4b}$ with the proviso that $(CH(R^{14}))_e$ is bonded to $E^0$;

$Y^0$ is optionally selected from the group consisting of $Q^b$—$Q^{ssss}$ and $Q^b$—$Q^{ssssr}$ wherein $Q^{ssss}$ is $(CH(R^{38}))_r$—$W^6$ and $Q^{ssssr}$ is $(CH(R^{38}))_r$—$W^6$, r is an integer selected from 1 through 2, and $W^5$ and $W^6$ are independently selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,7-imidazo(1,2-a)pyridinyl, 3,4-imidazo(1,2-a)pyridinyl, 3,5-imidazo(1,2-a)pyridinyl, 3,6-imidazo(1,2-a)pyridinyl, 3,7-imidazo(1,2-a) pyridinyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl, and each carbon and hyrido containing nitrogen member of the ring of the $W^5$ and of the ring of the $W^6$, other than the points of attachment of $W^5$ and $W^6$, is optionally substituted with one or more of the group consisting of $R^9$, $R^{10}$, $R^{11}$, and $R^{12}$, with the provisos that $Q^b$ is bonded to lowest number substituent position of each $W^5$, $Q^b$ is bonded to highest number substituent position of each $W^6$, and $(CH(R^{38}))_r$ is bonded to $E^0$.

In a more preferred embodiment of compounds of Formula I or a pharmaceutically acceptable salt thereof, J is O;

B is selected from the group consisting of aryl and heteroaryl wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, acetamido, haloacetamido, amidino, guanidino, alkylenedioxy, haloalkylthio, alkanoyloxy, alkoxy, hydroxy, amino, alkoxyamino, alkanoyl, haloalkanoyl, nitro, lower alkylamino, alkylthio, aryl, aralkyl, cycloalkyl, cycloalkylalkyl, heteroaryl, heterocyclyl, alkylsulfonamido, amidosulfonyl, monoalkyl amidosulfonyl, dialkyl amidosulfonyl, alkyl, alkenyl, halo, haloalkyl, haloalkenyl, haloalkoxy, hydroxyalkyl, alkylenylamino, carboalkoxy, carboxy, carboxamido, cyano, and $Q^b$;

B is optionally selected from the group consisting of hydrido, trialkylsilyl, C2–C8 alkyl, C3–C8 alkylenyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally selected from the group consisting of C3–C12 cycloalkyl and C4–C9 saturated heterocyclyl, wherein each ring carbon is optionally optionally substituted with $R^{35}$, a ring carbon other than the ring carbon at the point of attachment of B to A is optionally substituted with oxo provided that no more than one ring carbon is substituted by oxo at the same time, ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, a ring carbon or nitrogen atom adjacent to the $R^{13}$ position and two atoms from the point of attachment is optionally substituted with $R^{12}$, a ring carbon or nitrogen atom three atoms from the point of attachment and adjacent to the $R^{10}$ position is optionally substituted with $R^{11}$, a ring carbon or nitrogen atom three atoms from the point of attachment and adjacent to the $R^{12}$ position is optionally substituted with $R^{33}$, and a ring carbon or nitrogen atom four atoms from the point of attachment and adjacent to the $R^{11}$ and $R^{33}$ positions is optionally substituted with $R^{34}$;

$R^9$, $R^{10}$, $R^{11}$, $R^{12}$, and $R^{13}$ are independently selected from the group consisting of hydrido, acetamido, haloacetamido, alkoxyamino, alkanoyl, haloalkanoyl, amidino, guanidino, alkylenedioxy, haloalkylthio, alkoxy, hydroxy, amino, lower alkylamino, alkylthio, alkylsulfinyl, alkylsulfonyl, alkylsulfonamido, amidosulfonyl, monoalkyl amidosulfonyl, dialkyl amidosulfonyl, alkyl, halo, haloalkyl, haloalkoxy, hydroxyalkyl, aminoalkyl, carboalkoxy, carboxyalkyl, carboxy, carboxamido, and cyano;

A is selected from the group consisting of single covalent bond and $(CH(R^{15}))_{pa}$—$(W^7)_{rr}$ wherein rr is an integer selected from 0 through 1, pa is an integer selected from 0 through 3, and $W^7$ is selected from the group consisting of O, S, C(O), $(R^7)NC(O)$, $(R^7)NC(S)$, and $N(R^7)$;

$R^7$ is selected from the group consisting of hydrido, hydroxy and alkyl;

$R^{15}$ is selected from the group consisting of hydrido, hydroxy, halo, alkyl, and haloalkyl;

Ψ is NH;

$R^1$ is selected from the group consisting of hydrido, alkyl, cyano, halo, haloalkyl, haloalkoxy, amino, aminoalkyl, alkylamino, amidino, hydroxy, hydroxyamino, alkoxy, hydroxyalkyl, alkoxyamino, thiol, and alkylthio;

$R^2$ is $Z^0$—Q;

$Z^0$ is selected from the group consisting of covalent single bond and $(CR^{41}R^{42})_q$ wherein q is an integer selected from 1 through 2, $(CH(R^{41}))_g$—$W^0$—$(CH(R^{42}))_p$ wherein g and p are integers independently selected from 0 through 3 and $W^0$ is selected from the group consisting of O, S, and $N(R^{41})$, and $(CH(R^{41}))_e$—$W^{22}$—$(CH(R^{42}))_h$ wherein e and h are integers independently selected from 0 through 1 and $W^{22}$ is selected from the group consisting of $CR^{41}$=$CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, with the proviso that $Z^0$ is directly bonded to the pyrazinone ring;

$R^{41}$ and $R^{42}$ are independently selected from the group consisting of hydrido, hydroxy, and amino, Q is selected from the group consisting of hydrido, with the proviso that $Z^0$ is other than a covalent single bond, aryl, and heteroaryl, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

K is $CHR^{4a}$ wherein $R^{4a}$ is selected from the group consisting of hydrido, hydroxyalkyl, alkyl, alkoxyalkyl, alkylthioalkyl, and haloalkyl;

$E^0$ is selected from the group consisting of a covalent single bond, C(O)N(H), (H)NC(O), $(R^7)NS(O)_2$, and $S(O)_2N(R^7)$;

$Y^0$ is formula (IV):

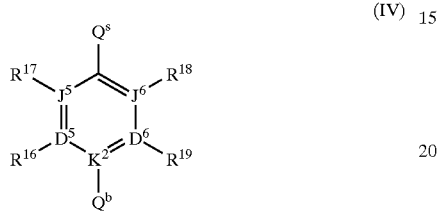

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkoxyamino, lower alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, $N(R^{26})C(NR^{25})N(R^{23})(R^{24})$, and $C(NR^{25})NR^{23}R^{24}$, with the provisos that no more than one of $R^{20}$ and $R^{21}$ is hydroxy, amino, alkylamino, or dialkylamino at the same time and that no more than one of $R^{23}$ and $R^{24}$ is hydroxy, amino, alkylamino, or dialkylamino at the same time;

$R^{20}$, $R^{21}$, $R^{23}$, $R^{24}$, $R^{25}$, and $R^{26}$ are independently selected from the group consisting of hydrido, alkyl, hydroxy, amino, alkylamino and dialkylamino;

$Q^s$ is selected from the group consisting of a single covalent bond, $(CR^{37}R^{38})_b$ wherein b is an integer selected from 1 through 4, and $(CH(R^{14}))_c$—$W^1$—$(CH(R^{15}))_d$ wherein c and d are integers independently selected from 1 through 3 and $W^1$ is selected from the group consisting of $C(O)N(R^{14})$, $(R^{14})NC(O)$, $S(O)$, $S(O)_2$, $S(O)_2N(R^{14})$, $N(R^{14})S(O)_2$, and $N(R^{14})$, with the provisos that $R^{14}$ is selected from other than halo when directly bonded to N and that $(CR^{37}R^{38})_b$ and $(CH(R^{14}))_c$ are bonded to $E^0$;

$R^{14}$ is selected from the group consisting of hydrido, halo, alkyl, and haloalkyl;

$R^{37}$ and $R^{38}$ are independently selected from the group consisting of hydrido, alkyl, and haloalkyl;

$R^{38}$ is optionally selected from the group consisting of aroyl and heteroaroyl;

$Y^0$ is optional $Q^b$—$Q^{ss}$ wherein $Q^{ss}$ is $(CH(R^{14}))_e$—$W^2$—$(CH(R^{15}))_h$, wherein e and h are integers independently selected from 1 through 2 and $W^2$ is $CR^{4a}$=CH with the proviso that $(CH(R^{14}))_e$ is bonded to $E^0$.

In an even more preferred embodiment of compounds of Formula I or a pharmaceutically acceptable salt thereof, J is O;

B is selected from the group consisting of aryl and heteroaryl wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, lower alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and $Q^b$;

A is selected from the group consisting of single covalent bond and $(CH(R^{15}))_{pa}$—$(W^7)_{rr}$ wherein rr is an integer selected from 0 through 1, pa is an integer selected from 0 through 3, and $W^7$ is selected from the group consisting of $(R^7)NC(O)$ and $N(R^7)$;

$R^7$ is selected from the group consisting of hydrido, hydroxy and alkyl;

$R^{15}$ is selected from the group consisting of hydrido, halo, alkyl, and haloalkyl;

Ψ is NH;

$R^1$ is selected from the group consisting of hydrido, alkyl, cyano, haloalkyl, and halo;

$R^2$ is $Z^0$—Q;

$Z^0$ is selected from the group consisting of a covalent single bond and $CH_2$;

Q is selected from the group consisting of aryl and heteroaryl wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, hydroxy, amino, amidino, guanidino, lower alkylamino, alkylthio, alkylsulfonamido, alkylsulfinyl, alkylsulfonyl, amidosulfonyl, monoalkyl amidosulfonyl, alkyl, alkoxy, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, hydroxy, amino, alkoxyamino, lower alkylamino, alkylsulfonamido, amidosulfonyl, monoalkyl amidosulfonyl, dialkyl amidosulfonyl, hydroxyalkyl, aminoalkyl, carboalkoxy, carboxy, carboxyalkyl, amidocarbonyl, halo, haloalkyl, and cyano;

K is $CH_2$;

$E^0$ is $C(O)N(H)$;

$Y^0$ is formula (IV):

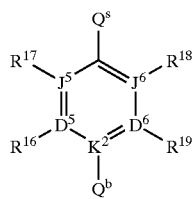

(IV)

wherein $D^5$, $D^6$, $J^5$ and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is optionally O, no more than one of $D^5$, $D^6$, $J^5$, and $J^6$ is optionally S, one of $D^5$, $D^6$, $J^6$, and $J^6$ must be acovalent bond when two of $D^5$, $D^5$, $J^5$, and $J^6$ are O and S, and no more than four of $D^5$, $D^6$, $J^5$, and $J^6$ are N;

$R^{16}$, $R^{17}$, $R^{18}$, and $R^{19}$ are independently selected from the group consisting of hydrido, amidino, guanidino, carboxy, haloalkylthio, alkoxy, hydroxy, amino, lower alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, and $C(NR^{25})NR^{23}R^{24}$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, and $R^{25}$ are independently selected from the group consisting of hydrido, alkyl, and hydroxy;

$Q^s$ is selected from the group consisting of a single covalent bond, $CH_2$, and $CH_2CH_2$.

In another even more preferred embodiment of compounds of Formula I or a pharmaceutically acceptable salt thereof, J is O;

B is optionally selected from the group consisting of hydrido, C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{36}$, and $R^{36}$ are independently selected from the group consisting of hydrido, acetamido, haloacetamido, amidino, guanidino, alkoxy, hydroxy, amino, alkoxyamino, lower alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and $Q^b$;

A is selected from the group consisting of single covalent bond and $(CH(R^{15}))_{pa}$—$(W^7)_{rr}$ wherein rr is an integer selected from 0 through 1, pa is an integer selected from 0 through 3, and $W^7$ is selected from the group consisting of $(R^7)NC(O)$ and $N(R^7)$;

$R^7$ is selected from the group consisting of hydrido, hydroxy and alkyl;

$R^{15}$ is selected from the group consisting of hydrido, halo, alkyl, and haloalkyl;

Ψ is NH;

$R^1$ is selected from the group consisting of hydrido, alkyl, cyano, haloalkyl, and halo;

$R^2$ is $Z^0$—Q;

$Z^0$ is selected from the group consisting of covalent single bond and $CH_2$;

Q is selected from the group consisting of aryl and heteroaryl wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, hydroxy, amino, amidino, guanidino, lower alkylamino, alkylthio, alkylsulfonamido, alkylsulfinyl, alkylsulfonyl, amidosulfonyl, monoalkyl amidosulfonyl, alkyl, alkoxy, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, hydroxy, amino, alkoxyamino, lower alkylamino, alkylsulfonamido, amidosulfonyl, monoalkyl amidosulfonyl, dialkyl amidosulfonyl, hydroxyalkyl, alkylenylamino, carboalkoxy, carboxy, carboxyalkyl, amidocarbonyl, halo, haloalkyl, and cyano;

K is $CH_2$;

$E^0$ is $C(O)N(H)$;

$Y^0$ is formula (IV):

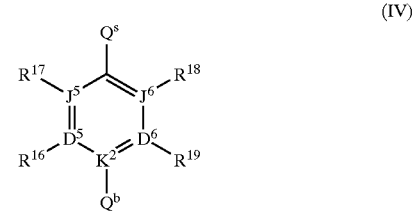

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$ and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$, $R^{17}$, $R^{18}$, and $R^{19}$ are independently selected from the group consisting of hydrido, amidino, guanidino, carboxy, haloalkylthio, alkoxy, hydroxy, amino, lower alkylamino, alkylthio, alkylsulfinyl, alkylsulfonyl, alkanoyl, haloalkanoyl, alkyl, halo, haloalkyl, haloalkoxy, hydroxyalkyl, alkylenylamino, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, $C(NR^{25})NR^{23}R^{24}$, and $N(R^{26})C(NR^{25})N(R^{23})(R^{24})$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, $R^{25}$, and $R^{26}$ are independently selected from the group consisting of hydrido, alkyl, and hydroxy;

$Q^s$ is selected from the group consisting of a single covalent bond, $CH_2$, and $CH_2CH_2$.

In still another even more preferred embodiment of compounds of Formula I or a pharmaceutically acceptable salt thereof, J is O;

B is optionally selected from the group consisting of C3–C7 cycloalkyl and C4–C6 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, a ring carbon or nitrogen atom adjacent to the $R^{13}$ position and two atoms from the point of attachment is optionally substituted with $R^{12}$, a ring carbon or nitrogen atom three atoms from the point of attachment and adjacent to the $R^{10}$ position is optionally substituted with $R^{11}$, a ring carbon or nitrogen atom three atoms from the point of attachment and adjacent to the $R^{12}$ position is optionally substituted with $R^{23}$, and a ring carbon or nitrogen atom four atoms from the point of attachment and adjacent to the $R^{11}$ and $R^{33}$ positions is optionally substituted with $R^{34}$;

$R^9$, $R^{11}$, and $R^{13}$ are independently selected from the group consisting of hydrido, hydroxy, amino, amidino, guanidino, lower alkylamino, alkylthio, alkylsulfonamido, alkylsulfinyl, alkylsulfonyl, amidosulfonyl, monoalkyl amidosulfonyl, alkyl, alkoxy, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, hydroxy, amino, alkoxyamino, lower alkylamino, alkylsulfonamido, amidosulfonyl, monoalkyl amidosulfonyl, dialkyl amidosulfonyl, hydroxyalkyl, alkylenylamino, carboalkoxy, carboxy, carboxyalkyl, amidocarbonyl, halo, haloalkyl, and cyano;

$R^{33}$ and $R^{34}$ are independently selected from the group consisting of hydrido, acetamido, haloacetamido, amidino, guanidino, alkoxy, hydroxy, amino, alkoxyamino, lower alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and $Q^b$;

A is selected from the group consisting of single covalent bond and $(CH(R^{15}))_{pa}—(W^7)_{rr}$ wherein rr is an integer selected from 0 through 1, pa is an integer selected from 0 through 3, and $W^7$ is selected from the group consisting of $(R^7)NC(O)$ and $N(R^7)$;

$R^7$ is selected from the group consisting of hydrido, hydroxy and alkyl;

$R^{15}$ is selected from the group consisting of hydrido, halo, alkyl and haloalkyl;

$\Psi$ is NH;

$R^1$ is selected from the group consisting of hydrido, alkyl, cyano, haloalkyl, and halo;

$R^2$ is $Z^0$—Q;

$Z^0$ is selected from the group consisting of covalent single bond and $CH_2$;

Q is selected from the group consisting of aryl and heteroaryl wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

K is $CH_2$;

$E^0$ is C(O)N(H);

$Y^0$ is formula (IV):

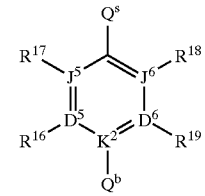

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$, and $J^6$ is S, one of $D^5$, $D^6$, $J^5$ and $J^6$ must be a covalent bond when two of $D^5$, $D^6$, $J^5$, and $J^6$ are O and S, and no more than four of $D^5$, $D^6$, $J^5$, and $J^6$ are N, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$, $R^{17}$, $R^{18}$, and $R^{19}$ are independently selected from the group consisting of hydrido, amidino, guanidino, carboxy, haloalkylthio, alkoxy, hydroxy, amino, lower alkylamino, alkylthio, alkylsulfinyl, alkylsulfonyl, alkanoyl, haloalkanoyl, alkyl, halo, haloalkyl, haloalkoxy, hydroxyalkyl, alkylenylamino, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, and $C(NR^{25})NR^{23}R^{24}$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, and $R^{25}$ are independently selected from the group consisting of hydrido, alkyl, and hydroxy;

$Q^s$ is selected from the group consisting of a single covalent bond, $CH_2$, and $CH_2CH_2$.

In a most preferred embodiment of compounds of Formula I or a pharmaceutically acceptable salt thereof, J is O;

B is selected from the group consisting of aryl and heteroaryl wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, lower alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and $Q^b$;

A is selected from the group consisting of single covalent bond and $(CH(R^{15}))_{pa}$—$(W^7)_{rr}$ wherein rr is an integer selected from 0 through 1, pa is an integer selected from 0 through 3, and $W^7$ is $N(R^7)$;

$R^7$ is selected from the group consisting of hydrido and alkyl;

$R^{15}$ is selected from the group consisting of hydrido, halo, alkyl, and haloalkyl;

Ψ is NH;

$R^1$ is selected from the group consisting of hydrido, cyano, haloalkyl, and halo;

$R^2$ is $Z^o$—Q;

$Z^o$ is a covalent single bond;

Q is selected from the group consisting of aryl and heteroaryl wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, hydroxy, amino, amidino, guanidino, lower alkylamino, alkylthio, alkoxy, alkylsulfinyl, alkylsulfonyl, amidosulfonyl, monoalkyl amidosulfonyl, alkyl, halo, haloalkyl, haloalkoxy, hydroxyalkyl, carboxy, carboxamido, and cyano;

$R^{10}$ and $R^{12}$ are independently selected from the group consistingof hydrido, acetamido, haloacetamido, amidino, guanidino, alkyl, alkoxy, alkoxyamino, aminoalkyl, hydroxy, amino, lower alkylamino, alkylsulfonamido, amidosulfonyl, monoalkyl amidosulfonyl, dialkyl amidosulfonyl, hydroxyalkyl, aminoalkyl, halo, haloalkyl, carboalkoxy, carboxy, carboxyalkyl, carboxyamido, and cyano;

K is $CH_2$;

$E^o$ is C(O)N(H);

$Y^o$ is formula (IV):

(IV)

wherein $D^5$, $D^6$, $J^5$ and $J^6$ are independently selected from the group consisting of C, N, O, S and a covalent bond with the provisos that no more than one is a covalent bond, $K^2$ is C, no more than one of $D^5$, $D^6$, $J^5$ and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$ and $J^6$ are O and S, and no more than four of $D^5$, $D^6$, $J^5$, and $J^6$ are N;

$R^{16}$, $R^{17}$, $R^{18}$, and $R^{19}$ are independently selected from the group consisting of hydrido, amidino, guanidino, carboxy, haloalkylthio, alkoxy, hydroxy, amino, lower alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, and $C(NR^{25})NR^{23}R^{24}$;

$R^{20}$, $R^{21}$, $R^{23}$, $R^{24}$, and $R^{25}$ are independently selected from the group consisting of hydrido and alkyl;

$Q^s$ is $CH_2$.

In another most preferred embodiment of compounds of Formula I or a pharmaceutically acceptable salt thereof, J is O;

B is optionally selected from the group consisting of hydrido, C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, lower alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and $Q^b$;

A is selected from the group consisting of single covalent bond and $(CH(R^{15}))_{pa}—(W^7)_{rr}$ wherein rr is an integer selected from 0 through 1, pa is an integer selected from 0 through 3, and $W^7$ is $N(R^7)$;

$R^7$ is selected from the group consisting of hydrido and alkyl;

$R^{15}$ is selected from the group consisting of hydrido, halo, alkyl, and haloalkyl;

Ψ is NH;

$R^1$ is selected from the group consisting of hydrido, cyano, haloalkyl, and halo;

$R^2$ is $Z^0$—Q;

$Z^0$ is a covalent single bond;

Q is selected from the group consisting of aryl and heteroaryl wherein a carbon adjacent to the carbon at the point of attachment is optionally substituted by $R^9$, the other carbon adjacent to the carbon at the point of attachment is optionally substituted by $R^{13}$, a carbon adjacent to R and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{12}$ and $R^{12}$ is optionally substituted by $R^{11}$;

$R^9$, $R^{11}$, and $R^{13}$ are independently selected from the group consisting of hydrido, hydroxy, amino, amidino, guanidino, lower alkylamino, alkylthio, alkoxy, alkylsulfinyl, alkylsulfonyl, amidosulfonyl, monoalkyl amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, aminoalkyl, hydroxy, amino, lower alkylamino, alkylsulfonamido, amidosulfonyl, monoalkyl amidosulfonyl, dialkyl amidosulfonyl, hydroxyalkyl, aminoalkyl, halo, haloalkyl, carboalkoxy, carboxy, carboxyalkyl, carboxyamido, and cyano;

K is $CH_2$;

$E^0$ is C(O)N(H);

$Y^0$ is formula (IV):

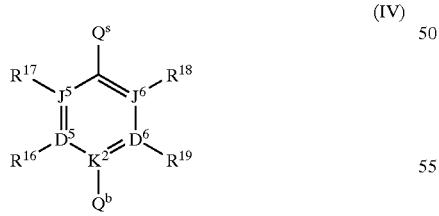

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$, and $J^6$ is S, one of $D^5$, $D^6$, $J^5$ and $J^6$ must be a covalent bond when two of $D^5$, $D^6$, $J^5$, and $J^6$ are O and S, and no more than four of $D^5$, $D^6$, $J^5$, and $J^6$ are N, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$, $R^{17}$, $R^{18}$, and $R^{19}$ are independently selected from the group consisting of hydrido, amidino, guanidino, carboxy, haloalkylthio, alkoxy, hydroxy, amino, lower alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, $N(R^{26})C(NR^{25})N(R^{23})(R^{24})$, and $C(NR^{25})NR^{23}R^{24}$;

$R^{20}$, $R^{21}$, $R^{23}$, $R^{24}$, $R^{25}$, and $R^{26}$ are independently selected from the group consisting of hydrido and alkyl;

$Q^s$ is $CH_2$.

In still another most preferred embodiment of compounds of Formula I or a pharmaceutically acceptable salt thereof, J is O;

B is optionally selected from the group consisting of C3–C7 cycloalkyl and C4–C6 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, a ring carbon or nitrogen atom adjacent to the $R^{13}$ position and two atoms from the point of attachment is optionally substituted with $R^{12}$, a ring carbon or nitrogen atom three atoms from the point of attachment and adjacent to the $R^{10}$ position is optionally substituted with $R^{11}$, a ring carbon or nitrogen atom three atoms from the point of attachment and adjacent to the $R^{12}$ position is optionally substituted with $R^{33}$, and a ring carbon or nitrogen atom four atoms from the point of attachment and adjacent to the $R^{11}$ and $R^{33}$ positions is optionally substituted with $R^{34}$;

$R^9$, $R^{11}$, and $R^{13}$ are independently selected from the group consisting of hydrido, hydroxy, amino, amidino, guanidino, lower alkylamino, alkylthio, alkoxy, alkylsulfinyl, alkylsulfonyl, amidosulfonyl, monoalkyl amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, aminoalkyl, hydroxy, amino, lower alkylamino, alkylsulfonamido, amidosulfonyl, monoalkyl amidosulfonyl, dialkyl amidosulfonyl, hydroxyalkyl, aminoalkyl, halo, haloalkyl, carboalkoxy, carboxy, carboxyalkyl, carboxyamido, and cyano;

$R^{33}$ and $R^{34}$ are independently selected from the group consisting of hydrido, amidino, guanidino, alkoxy, hydroxy, amino, alkoxyamino, lower alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, and cyano;

$R^{33}$ is optionally $Q^b$;

A is selected from the group consisting of single covalent bond and $(CH(R^{15}))_{pa}-(W^7)_{rr}$ wherein rr is an integer selected from 0 through 1, pa is an integer selected from 0 through 3, and $W^7$ is $N(R^7)$;

$R^7$ is selected from the group consisting of hydrido, hydroxy and alkyl;

$R^{15}$ is selected from the group consisting of hydrido, halo, alkyl, and haloalkyl;

$\Psi$ is NH;

$R^1$ is selected from the group consisting of hydrido, cyano, haloalkyl, and halo;

$R^2$ is $Z^0-Q$;

$Z^0$ is a covalent single bond;

Q is selected from the group consisting of aryl and heteroaryl wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

K is $CH_2$;

$E^0$ is C(O)N(H);

$Y^0$ is formula (IV):

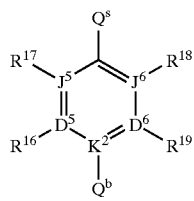

(IV)

wherein $D^5$, $D^6$, $J^5$, and $J^6$ are independently selected from the group consisting of C, N, O, S and a covalent bond with the provisos that no more than one is a covalent bond, $K^2$ is C, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N. with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$, $R^{17}$, $R^{18}$, and $R^{19}$ are independently selected from the group consisting of hydrido, amidino, guanidino, carboxy, haloalkylthio, alkoxy, hydroxy, amino, lower alkylamino, alkylthio, alkylsulfinyl, alkylsulfonyl, alkanoyl, haloalkanoyl, alkyl, halo, haloalkyl, haloalkoxy, hydroxyalkyl, alkylenylamino, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, and $C(NR^{25})NR^{23}R^{24}$;

$R^{20}$, $R^{21}$, $R^{23}$, $R^{24}$, and $R^{25}$ are independently selected from the group consisting of hydrido and alkyl;

$Q^s$ is $CH_2$.

In a preferred specific embodiment of Formula I, compounds have the Formula I-S:

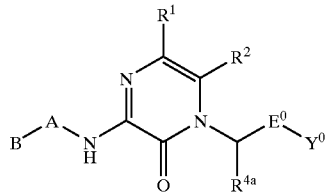

(I-S)

or a pharmaceutically acceptable salt thereof, wherein;

B is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 1,2,4-triazol-3-yl, 1,2,4-triazol-5-yl, 1,2,4-oxadiazol-3-yl, 1,2,4-oxadiazol-5-yl, 1,3,4-oxadiazol-3-yl, 1,3,4-oxadiazol-5-yl, 3-isothiazolyl, 5-isothiazolyl, 2-oxazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 1,3,5-triazin-2-yl, 1,2,4-triazin-3-yl, 1,2,4-triazin-5-yl, 1,2,4-triazin-6-yl, 1,2,3-triazin-4-yl, and 1,2,3-triazin-5-yl,, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, amidino, guanidino, carboxy, methyl, ethyl, isopropyl, propyl, methoxy, ethoxy, isopropoxy, propoxy, hydroxy, amino, methoxyamino, ethoxyamino, acetamido, trifluoroacetamido, nitro, aminomethyl, 1-aminoethyl, 2-aminoethyl, N-methylamino, dimethylamino, N-ethylamino, methylthio, ethylthio, isopropylthio, trifluoromethylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, acetyl, propanoyl, trifluoroacetyl, pentafluoropropanoyl, hydroxymethyl, 1-hydroxyethyl, 2-hydroxyethyl, 2,2,2-trifluoro-1-hydroxyethyl, 2,2,2-trifluoro-1-trifluoromethyl-1-hydroxyethyl, carboxymethyl, methoxycarbonyl, ethoxycarbonyl, amidocarbonyl, N-methylamidocarbonyl, N,N-dimethylamidocarbonyl, cyano, and $Q^b$;

B is selected from the group consisting of hydrido, trimethylsilyl, ethyl, 2-propenyl, 2-propynyl, propyl, isopropyl, butyl, 2-butenyl, 3-butenyl, 2-butynyl, sec-butyl, tert-butyl, isobutyl, 2-methylpropenyl, 1-pentyl, 2-pentenyl, 3-pentenyl, 4-pentenyl, 2-pentynyl, 3-pentynyl, 2-pentyl, 1-methyl-2-butenyl, 1-methyl-3-butenyl, 1-methyl-2-butynyl, 3-pentyl, 1-ethyl-2- propenyl, 2-methylbutyl, 2-methyl-2-butenyl, 2-methyl-3-butenyl, 2-methyl-3-butynyl, 3-methylbutyl, 3-methyl-2-butenyl, 3-methyl-3-butenyl, 1-hexyl, 2-hexenyl, 3-hexenyl, 4-hexenyl, 5-hexenyl, 2-hexynyl, 3-hexynyl, 4-hexynyl, 2-hexyl, 1-methyl-2-pentenyl, 1-methyl-3-pentenyl, 1-methyl-4-pentenyl, 1-methyl-2-pentynyl, 1-methyl-3-pentynyl, 3-hexyl, 1-ethyl-2-butenyl, 1-ethyl-3-butenyl, 1-propyl-2-propenyl, 1-ethyl-2-butynyl, 1-heptyl, 2-heptenyl, 3-heptenyl, 4-heptenyl, 5-heptenyl, 6-heptenyl, 2-heptynyl, 3-heptynyl, 4-heptynyl, 5-heptynyl, 2-heptyl, 1-methyl-2-hexenyl, 1-methyl-3-hexenyl, 1-methy-4-hexenyl, 1-methyl-5-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-4-pentenyl, 1-butyl-2-propenyl, 1-ethyl-2-pentynyl, 1-ethyl-3-pentynyl, 1-octyl, 2-octenyl, 3-octenyl, 4-octenyl, 5-octenyl, 6-octenyl, 7-octenyl, 2-octynyl, 3-octynyl, 4-octynyl, 5-octynyl, 6-octynyl, 2-octyl, 1-methyl-2-heptenyl, 1-methyl-3-heptenyl, 1-methyl-4-heptenyl, 1-methyl-5-heptenyl, 1-methyl-6-heptenyl, 1-methyl-2-heptynyl, 1-methyl-3-heptynyl, 1-methyl-4-heptynyl, 1-methyl-5-heptynyl, 1-methyl-6-heptynyl, 1-methyl-2-heptynyl, 1-methyl-3-heptynyl, 1-methyl-4-heptynyl, 1-methyl-5-heptynyl, 3-octyl, 1-ethyl-2-hexenyl, 1-ethyl-3-hexenyl, 1-ethyl-4-hexenyl, 1-ethyl-2-hexynyl, 1-ethyl-3-hexynyl, 1-ethyl-4-hexynyl, 1-ethyl-5-hexenyl, 1-pentyl-2-propenyl, 4-octyl, 1-propyl-2-pentenyl, 1-propyl-3-pentenyl, 1-propyl-4-pentenyl, 1-butyl-2-butenyl, 1-propyl-2-pentynyl, 1-propyl-3-pentynyl, 1-butyl-2-butynyl, 1-butyl-3-butenyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of $R^{32}$, $R^{33}$, $R^{34}$, $R^{35}$, and $R^{36}$;

B is optionally selected from the group consisting of cyclopropyl, cyclobutyl, oxetan-2-yl, oxetan-3-yl, azetidin-1-yl, azetidin-2-yl, azetidin-3-yl, thiaetan-2-yl, thiaetan-3-yl, cyclopentyl, cyclohexyl, adamantyl, norbornyl, 3-trifluoromethylnorbornyl, 7-oxabicyclo[2.2.1]heptan-2-yl, bicyclo[3.1.0]hexan-6-yl, cycloheptyl, cyclooctyl, 2-morpholinyl, 3-morpholinyl, 4-morpholinyl, 1-piperazinyl, 2-piperazinyl, 1-piperidinyl, 2-piperidinyl, 3-piperidinyl, 4-piperidinyl, 1-pyrrolidinyl, 2-pyrrolidinyl, 3-pyrrolidinyl, 2-dioxanyl, 4H-2-pyranyl, 4H-3-pyranyl, 4H-4-pyranyl, 4H-pyran-4-one-2-yl, 4H-pyran-4-one-3-yl, 2-tetrahydrofuranyl, 3-tetrahydrofuranyl, 2-tetrahydropyranyl, 3-tetrahydropyranyl, 4-tetrahydropyranyl, 2-tetrahydrothienyl, and 3-tetrahydrothienyl, wherein each ring carbon is optionally substituted with $R^{33}$, a ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, and a ring carbon or nitrogen atom adjacent to the $R^{13}$ position and two atoms from the point of attachment is optionally substituted with $R^{12}$;

$R^9$, $R^{10}$, $R^{11}$, $R^{12}$, and $R^{13}$ are independently selected from the group consisting of hydrido, amidino, guanidino, carboxy, carboxymethyl, methyl, ethyl, isopropyl, propyl, methoxy, ethoxy, isopropoxy, propoxy, hydroxy, amino, methoxyamino, ethoxyamino, acetamido, trifluoroacetamido, nitro, aminomethyl, 1-aminoethyl, 2-aminoethyl, N-methylamino, dimethylamino, N-ethylamino, methylthio, ethylthio, isopropylthio, trifluoromethylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, methanesulfonamido, amidosulfonyl, N-methylamidosulfonyl, N,N-dimethylamidosulfonyl, acetyl, propanoyl, trifluoroacetyl, pentafluoropropanoyl, hydroxymethyl, 1-hydroxyethyl, 2-hydroxyethyl, 2,2,2-trifluoro-1-hydroxyethyl, 2,2,2-trifluoro-1-trifluoromethyl-1-hydroxyethyl, carboxymethyl, methoxycarbonyl, ethoxycarbonyl, amidocarbonyl, N-methylamidocarbonyl, N,N-dimethylamidocarbonyl, and cyano;

A is selected from the group consisting of single covalent bond, O, S, NH, N(CH$_3$), N(OH), C(O), CH$_2$, CH$_3$CH, CF$_3$CH, NHC(O), N(CH$_3$)C(O), C(O)NH, C(O)N(CH$_3$), CF$_3$CC(O), C(O)CCH$_3$, C(O)CCF$_3$, CH$_2$C(O), (O)CCH$_2$, CH$_2$CH$_2$, CH$_2$CH$_2$CH$_2$, CH$_3$CHCH$_2$, CF$_3$CHCH$_2$, CH$_3$CC(O)CH$_2$, CF$_3$CC(O)CH$_2$, CH$_2$C(O)CCH$_3$, CH$_2$C(O)CCF$_3$, CH$_2$CH$_2$C(O), and CH$_2$(O)CCH$_2$;

A is optionally selected from the group consisting of CH$_2$N(CH$_3$), CH$_2$N(CH$_2$CH$_3$), CH$_2$CH$_2$N(CH$_3$), and CH$_2$CH$_2$N(CH$_2$CH$_3$) with the proviso that B is hydrido;

$R^1$ is selected from the group consisting of hydrido, cyano, methyl, ethyl, propyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, and bromo;

$R^2$ is $Z^0$—Q;

$Z^0$ is selected from the group consisting of covalent single bond, CH$_2$, CH$_2$CH$_2$, CH(OH), CH(NH$_2$), CH$_2$CH(OH), CH$_2$CHNH$_2$, CH(OH)CH$_2$, and CH(NH$_2$)CH$_2$;

Q is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 1,2,4-triazol-3-yl, 1,2,4-triazol-5-yl, 1,2,4-oxadiazol-3-yl, 1,2,4-oxadiazol-5-yl, 1,3,4-oxadiazol-3-yl, 1,3,4-oxadiazol-5-yl, 3-isothiazolyl, 5-isothiazolyl, 2-oxazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 1,3,5-triazin-2-yl, 1,2,4-triazin-3-yl, 1,2,4-triazin-5-yl, 1,2,4-triazin-6-yl, 1,2,3-triazin-4-yl, and 1,2,3-triazin-5-yl, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

K is CHR$^{4a}$ wherein $R^{4a}$ is selected from the group consisting of methyl, ethyl, propyl, isopropyl, hydroxymethyl, 1-hydroxyethyl, methoxymethyl, trifluoromethyl, pentafluoroethyl, 2,2,2-trifluoromethyl, methylthiomethyl, and hydrido;

$E^0$ is a covalent single bond, C(O)N(H), (H)NC(O), and $S(O)_2N(H)$;

$Y^0$ is selected from the group of formulas consisting of:

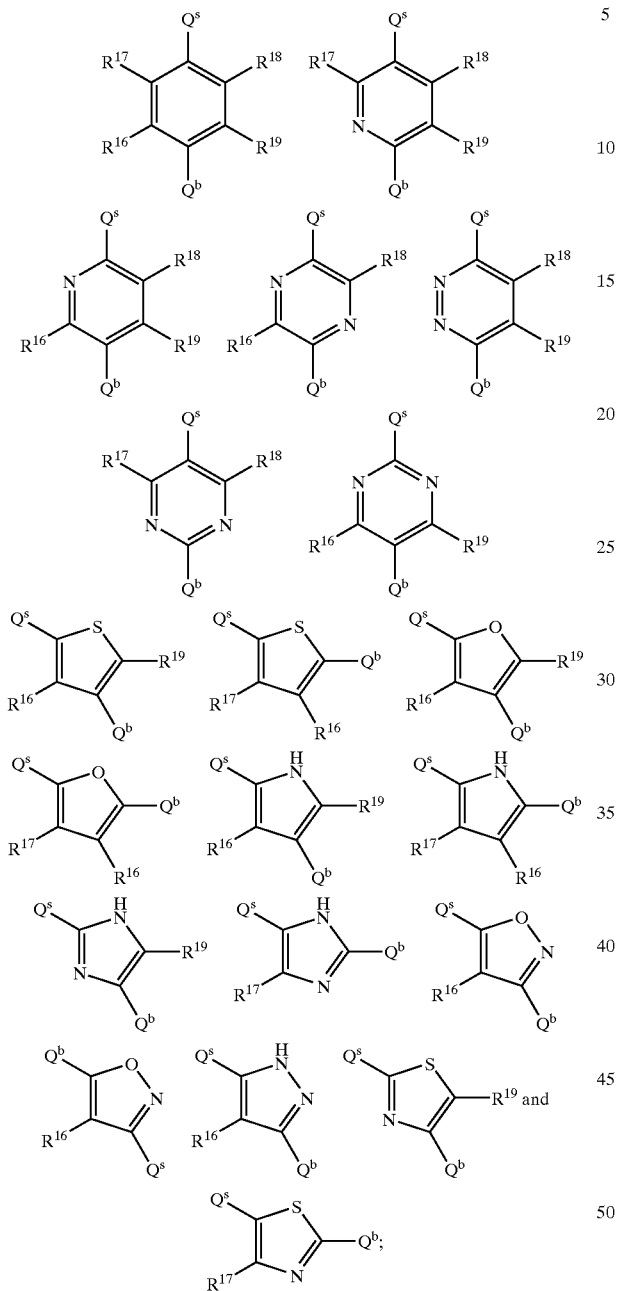

$R^{16}$, $R^{17}$, $R^{18}$, and $R^{19}$ are independently selected from the group consisting of hydrido, methyl, ethyl, isopropyl, propyl, amidino, guanidino, carboxy, methoxy, ethoxy, isopropoxy, propoxy, hydroxy, amino, methoxyamino, ethoxyamino, aminomethyl, 1-aminoethyl, 2-aminoethyl, N-N-methylamino, dimethylamino, N-ethylamnino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, acetyl, propanoyl, trifluoroacetyl, pentafluoropropanoyl, hydroxymethyl, 1-hydroxyethyl, 2-hydroxyethyl, 2,2,2-trifluoro-1-hydroxyethyl, and cyano;

$R^{16}$ and $R^{19}$ are optionally $Q^b$ with the proviso that no more than one of $R^{16}$ and $R^{19}$ is $Q^b$ at the same time and that $Q^b$ is $Q^{be}$;

$Q^b$ is selected from the group consisting of $NR^{20}R^{21}$, $Q^{be}$ wherein $Q^{be}$ is hydrido, $C(NR^{25})NR^{23}R^{24}$ and $N(R^{26})C(NR^{25})N(R^{23})(R^{24})$, with the proviso that no more than one of $R^{20}$ and $R^{21}$ is hydroxy, N-methylamino, and N,N-dimethylamino at the same time and that no more than one of $R^{23}$ and $R^{24}$ is hydroxy, N-methylamino, and N,N-dimethylamino at the same time;

$R^{20}$, $R^{21}$, $R^{23}$, $R^{24}$, $R^{25}$, and $R^{26}$ are independently selected from the group consisting of hydrido, methyl, ethyl, propyl, butyl, isopropyl, hydroxy, 2-aminoethyl, 2-(N-methylamino)ethyl, and 2-(N,N-dimethylamino)ethyl;

$Q^s$ is selected from the group consisting of a single covalent bond, $CH_2$, $CH_2CH_2$, $CH_3CH$, $CF_3CH$, $CH_3CHCH_2$, $CF_3CHCH_2$, $CH_2(CH_3)CH$, CH=CH, CF=CH, $C(CH_3)$=CH, CH=$CHCH_2$, CF=$CHCH_2$, $C(CH_3)$=$CHCH_2$, $CH_2CH$=CH, $CH_2CF$=CH, $CH_2C(CH_3)$=CH, $CH_2CH$=$CHCH_2$, $CH_2CF$=$CHCH_2$, $CH_2C(CH_3)$=$CHCH_2$, $CH_2CH$=$CHCH_2CH_2$, $CH_2CF$=$CHCH_2CH_2$, and $CH_2C(CH_3)$=$CHCH_2CH_2$.

In a more preferred specific embodiment of Formula I, compounds have the Formula I-MPS wherein B is an aromatic:

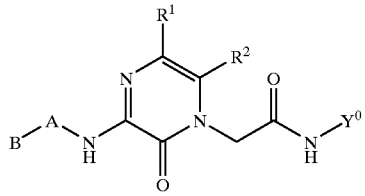

(I-MPS wherein B is aromatic)

or a pharmaceutically acceptable salt thereof, wherein;

B is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, cyano, and $Q^b$;

A is selected from the group consisting of single covalent bond, NH, N(CH$_3$), N(OH), CH$_2$, CH$_3$CH, CF$_3$CH, NHC(O), N(CH$_3$)C(O), C(O)NH, C(O)N(CH$_3$), CH$_2$CH$_2$, CH$_2$CH$_2$CH$_2$, CH$_3$CHCH$_2$, and CF$_3$CHCH$_2$;

$Q^b$ is selected from the group consisting of NR$^{20}$R$^{21}$, $Q^{be}$ wherein $Q^{be}$ is hydrido, and C(NR$^{25}$)NR$^{23}$R$^{24}$, with the provisos that no more than one of R$^{20}$ and R$^{21}$ is hydroxy at the same time and that no more than one of R$^{23}$ and R$^{24}$ is hydroxy at the same time;

R$^{20}$, R$^{21}$, R$^{23}$, R$^{24}$, and R$^{25}$ are independently selected from the group consisting of hydrido, methyl, ethyl, propyl, butyl, isopropyl, and hydroxy;

$Q^s$ is selected from the group consisting of a single covalent bond, CH$_2$, and CH$_2$CH$_2$.

In another more preferred specific embodiment of Formula I, compounds have the Formula I-MPS wherein B is a non-cyclic substituent:

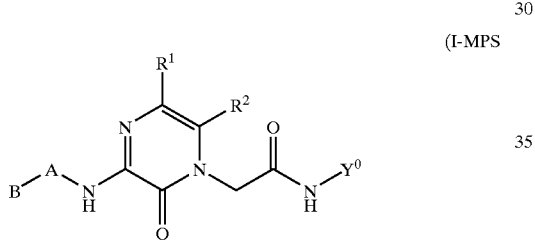

(I-MPS)

wherein B is a non-cyclic substituent)
or a pharmaceutically acceptable salt thereof, wherein;

B is selected from the group consisting of hydrido, ethyl, 2-propenyl, 2-propynyl, propyl, isopropyl, butyl, 2-butenyl, 3-butenyl, 2-butynyl, sec-butyl, tert-butyl, isobutyl, 2-methylpropenyl, 1-pentyl, 2-pentenyl, 3-pentenyl, 4-pentenyl, 2-pentynyl, 3-pentynyl, 2-pentyl, 1-methyl-2-butenyl, 1-methyl-3-butenyl, 1-methyl-2-butynyl, 3-pentyl, 1-ethyl-2-propenyl, 2-methylbutyl, 2-methyl-2-butenyl, 2-methyl-3-butenyl, 2-methyl-3-butynyl, 3-methylbutyl, 3-methyl-2-butenyl, 3-methyl-3-butenyl, 1-hexyl, 2-hexenyl, 3-hexenyl, 4-hexenyl, 5-hexenyl, 2-hexynyl, 3-hexynyl, 4-hexynyl, 2-hexyl, 1-methyl-2-pentenyl, 1-methyl-3-pentenyl, 1-methyl-4-pentenyl, 1-methyl-2-pentynyl, 1-methyl-3-pentynyl, 3-hexyl, 1-ethyl-2-butenyl, 1-ethyl-3-butenyl, 1-propyl-2-propenyl, 1-ethyl-2-butynyl, 1-heptyl, 2-heptenyl, 3-heptenyl, 4-heptenyl, 5-heptenyl, 6-heptenyl, 2-heptynyl, 3-heptynyl, 4-heptynyl, 5-heptynyl, 2-heptyl, 1-methyl-2-hexenyl, 1-methyl-3-hexenyl, 1-methyl-4-hexenyl, 1-methyl-5-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-4-pentenyl, 1-butyl-2-propenyl, 1-ethyl-2-pentynyl, 1-ethyl-3-pentynyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of R$^{32}$, R$^{33}$, R$^{34}$, and R$^{36}$;

R$^{32}$, R$^{33}$, R$^{34}$, R$^{35}$, and R$^{36}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, cyano, and $Q^b$;

A is selected from the group consisting of single covalent bond, NH, N(CH$_3$), N(OH), CH$_2$, CH$_3$CH, CF$_3$CH, NHC(O), N(CH$_3$)C(O), C(O)NH, C(O)N(CH$_3$), CH$_2$CH$_2$, CH$_2$CH$_2$CH$_2$, CH$_3$CHCH$_2$, and CF$_3$CHCH$_2$;

A is optionally selected from the group consisting of CH$_2$N(CH$_3$), CH$_2$N(CH$_2$CH$_3$), CH$_2$CH$_2$N(CH$_3$), and CH$_2$CH$_2$N(CH$_2$CH$_3$) with the proviso that B is hydrido;

$Q^b$ is selected from the group consisting of NR$^{20}$R$^{21}$, $Q^{be}$, wherein $Q^{be}$ is hydrido, C(NR$^{25}$)N$^{23}$R$^{24}$, and N(R$^{26}$) C(NR$^{25}$)N(R$^{23}$)(R$^{24}$), with the provisos that no more than one of R$^{20}$ and R$^{21}$ is hydroxy at the same time and that no more than one of R$^{23}$ and R$^{24}$ is hydroxy at the same time;

R$^{20}$, R$^{21}$, R$^{23}$, R$^{24}$, R$^{25}$, and R$^{26}$ are independently selected from the group consisting of hydrido, methyl, ethyl, propyl, butyl, isopropyl, and hydroxy;

$Q^s$ is selected from the group consisting of a single covalent bond, CH$_2$, and CH$_2$CH$_2$.

In still another more preferred specific embodiment of Formula I, compounds have the Formula I-MPS wherein B is a non-aromatic cyclic substituent:

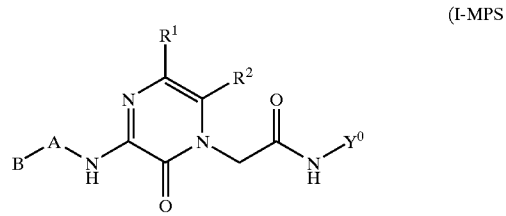

(I-MPS)

wherein B is a non-aromatic cyclic substituent)
or a pharmaceutically acceptable salt thereof, wherein;

B is optionally selected from the group consisting of cyclopropyl, cyclobutyl, oxetan-3-yl, azetidin-1-yl, azetidin-2-yl, azetidin-3-yl, thiaetan-3-yl, cyclopentyl, cyclohexyl, norbornyl, 7-oxabicyclo[2.2.1]heptan-2-yl, bicyclo[3.1.0]hexan-6-yl, cycloheptyl, 2-morpholinyl, 3-morpholinyl, 4-morpholinyl, 1-piperazinyl, 2-piperazinyl, 1-piperidinyl, 2-piperidinyl, 3-piperidinyl, 4-piperidinyl, 1-pyrrolidinyl, 2-pyrrolidinyl, 3-pyrrolidinyl, 2-dioxanyl, 4H-2- pyranyl, 4H-3-pyranyl, 4H-4-pyranyl, 4H-pyran-4-one-2-yl, 4H-pyran-4-one-3-yl, 2-tetrahydrofuranyl, 3-tetrahydrofuranyl, 2-tetrahydropyranyl, 3-tetrahydropyranyl, 4-tetrahydropyranyl, 2-tetrahydrothienyl, and 3-tetrahydrothienyl, wherein each ring carbon is optionally substituted with $R^{33}$, a ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, and a ring carbon or nitrogen atom adjacent to the $R^{13}$ position and two atoms from the point of attachment is optionally substituted with $R^{12}$;

A is selected from the group consisting of single covalent bond, NH, $N(CH_3)$, $N(OH)$, $CH_2$, $CH_3CH$, $CF_3CH$, $NHC(O)$, $N(CH_3)C(O)$, $C(O)NH$, $C(O)N(CH_3)$, $CH_2CH_2$, $CH_2CH_2CH_2$, $CH_3CHCH_2$, and $CF_3CHCH_2$;

$R^{33}$ and $R^{34}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amnidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, cyano, and $Q^b$;

$Q^b$ is selected from the group consisting of $NR^{20}R^{21}$, $Q^{be}$ wherein Q is hydrido, and $C(NR^{25})NR^{23}R^{24}$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, and $R^{25}$ are independently selected from the group consisting of hydrido, methyl, ethyl, propyl, butyl, isopropyl, and hydroxy;

$Q^s$ is selected from the group consisting of a single covalent bond, $CH_2$, and $CH_2CH_2$.

The more preferred specific embodiment (I-MPS) compounds of the present invention having the Formula:

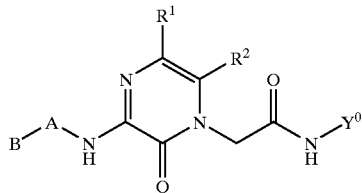

or a pharmaceutically acceptable salt thereof, have common structural units, wherein;

$R^1$ is selected from the group consisting of hydrido, methyl, ethyl, propyl, trifluoromethyl, pentafluoroethyl, 2,2,2-trifluoroethyl, 2,2,3,3,3-pentafluoropropyl, fluoro, chloro, and bromo;

$R^2$ is $Z^0$—Q;

$Z^0$ is selected from the group consisting of covalent single bond and $CH_2$;

Q is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, amidino, guanidino, carboxy, methyl, ethyl, propyl, isopropyl, methoxy, ethoxy, isopropoxy, propoxy, hydroxy, amino, N-methylamino, N,N-dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, amidocarbonyl, N-methylamidocarbonyl, N,N-dimethylamidocarbonyl, and cyano;

$R^{10}$ and $R^{12}$ are independently selected from the group consisting of hydrido, amidino, guanidino, carboxy, carboxymethyl, methyl, ethyl, propyl, isopropyl, methoxy, ethoxy, isopropoxy, propoxy, hydroxy, amino, methoxyamino, ethoxyamino, acetamido, trifluoroacetamido, aminomethyl, 1-aminoethyl, 2-aminoethyl, N-methylamino, dimethylamino, N-ethylamino, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, fluoro, chloro, bromo, and cyano;

$Y^0$ is selected from the group of formulas consisting of:

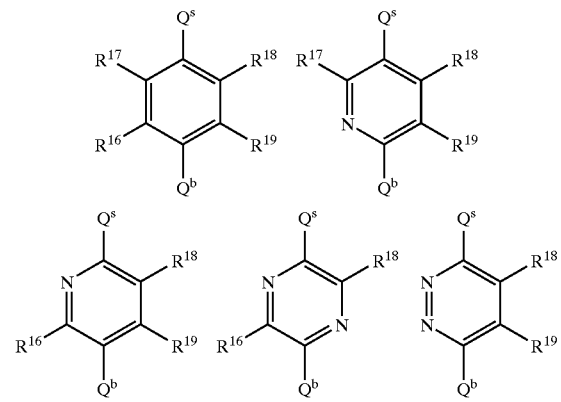

-continued

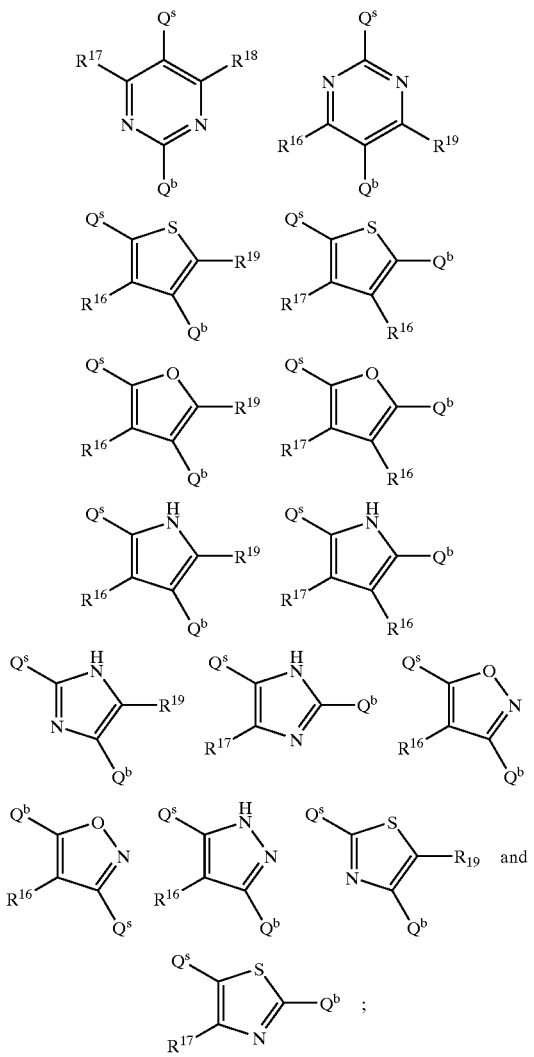

R$^{16}$, R$^{17}$, R$^{18}$, and R$^{19}$ are independently selected from the group consisting of hydrido, methyl, ethyl, isopropyl, propyl, carboxy, amidino, guanidino, methoxy, ethoxy, isopropoxy, propoxy, hydroxy, amino, aminomethyl, 1-aminoethyl, 2-aminoethyl, N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, and cyano;

R$^{16}$ and R$^{19}$ are optionally Q$^b$ with the proviso that no more than one of R$^{16}$ and R$^{19}$ is Q$^b$ at the same time and that Q$^b$ is Q$^{be}$.

In a most preferred specific embodiment of Formula I, compounds have the Formula I-EMPS wherein B is an aromatic:

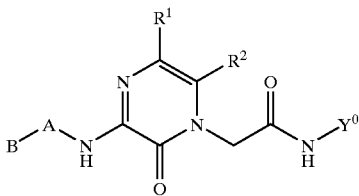

(I-EMPS wherein B is aromatic)

or a pharmaceutically acceptable salt thereof, wherein;

B is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, and 5-isoxazolyl, wherein a carbon adjacent to the carbon at the point of attachment is optionally substituted by R$^{32}$, the other carbon adjacent to the carbon at the point of attachment is optionally substituted by R$^{36}$, a carbon adjacent to R$^{32}$ and two atoms from the carbon at the point of attachment is optionally substituted by R$^{33}$, a carbon adjacent to R$^{36}$ and two atoms from the carbon at the point of attachment is optionally substituted by R$^{35}$, and any carbon adjacent to both R$^{33}$ and R$^{35}$ is optionally substituted by R$^{34}$;

R$^{32}$, R$^{33}$, R$^{34}$, R$^{35}$, and R$^{36}$ are independently selected from the group consisting of hydrido, amidino, guanidino, methyl, ethyl, methoxy, ethoxy, hydroxy, amino, N-methylamino, dimethylamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, carboxy, cyano, and Q$^b$;

A is selected from the group consisting of single covalent bond, NH, N(CH$_3$), CH$_2$, CH$_3$CH, and CH$_2$CH$_2$;

Q$^b$ is selected from the group consisting of N$^{20}$R$^{21}$ and C(NR$^{25}$)NR$^{23}$R$^{24}$, with the proviso that said Q$^b$ group is bonded directly to a carbon atom;

R$^{20}$, R$^{21}$, R$^{23}$, R$^{24}$, and R$^{25}$ are independently selected from the group consisting of hydrido, methyl, and ethyl;

Q$^s$ is CH$_2$.

In another most preferred specific embodiment of Formula I, compounds have the Formula I-EMPS wherein B is a non-cyclic substituent:

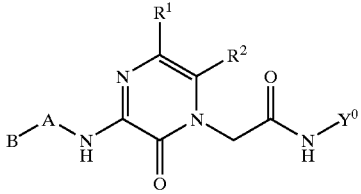

(I-EMPS wherein B is a non-cyclic substituent)

or a pharmaceutically acceptable salt thereof, wherein;

B is selected from the group consisting of hydrido, ethyl, 2-propenyl, 2-propynyl, propyl, isopropyl, butyl, 2-butenyl, 2-butynyl, sec-butyl, tert-butyl, isobutyl, 2-methylpropenyl, 1-pentyl, 2-pentenyl, 3-pentenyl, 2-pentynyl, 3-pentynyl, 2-pentyl, 3-pentyl, 2-methylbutyl, 2-methyl-2-butenyl, 3-methylbutyl, 3-methyl-2-butenyl, 1-hexyl, 2-hexenyl, 3-hexenyl, 4-hexenyl, 2-hexynyl, 3-hexynyl, 4-hexynyl, 2-hexyl, 1-methyl-2-pentenyl, 1-methyl-3-pentenyl, 1-methyl-2-pentynyl, 1-methyl-3-pentynyl, 3-hexyl, 1-ethyl-2-butenyl, 1-heptyl, 2-heptenyl, 3-heptenyl, 4-heptenyl, 5-heptenyl, 2-heptynyl, 3-heptynyl, 4-heptynyl, 5-heptynyl, 2-heptyl, 1-methyl-2-hexenyl, 1-methyl-3-hexenyl, 1-methyl-4-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-2-pentynyl, 1-ethyl-3-pentynyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, amidino, guanidino, methyl, ethyl, methoxy, ethoxy, hydroxy, amino, N-methylamino, dimethylamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, carboxy, cyano, and $Q^b$;

A is selected from the group consisting of single covalent bond, NH, N(CH$_3$), CH$_2$, CH$_3$CH, and CH$_2$CH$_2$;

A is optionally selected from the group consisting of CH$_2$N(CH$_3$), CH$_2$N(CH$_2$CH$_3$), CH$_2$CH$_2$N(CH$_3$), and CH$_2$CH$_2$N(CH$_2$CH$_3$) with the proviso that B is hydrido;

$Q^b$ is selected from the group consisting of NR$^{20}$R$^{21}$, C(NR$^{25}$)NR$^{23}$R$^{24}$, and N(R$^{26}$)C(NR$^{25}$)N(R$^{23}$)(R$^{24}$), with the proviso that said $Q^b$ group is bonded directly to a carbon atom;

$R^{20}$, $R^{21}$, $R^{23}$, $R^{24}$, $R^{25}$, and $R^{26}$ are independently selected from the group consisting of hydrido, methyl, and ethyl;

$Q^s$ is CH$_2$.

In still another most preferred specific embodiment of Formula I, compounds have the Formula I-EMPS wherein B is a non-aromatic cyclic substituent:

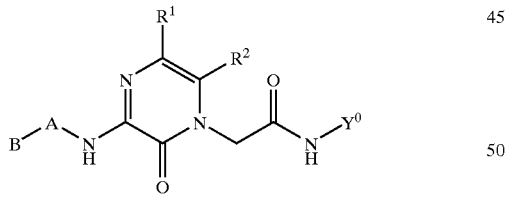

(I-EMPS wherein B is a non-aromatic cyclic substituent) or a pharmaceutically acceptable salt thereof, wherein;

B is optionally selected from the group consisting of cyclopropyl, cyclobutyl, oxetan-3-yl, azetidin-3-yl, thiaetan-3-yl, cyclopentyl, cyclohexyl, 1-pyrrolidinyl, 2-pyrrolidinyl, 3-pyrrolidinyl, 2-tetrahydrofuranyl, 3-tetrahydrofuranyl, 2-tetrahydrothienyl, and 3-tetrahydrothienyl, wherein each ring carbon is optionally substituted with $R^{33}$, a ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, and a ring carbon or nitrogen atom adjacent to the $R^{13}$ position and two atoms from the point of attachment is optionally substituted with $R^{12}$;

$R^{33}$ are independently selected from the group consisting of hydrido, amidino, guanidino, methyl, ethyl, methoxy, ethoxy, hydroxy, carboxy, amino, N-methylamino, dimethylamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, cyano, and $Q^b$;

A is selected from the group consisting of single covalent bond, NH, N(CH$_3$), CH$_2$, CH$_3$CH, and CH$_2$CH$_2$;

$Q^b$ is selected from the group consisting of NR$^{20}$R$^{21}$ and C(NR$^{25}$)NR$^{23}$R$^{24}$, with the proviso that said $Q^b$ group is bonded directly to a carbon atom;

$R^{20}$, $R^{21}$, $R^{23}$, $R^{24}$, and $R^{25}$ are independently selected from the group consisting of hydrido, methyl, and ethyl;

$Q^s$ is CH$_2$.

The most preferred specific embodiment (I-EMPS) compounds of the present invention having the Formula:

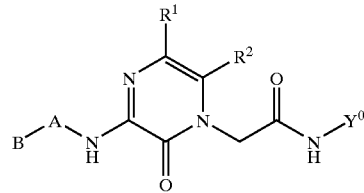

or a pharmaceutically acceptable salt thereof, have common structural units, wherein;

$R^1$ is selected from the group consisting of hydrido, trifluoromethyl, pentafluoroethyl, fluoro, and chloro;

$R^2$ is $Z^0$—Q;

$Z^0$ is a covalent single bond;

Q is selected from the group consisting of phenyl, 2-thienyl, 2-furyl, 2-pyrrolyl, 2-imidazolyl, 2-thiazolyl, 3-isoxazolyl, 2-pyridyl, and 3-pyridyl, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, methyl, ethyl, methoxy, ethoxy, hydroxy, amino, N-methylamino, N,N-dimethylamino, methylthio, trifluoromethyl, pentafluoroethyl, 2,2,2-trifluoroethyl, fluoro, chloro, bromo, amidosulfonyl, N-methylamidosulfonyl, N,N-dimethylamidosulfonyl, hydroxymethyl, 1-hydroxyethyl, amidocarbonyl, N-methylamidocarbonyl, carboxy, and cyano;

$R^{10}$ and $R^{12}$ are independently selected from the group consisting of hydrido, amidino, amidocarbonyl, N-methylamidocarbonyl, guanidino, methyl, ethyl, methoxy, ethoxy, hydroxy, hydroxymethyl, 1-hydroxyethyl, 2-hydroxyethyl, carboxy, carboxymethyl, amino, acetamido, trifluoromethyl, pentafluoroethyl, 2,2,2-trifluoroethyl, trifluoroacetamido, aminomethyl, N-methylamino, dimethylamino, amidosulfonyl, N-methylamidosulfonyl, N,N-dimethylamidosulfonyl, methoxycarbonyl, fluoro, chloro, bromo, and cyano;

$Y^0$ is selected from the group of formulas consisting of:

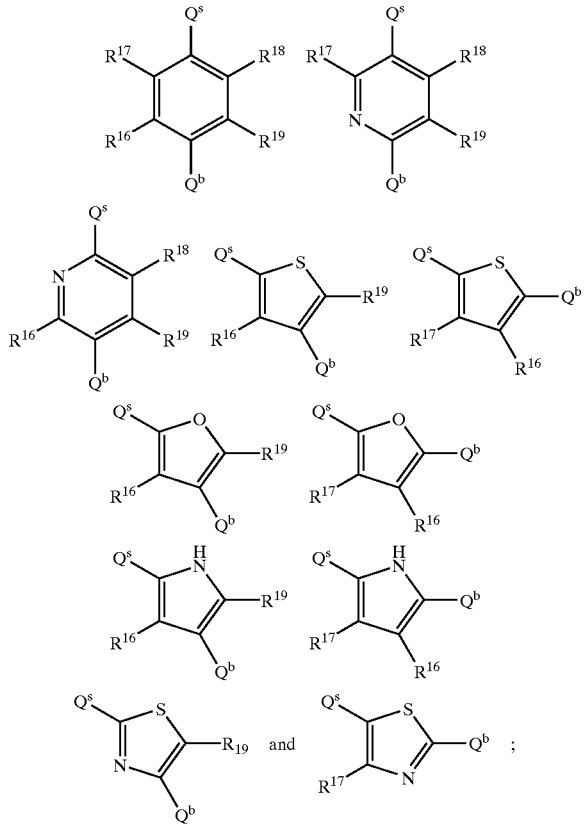

$R^{16}$, $R^{17}$, $R^{18}$, and $R^{19}$ are independently selected from the group consisting of hydrido, methyl, ethyl, amidino, guanidino, methoxy, hydroxy, amino, aminomethyl, 1-aminoethyl, 2-aminoethyl, N-methylamino, dimethylamino, methylthio, ethylthio, trifluoromethylthio, methylsulfinyl, methylsulfonyl, trifluoromethyl, pentafluoroethyl, 2,2,2-trifluoroethyl, trifluoromethoxy, fluoro, chloro, amidosulfonyl, N-methylamidosulfonyl, hydroxymethyl, carboxy, and cyano.

The compounds of this invention can be used in anticoagulant therapy for the treatment and prevention of a variety of thrombotic conditions including coronary artery and cerebrovascular disease. The compounds of this invention can be used to inhibit serine protease associated with the coagulation cascade and factors II, VII, VIII, IX, X, XI, or XII. The compounds of the invention can inhibit the formation of blood platelet aggregates, inhibit the formation of fibrin, inhibit thrombus formation. and inhibiting embolus formation in a mammal, in blood, in blood products, and in mammalian organs. The compounds also can be used for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels in a mammal. The compounds can also be used in prophylactic treatment of subjects who are at risk of developing such disorders. The compounds can be used to lower the risk of atherosclerosis. The compounds of Formula (I) would also be useful in prevention of cerebral vascular accident (CVA) or stroke.

Besides being useful for human treatment, these compounds are also useful for veterinary treatment of companion animals, exotic animals and farm animals, including mammals, rodents, and the like. More preferred animals include horses, dogs, and cats.

In yet another embodiment of the present invention, the novel compounds are selected from the compounds set forth in Examples 1 through Example 109 and Tables 1 through Table 7.

The use of generic terms in the description of the compounds are herein defined for clarity.

Standard single letter elemental symbols are used to represent specific types of atoms unless otherwise defined. The symbol "C" represents a carbon atom. The symbol "O" represents an oxygen atom. The symbol "N" represents a nitrogen atom. The symbol "P" represents a phosphorus atom. The symbol "S" represents a sulfur atom. The symbol "H" represents a hydrido atom. Double letter elemental symbols are used as defined for the elements of the periodical table (i.e., Cl represents chlorine, Se represents selenium, etc.).

As utilized herein, the term "alkyl", either alone or within other terms such as "haloalkyl" and "alkylthio", means an acyclic alkyl radical containing from 1 to about 10, preferably from 3 to about 8 carbon atoms and more preferably 3 to about 6 carbon atoms. Said alkyl radicals may be optionally substituted with groups as defined below. Examples of such radicals include methyl, ethyl, chloroethyl, hydroxyethyl, n-propyl, oxopropyl, isopropyl, n-butyl, cyanobutyl, isobutyl, sec-butyl, tert-butyl, pentyl, aminopentyl, iso-amyl, hexyl, octyl and the like.

The term "alkenyl" refers to an unsaturated, acyclic hydrocarbon radical in so much as it contains at least one double bond. Such alkenyl radicals contain from about 2 to about 10 carbon atoms, preferably from about 3 to about 8 carbon atoms and more preferably 3 to about 6 carbon atoms. Said alkenyl radicals may be optionally substituted with groups as defined below. Examples of suitable alkenyl radicals include propenyl, 2-chloropropenyl, buten-1-yl, isobutenyl, penten-1-yl, 2-2-methylbuten-1-yl, 3-methylbuten-1-yl, hexen-1-yl, 3-hydroxyhexen-1-yl, hepten-1-yl, and octen-1-yl, and the like.

The term "alkynyl" refers to an unsaturated, acyclic hydrocarbon radical in so much as it contains one or more triple bonds, such radicals containing about 2 to about 10 carbon atoms, preferably having from about 3 to about 8 carbon atoms and more preferably having 3 to about 6 carbon atoms. Said alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl. hexyn-1-yl, hexyn-2-yl, hexyn-3-yl, 3,3-dimethylbutyn-1-yl radicals and the like.

The term "hydrido" denotes a single hydrogen atom (H). This hydrido radical may be attached, for example, to an oxygen atom to form a "hydroxyl" radical, one hydrido radical may be attached to a carbon atom to form a "methine" radical —CH=, or two hydrido radicals may be attached to a carbon atom to form a "methylene" (—CH$_2$—) radical.

The term "carbon" radical denotes a carbon atom without any covalent bonds and capable of forming four covalent bonds.

The term "cyano" radical denotes a carbon radical having three of four covalent bonds shared by a nitrogen atom.

The term "hydroxyalkyl" embraces radicals wherein any one or more of the alkyl carbon atoms is substituted with a hydroxyl as defined above. Specifically embraced are monohydroxyalkyl, dihydroxyalkyl and polyhydroxyalkyl radicals.

The term "alkanoyl" embraces radicals wherein one or more of the terminal alkyl carbon atoms are substituted with one or more carbonyl radicals as defined below. Specifically embraced are monocarbonylalkyl and dicarbonylalkyl radicals. Examples of monocarbonylalkyl radicals include formyl, acetyl, and pentanoyl. Examples of dicarbonylalkyl radicals include oxalyl, malonyl, and succinyl.

The term "alkylene" radical denotes linear or branched radicals having from 1 to about 10 carbon atoms and having attachment points for two or more covalent bonds. Examples of such radicals are methylene, ethylene, methylethylene, and isopropylidene.

The term "alkenylene" radical denotes linear or branched radicals having from 2 to about 10 carbon atoms, at least one double bond, and having attachment points for two or more covalent bonds. Examples of such radicals are 1,1-vinylidene ($CH_2=C$), 1,2-vinylidene ($-CH=CH-$), and 1,4-butadienyl ($-CH=CH-CH=CH-$).

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo radicals may have two or more of the same halo atoms or a combination of different halo radicals and polyhaloalkyl radicals may have more than two of the same halo atoms or a combination of different halo radicals. More preferred haloalkyl radicals are "lower haloalkyl" radicals having one to about six carbon atoms. Examples of such haloalkyl radicals include fluoromethyl, difluoromethyl, trifluoromethyl, chloromethyl, dichloromethyl, trichloromethyl, trifluoroethyl, pentafluoroethyl, heptafluoropropyl, difluoroceloromethyl, dichiorofluoromethyl, difluoroethyl, difluoropropyl, dichloroethyl and dichloropropyl.

The term "hydroxyhaloalkyl" embraces radicals wherein any one or more of the haloalkyl carbon atoms is substituted with hydroxy as defined above. Examples of "hydroxyhaloalkyl" radicals include hexafluorohydroxypropyl.

The term "haloalkylene radical" denotes alkylene radicals wherein any one or more of the alkylene carbon atoms is substituted with halo as defined above. Dihalo alkylene radicals may have two or more of the same halo atoms or a combination of different halo radicals and polyhaloalkylene radicals may have more than two of the same halo atoms or a combination of different halo radicals. More preferred haloalkylene radicals are "lower haloalkylene" radicals having one to about six carbon atoms. Examples of "haloalkylene" radicals include difluoromethylene, tetrafluoroethylene, tetrachloroethylene, alkyl substituted monofluoromethylene, and aryl substituted trifluoromethylene.

The term "haloalkenyl" denotes linear or branched radicals having from 1 to about 10 carbon atoms and having one or more double bonds wherein any one or more of the alkenyl carbon atoms is substituted with halo as defined above. Dihaloalkenyl radicals may have two or more of the same halo atoms or a combination of different halo radicals and polyhaloalkenyl radicals may have more than two of the same halo atoms or a combination of different halo radicals.

The terms "alkoxy" and "alkoxyalkyl" embrace linear or branched oxy-containing radicals each having alkyl portions of one to about ten carbon atoms, such as methoxy radical. The term "alkoxyalkyl" also embraces alkyl radicals having one or more alkoxy radicals attached to the alkyl radical, that is, to form monoalkoxyalkyl and dialkoxyalkyl radicals. More preferred alkoxy radicals are "lower alkoxy" radicals having one to six carbon atoms. Examples of such radicals include methoxy, ethoxy, propoxy, butoxy, isopropoxy and tert-butoxy alkyls. The "alkoxy" radicals may be further substituted with one or more halo atoms, such as fluoro, chloro or bromo, to provide "haloalkoxy" and "haloalkoxyalkyl" radicals. Examples of such haloalkoxy radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy. Examples of such haloalkoxyalkyl radicals include fluoromethoxymethyl, chloromethoxyethyl, trifluoromethoxymethyl, difluoromethoxyethyl, and trifluoroethoxymethyl.

The terms "alkenyloxy" and "alkenyloxyalkyl" embrace linear or branched oxy-containing radicals each having alkenyl portions of two to about ten carbon atoms, such as ethenyloxy or propenyloxy radical. The term "alkenyloxyalkyl" also embraces alkenyl radicals having one or more alkenyloxy radicals attached to the alkyl radical, that is, to form monoalkenyloxyalkyl and dialkenyloxyalkyl radicals. More preferred alkenyloxy radicals are "lower alkenyloxy" radicals having two to six carbon atoms. Examples of such radicals include ethenyloxy, propenyloxy, butenyloxy, and isopropenyloxy alkyls. The "alkenyloxy" radicals may be further substituted with one or more halo atoms, such as fluoro, chloro or bromo, to provide "haloalkenyloxy" radicals. Examples of such radicals include trifluoroethenyloxy, fluoroethenyloxy, difluoroethenyhloxy, and fluoropropenyloxy.

The term "haloalkoxyalkyl" also embraces alkyl radicals having one or more haloalkoxy radicals attached to the alkyl radical, that is, to form monohaloalkoxyalkyl and dihaloalkoxyalkyl radicals. The term "haloalkenyloxy" also embraces oxygen radicals having one or more haloalkenyloxy radicals attached to the oxygen radical, that is, to form monohaloalkenyloxy and dihaloalkenyloxy radicals. The term "haloalkenyloxyalkyl" also embraces alkyl radicals having one or more haloalkenyloxy radicals attached to the alkyl radical, that is, to form monohaloalkenyloxyalkyl and dihaloalkenyloxyalkyl radicals.

The term "alkylenedioxy" radicals denotes alkylene radicals having at least two oxygens bonded to a single alkylene group. Examples of "alkylenedioxy" radicals include methylenedioxy, ethylenedioxy, alkylsubstituted methylenedioxy, and arylsubstituted methylenedioxy. The term "haloalkylenedioxy" radicals denotes haloalkylene radicals having at least two oxy groups bonded to a single haloalkyl group. Examples of "haloalkylenedioxy" radicals include difluoromethylenedioxy, tetrafluoroethylenedioxy, tetrachloroethylenedioxy, alkylsubstituted monofluoromethylenedioxy, and arylsubstituted monofluoromethylenedioxy.

The term "aryl", alone or in combination, means a carbocyclic aromatic system containing one, two or three rings wherein such rings may be attached together in a pendant manner or may be fused. The term "fused" means that a second ring is present (ie, attached or formed) by having two adjacent atoms in common (ie, shared) with the first ring.

The term "fused" is equivalent to the term "condensed". The term "aryl" embraces aromatic radicals such as phenyl, naphthyl, tetrahydronaphthyl, indane and biphenyl.

The term "perhaloaryl" embraces aromatic radicals such as phenyl, naphthyl, tetrahydronaphthyl, indane and biphenyl wherein the aryl radical is substituted with 3 or more halo radicals as defined below.

The term "heterocyclyl" embraces saturated and partially saturated heteroatom-containing ring-shaped radicals having from 4 through 15 ring members, herein referred to as "C4–C15 heterocyclyl", selected from carbon, nitrogen, sulfur and oxygen, wherein at least one ring atom is a heteroatom. Heterocyclyl radicals may contain one, two or three rings wherein such rings may be attached in a pendant manner or may be fused. Examples of saturated heterocyclic radicals include saturated 3 to 6-membered heteromonocylic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclyl radicals include dihydrothiophene, dihydropyran, dihydrofuran and dihydrothiazole. Non-limiting examples of heterocyclic radicals include 2-pyrrolinyl, 3-pyrrolinyl, pyrrolindinyl, 1,3-dioxolanyl, 2H-pyranyl, 4H-pyranyl, piperidinyl, 1,4-dioxanyl, morpholinyl, 1,4-dithianyl, thiomorpholinyl, and the like.

The term "heteroaryl" embraces fully unsaturated heteroatom-containing ring-shaped aromatic radicals having from 4 through 15 ring members selected from carbon, nitrogen, sulfur and oxygen, wherein at least one ring atom is a heteroatom. Heteroaryl radicals may contain one, two or three rings wherein such rings may be attached in a pendant manner or may be fused. Examples of "heteroaryl" radicals, include unsaturated 5 to 6 membered heteromonocyclyl group containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl, etc.], etc.; unsaturated 3 to 6-membered heteromonocyclic group containing an oxygen atom, for example, pyranyl, 2-furyl, 3-furyl, etc.: unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4oxadiazolyl, 1,3,4-oxadiazolyl, 1,2,-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like.

Said "heterocyclyl" group may have 1 to 3 substituents as defined below. Preferred heterocyclic radicals include five to twelve membered fused or unfused radicals. Non-limiting examples of heteroaryl radicals include pyrrolyl, pyridinyl, pyridyloxy, pyrazolyl, triazolyl, pyrimidinyl, pyridazinyl, oxazolyl, thiazolyl, imidazolyl, indolyl, thiophenyl, furanyl, tetrazolyl, 2-imidazolinyl, imidazolidinyl, 2-pyrazolinyl, pyrazolidinyl, isoxazolyl, isothiazolyl, 1,2,3-oxadiazolyl, 1,2,3-triazolyl, 1,3,4-thiadiazolyl, pyrazinyl, piperazinyl, 1,3,5-triazinyl, 1,3,5-trithianyl, benzo(b)thiophenyl, benzimidazoyl, quinolinyl, tetraazolyl, and the like.

The term "sulfonyl", whether used alone or linked to other terms such as alkylsulfonyl, denotes respectively divalent radicals —$SO_2$—. "Alkylsulfonyl", 30 embraces alkyl radicals attached to a sulfonyl radical, where alkyl is defined as above. "Alkylsulfonylalkyl", embraces alkylsulfonyl radicals attached to an alkyl radical, where alkyl is defined as above. "Haloalkylsulfonyl", embraces haloalkyl radicals attached to a sulfonyl radical, where haloalkyl is defined as above. "Haloalkylsulfonylalkyl", embraces haloalkylsulfonyl radicals attached to an alkyl radical, where alkyl is defined as above. The term "aminosulfonyl" denotes an amino radical attached to a sulfonyl radical.

The term "sulfinyl", whether used alone or linked to other terms such as alkylsulfinyl, denotes respectively divalent radicals —S(O)—. "Alkylsulfinyl", embraces alkyl radicals attached to a sulfinyl radical, where alkyl is defined as above. "Alkylsulfinylalkyl", embraces alkylsulfinyl radicals attached to an alkyl radical, where alkyl is defined as above. "Haloalkylsulfinyl", embraces haloalkyl radicals attached to a sulfinyl radical, where haloalkyl is defined as above. "Haloalkylsulfonylalkyl", embraces haloalkylsulfinyl radicals attached to an alkyl radical, where alkyl is defined as above.

The term "aralkyl" embraces aryl-substituted alkyl radicals. Preferable aralkyl radicals are "lower aralkyl" radicals having aryl radicals attached to alkyl radicals having one to six carbon atoms. Examples of such radicals include benzyl, diphenylmethyl, triphenylmethyl, phenylethyl and diphenylethyl. The terms benzyl and phenylmethyl are interchangeable.

The term "heteroaralkyl" embraces heteroaryl-substituted alkyl radicals wherein the heteroaralkyl radical may be additionally substituted with three or more substituents as defined above for aralkyl radicals. The term "perhaloaralkyl" embraces aryl-substituted alkyl radicals wherein the aralkyl radical is substituted with three or more halo radicals as defined above.

The term "aralkylsulfinyl", embraces aralkyl radicals attached to a sulfinyl radical, where aralkyl is defined as above. "Aralkylsulfinylalkyl", embraces aralkylsulfinyl radicals attached to an alkyl radical, where alkyl is defined as above.

The term "aralkylsulfonyl", embraces aralkyl radicals attached to a sulfonyl radical, where aralkyl is defined as above. "Aralkylsulfonylalkyl", embraces aralkylsulfonyl radicals attached to an alkyl radical, where alkyl is defined as above.

The term "cycloalkyl" embraces radicals having three to 15 carbon atoms. More preferred cycloalkyl radicals are "lower cycloalkyl" radicals having three to seven carbon atoms. Examples include radicals such as cyclopropyl, cyclobutyl, cyclopentyl, cyclohexyl and cycloheptyl. The term cycloalkyl embraces radicals having seven to 15 carbon atoms and having two to four rings. Exmaples incude radicals such as norbornyl (i.e., bicyclo[2.2.1]heptyl) and adamantyl. The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Examples of such radicals include cyclohexylhexyl. The term "cycloalkenyl" embraces radicals having three to ten carbon atoms and one or more carbon-carbon double bonds. Preferred cycloalkenyl radicals are "lower cycloalkenyl" radicals having three to seven carbon atoms. Examples include radicals such as cyclobutenyl, cyclopentenyl, cyclohexenyl and cycloheptenyl. The term "halocycloalkyl" embraces radicals wherein any one or more of the cycloalkyl carbon atoms is substituted with halo as defined above. Specifically embraced are monohalocycloalkyl, dihalocycloalkyl and polyhalocycloalkyl radicals. A monohalocycloalkyl radical, for one example, may have either a bromo, chloro or a fluoro atom within the radical. Dihalo radicals may have two or more of the same halo atoms or a combination of different halo radicals and polyhalocycloalkyl radicals may have more than two of the same halo atoms or a combination of different halo radicals. More preferred halocycloalkyl radicals are "lower halocycloalkyl" radicals having three to about eight carbon atoms. Examples of such halocycloalkyl radicals include fluorocyclopropyl, difluorocyclobutyl, trifluorocyclopentyl, tetrafluorocyclohexyl, and dichlorocyclopropyl. The term "halocycloalkenyl" embraces radicals wherein any one or more of the cycloalkenyl carbon atoms is substituted with halo as defined above. Specifically embraced are monohalocycloalkenyl, dihalocycloalkenyl and polyhalocycloalkenyl radicals.

The term "cycloalkoxy" embraces cycloalkyl radicals attached to an oxy radical. Examples of such radicals includes cyclohexoxy and cyclopentoxy. The term "cycloalkoxyalkyl" also embraces alkyl radicals having one or more cycloalkoxy radicals attached to the alkyl radical, that is, to form monocycloalkoxyalkyl and dicycloalkoxyalkyl radicals. Examples of such radicals include cyclohexoxyethyl. The "cycloalkoxy" radicals may be further substituted with one or more halo atoms, such as fluoro, chloro or bromo, to provide "halocycloalkoxy" and "halocycloalkoxyalkyl" radicals.

The term "cycloalkylalkoxy" embraces cycloalkyl radicals attached to an alkoxy radical. Examples of such radicals includes cyclohexylmethoxy and cyclopentylmethoxy.

The term "cycloalkenyloxy" embraces cycloalkenyl radicals attached to an oxy radical. Examples of such radicals includes cyclohexenyloxy and cyclopentenyloxy. The term "cycloalkenyloxyalkyl" also embraces alkyl radicals having one or more cycloalkenyloxy radicals attached to the alkyl radical, that is, to form monocycloalkenyloxyalkyl and dicycloalkenyloxyalkyl radicals. Examples of such radicals include cyclohexenyloxyethyl. The "cycloalkenyloxy" radicals may be further substituted with one or more halo atoms, such as fluoro, chloro or bromo, to provide "halocycloalkenyloxy" and "halocycloalkenyloxyalkyl" radicals.

The term "cycloalkylenedioxy" radicals denotes cycloalkylene radicals having at least two oxygens bonded to a single cycloalkylene group. Examples of "alkylenedioxy" radicals include 1,2-dioxycyclohexylene.

The term "cycloalkylsulfinyl", embraces cycloalkyl radicals attached to a sulfinyl radical, where cycloalkyl is defined as above. "Cycloalkylsulfinylalkyl", embraces cycloalkylsulfinyl radicals attached to an alkyl radical, where alkyl is defined as above. The term "Cycloalkylsulfonyl", embraces cycloalkyl radicals attached to a sulfonyl radical, where cycloalkyl is defined as above. "Cycloalkylsulfonylalkyl", embraces cycloalkylsulfonyl radicals attached to an alkyl radical, where alkyl is defined as above.

The term "cycloalkylalkanoyl" embraces radicals wherein one or more of the cycloalkyl carbon atoms are substituted with one or more carbonyl radicals as defined below. Specifically embraced are monocarbonylcycloalkyl and dicarbonylcycloalkyl radicals. Examples of monocarbonylcycloalkyl radicals include cyclohexylcarbonyl, cyclohexylacetyl, and cyclopentylcarbonyl. Examples of dicarbonylcycloalkyl radicals include 1,2-dicarbonylcyclohexane.

The term "alkylthio" embraces radicals containing a linear or branched alkyl radical, of one to ten carbon atoms, attached to a divalent sulfur atom. More preferred alkylthio radicals are "lower alkylthio" radicals having one to six carbon atoms. An example of "lower alkylthio" is methylthio ($CH_3$—S—). The "alkylthio" radicals may be further substituted with one or more halo atoms, such as fluoro, chloro or bromo, to provide "haloalkylthio" radicals. Examples of such radicals include fluoromethylthio, chloromethylthio, trifluoromethylthio, difluoromethylthio, trifluoroethylthio, fluoroethylthio, tetrafluoroethylthio, pentafluoroethylthio, and fluoropropylthio.

The term "alkyl aryl amino" embraces radicals containing a linear or branched alkyl radical, of one to ten carbon atoms, and one aryl radical both attached to an amino radical. Examples include N-methyl-4-methoxyaniline, N-ethyl-4-methoxyaniline, and N-methyl-4-trifluoromethoxyaniline.

The terms alkylamino denotes "monoalkylamino" and "dialkylamino" containing one or two alkyl radicals, respectively, attached to an amino radical.

The terms arylamino denotes "monoarylamino" and "diarylamino" containing one or two aryl radicals, respectively, attached to an amino radical. Examples of such radicals include N-phenylamino and N-naphthylamino.

The term "aralkylamino", embraces aralkyl radicals attached to an amino radical, where aralkyl is defined as above. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "arylsulfinyl" embraces radicals containing an aryl radical, as defined above, attached to a divalent S(O) atom. The term "arylsulfinylalkyl" denotes arylsulfinyl radicals attached to a linear or branched alkyl radical, of one to ten carbon atoms.

The term "arylsulfonyl", embraces aryl radicals attached to a sulfonyl radical, where aryl is defined as above. "arylsulfonylalkyl", embraces arylsulfonyl radicals attached to an alkyl radical, where alkyl is defined as above. The term "heteroarylsulfinyl" embraces radicals containing an heteroaryl radical, as defined above, attached to a divalent S(O) atom. The term "heteroarylsulfinylalkyl" denotes heteroarylsulfinyl radicals attached to a linear or branched alkyl radical, of one to ten carbon atoms. The term "Heteroarylsulfonyl", embraces heteroaryl radicals attached to a sulfonyl radical, where heteroaryl is defined as above. "Heteroarylsulfonylalkyl", embraces heteroarylsulfonyl radicals attached to an alkyl radical, where alkyl is defined as above.

The term "aryloxy" embraces aryl radicals, as defined above, attached to an oxygen atom. Examples of such radicals include phenoxy, 4-chloro-3-ethylphenoxy, 4-chloro-3-methylphenoxy, 3-chloro-4-ethylphenoxy, 3,4-dichlorophenoxy, 4-methylphenoxy, 3-trifluoromethoxyphenoxy, 3-trifluoromethylphenoxy, 4-fluorophenoxy, 3,4-dimethylphenoxy, 5-bromo-2-fluorophenoxy, 4-bromo-3-fluorophenoxy, 4-fluoro-3-methylphenoxy, 5,6,7,8-tetrahydronaphthyloxy, 3-isopropylphenoxy, 3-cyclopropylphenoxy, 3-ethylphenoxy, 3-pentafluoroethylphenoxy, 3-(1,1,2,2-tetrafluoroethoxy)-phenoxy, and 4-tert-butylphenoxy.

The term "aroyl" embraces aryl radicals, as defined above, attached to an carbonyl radical as defined above. Examples of such radicals include benzoyl and toluoyl.

The term "aralkanoyl" embraces aralkyl radicals, as defined herein, attached to an carbonyl radical as defined above. Examples of such radicals include, for example, phenylacetyl.

The term "aralkoxy" embraces oxy-containing aralkyl radicals attached through an oxygen atom to other radicals. More preferred aralkoxy radicals are "lower aralkoxy" radicals having phenyl radicals attached to lower alkoxy radical as described above. Examples of such radicals include benzyloxy, 1-phenylethoxy, 3-trifluoromethoxybenzyloxy, 3-trifluoromethylbenzyloxy, 3,5-difluorobenyloxy, 3-bromobenzyloxy, 4-propylbenzyloxy, 2-fluoro-3-trifluoromethylbenzyloxy, and 2-phenylethoxy.

The term "aryloxyalkyl" embraces aryloxy radicals, as defined above, attached to an alkyl group. Examples of such radicals include phenoxymethyl.

The term "haloaryloxyalkyl" embraces aryloxyalkyl radicals, as defined above, wherein one to five halo radicals are attached to an aryloxy group.

The term "heteroaroyl" embraces heteroaryl radicals, as defined above, attached to an carbonyl radical as defined above. Examples of such radicals include furoyl and nicotinyl.

The term "heteroaralkanoyl" embraces heteroaralkyl radicals, as defined herein, attached to an carbonyl radical as defined above. Examples of such radicals include, for example, pyridylacetyl and furylbutyryl.

The term "heteroaralkoxy" embraces oxy-containing heteroaralkyl radicals attached through an oxygen atom to other radicals. More preferred heteroaralkoxy radicals are "lower heteroaralkoxy" radicals having heteroaryl radicals attached to lower alkoxy radical as described above.

The term "haloheteroaryloxyalkyl" embraces heteroaryloxyalkyl radicals, as defined above, wherein one to four halo radicals are attached to an heteroaryloxy group.

The term "heteroarylamino" embraces heterocyclyl radicals, as defined above, attached to an amino group. Examples of such radicals include pyridylamino.

The term "heteroarylaminoalkyl" embraces heteroarylamino radicals, as defined above, attached to an alkyl group. Examples of such radicals include pyridylmethylamino.

The term "heteroaryloxy" embraces heterocyclyl radicals, as defined above, attached to an oxy group. Examples of such radicals include 2-thiophenyloxy, 2-pyrimidyloxy, 2-pyridyloxy, 3-pyridyloxy, and 4-pyridyloxy.

The term "heteroaryloxyalkyl" embraces heteroaryloxy radicals, as defined above, attached to an alkyl group. Examples of such radicals include 2-pyridyloxymethyl, 3-pyridyloxyethyl, and 4-pyridyloxymethyl.

The term "arylthio" embraces aryl radicals, as defined above, attached to an sulfur atom. Examples of such radicals include phenylthio.

The term "arylthioalkyl" embraces arylthio radicals, as defined above, attached to an alkyl group. Examples of such radicals include phenylthiomethyl.

The term "alkylthioalkyl" embraces alkylthio radicals, as defined above, attached to an alkyl group. Examples of such radicals include methylthiomethyl. The term "alkoxyalkyl" embraces alkoxy radicals, as defined above, attached to an alkyl group. Examples of such radicals include methoxymethyl.

The term "carbonyl" denotes a carbon radical having two of the four covalent bonds shared with an oxygen atom. The term "carboxy" embraces a hydroxyl radical, as defined above, attached to one of two unshared bonds in a carbonyl group. The term "carboxamide" embraces amino, monoalkylamino, dialkylamino, monocycloalkylamino, alkylcycloalkylamino, and dicycloalkylamino radicals, attached to one of two unshared bonds in a carbonyl group. The term "carboxamidoalkyl" embraces carboxamide radicals, as defined above, attached to an alkyl group. The term "carboxyalkyl" embraces a carboxy radical, as defined above, attached to an alkyl group. The term "carboalkoxy" embraces alkoxy radicals, as defined above, attached to one of two unshared bonds in a carbonyl group. The term "carboaralkoxy" embraces aralkoxy radicals, as defined above, attached to one of two unshared bonds in a carbonyl group. The term "monocarboalkoxyalkyl" embraces one carboalkoxy radical, as defined above, attached to an alkyl group. The term "dicarboalkoxyalkyl" embraces two carboalkoxy radicals, as defined above, attached to an alkylene group. The term "monocyanoalkyl" embraces one cyano radical, as defined above, attached to an alkyl group. The term "dicyanoalkylene" embraces two cyano radicals, as defined above, attached to an alkyl group. The term "carboalkoxycyanoalkyl" embraces one cyano radical, as defined above, attached to an carboalkoxyalkyl group.

The term "acyl", alone or in combination, means a carbonyl or thionocarbonyl group bonded to a radical selected from, for example, hydrido, alkyl, alkenyl, alkynyl, haloalkyl, alkoxy, alkoxyalkyl, haloalkoxy, aryl, heterocyclyl, heteroaryl, alkylsulfinylalkyl, alkylsulfonylalkyl, aralkyl, cycloalkyl, cycloalkylalkyl, cycloalkenyl, alkylthio, arylthio, amino, alkylamino, dialkylamino, aralkoxy, arylthio, and alkylthioalkyl. Examples of "acyl" are formyl, acetyl, benzoyl, trifluoroacetyl, phthaloyl, malonyl, nicotinyl, and the like. The term "haloalkanoyl" embraces one or more halo radicals, as defined herein, attached to an alkanoyl radical as defined above. Examples of such radicals include, for example, chloroacetyl, trifluoroacetyl, bromopropanoyl, and heptafluorobutanoyl.

The term "phosphono" embraces a pentavalent phosphorus attached with two covalent bonds to an oxygen radical. The term "dialkoxyphosphono" denotes two alkoxy radicals, as defined above, attached to a phosphono radical with two covalent bonds. The term "diaralkoxyphosphono" denotes two aralkoxy radicals, as defined above, attached to a phosphono radical with two covalent bonds. The term "dialkoxyphosphonoalkyl" denotes dialkoxyphosphono radicals, as defined above, attached to an alkyl radical. The term "diaralkoxyphosphonoalkyl" denotes diaralkoxyphosphono radicals, as defined above, attached to an alkyl radical.

The term "amino" denotes a nitrogen atom containing two substituents such as hydrido, hydroxy or alkyl and having one covalent bond available for bonding to a single atom such as carbon. Examples of such amino radicals include, for example, $-NH_2$, $-NHCH_3$, $-NHOH$, and $-NHOCH_3$. The term "imino" denotes a nitrogen atom containing one substituent such as hydrido, hydroxy or alkyl and having two covalent bonds available for bonding to a single atom such as carbon. Examples of such imino radicals include, for example, $=NH$, $=NCH_3$, $=NOH$, and $=NOCH_3$. The term "imino carbonyl" denotes a carbon radical having two of the four covalent bond sites shared with an imino group. Examples of such imino carbonyl radicals include, for example, C=NH, C=NCH$_3$, C=NOH, and C=NOCH$_3$. The term "amidino" embraces a substituted or unsubstituted amino group bonded to one of two available bonds of an iminocarbonyl radical. Examples of such amidino radicals include, for example, NH$_2$—C=NH, NH$_2$—C=NCH$_3$, NH$_2$—C=NOCH$_3$ and CH$_3$NH—C=NOH. The term "guanidino" denotes an amidino group bonded to an amino group as defined above where said amino group can be bonded to a third group. Examples of such guanidino radicals include, for example, NH$_2$—C(NH)—NH—, NH$_2$—C(NCH$_3$)—NH—, NH$_2$—C(NOCH$_3$)—NH—, and CH$_3$NH—C(NOH)—NH—.

The term "sulfonium" denotes a positively charged trivalent sulfur atom where said sulfur is substituted with three carbon based groups such as alkyl, alkenyl, aralkyl, or aryl. The term "dialkyl sulfonium" denotes a sulfonium group where said sulfur is substituted with two alkyl groups. Examples of such dialkylsulfonium radicals include, for example, (CH$_3$)$_2$S$^+$—. The term "dialkyl sulfonium alkyl" denotes a dialkyl sulfonium group where said group is bonded to one bond of an alkylene group as defined above. Examples of such dialkylsulfoniumalkyl radicals include (CH$_3$)$_2$S$^+$—CH$_2$CH$_2$—.

The term "phosphonium" denotes a positively charged tetravalent phosphorus atom where said phosphorus is substituted with four carbon based groups such as alkyl, alkenyl, aralkyl, or aryl. The term "trialkyl phosphonium" denotes a phosphonium group where said phosphorus is substituted with three alkyl groups. Examples of such trialkylphosphonium radicals include, for example, (CH$_3$)$_3$P$^+$—.

Said "alkyl", "alkenyl", "alkynyl", "alkanoyl", "alkylene", "alkenylene", "hydroxyalkyl", "haloalkyl", "haloalkylene", "haloalkenyl", "alkoxy", "alkenyloxy", "alkenyloxyalkyl", "alkoxyalkyl", "aryl", "perhaloaryl", "haloalkoxy", "haloalkoxyalkyl", "haloalkenyloxy", "haloalkenyloxyalkyl", "alkylenedioxy", "haloalkylenedioxy", "heterocyclyl", "heteroaryl", "hydroxyhaloalkyl", "alkylsulfonyl", "haloalkylsulfonyl", "alkylsulfonylalkyl", "haloalkylsulfonylalkyl", "alkylsulfinyl", "alkylsulfinylalkyl", "haloalkylsulfinylalkyl", "aralkyl", "heteroaralkyl", "perhaloaralkyl", "aralkylsulfonyl", "aralkylsulfonylalkyl", "aralkylsulfinyl", "aralkylsulfinylalkyl", "cycloalkyl", "cycloalkylalkanoyl", "cycloalkylalkyl", "cycloalkenyl", "halocycloalkyl", "halocycloalkenyl", "cycloalkylsulfinyl", "cycloalkylsulfinylalkyl", "cycloalkylsulfonyl", "cycloalkylsulfonylalkyl", "cycloalkoxy", "cycloalkoxyalkyl", "cycloalkylalkoxy", "cycloalkenyloxy", "cycloalkenyloxyalkyl", "cycloalkylenedioxy", "halocycloalkoxy", "halocycloalkoxyalkyl", "halocycloalkenyloxy", "halocycloalkenyloxyalkyl", "alkylthio", "haloalkylthio", "alkylsulfinyl", "amino", "oxy", "thio", "alkylamino", "arylamino", "aralkylamino", "arylsulfinyl", "arylsulfinylalkyl", "arylsulfonyl", "arylsulfonylalkyl", "heteroarylsulfinyl", "heteroarylsulfinylalkyl", "heteroarylsulfonyl", "heteroarylsulfonylalkyl", "heteroarylamino", "heteroarylaminoalkyl", "heteroaryloxy", "heteroaryloxylalkyl", "aryloxy", "aroyl", "aralkanoyl", "aralkoxy", "aryloxyalkyl", "haloaryloxyalkyl", "heteroaroyl", "heteroaralkanoyl", "heteroaralkoxy", "heteroaralkoxyalkyl", "arylthio", "arylthioalkyl", "alkoxyalkyl", "acyl", "amidino", "guanidino", "dialkylsulfonium", "trialkylphosphonium", and "dialkylsulfoniumalkyl" groups defined above may optionally have 1 or more non-hydrido substituents such as amidino, guanidino, dialkylsulfonium, trialkylphosphonium, dialkylsulfoniumalkyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, heteroaryloxy, heteroaryloxylalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, hatocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, aminoalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, alkoxycarbonyl, carboaralkoxy. carboxamido, carboxamidoalkyl, cyano, carbohaloalkoxy, phosphono, phosphonoalkyl, diaralkoxyphosphono, and diaralkoxyphosphonoalkyl.

The term "spacer" can include a covalent bond and a linear moiety having a backbone of 1 to 7 contiguous atoms. The spacer may have 1 to 7 atoms of a univalent or multi-valent chain. Univalent chains may be constituted by a radical selected from =C(H)—, =C(R$^{2a}$)—, —O—, —S—, —S(O)—, —S(O)$_2$—, —NH—, —N(R$^{2a}$)—, —N=, —CH(OH)—, =C(OH)—, —CH(OR$^{2a}$)—, =C(OR$^{2a}$)—, and —C(O)— wherein R$^{2a}$ is selected from alkyl, alkenyl, alkynyl, aryl, heteroaryl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, heteroaryloxyalkyl, heteroarylthioalkyl, and heteroarylalkenyl. Multi-valent chains may consist of a straight chain of 1 or 2 or 3 or 4 or 5 or 6 or 7 atoms or a straight chain of 1 or 2 or 3 or 4 or 5 or 6 atoms with a side chain. The chain may be constituted of one or more radicals selected from: lower alkylene, lower alkenyl, —O—, —O—CH$_2$—, —S—CH$_2$—, —CH$_2$CH$_2$—, ethenyl, —CH=CH(OH)—, —OCH$_2$O—, —O(CH$_2$)$_2$O—, —NHCH$_2$—, —OCH(R$^{2a}$)O—, —O(CH$_2$CHR$^{2a}$)O—, —OCF$_2$O—, —(CF$_2$)$_2$O—, —S—, —S(O)—, —S(O)$_2$—, —N(H)—, —N(H)O—, —N(R$^{2a}$)O—, —N(R$^{2a}$)—, —C(O)—, —C(O)NH—, —C(O)NR$^{2a}$—, —N=, —OCH$_2$—, —SCH$_2$—, S(O)CH$_2$—, —CH$_2$C(O)—, —CH(OH)—, =C(OH)—, —CH(OR$^{2a}$)—, =C(OR$^{2a}$)—, S(O)$_2$CH$_2$—, and —NR$^{2a}$CH$_2$— and many other radicals defined above or generally known or ascertained by one of skill-in-the art. Side chains may include substituents such as 1 or more non-hydrido substituents such as amidino, guanidino, dialkylsulfonium, trialkylphosphonium, dialkylsulfoniumalkyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylaminno, N-heteroarylamino-N-alkylamino, heteroarylaminoalkyl, heteroaryloxy, heteroaryloxylalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamindo, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, aminoalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, carboaralkoxy, carboxamido, carboxamidoalkyl, cyano, carbohaloalkoxy, phosphono, phosphonoalkyl, diaralkoxyphosphono, and diaralkoxyphosphonoalkyl.

Compounds of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, 1-isomers, the racemic mixtures thereof and other mixtures thereof, as falling within the scope of the invention. Pharmaceutically acceptable sales of such tautomeric, geometric or stereoisomeric forms are also included within the invention.

The terms "cis" and "trans" denote a form of geometric isomerism in which two carbon atoms connected by a double bond will each have a hydrogen atom on the same side of the double bond ("cis") or on opposite sides of the double bond ("trans").

Some of the compounds described contain alkenyl groups, and are meant to include both cis and trans or "E" and "Z" geometric forms.

Some of the compounds described contain one or more stereocenters and are meant to include R, S, and mixtures of R and S forms for each stereocenter present.

Some of the compounds described herein may contain one or more ketonic or aldehydic carbonyl groups or combinations thereof alone or as part of a heterocyclic ring system. Such carbonyl groups may exist in part or principally in the "keto" form and in part or principally as one or more "enol" forms of each aldehyde and ketone group present. Compounds of the present invention having aldehydic or ketonic carbonyl groups are meant to include both "keto" and "enol" tautomeric forms.

Some of the compounds described herein may contain one or more amide carbonyl groups or combinations thereof alone or as part of a heterocyclic ring system. Such carbonyl groups may exist in part or principally in the "keto" form and in part or principally as one or more "enol" forms of each amide group present. Compounds of the present invention having amidic carbonyl groups are meant to include both "keto" and "enol" tautomeric forms. Said amide carbonyl groups may be both oxo (C=O) and thiono (C=S) in type.

Some of the compounds described herein may contain one or more imine or enamine groups or combinations thereof. Such groups may exist in part or principally in the "imine" form and in part or principally as one or more "enamine" forms of each group present. Compounds of the present invention having said imine or enamine groups are meant to include both "imine" and "enamine" tautomeric forms.

The present invention also comprises a treatment and prophylaxis in anticoagulant therapy for the treatment and prevention of a variety of thrombotic conditions including coronary artery and cerebrovascular disease in a subject, comprising administering to the subject having such disorder a therapeutically-effective amount of a compound of Formula (I):

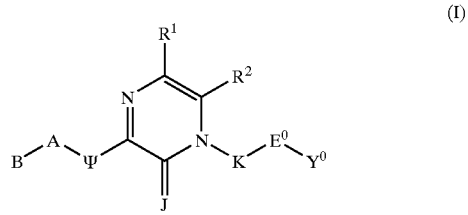

(I)

or a pharmaceutically-acceptable salt thereof.

As a further embodiment, compounds of the present invention of Formula (I) or a pharmaceutically-acceptable salt thereof as defined above, comprise a treatment and prophylaxis of coronary artery disease, cerebrovascular disease and other coagulation cascade related disorders in a subject, comprising administering to the subject having such disorder a therapeutically-effective amount of compounds of formula (I) of the present invention or a pharmaceutically-acceptable salt thereof.

Compounds of the present invention of Formula (I) or a pharmaceutically-acceptable salt thereof can also be used whenever inhibition of blood coagulation is required such as to prevent coagulation of stored whole blood and to prevent coagulation in other biological samples for testing or storage. Thus coagulation inhibitors of the present inhibition can be added to or contacted with stored whole blood and any medium containing or suspected of containing plasma coagulation factors and in which it is desired that blood coagulation be inhibited, e.g. when contacting the mammal's blood with material selected from the group consisting of vascular grafts, stents, orthopedic prothesis, cardiac prosthesis, and extracorporeal circulation systems.

Compounds of Formula (I) are capable of inhibiting activity of serine proteases related to the coagulation cascade, and thus could be used in the manufacture of a medicament, a method for the prophylactic or therapeutic treatment of diseases mediated by coagulation cascade serine proteases, such as inhibiting the formation of blood platelet aggregates, inhibiting the formation of fibrin, inhibiting thrombus formation, and inhibiting embolus formation in a mammal, in blood, in blood products, and in mammalian organs. The compounds also can be used for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels in a mammal. The compounds also can be used to study the mechanism of action of coagulation cascade serine proteases to enable the design of better inhibitors and development of better assay methods. The compounds of Formula (I) would be also useful in prevention of cerebral vascular accident (CVA) or stroke.

Also included in the family of compounds of Formula (I) are the pharmaceutically-acceptable salts thereof. The term "pharmaceutically-acceptable salt" embraces salts commonly used to form alkali metal salts and to form addition salts of free acids or free bases. The nature of the salt is not critical, provided that it is pharmaceutically acceptable. Suitable pharmaceutically-acceptable acid addition salts of compounds of Formula (I) may be prepared from inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of Formula (I) include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compound of Formula (I) by reacting, for example, the appropriate acid or base with the compound of Formula (I).

The present invention also comprises a pharmaceutical composition comprising a therapeutically-effective amount of a compound of Formulas (I) in association with at least one pharmaceutically-acceptable carrier, adjuvant or diluent. Pharmaceutical compositions of the present invention can comprise the active compounds of Formula (I) in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended.

The active compounds and composition may, for example, be administered orally, intravascularly, intraperitoneally, subcutaneously, intramuscularly, ocularly, or topically. For treating ocular build up of fibrin, the compounds may be administered intraocularly or topically as well as orally or parenterally.

The compounds can be administered in the form of a depot injection or implant preparation which may be formulated in such a manner as to permit a sustained release of the active ingredient. The active ingredient can be compressed into pellets or small cylinders and implanted subcutaneously or intramusculary as depot injections or implants. Implants may employ inert materials such as biodegradable polymers or synthetic silicones, for example, Silastic, silicone rubber or other silicon containing polymers.

The compounds can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxy-propyl-methacrylamide-phenol, polyhydroxyethyl-aspartamide-phenol, or ployethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphitpathic block copolymers of hydrogels.

For oral administration, the pharmaceutical composition may be in the form of, for example, tablets, capsules (each of which includes sustained release or timed release formulations), pills, powders, granules, elixers, tinctures, suspensions, liquids including syrups, and emulsions. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds which are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely.

The pharmaceutical compositions may contain active ingredients in the range of about 0.1 to 2000 mg, and preferably in the range of about 0.5 to 500 mg. A daily dose of about 0.01 to 100 mg/kg body weight, and preferably between about 0.5 and about 20 mg/kg body weight, may be appropriate. The daily dose can be administered in one to four doses per day.

The compounds may be formulated in topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

For therapeutic purposes, the active compounds of the present invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

In practicing the methods of the present invention for the treatment and prevention of a variety of thrombotic conditions including coronary artery and cerebrovascular disease, the compounds and pharmaceutical compositions of the present invention are administered alone or in combination with one another, or in combination with other therapeutics or in vivo diagnostic agents. The coagulation cascade inhibitors of the present invention can also be coadministered with suitable anti-platelet agreggation agents, including, but not limited to ticlopidine or clopidrogel, fibrinogen receptor antagonists (e.g. to treat or prevent unstable angina or to prevent reocculsion after angioplasty and restenosis), anticoagulants such as aspirin, warfarin or heparins, thrombolytic agents such as plasminogen activators or streptokinase to achieve synergistic effects in the treatment of various pathologies, lipid lowering agents including antihypercholesterolemics (e.g. HMG CoA reductase inhibitors such as mevastatin, lovastatin, simvastatin, pravastatin, and fluvastatin, HMG CoA synthatase inhibitors, etc.), anti-diabetic drugs, or other cardiovascular agents (loop diuretics, thiazide type diuretics, nitrates, aldosterone antagonistics (i.e., spironolactone and epoxymexlerenone), angiotensin converting enzyme (e.g. ACE) inhibitors, angiotensin II receptor antagonists, beta-blockers, antiarrythmics, anti-hypertension agents, and calcium channel blockers) to treat or prevent atheriosclerosis. For example, patients suffering from coronary artery disease, and patients subjected to angioplasty procedures, would benefit from coadministration of fibrinogen receptor antagonists and coagulation cascade inhibitors of the present invention. Also, coagulation cascade inhibitors could enhance the efficiency of tissue plasminogen activator-mediated thrombolytic reperfusion.

Typical doses of coagulation cascade inhibitors of the present invention with other suitable anti-platelet agents, anticoagulation agents, cardiovascular therapeutic agents, or thrombolytic agents may be the same as those doses of coagulation cascade inhibitors administered without coadministration of additional anti-platelet agents, anticoagulation agents, cardiovascular therapeutic agents, or thrombolytic agents, or may be substantially less than those doses of coagulation cascade inhibitors administered without coadministration of additional anti-platelet agents, anticoagulation agents, cardiovascular therapeutic agents, or thrombolytic agents, depending on a patient's therapeutic needs.

All mentioned references are incorporated by reference as if here written.

Although this invention has been described with respect to specific embodiments, the details of these embodiments are not to be construed as limitations. The following examples are provided to illustrate the present invention and are not intended to limit the scope thereof. Without further elaboration, it is believed that one skilled in the art can, using the preceding descriptions, utilize the present invention to its fullest extent. Therefore the following preferred specific embodiments are to be construed as merely illustrative and not limitative of the remainder of the disclosure in any way whatsoever. Compounds containing multiple variations of the structural modifications illustrated in the schemes or the following Examples are also contemplated. Those skilled in the art will readily understand that known variations of the conditions and processes of the following preparative procedures can be used to prepare these compounds.

One skilled in the art may use these generic methods to prepare the following specific examples, which have been or may be properly characterized by $^1$H NMR, mass spectrometry, elemental composition, and similar procedures. These compounds also may be formed in vivo. The following examples contain detailed descriptions of the methods of preparation of compounds of Formula (I). These detailed descriptions fall within the scope and are presented for illustrative purposes only and are not intended as a restriction on the scope of the invention. All parts are by weight and temperatures are Degrees centigrade unless otherwise indicated.

The following general synthetic sequences are useful in making the present invention. Abbreviations used in the schemes and tables include: "AA" represents amino acids, "AcCN" represents acetonitrile, "AcOH" represents acetic acid, "BINAP" represents 2,2'-bis(diphenylphosphino)-1,1'-binaphthyl, "BnOH" represents benzyl alcohol, "BnCHO" represents 2-phenylethanal, "BnSO$_2$Cl" represents benzylsulfonyl chloride, "Boc" represents tert-butyloxycarbonyl, "BOP" represents benzotriazol-1-yl-oxy-tris-(dimethylamino), "bu" represents butyl, "dba" represents dibenzylidene-acetone, "DCC" represents 1,3-dicyclohexylcarbodiimide, "DCM" represents dichloromethane or methylene chloride, "DIBAH" or "DIBAL" represents diisobutylaluminum hydride, "DMF" represents dimethylformamide, "DMSO" represents dimethylsulfoxide, "DPPA" represents diphenylphosphoryl azide", "EDC" represents 1-[3-(dimethylamino)propyl]-3-ethylcarbodiimide hydrochloride, "Ex. No." represents Example Number, "Fmoc" represents 9-fluorenylmethoxycarbonyl, "HOBt" represents hydroxybenzoltriazole", "LDA" represents lithium diisopropylamide, "MW" represents molecular weight, "NMM" represents N-methylmorpholine, "Ph" represents phenyl or aryl, "PHTH" represents a phthaloyl group, "pnZ" represents 4-nitrobenzyloxycarbonyl, "PTC" represents a phase transfer catalyst, "py" represents pyridine, "RNH$_2$" represents a primary organic amine, "p-TsOH" represents paratoluenesulfonic acid, "TBAF" represents tetrabutylammonium fluoride, "TBTU" represents 2-(1H-benzotriozole-1-yl)-1,1,3,3-tetramethyl uronium tetrafluoroborate, "TEA" represents triethylamine, "TFA" represents trifluoroacetic acid, "THF" represents tetrahydrofuran, "TMS" represents trimethylsilyl, "TMSCN" represents trimethylsilyl cyanide, and "Cbz" or "Z" represents benzyloxycarbonyl.

GENERAL SYNTHETIC PROCEDURES AND SPECIFIC EXAMPLES

The compounds of the present invention can be synthesized, for example, according to the following procedures and Schemes given below. The general synthetic approach to substituted pyrazinones is shown in Schemes 1 and 2 below. Treatment of benzyl glycine under Strecker reaction conditions followed by cyclocondensation with oxalyl chloride provides the pyrazinone heterocyclic core with an acetic acid ester at N-1. Heating a solution of the pyrazinone in ethyl acetate in the presence of excess amine results in the nucleophilic displacement of the C-3 chlorine atom by the amine. Stirring the substituted pyrazinone in the presence of lithium hydroxide results in the unmasking of the acid functional group. Alternatively, treatment of the pyrazinone with potassium hydroxide and catalytic palladium on carbon under an atmosphere of hydrogen results in the reductive dechlorination of the C-5 chlorine atom as well as the unmasking of the acid functional group. These acids are then coupled under standard peptide coupling conditions with various amines. These amines are typically multifunctional, and are introduced in a protected form. Removal of these protecting groups in any of several ways provides the compounds for screening. These synthetic schemes are exemplified in specific examples disclosed herein.

SCHEME 1
General Pyrazinone Synthesis

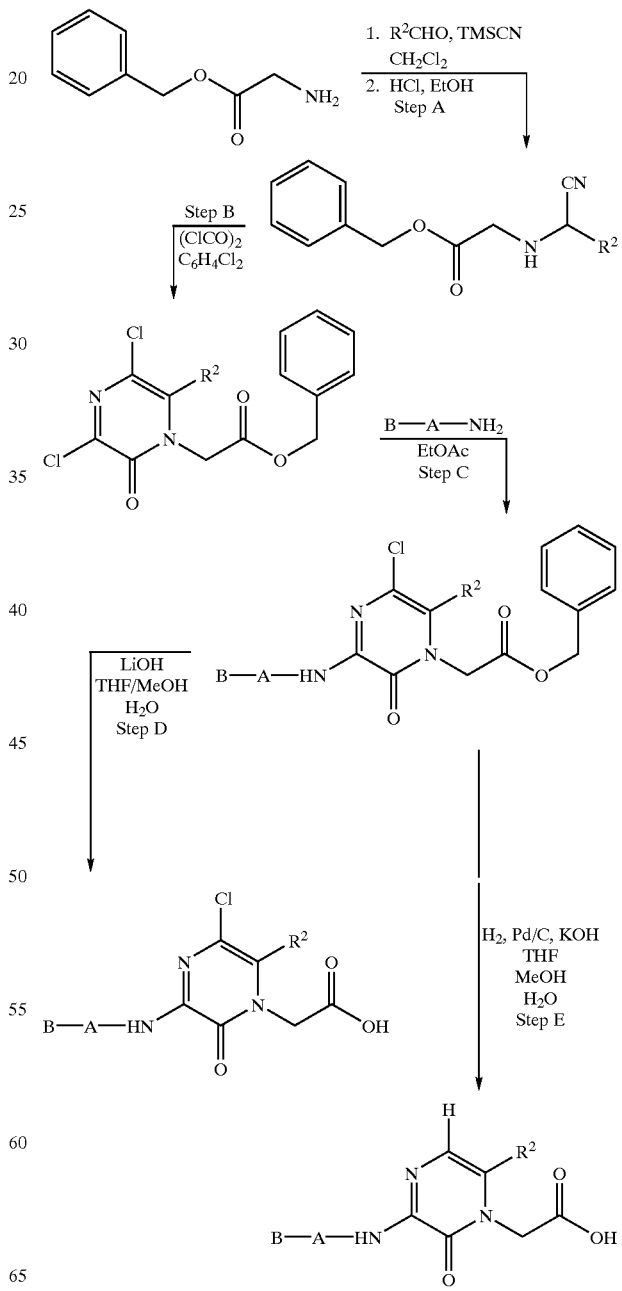

Scheme 2
General Pyrazinone Synthesis (Continued)

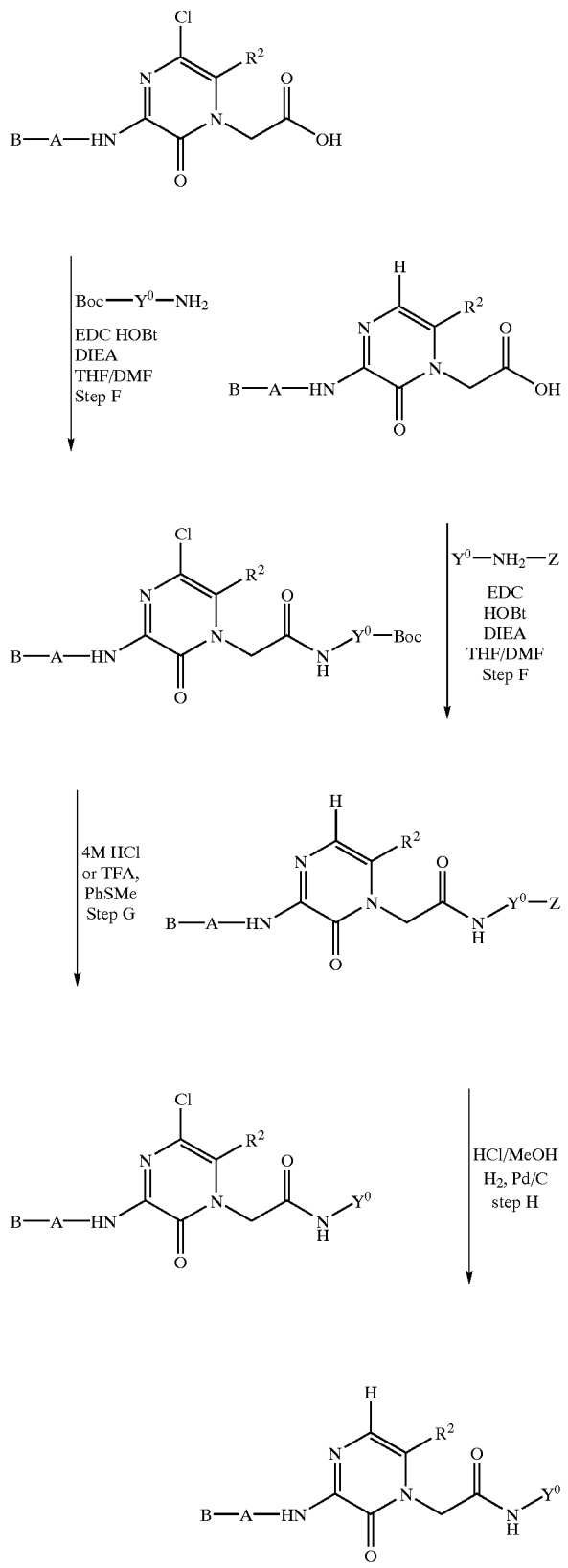

Example 1

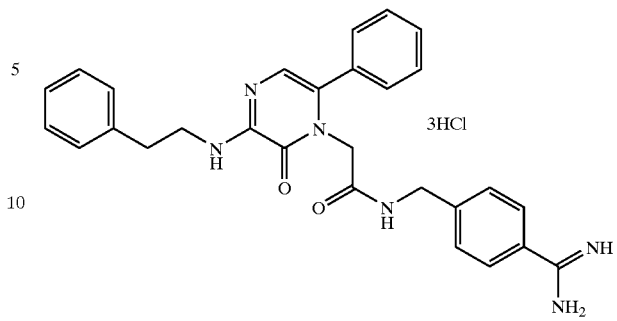

A solution of benzyl glycine hydrochloride (78.00 g, 386.8 mmol) in 1.2 L ethyl acetate was washed with brine and saturated $Na_2CO_3$ (1:1, 3×1 L). The organic solution was dried ($MgSO_4$), filtered, and concentrated. The resulting light yellow oil was placed on the high vacuum for approximately 15 minutes to remove residual solvent. The yellow oil was then diluted with 137.0 mL dichloromethane (2.82 M) and added benzaldehyde (39.30 mL, 386.6 mmol) slowly by syringe at room temperature. The reaction becomes slightly exothermic and turbid. The mixture was then added trimethylsilyl nitrile (51.60 mL, 386.9 mmol) drop wise via syringe over a 10 minute period, upon which a slight exotherm occurs and the reaction becomes clear and golden brown in color. The reaction was stirred for 4 hours at room temperature. The reaction mixture was then concentrated under reduced pressure. The resulting brown oil was diluted with ethyl acetate (500.0 mL), washed with brine (3×150 mL), dried ($MgSO_4$), and concentrated to leave a yellow oil. The oil was diluted ethyl acetate (80 mL) and added 9.9 M HCl (406.4 mmol) in ethanol (prepared by addition of 28.90 mL acetyl chloride to 41.0 mL cold ethanol). Upon which a white precipitate forms exothermically. The precipitate was collected by filtration, washed with ethyl ether, and dried which gave pure benzyl-N-(1-cyanobenzyl)glycine hydrochloride (EX-1A) in 35% yield: $^1$H NMR (300 MHz, DMSO) δ9.13–9.00 (br s, 1H) 7.68–7.60 (m, 2H), 7.55–7.32 (m, 8H) 5.70 (s, 1H), 5.19 (s, 2H), 3.81 (d, J=5.4 Hz, 1H); $^{13}$C NMR (75 MHz, DMSO) d 168.6, 136.1, 130.7, 129.78, 129.49, 129.17, 128.99, 128.92, 127.10, 67.3, 51.7, 47.1; HRMS (ES) calcd for $C_{17}H_{17}N_2O_2$ 281.1290, found 281.1311.

A suspension of benzyl-N-(1-cyanobenzyl)glycine hydrochloride (EX-1A) (42.90 g, 135.4 mmol) in 135.0 mL dry 1,2-dichlorobenzene (1.0 M) was added to oxalyl chloride (47.50 mL, 544.5 mmol) with stirring at room temperature. The resulting light brown suspension was heated to 100° C. for approximately 18 hours. Upon heating to mixture 100° C., the mixture became homogeneous and dark brown in color with gaseous HCl being evolved. The reaction was allowed to cool to room temperature and the volatiles were removed under reduced pressure. The remaining solution was passed through a silica gel column (1 L hexane flush, followed by 2 L 50% ethyl acetate/hexanes). Concentration of the solution gave a dark brown solid. The crude product was purified by MPLC (2 L hexane flush to 25% ethyl acetate/hexanes) to gave pure 1-Benzyloxycarbonylmethyl-3,5-dichloro-6-phenylpyrazinone (EX-1B) in 60% yield as a yellow solid: $^1$H NMR (300 MHz, $CDCl_3$) δ7.58–7.37 (m, 6H), 7.31–7.26 (m, 4H), 5.18 (s, 2H), 4.53 (s, 2H); $^{13}$C NMR (75 MHz, $CDCl_3$) δ166.4, 152.4, 146.0, 138.3, 134.9, 131.1, 130.0, 129.8, 129.1, 129.0, 128.8, 124.3, 68.2, 49.5; HRMS (ES) calcd for $C_{19}H_{15}Cl_2N_2O_3$ 389.0460, found 389.0475.

A solution of 1-benzyloxycarbonylmethyl-3,5-dichloro-6-phenylpyrazinone (EX-1B) (10.19 g, 26.19 mmol) in 103.0 mL ethyl acetate (0.255M) was added 9.90 mL phenethyl amine in one portion at room temperature. The resulting solution was heated to reflux for 18 hours. The solution was allowed to cool to room temperature which resulted in a thick precipitate forming. The reaction mixture was diluted with ethyl acetate (750.0 mL) and was washed with 0.5 N HCl (1×250 mL), saturated $NaHCO_3$ (1×250 mL) and brine (1×250 mL). The organic solution was dried ($MgSO_4$), filtered and concentrated to give the crude product. Recrystallization from ethyl acetate and hexanes afforded pure 3-(2-phenylethylamino)-5-chloro-6-phenyl-1-benzyloxycarbonylmethylpyrazinone (EX-1C) as light yellow crystals in 96% yield: $^1$H NMR (300 MHz, $CDCl_3$) δ7.46–7.28 (m, 15H), 6.39 (br s, 1H), 5.25 (s, 2H), 4.54 (s, 2H), 3.81–3.79 (m, 2H), 3.04–3.00 (m, 2H); $^{13}$C NMR (75 MHz, $CDCl_3$) δ167.2, 151.3, 149.2, 138.9, 135.2, 131.9, 130.7, 129.9, 129.3, 129.0, 128.95, 128.86, 128.83, 128.7, 126.9, 123.3, 67.7, 47.9, 42.5, 35.4; HRMS (EI) calcd for $C_{27}H_{25}ClN_3O_3$ 474.1584, found 474.1591.

A suspension of 3-(2-phenylethylamino)-5-chloro-6-phenyl-1-benzyloxycarbonylmethylpyrazinone (EX-1C) (1.26 g, 2.66 mmol) in 27.0 mL tetrahydrofuran and ethanol (1:1, 0.12 M) was added potassium hydroxide (463.1 mg, 8.25 mmol) in 4.0 mL water. The resulting solution was degassed (via high vacuum) three times. The solution was then added 421.1 mg 5% Pd/C in one portion. The resulting mixture was then stirred under an atmosphere of hydrogen overnight. The reaction mixture was filtered through a pad of Celite 545 then concentrated under reduced pressure to half of the original volume. The solution was then diluted with brine and acidified with 20% (w/w) $KHSO_4$ to a pH of 1. The resulting turbid solution was extracted with ethyl acetate (4×25 mL). The combined organic solutions were washed with brine (1×25 mL), dried ($MgSO_4$), filtered, concentrated to give pure 3-(2-phenethylamino)-6-phenyl-1-methylenecarboxypyrazinone (EX-1D) in 97 % yield as a white solid: $^1$H NMR (300 MHz, DMSO) δ7.49–7.48 (m, 3H), 7.40–7.23 (m, 7H), 6.77 (s, 1H), 4.52 (s, 1H), 4.40 (s, 2H), 3.64–3.57 (m, 2H), 2.93 (t, J=7.4Hz, 2H); $^{13}$C NMR (75 MHz, DMSO) δ169.6, 151.8, 150.6, 150.5, 143.2, 140.3, 133.2, 130.2, 129.6, 129.4, 129.3, 129.1, 128.8, 128;7, 127.3, 127.1, 126.8, 122.3, 63.6, 47.5, 42.5, 35.2; HRMS (EI) calcd for $C_{20}H_{20}N_3O_3$ 350.1505, found 350.1502.

p-Cyanobenzaldehyde (38.13 mmoles, 5 g) was stirred in 50 mL of tetrahydrofuran at 0° C. under nitrogen while lithium bis(trimethylsilyl)amide (83.89 mmoles, 84 mL of a 1.0M solution in tetrahydrofuran) was added dropwise over 10 min. After addition the mixture was allowed to warm to room temperature and stirred for 3 hr. Water (50 mL) was then added and stirring continued for 30 min. Then 2.5N sodium hydroxide (763 mmoles, 305 mL) and di-tert-butyl dicarbonate (83.89 mmoles, 18.309 g) were added along with tetrahydrofuran (100 mL) and the mixture was allowed to stir for 3 hr. The layers were then separated. The tetrahydrofuran layer was diluted with ethyl acetate and washed with brine. The water layer was extracted twice with ethyl acetate. The combined organic layers were dried over magnesium sulfate, filtered, the solvent removed in vacuo. The residue was chromatographed medium pressure liquid chromatography with 30% ethyl acetate/hexanes to give 4.03 g of desired 4-(t-butoxycarbonylamidino)benzaldehyde in 43% yield. $^1$H NMR (300 MHz, $CDCl_3$) δ10.03 (s, 1H), 7.97 (d, 2H) 7.89 (d, 2H), 1.53 (s, 9H).

The 4-(t-butoxycarbonylamidino)benzaldehyde (4.03 mmoles, 1.0 g) was stirred in tetrahydrofuran (20 mL) at room temperature under nitrogen while allylamine (6.05 mmoles, 453 uL) was added dropwise. After addition the mixture was allowed to stir for 6 hr. The mixture was diluted with methanol (20 mL) and cooled to 0° C. Then sodium borohydride (6.04 mmoles, 22.8 mg) added in small amounts and allowed to warm to room temperature. After 2 hr the reaction was quenched with water and extracted with dichloromethane. The organic layer was dried over magnesium sulfate, filtered, and the solvent removed in vacuo. The oily residue solidified on standing. The N-allyl-4-(t-butoxycarbonylamidino)benzylamine product was used without further purification. $^1$H NMR (300 MHz, $CDCl_3$) δ7.79 (d, 2H), 7.37 (d, 2H), 5.90–6.10 (m, 1H), 5.19 (dd, 2H), 3.81 (s, 2H), 3.24 (d, 2H), 1.53 (s, 9H)

The N-allyl-4-(t-butoxycarbonylamidino)benzylamine (3.97 mmoles, 1.15 g) and chlorotris(triphenylphosphine)-rhodium(I) (0.21 mmoles, 195 mg) was stirred in acetonitrile/water (84:16, 92 mL) under nitroen. The mixture was refluxed for 3 hr and allowed to cool to room temperature. Then the mixture was filtered through a pad of celite and the solvent removed in vacuo. The residue was dried on a high vacuum pump to yield an orange glassy product. 4-(t-Butoxycarbonylamidino)benzylamine product was verified by HPLC/MS and used without further purification.

A solution of 3-(2-phenethylamino)-6-phenyl-1-methylenecarboxypyrazinone (EX-1D) (521.1 mg, 1.491 mmol) in 15.0 mL tetrahydrofuran and dimethylformamide (1:1, 0.1 M) was added N,N-diisopropylethylamine (1.30 mL, 7.463 mmol), N-hydroxybenzotriazole (610.5 mg, 4.518 mmol), and 1-[3-(dimethylamino)propyl]-3-ethylcarbodiimide hydrochloride (855.3 mg, 4.461 mmol). The resulting mixture was allowed to stir for 30 minutes. The reaction mixture was then added 4-(t-butoxycarbonylamidino)benzylamine (763.1 mg, 3.061 mmol) prepared above in one portion. The resulting mixture was allowed to stir over night. The reaction mixture was diluted with ethyl acetate (50 mL) and washed with 5% citric acid (1×25 mL), saturated $NaHCO_3$ (1×25 mL), and brine (1×25 mL). The organic solution was dried ($MgSO_4$), filtered and concentrated. The crude reaction was purified by MPLC (75% ethyl acetate/hexanes) to give the product (EX-1E): $^1$H NMR (300 MHz, DMSO) δ9.06 (br s, 1H), 8.65 (t, J=5.6 Hz, 1H), 7.94 (d, J=8.1 Hz, 2H), 7.47–7.40 (m, 6H), 7.35–7.21 (m, 8H), 6.75 (s, 1H), 4.41 (s, 2H), 4.36–4.34 (m, 2H), 3.63–3.57 (m, 2H), 2.93 (t, J =7.3 Hz, 2H), 1.48 (s, 9H); $^{13}$C NMR (75 MHz, DMSO) δ167.3, 151.9, 150.7, 143.7, 140.4, 133.8, 133.4, 130.3, 129.4, 129.34, 129.29, 129.15, 129.10, 128.3, 127.6, 126.8. 122.2, 78.5, 48.7, 42.6,35.2, 28.7; HRMS (EI) calcd for $C_{33}H_{37}N_6O_4$ 581.2876, found 581.2871.

A flask of protected pyrazinone (260.7 mg, 0.449 mmol) was added 5.0 mL of 4 M HCl in dioxane. The resulting solution was allowed to stir overnight (approximately 18 hours). The solution was concentrated and the crude product was triturated from ethyl ether. The resulting white solid was collected by filtration, washed with ethyl ether and dried to give pure product. $^1$H NMR (300 MHz, DMSO) δ9.57 (br s, 2H), 9.38 (br s, 2H), 9.06 (br s, 1H), 7.88 (d, J=7.9 Hz, 2H), 7.55–7.52 (m, 3H), 7.42–7.24 (m, 9H), 6.66 (s, 1H), 4.43 (s, 2H), 4.38–4.37 (m, 2H), 3.83 (br s, 2H), 3.03–2.98 (m, 2H); HRMS (EI) calcd for $C_{28}H_{29}N_6O_2$ 481.2352, found 481.2348.

Example 2

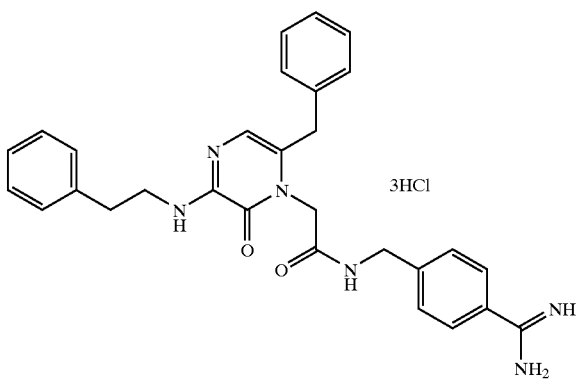

By following the method of Example 1 and substituting phenylacetaldehyde for benzaldehyde, the compound was prepared: $^1$H NMR (400 MHz, DMSO) δ9.43 (s, 2H), 9.25 (s, 2H), 8.84 (br s, 1 H), 7.79 (d, J=8.1 Hz, 2H), 7.40–7.16 (m, 12H), 6.61 (s, 1H), 4.47 (s, 2H), 4.27 (s, 2H), 3.86 (s, 2H), 3.75 (br s, 2H), 2.94–2.90 (m, 2H); HRMS (EI) calcd for $C_{29}H_{30}N_6O_2$ 494.2430, found 494.2438.

Example 3

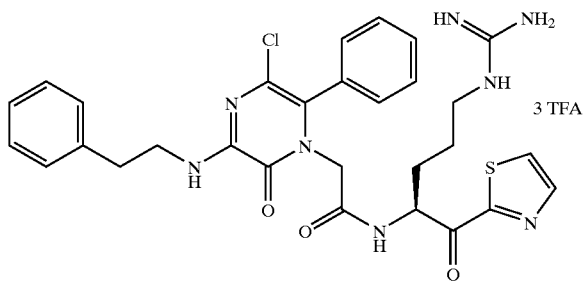

A suspension of 3-(2-phenylethylamino)-5-chlorophenyl-1-benzyloxycarbonylmethylpyrazinone (1.35 g, 2.85 mmol) in 28.0 mL tetrahydrofuran, methanol and water (3:3:1, 0.10 M) was added potassium hydroxide (0.50 g, 8.93 mmol). The mixture was then stirred 3 hours. The reaction mixture was concentrated under reduced pressure to half of the original volume. The solution was then diluted with brine and acidified with 20% (w/w) $KHSO_4$ to a pH of 1. The resulting turbid solution was extracted with ethyl acetate (4×25 mL). The combined organic solutions were washed with brine (1×25 mL), dried ($MgSO_4$), filtered, concentrated to give pure EX-3A (3-(2-phenethylamino)-5-chloro-6-phenyl-1-methylenecarboxypyrazinone) in 88% yield as a white solid; $^1$H NMR (300 MHz, DMSO) δ13.15 (br s, 1H), 7.84 (br s, 1H), 7.51–7.50 (br m, 3H), 7.33–7.24 (m, 7H), 4.24 (s, 2H), 3.58 (br s, 2H), 2.94 (br s, 2H); $^{13}$C NMR (75 MHz, DMSO) δ169.2, 151.0, 149.6, 140.1, 132.4, 131.1, 130.2, 129.6, 129.3, 129.1, 126.9, 125.4, 123.4, 48.1, 42.8, 34.8; HRMS (EI) calcd for $C_{20}H_{19}ClN_3O_3$ 384.1115, found 384.1118.

A solution of (S)-N-[[[4-amino-5-oxo-5-(thiazolyl)pentyl]amino]iminomethyl]-4-methoxy-2,3,6-trimethylbenzenesulfonamide dihydrochloride (1.664 g, 3.161 mmol) in 29.0 mL tetrahydrofuran and dimethylformamide (1:1, 0.10 M) was added N,N-diisopropylethylamine (5.00 mL, 28.70 mmol). The resulting mixture was allowed to stir for 10 minutes at room temperature. The solution was then added 3-(2-Phenylethylamino)-5-chloro-6-phenyl-1-methylenecarboxypyrazinone (1.104 g, 2.877 mmol), N-hydroxybenzotriazole (466.8 mg, 3.454 mmol), and 1-[3-(dimethylamino)propyl]-3-ethylcarbodiimide hydrochloride (673.1 mg, 3.511 mmol). After the addition was complete the solution was allowed to stir over night. The reaction mixture was diluted with ethyl acetate (50 mL). The organic solution was washed with 5% citric acid (1×25 mL), saturated $NaHCO_3$ (1×25 mL), and brine (1×25 mL). The organic solution was dried ($MgSO_4$), filtered and concentrated. The crude reaction mixture was purified by MPLC (75% ethyl acetate/hexanes) to give pure product EX-3B: $^1$H NMR (300 MHz, $CDCl_3$) δ8.04 (d, J=3.0 Hz, 1H), 7.75 (d, J=2.8 Hz, 1H), 7.57 (br s, 1H), 7.42–7.21 (m, 11H), 6.54 (s, 2H), 6.31 (s, 2H), 5.63 (br s, 1H), 4.60 (d, J=16.2 Hz, 1H), 4.21 (d, J=16.5 Hz, 1H), 3.84 (s, 3H), 3.77–3.66 (m, 2H), 3.17 (br s, 1H), 2.96 (d, J=7.2 Hz, 2H), 2.68 (s, 3H), 2.60 (s, 3H), 2.14 (s, 3H), 1.79–1.66 (m, 3H); HRMS (EI) calcd for $C_{39}H_{44}ClN_8O_6S_2$ 819.2514, found 819.2512.

A solution of material EX-3B (928.1 mg, 1.133 mmol) in 11.3 mL trifluoroacetic acid (0.1 M) was added to thioanisole (0.400 mL, 3.407 mmol) at room temperature with stirring. The resulting mixture was allowed to stir 6 hours. The reaction mixture was concentrated under reduced pressure. The crude product was purified by trituration from ethyl ether. A yellow powder was collected by filtration, washed with ethyl ether to give the pure product: $^1$H NMR (300 MHz, DMF) δ8.76 (d, J=7.2 Hz, 1H), 8.51–8.50 (m, 1H), 8.42–8.41 (m, 1H), 8.17 (br s, 1H), 7.92–7.45 (m, 10 H), 5.74 (br s, 1H), 4.67–4.65 (m, 2H), 3.89–3.87 (m, 2H), 3.52 (br s, 2H), 3.23–3.20 (m, 2H), 2.73 (s, 2H), 2.19 (br s, 1H), 1.88 (br s, 3H); HRMS (EI) calcd for $C_{29}H_{32}ClN_8O_3S$ 607.2007, found 607.2000.

Example 4

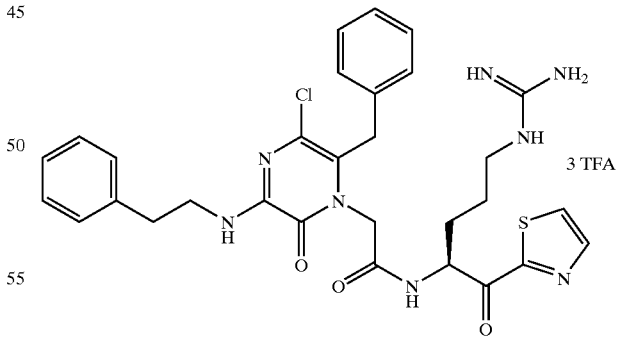

By following the method of Example 3 and substituting 3-(2-phenethylamino)-5-chloro-6-benzyl-1-methylenecarboxypyrazinone for 3-(2-phenethylamino)-5-chloro-6-phenyl-1-methylenecarboxypyrazinone, the title compound was prepared: HRMS (EI) calcd for $C_{30}H_{34}ClN_8O_3S$ 621.2163, found 621.2171.

Example 5

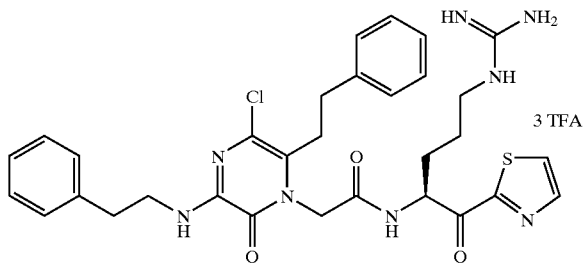

By following the method of Example 3 and substituting 3-(2-phenethylamino)-5-chloro-6-(2-phenylethyl)-1-methylenecarboxypyrazinone for 3-(2-phenethylamino)-5-chloro-6-phenyl-1-methylenecarboxypyrazinone, the title compound was prepared: HRMS (EI) calcd for $C_{31}H_{36}ClN_8O_3S$ 635.2320, found 635.2330.

Example 6

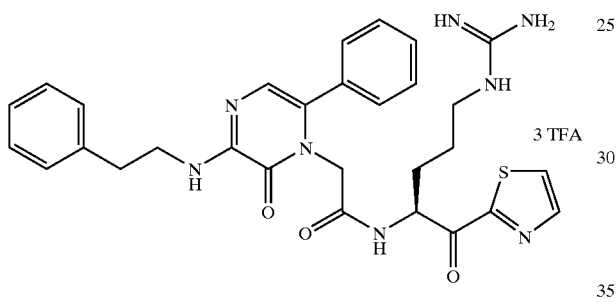

By following the method of Example 3 and substituting 3-(2-phenethylamino)-6-phenyl-1-methylenecarboxypyrazinone for 3-(2-phenethylamino)-5-chloro-6-phenyl-1-methylenecarboxypyrazinone, the title compound was prepared: HRMS (EI) calcd for $C_{29}H_{33}N_6O_3S$ 573.2396, found 573.2399.

Example 7

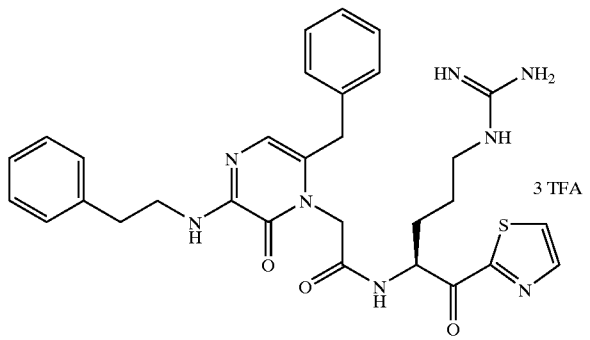

By following the method of Example 3 and substituting 3-(2-phenethylamino)-6-benzyl-1-methylenecarboxypyrazinone for 3-(2-phenethylamino)-5-chlorophenyl-1-methylenecarboxypyrazinone, the title compound was prepared: HRMS (EI) calcd for $C_{30}H_{35}N_8O_3S$ 587.2553, found 587.2564.

Example 8

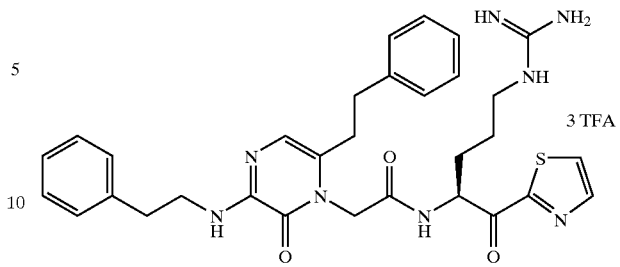

By following the method of Example 3 and substituting 3-(2-phenethylamino)-6-(2-phenylethyl)-1-methylenecarboxypyrazinone for 3-(2-phenethylamino)-5-chloro-6-phenyl-1-methylenecarboxypyrazinone, the title compound was prepared: HRMS (EI) calcd for $C_{31}H_{37}N_8O_3S$ 601.2709, found 601.2714.

Example 9

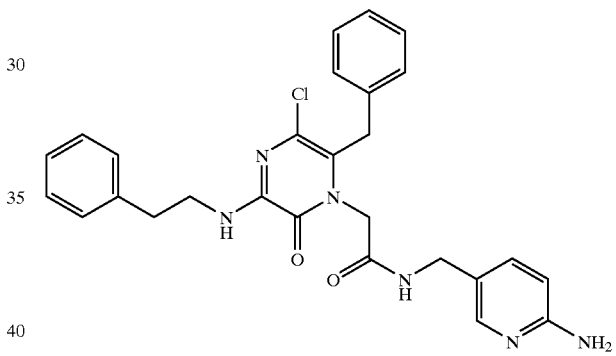

A solution of 2-amino-5-aminomethylpyridine in 1.60 mL tetrahydrofuran (0.13 M) was added to N,N-diisopropylethylamine (0.145 mL, 0.832 mmol). The resulting mixture was allowed to stir for 10 minutes at room temperature. The solution was then added to 3-(2-Phenylethylamino)-6-benzyl-5-chloro-1-methylenecarboxypyrazinone (81.6 mg, 0.2051 mmol), N-hydroxybenzotriazole (38.1 mg, 0.2819 mmol), and 1-[3-(dimethylamino)propyl]-3-ethylcarbodiimide hydrochloride (49.6 mg, 3.511 mmol). The reaction mixture was then allowed to stir over night. The reaction mixture was diluted with ethyl acetate (50 mL). The organic solution was washed with 5% citric acid (1×25 mL), saturated $NaHCO_3$ (1×25 mL), and brine (1×25 mL). The organic solution was dried ($MgSO_4$), filtered and concentrated. The crude reaction mixture was purified by MPLC (ethyl acetate) to give pure product: $^1$H NMR (300 MHz, DMSO) δ8.50 (br s, 1 H), 7.83 (s, 1H), 7.68 (br s, 1H), 7.34–7.19 (m, 13H), 6.46–6.43 (m, 1H), 5.90 (br s, 1H), 4.42 (s, 2H), 4.09 (br s, 2H), 3.98 (br s, 2H), 3.56 (br s, 3H), 2.94 (br s, 3H); HRMS (EI) calcd for $C_{27}H_{28}ClN_6O_2$ 503.1962, found 503.1968.

Example 10

3-(2-Phenylethylamino)-5-chloro-6-phenethyl-1-(2-amino-5-methylcarboxamidomethylpyridinyl)pyrazinone

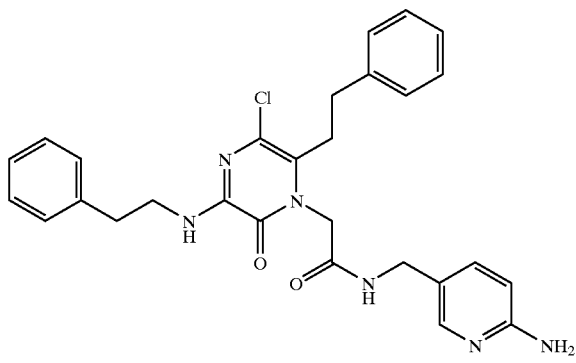

By following the method of Example 9 and substituting 3-(2-phenethylamino)-5-chloro-6-(2-phenylethyl)-1-methylenecarboxypyrazinone for 3-(2-phenethylamino)-5-chlorobenzyl-1-methylenecarboxypyrazinone, the title compound was prepared: HRMS (EI) calcd for $C_{28}H_{30}N_6O_2$ 517.2119, found 517.2127.

Example 11

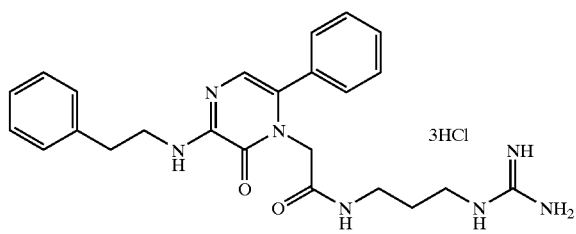

A solution of 3-(2-phenethylamino)-6-phenyl-1-methylenecarboxypyrazinone (217.6 mg, 0.6228 mmol) in 6.3 mL tetrahydrofuran and dimethylformamide (1:1, 0.1 M) was added N,N-diisopropylethylamine (1.00 mL, 5.741 mmol), N-hydroxybenzotriazole (171.1 mg, 1.266 mmol), and 1-[3-(dimethylamino)propyl]-3-ethylcarbodiimide hydrochloride (240.0 mg, 1.252 mmol). The resulting mixture was allowed to stir for 30 minutes. The reaction mixture was then added to the 3-(di-Boc-guanidino)propanamine (1.30 mg, 3.684 mmol) in one portion. The resulting mixture was allowed to stir over night. The reaction mixture was diluted with ethyl acetate (50 mL) and washed with 5% citric acid (1×25 mL), saturated NaHCO₃ (1×25 mL), and brine (1×25 mL). The organic solution was dried (MgSO₄), filtered and concentrated. The crude reaction was purified by MPLC (75% ethyl acetate/hexanes) to give the product EX-11A: $^1$H NMR (300 MHz, DMSO) δ11.42 (s, 1H), 8.46 (t, J=6.3 Hz, 1H), 7.92 (t, J=6.0 Hz, 1H), 7.46–7.41 (m, 5H), 7.37–7.23 (m, 5H), 6.86 (s, 1H), 6.24 (br s, 1H), 4.49 (s, 2H), 3.79–3.72 (m, 2H), 3.48–3.42 (m, 2H), 3.31–3.25 (m, 2H), 3.00 (t, J=7.1 Hz, 2 H), 1.53 (s, 9H), 1.40 (s, 9H); HRMS (EI) calcd for $C_{34}H_{45}N_7O_6$ 648.3510, found 648.3498.

A flask of protected guanidine EX-11A (260.7 mg, 0.449 mmol) was added to 5.0 mL of 4 M HCl in dioxane. The resulting solution was allowed to stir for 4 hours. The solution was concentrated and the crude product was triturated from ethyl ether. The resulting white solid was collected by filtration, washed with ethyl ether and dried to give pure product: $^1$H NMR (300 MHz, DMSO) δ9.65 (br s, 1H), 8.48 (t, J=5.1 Hz, 1H), 7.96 (t, J=5.4 Hz, 1H), 7.60–7.22 (m, 13H), 6.66 (s, 1H), 4.32 (s, 2H), 3.82 (br s, 2H), 3.13–3.09 (m, 2H), 3.03–2.98 (m, 2H), 1.59–1.54 (m, 2H); HRMS (EI) calcd for $C_{24}H_{29}N_7O_2$ 448.2461, found 448.2425.

Example 12

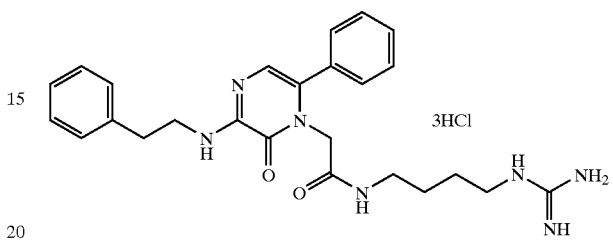

By following the method of Example 11 and using the appropriate butanamine, the title compound was prepared: HRMS (EI) calcd for $C_{25}H_{31}N_7O_2$ 462.2617, found 462.2575.

Example 13

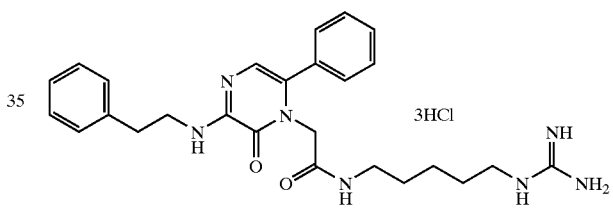

By following the method of Example 11 and using the appropriate pentanamine, the title compound was prepared: FRMS (EI) calcd for $C_{26}H_{33}N_7O_2$ 476.2774, found 476.2783.

Example 14

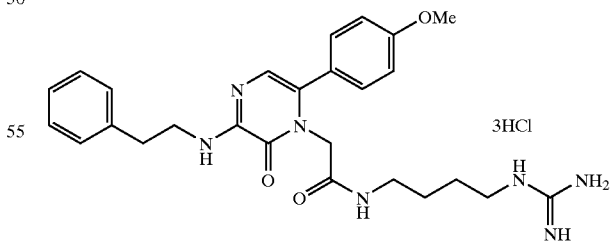

By following the method of Example 11 and using the appropriate butanamine with 3-(2-phenethylamino)-6-(4-methoxyphenyl)-1-methylenecarboxypyrazinone, title compound was prepared: HRMS (EI) calcd for $C_{26}H_{34}N_7O_3$ 492.2723, found 492.2693.

Example 15

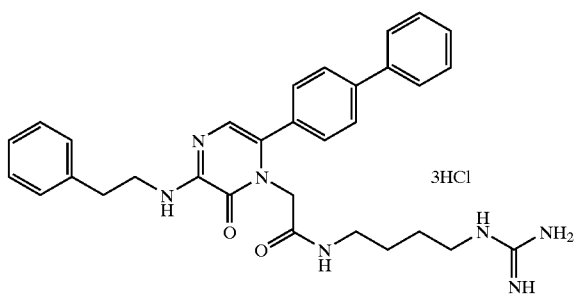

By following the method of Example 11 and using the appropriate butanamine with 3-(2-phenethylamino)-6-(4-biphenyl)-1-methylenecarboxypyrazinone, the title compound was prepared: HRMS (EI) calcd for $C_{31}H_{36}N_7O_2$ 538.2930, found 538.2918.

Example 16

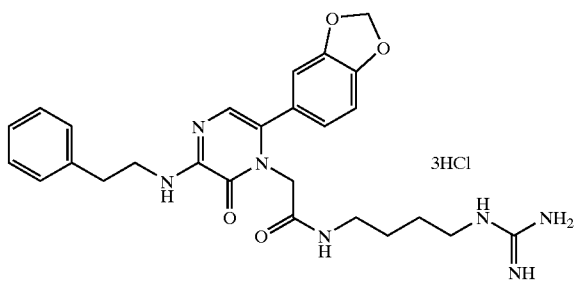

By following the method of Example 11 and using the appropriate butanamine with 3-(2-phenethylamino)-6-(3,4-methylenedioxyphenyl)-1-methylenecarboxypyrazinone, the title compound was prepared: HRMS (EI) calcd for $C_{26}H_{32}N_7O_4$ 506.2516, found 506.2506.

Example 17

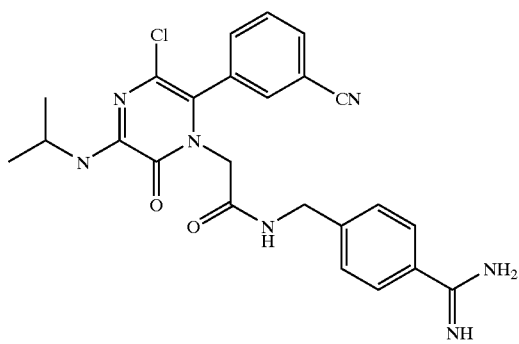

Using the procedures of Schemes 1 and 2 and Example 1, 2-{5-chloro-6-(3-bromophenyl)-3-[(methylethyl)amino]-2-oxohydropyrazinyl}acetic acid was prepared.

A solution of 2-{5-chloro-6-(3-bromophenyl)-3-[(methylethyl)amino]-2-oxohydropyrazinyl}acetic acid (7.4 g, 18.47 mmol) and copper (1) cyanide (1.75 g, 19.55 mmol) in 75.0 mL dimethylsulfoxide was heated at 150° C. for 20 hours. The flask was then cooled and the contents were poured into a solution of 500 mL water and 100 mL 1M HCl. The mixture was then extracted with ethyl acetate (2×1 L). The ethyl acetate layers were separated, combined, dried over magnesium sulfate, filtered, and stripped of solvent under reduced pressure. Purification by HPLC (25% ethyl acetate in hexanes) provided 2-{5-chloro-6-(3-cyanophenyl)-3-[(methylethyl)amino]-2-oxohydropyrazinyl}acetic acid (EX-17A) of adequate purity: $^1$H NMR (400 MHz, CDCl$_3$) δ7.8–7.4 (br, 4H), 4.4 (br, 2H), 2.2 (br, 1H), 1.3 (br d, 6H); MS (ES) calcd for $C_{15}H_{15}ClN_4O_3$ 346, found 347 (M+H).

2-{5-chloro-6-(3-cyanophenyl)-3-[(methylethyl)amino]-2-oxohydropyrazinyl}acetic acid (EX-17A) was converted to the product as described in Example 1. Mass spectral analysis gave an m/z+1 of 478.

Example 18

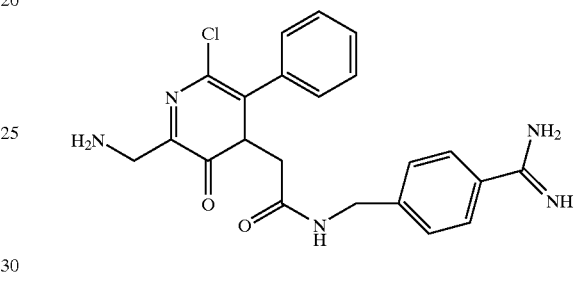

A solution of 3.90 g (10 mmol) of EX-1B in 50 mL of CH$_3$NO$_2$ was treated with 4.5 mL of 1,8-diazabicyclo[5.4.0] undec-7-ene (DBU). After 30 minutes, the reaction was poured into 300 mL of ethyl acetate and washed with 2×25 mL 1 N HCl (aq). The excess organic solvent was removed under reduced pressure. The resulting oil was treated with 25 mL H$_2$O and 25 mL CH$_3$OH. The solution was treated with 2.8 g of KOH. After 60 minutes, the reaction was diluted with 300 mL of acetonitrile. The resulting solid was washed with 100 mL of acetonitrile. The solid was dissolved in 50 mL 1N HCl (aq) and extracted with 2×100 mL CH$_2$Cl$_2$. The organic layer was dried with MgSO$_4$, and the excess solvent removed under reduced pressure. The resulting solid was washed with diethyl ether and dried in ambient conditions to give 2.1 g (6.4 mmol; 64% yield) of desired product (EX-18A). LC/MS showed a single peak at 254 nm and a M+Na at 346. $^1$H-NMR (dmso-d$_6$): 4.4 ppm (2H, s); 5.6 ppm (2H, s); 7.3–7.5 ppm (5H, m).

The product was obtained using standard coupling conditions and deprotection methods under reducing conditions of Example 1 to give the desired product after purification by HPLC. LC/MS showed a single peak at 254 nm and a M+H at 425. $^1$H-NMR (dmso-d$_6$): 4.2 ppm (2H, s); 4.4 ppm (2H, m); 4.6 ppm (2H, m); 7.4 ppm (5H, m) 7.6–7.8 ppm (4H, m); 8.4 ppm (2H, bs); 8.7 (1H,m); 9.1 ppm (2H, bs); 9.3 ppm (2H,bs).

Using the procedures of Scheme 1, Scheme 2, and Example 1 through Example 18 with suitable reagents, starting materials, intermediates, and additional pyrazinones of the present invention were prepared by one skilled in the art using similar methods and these pryazinones summarized in Table 1.

TABLE 1

Additional Substituted Pyrazinones Prepared by Procedures of Scheme 1, Scheme 2, and Examples 1 through 18

General Structure

| Ex. No. | R² | B-A | Y⁰ | MW (m/z + 1) |
|---|---|---|---|---|
| 19 | phenyl | 2-(4-pyridyl)ethyl | 4-amidinobenzyl | 516.3 |
| 20 | benzyl | 2-phenylethyl | 4-amidinobenzyl | 528.9 |
| 21 | biphenyl | 2-(3-pyridyl)ethyl | 4-amidinobenzyl | 591.9 |
| 22 | biphenyl | 2-(4-chlorophenyl)-ethyl | 4-amidinobenzyl | 625.5 |
| 23 | 3-chlorophenyl | benzyl | 4-amidinobenzyl | 535.3 |
| 24 | biphenyl | 2-phenylethyl | 4-amidinobenzyl | 591.5 |

Example 25

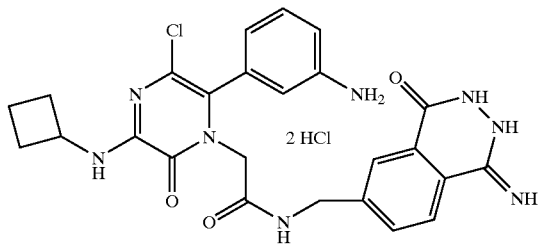

To a solution of 2-iodo-5-methyl benzoic acid (10.0 g, 0.038 mol) in toluene (200 mL) was added trimethylorthoacetate (25 mL) at room temperature. The reaction mixture was refluxed for 12 hours. The reaction mixture was cooled to room temperature and diluted with saturated sodium bicarbonate and ethyl acetate. The layers were separated and the organic layer washed with brine. The organic layer was dried (MgSO$_4$) and solvent removed to give 10.35 g of methyl 2-iodo-5-methylbenzoate (EX-25A) as a yellow oil with an m/z+1=277.

A degasssed mixture of ester EX-25A (10.35 g, 0.037 mol)), Pd(dba)$_3$ (0.017 g, 0.018 mmol)), dppf (0.025 g, 0.045 mmol)) and Zn(CN)$_2$ (2.6 g, 0.02 mol) in DMF (100 mL) was heated to 120° C. for 2 hours. The reaction mixture was poured into water and ethyl acetate. The organic layer was washed with water (2x) and brine (1x). The organic layer was collected, dried (MgSO$_4$) and the solvent removed in vacuo to give 5.28 g methyl 2-cyano-5-methylbenzoate (EX-25B) as a brownish oil with m/z+1=176.

To a solution of EX-25B (5.28 g, 0.03 mol) in CCl$_4$ (100 mL) was added NBS (5.37 g, 0.03 mol) and benzoyl peroxide (0.36 g, 0.0015 mol) at room temperature. The reaction mixture was heated to reflux for 15 hours. The reaction was cooled and the precipitate filtered away. The organic filtrate was diluted with ether and washed with saturated sodium bicarbonate. The organic layer was dried (MgSO$_4$) and the solvent removed in vacuo to give an oil, which after chromatography (silica, hexanes to 30% ether/hexanes) gave 1.57 g methyl 2-cyano-5-bromomethylbenzoate (EX-25C) as a tan solid with m/z+1=255.

To a solution of di-tert-butyl iminodicarboxylate (1.48 g, 7.5 mmol) in THF at 0° C. was added NaH (0.31 g, 7.8 mmol). After stirring at room temperature for 30 minutes, EX-25C (1.57 g, 6.0 mmol) was added as a solution in THF via canula. The reaction was complete after 2.5 hours at room temperature. The reaction was quenched by addition of water and ether. The layers were separated and the organic layer washed with brine (2x), dried (MgSO$_4$) and the solvent removed in vacuo to give 2.36 g methyl 2-cyano-5-(N,N-bis-Bocaminomethylbenzoate (EX-25D) as a yellowish solid with m/z+1=391.

To a solution of EX-25D (0.20 g, 0.5 mmol) in anhydrous methanol (10 mL) was added anhydrous hydrazine (1 mL, 32 mmol)) at room temperature. The reaction was heated to 70° C. overnight. The solvent was removed in vacuo to give a solid, which was suspended in ether and filtered to give 0.11 g of the product EX-25E as a white solid with an m/z+1=291.

To a solution of EX-25E (0.22 g, 0.78 mmol) in dichloromethane (5 mL) at room temperature was added trifluoroacetic acid (5 mL). After 30 min, the solvent was removed in vacuo to give a clear residue, which upon drying on high vacuum became a white solid EX-25F (0.39 g) with m/z+1=191.

To a solution of 2-{5-chloro-6-(3-aminophenyl)-3-cyclobutylamino-2-oxohydropyrazinyl}acetic acid (0.93 g, 2.6 mmol) in DMF (20 mL) was added EDC (0.64 g, 3.3 mmol) and HOBt (0.44 g, 3.2 mmol) at room temperature. After 30 min, the amine EX-25F in a solution of DMF and triethylamine (1.76 mL, 0.01 mol) was added to the acid. The reaction mixture was stirred for 1 hour and then poured into NaHCO$_3$ $_{(aq)}$ and ethyl acetate. The layers were separated and the aqueous layer extracted with ethyl acetate (2x) The organic layer was washed with brine (1x), dried (MgSO$_4$), and the solvent removed in vacuo to give a brown oil, which after chromatography (silica, dicholoromethane to 10% methanol/dichloromethane) gave the product EX-25G (0.29 g) with m/z+1=521.

To a suspension of EX-25G (0.29 g, 5.6 mmol) in ether (5 mL) was added 25 mL of 2.0 M HCl in ether. The reaction was stirred for 30 min to give a fine precipitate which was filtered and dried to give the product (0.37 g) with m/z+1= 521. Analysis C$_{25}$H$_{25}$Cl$_2$N$_8$O$_3$+1.8 HCl+2.15 H$_2$O gave C, 47.78%; H, 5.22%; N, 16.29%; O, 12.59%; Cl, 15.43%.

Example 26

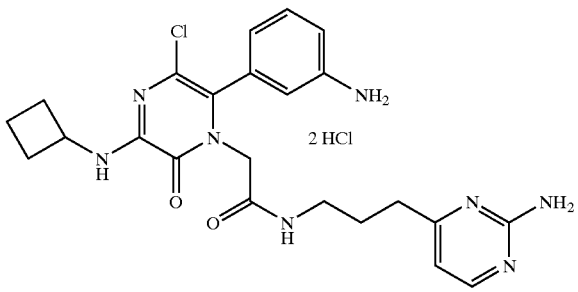

To a solution of 2-Amino-4-methylpyrimidine (1.0 g, 9.0 mmol) in THF (100 mL) at 0° C. was added TMEDA (4.15 mL, 27.0 mmol) and n-butyl lithium (17.2 mL, 27.0 mmol).

After stirring at 0° C. for 30 min, (2-bromoethoxy)-tert-butyldimethylsilane (2.16 mL, 10 mmol) was added in a solution of THF (20 mL) dropwise via canula. The reaction was allowed to warm to room temperature overnight. The reaction was diluted with water and ether. The aqueous layer was extracted (2×) with ether. The organic layer was washed with brine, dried (MgSO$_4$), and solvent removed in vacuo to give a brown oil, which after chromatography (silica, dichloromethane to 10% methanol/dicholoromethane) gave EX-26A (1.26 g) with m/z+1=268.

To a solution of EX-26A (4.36 g, 16.0 mmol) in dichloromethane (100 mL) was added triethylamine (3.4 mL, 24 mmol), di-tert-butyl dicarbonate (4.53 g, 24 mmol) and DMAP (0.2 g, 0.16 mmol). After stirring at room temperature for 24 hours the reaction was poured into aqueous sodium bicarbonate and ether. The layers were separated and the aqueous layer extracted (2×) with ether. The organic layer was washed with brine, and the solvent removed in vacuo to give a red oil (4.4 g). The oil was purified by chromatography (silica, 60% ethyl acetate/hexanes) to give a yellow oil EX-26B (2.77 g) with m/z+1=468.

To a solution of EX-26B (2.77 g, 6.0 mmol) in THF (100 mL) was added TBAF (7.1 mL, 1 M in THF) dropwise. After 4 hours at room temperature the reaction was complete. The reaction mixture was poured into ethyl acetate and brine. The aqueous layer was extracted 2× with ethyl acetate. The organic layer was dried (MgSO$_4$) and the solvent removed to give a yellow oil, which after chromatography (silica, 70% ethyl acetate/hexanes to 100% ethyl acetate) gave 1.51 g of the alcohol 2-(bis-Boc-amino)-4-(3-hydroxypropyl) pyrimidine (EX-26C) as a yellow oil with an m/z+1=354.

To a solution of EX-26C (1.38 g, 4.0 mmol) in toluene (20 mL) was added triethylamine (0.54 mL, 4.0 mmol) and methanesulfonyl chloride (0.30 mL, 4.0 mmol). After 10 min, no starting material was observed by TLC. The reaction mixture was poured into dichloromethane and water. The layers were separated and the organic layer was washed with brine and dried (Na$_2$SO$_4$). The solvent was removed to give a yellow oil EX-26D which was used without further purification. To the crude mesylate EX-26D (1.73 g, 4.0 mmol) in DMF (10 mL) was added NaN$_3$ (2.6 g, 40 mmol) and water (1 mL). The reaction mixture was stirred at room temperature for 18 hours. The reaction was diluted with ether and water. The layers were separated and the organic layer washed with brine and dried (Na$_2$SO$_4$). The solvent was removed to give an oil, which after chromatography (silica, 60% ethyl acetate/hexanes) gave the azide EX-26E (0.91 g) with a m/z+1=379.

To a solution of 2-(bis-Boc-amino)-4-(3-azidopropyl) pyrimidine (EX-26E) (0.39 g, 1.0 mmol) in ethanol at room temperature was added 10% Pd/C and a hydrogen balloon. After stirring at room temperature for 3 hours the reaction was complete by TLC. The reaction mixture was filtered through a pad of celite and washed with ethanol. The solvent was removed in vacuo to give an oil (0.35 g) which was a mixture of Boc derivatives EX-26F. To a solution of EX-26F (0.32 g) in dichloromethane (7 mL) was added trifluoroacetic acid (3 mL) dropwise. After 30 min, the solvent was removed in vacuo to give 0.34 g of the free amine 2-amino-4-(3-aminopropyl)pyrimidine (EX-26G) as an oil with an m/z+1=353.

To a solution of anilino-acid 2-{5-chloro-6-(3-aminophenyl)-3-cyclobutylamino-2-oxohydropyrazinyl}acetic acid (1.46 g, 4.2 mmol) in DMF (30 mL) was added HOBt (0.91 g, 6.7 mmol) and EDAC (1.29 g, 6.7 mmol) at room temperature. After stirring for 30 min, EX-26G (1.59 g, 4.2 mmol) in DMF (8 mL) and triethylamine (3.5 mL, 25.2 mmol) was added. After 30 min, the reaction was diluted with aqueous sodium bicarbonate and ethyl acetate. The layers were separated and aqueous layer extracted (2×) with ethyl acetate. The organic layer was washed with brine and dried (MgSO$_4$). The solvent was removed in vacuo to give an oil, which after chromatography (dichloromethane to 15% methanol dichloromethane) gave the product EX-26H (1.20 g) as a yellow foam with an m/z+1=483.

To a solution of EX-26H (0.32 g, 0.67 mmol) in 5 mL of ether was added 20 mL of 3.0 M HCl in ether at room temperature. The reaction mixture was stirred at room temperature for 20 minutes to give a precipitate which was filtered to give a yellow solid (0.34 g) of the di-hydrochloride salt. The solid was purified by RP-HPLC to give (0.22 g) with an m/z+1=483.

Example 27

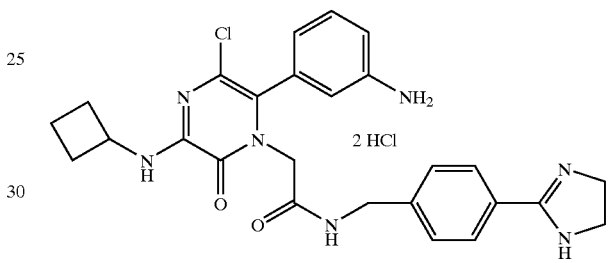

To a solution of the mixture N-Boc and N,N-bis-Boc 4-(N'-Z-amidino)benzylamines (3.0 g, 6.2 mmol) in 50 mL of EtOH and 20 mL THF was added 300 mg of 5% Pd(C). The solution was hydrogenated at 40 psi H$_2$ in a Parr shaker for 18 hrs. The catalyst was filtered off, and the filtrate concentrated in-vacuo to afford the mixture EX-27A (2.1 g, 6.0 mmol) of N-Boc and N,N-bis-Boc 4-amidinobenzylamines as a brownish oil with M+H of 250 (monoBoc) and M+H of 350 (diBoc).

A solution of EX-27A (2.1 g, 6.0 mmol) in MeOH was treated with ethylenediamine (1.13 g, 18.9 mmol). The mixture was heated to reflux for 18 hrs, cooled to room temperature and concentrated in vacuo. 50 mL of H$_2$O was added and extracted 3× with CH$_2$Cl$_2$. The organic extracts were dried over MgSO$_4$, filtered and condensed in vacuo to afford the mixture EX-27B (2.2 g, 5.9 mmol) as a tan solid with M+H of 276 (monoBoc) and M+H of 376 (diBoc).

A solution of the mixture EX-27B (2.2 g, 5.9 mmol) in 20 mL methylene chloride and 5 mL pyridine was treated with benzyl chloroformate (1.3 g, 7.7 mmol). The mixture was stirred for 1.5 hrs and then was added 100 mL methylene chloride and 100 mL 0.5 N HCl. The layers were seperated, and the aqueous extracted 2× with methylene chloride The organics were combined, washed 1× with brine, dried over MgSO$_4$, filtered and condensed in vacuo. Purification by column chromatography (silica gel 200–400 mesh) using 50% ethyl acetate as elutant afforded the mixture EX-27C (1.1 g, 2.2 mmol) as a tan oil with M+H 410 (monoBoc) and M+H 510 (diBoc).

A solution of the mixture EX-27C (800 mg, 1.6 mmol) in 10 mL of methylene chloride was treated with 5 mL of 4N HCl in dioxane. The mixture was stirred for 1.5 hrs. and then diethyl ether was added to precipitate the product. The precipitate was filtered off and washed extensively with diethyl ether to afford the HCl salt EX-27D (520 mg, 1.7 mmol) as a tan soild with an M+H of 310.

A solution of 2-{5-chloro-6-(3-nitrophenyl)-3-cyclobutylamino-2-oxohydropyrazinyl}acetic acid (329 mg, 0.86 mmol) in 10 mL of methylene chloride was treated with HOBt (127 mg, 0.94 mmol) for 20 min. Then was added EDC (180 mg, 0.94 mmol), DIEA (335 mg, 2.6 mmol), and EX-27D (300 mg, 0.86 mmol), and the reaction was allowed to stir for 1 hr. Water was then added, and the reaction mixture extracted 3× with methylene chloride. The organics were then washed 1× with brine, dried over MgSO$_4$, filtered and condensed in vacuo. Purification by column chromatography (silica gel 200–400 mesh) eluting with 90% ethyl acetate/hexane and then 100% ethyl acetate afforded EX-27E (325 mg, 0.48 mmol) as a yellow solid which gave an M+H of 670.

A solution of EX-27E (325 mg, 0.48 mmol) in 10 mL of MeOH was treated with 0.7 mL of 3N HCl in MeOH and 5% Pd(C) (50 mg). The mixture was hydrogenated at 45 psi on a Parr shaker apparatus for 2 hrs. The catalyst was then filtered off and washed extensively with MeOH. The filtrate was concentrated in vacuo. The residue was dissolved in EtOH and triturated with diethyl ether. The solid formed was filtered and extensively washed with diethyl ether to afford the HCl salt product (220 mg, 0.43 mmol) as an off-white solid which gave M+H's of 506 (100%) and 508 (60%).

Example 28

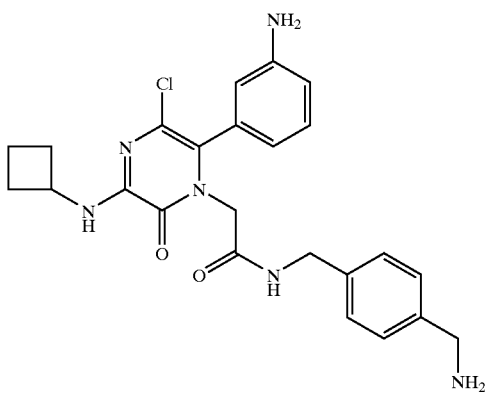

Using the procedures of Scheme 1, Scheme 2, and Example 1 through Example 18 with suitable reagents, starting materials, 2-{5-chloro-6-(3-nitrophenyl)-3-cyclobutylamino-2-oxohydropyrazinyl}acetic acid and 4-(N-Boc-aminomethyl)benzylamine prepared according to the literature reference (Callahan, J. F., Ashton-Shue, D., et al., *J. Med. Chem.* 1989, 32, 391–396), the product was obtained and gave an m/z(M+H)$^+$ of 467.

Example 29

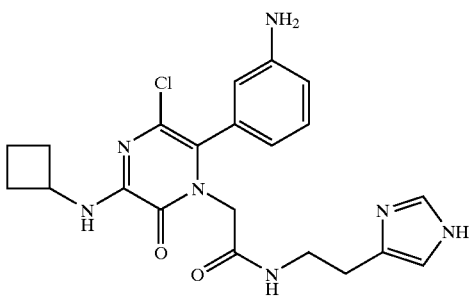

Using the procedures of Scheme 1, Scheme 2, and Example 1 through Example 18 with suitable reagents, starting materials, 2-{5-chloro-6-(3-nitrophenyl)-3-cyclobutylamino-2-oxohydropyrazinyl}acetic acid, and 2-(4-imidazoyl)ethanamine commercially available form Fluka, the product was obtained and gave an m/z(M+H)$^+$ of 442.

Example 30

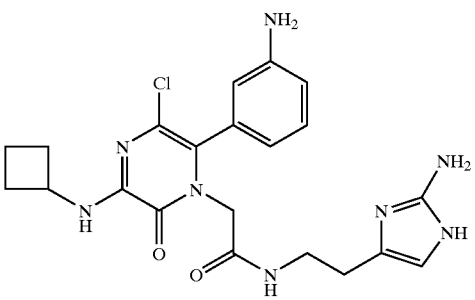

Using the procedures of Scheme 1, Scheme 2, and Example 1 through Example 18 with suitable reagents, starting materials, 2-{5-chloro-6-(3-nitrophenyl)-3-cyclobutylamino-2-oxohydropyrazinyl}acetic acid and 2-(4-(2-aminoimidazoyl))ethanamine prepared according to the literature reference (Nagai, W. Kirk, K. L., Cohen, L. A., *J. Org. Chem.* 1973, 33, 1971–1974), the product was obtained and gave an m/z(M+H)$^+$ of 457.

Example 31

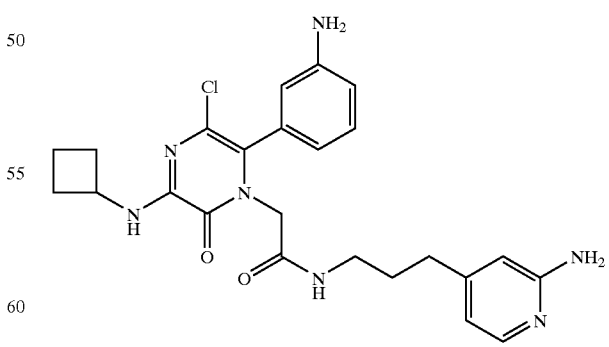

2-Amino-4-picoline (5.00 g, 46.2 mmol) and 11.20 g of di-tert-butyl dicarbonate (50.8 mmol) were stirred in 100 mL of tert-butanol at 30° C. overnight. The reaction mixture was concentrated in vacuo and chromatographed on silica gel with 25% EtOAc/Hexane to give 8.20 g (85% yield) of the product EX-31A.

To a solution of 3.00 g of N-Boc-2-amino-4-picoline (EX-31A, 14.4 mmol) in 150 mL of THF at −78° C. was added 14.4 mL of 2.5 M n-BuLi/Hexanes solution. The reaction mixture was allowed to warm up to room temperature and stirred for 40 min. The reaction mixture was cooled down to −78° C. and 1-bromo-2-chloroethane was added. The mixture was stirred at −78° C. for overnight. The reaction mixture was quenched with HOAc at −78° C. and concentrated in vacuo. The crude was dissolved in EtOAc and washed with brine. The EtOAc layer was dried over $MgSO_4$ and concentrated in vacuo. The crude product was purified by silica gel chromatography with 20% EtOAc/Hexane to give 2.00 g (50%) of the product EX-31B.

To a solution of 2.00 g of the chloride EX-31B (6.91 mmol) and 0.50 g of sodium azide (7.69 mmol) in 80 mL of DMF was added 10 mL of water and 0.52 g of sodium iodide. The reaction mixture was stirred at 55° C. overnight. The mixture was washed with brine and extracted with EtOAc. The EtOAc layer was dried over $MgSO_4$ and concentrated in vacuo. The crude product was chromatographed on silica gel with 20% EtOAc/Hexane to give 1.80 g (94%) of the product EX-31C.

To a solution of 1.74 g of the azide EX-31C (6.27 mmol) in 30 mL of THF was added 1.64 g of triphenylphosphine (6.27 mmol) and 1 mL of water. The reaction mixture was stirred at room temperature overnight. The reaction mixture was concentrated in vacuo and chromatographed on silica gel with 10% $CH_3OH/CH_2Cl_2$ to give 1.26 g (80%) of the amine product EX-31D.

To a solution of 0.77 g of 2-{5-chloro-6-(3-aminophenyl)-3-cyclobutylamino-2-oxohydropyrazinyl}acetic acid (2.21 mmol) in 50 mL of DMF was added 0.47 g of EDC.HCl and 0.33 g of HOBt. The mixture was stirred at room temperature for 30 min. After the addition of 0.61 g of the amine EX-31D (2.43 mmol) and 0.50 g of triethylamine the reaction mixture was stirred at room temperature overnight. The mixture was washed with water and extracted with EtOAc. The EtOAc layer was washed with brine and concentrated in vacuo. The crude product was chromatographed on silica gel with 3% $CH_3OH/CH_2Cl_2$ to afford 1.10 g (86%) of the Boc protected product EX-31E.

The Boc protected product EX-31E (0.50 g) was treated with 2.0 M of HCl/ether solution for overnight. The mixture was concentrated in vacuo and chromatographed by DeltaP-rep with 10% $CH_3CN/H_2O$ to give 0.32 g of the product (78%) as a TFA salt. The TFA salt was converted to the HCl salt by ion exchange chromatography with BioRad AG 2-X8 resin and 10% $CH_3CN/H_2O$ and analyzed by mass sprectrometry to give an (M+H) of 482.16.

Example 32

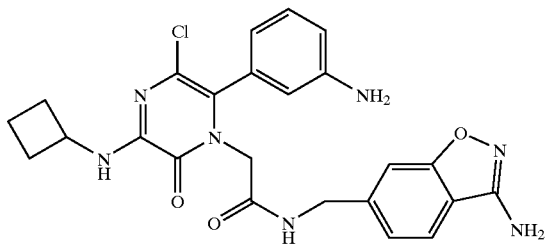

A mixture of 26.5 mmol of 4-bromo-3-fluorotoluene, 29 mmol of copper cyanide and 25 ml of dry DMF is refluxed for 12 hr, then 150 ml water was added and the reaction mixture filtered. The precipitate was triturated with 100 ml of concentrated ammonium hydroxide, extracted twice with 50 ml of dichloromethane. The organic layer was washed with ammonium hydroxide (100 ml) and water (100) and then concentrated and recrystallized (hexane) to yield 2 g solid 4-cyano-3-fluorotoluene (EX-32A). NMR and MS confirmed the structure of EX-32A.

A mixture of 2-fluoro-4-methylbenzonitrile (EX-32A) (2 g, 14.8 mmol), NBS (2.6 g, 14.8 mmol) and benzoyl peroxide (178 mg, 0.74 mmol) in $CCl_4$ (30 ml) was refluxed for 16 hr, then cooled and filtered. The mixture was then concentrated and purified with silica-gel column to yield 1.5 g oil EX-32B. NMR and MS confirmed the structure of EX-32B.

N,N-(Boc)$_2$NH (1.1 g, 5.17 mmol) in THF (20 ml) was cooled to 0° C. and NaH (60%, 0.25 g, 6.11 mmol) was added. The mixture was kept stirring for 30 min., then benzylbromide EX-32B (1 g, 4.7 mmol) in THF (2 ml) was added. The mixture was stirred for 3 hr. Then water was added and extracted with EtOAc (3×15 ml). The combined EtOAc was then concentrated and recrystalized in hexane to yield 0.6 g white solid EX-32C. NMR and MS all confirmed the structure of EX-32C.

To the compound EX-32C (200 mg) in $CH_2Cl_2$ (3 ml) was added TFA (1.5 ml). The reaction mixture was stirred at RT for 3 h and concentrated to afford oil EX-32D which was directly used for next amide coupling reaction.

To 2-{5-chloro-6-(3-nitrophenyl)-3-cyclobutylamino-2-oxohydropyrazinyl}acetic acid (227 mg, 0.6 mmol) was added HOBt (106.1 mg, 0.7 mmol) and EDC (126.7 mg, 0.7 mmol) in DMF (3mnl). The mixture was stirred at RT for 30 min. Then the amine TFA salt EX-32D in DMF (1 ml) and triethyl amine (0.2 ml) was added to the mixture which was stirred overnight. The mixture was concentrated, purified to yield 200 mg solid EX-32E, confirmed by NMR and MS.

EX-32E(0.2 g) in THF (5 ml) was added with Pd/C (10%, 20 mg). The mixture was stirred at RT under $N_2$, and then $H_2$ gas balloon was connected to the flask. The reaction was stirred for 24 hr to complete reaction. The mixture was filtered, washed with ethanol, and then dried to yield 0.16 g white solid EX-32F which was directly used for next cyclization reaction.

To acetohydroxamic acid (37 mg, 0.5 mmol) in DMF (2 ml) was added potassium t-butoxide (1M, 0.5 ml, 0.5 mmol) at room temperature. After stirring for 30 min, benzonitrile EX-32F (160 mg, 0.33 mmol) in DMF (2 ml) was added. The reaction mixture was stirred overnight, and then poured into a mixture of brine and ethyl acetate. The aqueous layer was extracted with EtOAc (3×2 ml), and the combined EtOAc was washed with brine, dried, concentrated and purified on reverse-phase HPLC to yield 60 mg of the HCl salt. NMR and MS both confirmed the structure of product.

Example 33

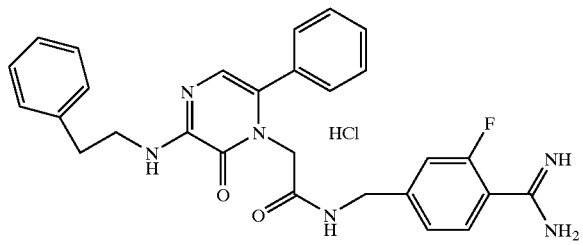

By substituting 2-fluoro-4-methylbenzonitrile for 4-methylbenzonitrile, 2-fluoro-4-methylbenzonitrile (EX-32A) was converted to the protected amidine, 4-(N-benzyloxycarbonylamidino)-3-fluorobenzylamine hydrogen chloride salt (EX-33A), using the procedure outlined in Synthetic Communications, 28(23), 4419–4429 (1998) for preparing 4-(N-benzyloxycarbonylamidino)benzylamine hydrogen chloride salt. EX-33A was characterized by: MS (LR-ESI) m/z 302 (M+H)+; $^1$HNMR (DMSO, 300 MHz) δ8.75 (bs, 3H, CH$_2$NH$_3$), δ7.79–7.02 (m, 8H, aromatic CH), δ5.31–5.07 (m, 2H, C$_6$H$_5$CH$_2$), δ4.10 (s, 2H, CH$_2$NH$_3$).

Using the procedure of Example 44 by substituting 2-[3-(N-{2-phenylethyl}amino)-2-oxo-6-phenylhydropyrazinyl]acetic acid (EX-1D) for 2-[3-({2-[(tert-butoxy)carbonylamino]ethyl}amino)-5-chloro-2-oxo-6-phenylhydropyrazinyl]acetic acid, EX-33A was converted to the product which gave an m/z+1 of 499.

Example 34

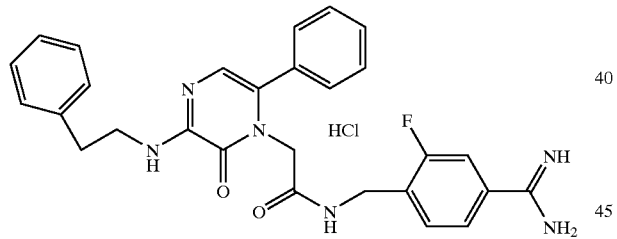

By substituting 3-fluoro-4-methylbenzonitrile for 4-methylbenzonitrile, 3-fluoro-4-methylbenzonitrile was converted to the protected amidine, 4-(N-benzyloxycarbonylamidino)-2-fluorobenzylamine hydrogen chloride salt (EX-34A), using the procedure outlined in Synthetic Communications, 28(23), 4419–4429 (1998) for preparing 4-(N-benzyloxycarbonylamidino)benzylamine hydrogen chloride salt. EX-34A was characterized by: MS (LR-ESI) m/z 302 (M+H)+; $^1$HNMR (DMSO, 300 MHz) δ8.82 (bs, 3H, CH$_2$NH$_3$), δ7.92–7.26 (m, 8H, aromatic CH), δ5.32 (s, 2H, C$_6$H$_5$CH$_2$), δ4.10 (s, 2H, CH$_2$NH$_3$).

Using the procedure of Example 44 by substituting 2-[3-(N-{2-phenylethyl}amino)-2-oxo-6-phenylhydropyrazinyl]acetic acid (EX-1D) for 2-[3-({2-[(tert-butoxy)carbonylamino]ethyl}amino)-5-chloro-2-oxo-6-phenylhydropyrazinyl]acetic acid, EX-34A was converted to the product which gave an m/z+1 of 499.

Example 35

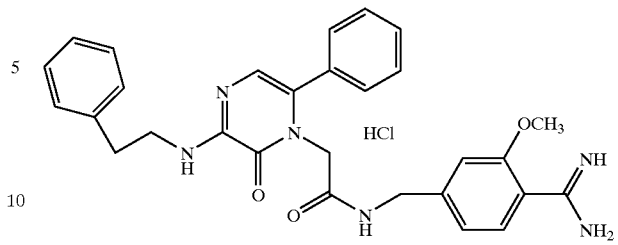

By substituting 2-methoxy-4-methylbenzonitrile for 4-methylbenzonitrile, 2-methoxy-4-methylbenzonitrile was converted to the protected amidine, 4-(N-benzyloxycarbonylamidino)-3-methoxybenzylamine hydrogen chloride salt (EX-35A), using the procedure outlined in Synthetic Communications, 28(23), 4419–4429 (1998) for preparing 4-(N-benzyloxycarbonylamidino)benzylamine hydrogen chloride salt. EX-35A was characterized by: MS (LR-ESI) m/z 314 (M+H)+; $^1$HNMR (DMSO, 300 MHz) δ7.77–6.95 (m, 8H, aromatic CH), δ4.74 (bs, 2H, C$_6$H$_5$CH$_2$), δ4.10–3.95 (m, 2H, CH$_2$NH$_3$), δ3.80 (s, 3H, OCH$_3$).

Using the procedure of Example 44 by substituting 2-[3-(N-{2-phenylethyl}amino)-2-oxophenylhydropyrazinyl]acetic acid (EX-1D) for 2-[3-({2-[(tert-butoxy)carbonylamino]ethyl}amino)-5-chloro-2-oxo-6-phenylhydropyrazinyl]acetic acid, EX-35A was converted to the product which gave an m/z+1 of 511.

Using the procedures of Scheme 1, Scheme 2, and the Examples herein with suitable reagents, starting materials, and intermediates, additional pyrazinones of the present invention were prepared and these pryazinones are summarized in Table 2.

TABLE 2

Additional Substituted Pyrazinones of the Present Invention Prepared based on the Procedures of Scheme 1, Scheme 2, and Examples herein.

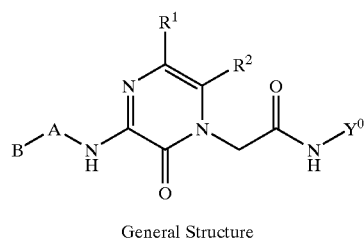

General Structure

| Ex. No. | R² | R¹ | B-A- | Y⁰ | MW (m/z + 1) |
|---|---|---|---|---|---|
| 36 | Phenyl | H | 2-phenethyl | 1-(4-guanidino)-2-butynyl | 458 |
| 37 | Phenyl | H | 2-phenylethyl | 1-(4-guanidino)-cis-2-butenyl | 460 |
| 38 | Phenyl | H | 2-phenylethyl | (3-aminoindazol-5-yl)methyl | 494 |
| 39 | Phenyl | H | 2-phenylethyl | (3-aminoindazol-6-yl)methyl | 494 |
| 40 | 3-amino-phenyl | Cl | cyclobutyl | (4-amidino-3-fluoro)-benzyl | 498 |
| 41 | 3-amino-phenyl | Cl | cyclobutyl | (4-amidino-2-fluoro)-benzyl | 511 |
| 42 | 3-amino-phenyl | Cl | isopropyl | (4-amidino-3-fluoro)-benzyl | 486 |

TABLE 2-continued

Additional Substituted Pyrazinones of the Present Invention Prepared based on the Procedures of Scheme 1, Scheme 2, and Examples herein.

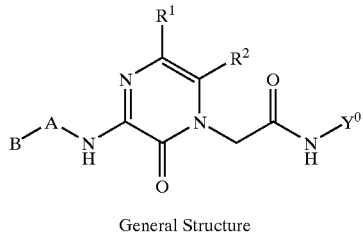

General Structure

| Ex. No. | R² | R¹ | B-A- | Y⁰ | MW (m/z + 1) |
|---|---|---|---|---|---|
| 43 | 3-amino-phenyl | H | isopropyl | (4-amidino-3-fluoro)-benzyl | 452 |

Example 44

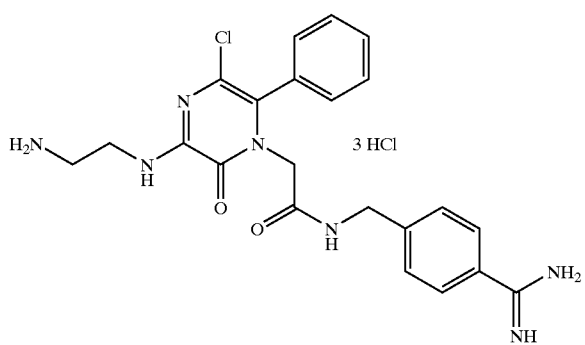

To a solution of 2-[3-({2-[(tert-butoxy)carbonylamino]ethyl}amino)-5-chloro-2-oxo-6-phenylhydropyrazinyl] acetic acid (6.50 g, 15.38 mmol) prepared as described in EX-1C using 2-(tert-butoxycarbonylamino)ethylamine in place of 2-phenethylamine in 100.0 mL dimethylformamide was added N,N-diisopropylethylamine (21.0 mL, 120.56 mmol), N-hydroxybenzotriazole (2.73 g, 20.21 mmol), and 1-[3-(dimethylamino)propyl]-3-ethylcarbodiimide hydrochloride (3.84 g, 20.04 mmol). The resulting mixture was stirred for 30 minutes. To the reaction mixture was added in one portion (5.9723 g, 18.68 mmol) of the protected amidine, 4-(N-benzyloxycarbonylamidino)benzylamine hydrogen chloride salt, prepared using the procedure outlined Synthetic Communications, 28(23), 4419–4429 (1998). The resulting mixture was stirred over night. The reaction mixture was diluted with ethyl acetate (250 mL) and washed with 5% citric acid (1×50 mL), saturated NaHCO₃ (1×50 mL), and brine (1×50 mL). The organic solution was dried (MgSO₄), filtered and concentrated. The crude reaction was purified by MPLC (80% ethyl acetate/hexanes) to give pure product EX-44A: $^1$H NMR (300 MHz, DMSO) δ8.59–8.53 (1H), 7.99–7.96 (m, 2H), 7.81–7.75 (m, 1H), 7.51–7.25 (m, 12H), 6.99 (br m, 1H), 5.14 (s, 2H), 4.32–4.27 (m, 4H), 3.42–3.35 (m, 4H), 3.24–3.20 (m, 2H), 1.41 (s, 9H); $^{13}$C NMR (75 MHz, CDCl₃) δ166.6, 163.0, 156.5, 151.3, 149.9, 143.9, 137.8, 133.5, 132.6, 131.3, 130.1, 129.5, 129.2, 129.1, 128.9, 128.7, 128.4, 127.7, 124.0, 78.5, 66.8, 49.3, 42.6, 36.5, 31.5, 29.0; HRMS (EI) calcd for C₃₅H₃₈ClN₇O₆ 688.2650, found 688.2614.

A solution of pyrazinone EX-44A (334.4 mg, 0.4593 mmol) in 5.0 mL ethanol/4 M HCl in dioxane (3:1, 0.1 M) was flushed with hydrogen gas. To the solution was then added 113.1 mg 10% Pd/C (wet), and the resulting suspension was stirred at room temperature under an atmosphere of hydrogen (balloon pressure) for approximately 18 hours. The reaction mixture was filtered through a pad of Celite 545 and rinsed with ethanol. The solvent was removed under reduced pressure. The resulting oil was triturated with ethyl ether to provide pure product as a white solid: $^1$H NMR (400 MHz, DMSO) d 9.50 (s, 2H), 9.29 (s, 2H), 8.8/0 (s, 1H), 8.22 (s, 3H), 7.85–7.80 (m, 3H), 7.44 (br s, 3H), 7.27–7.24 (m, 4H), 4.23 (s, 4H), 3.58–3.54 (m, 4H); HRMS (ES) calcd for C₂₂H₂₅ClN₇O₂ 454.1758, found 454.1741.

Example 45

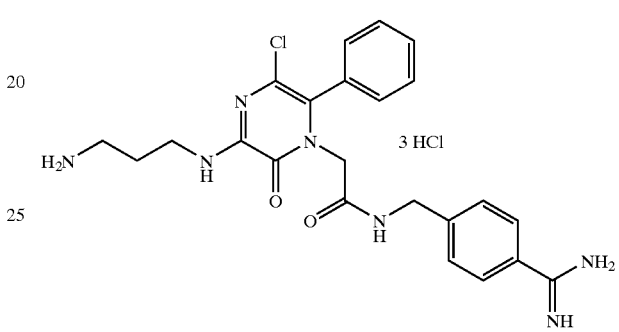

By following the method of Example 45 and substituting 2-[3-({3-[(tert-butoxy)carbonylamino]propyl}amino)-5-chloro-2-oxo-6-phenylhydropyrazinyl]acetic acid for 2-[3-({2-[(tert-butoxy)carbonylamino]ethyl}amino)-5-chloro-2-oxo-6-phenylhydropyrazinyl]acetic acid, the product was prepared: $^1$H NMR (400 MHz, DMSO) d 9.51 (br s, 2H), 8.28 (br s, 2H), 8.77 (s, 1H), 8.15 (3, 3H), 7.86–7.79 (m, 3H), 7.42 (s, 3H), 7.26–7.24 (m, 4H), 5.37 (br s, 2H), 4.21 (s 4H), 3.39–3.29 (m, 2H), 2.81–2.76 (br s, 2H), 1.86 (br s, 2H); $^{13}$C NMR (100 MHz, DMSO) d 166.7, 166.0, 151.2, 149.7, 146.0, 132.5, 131.1, 129.5, 128.8, 127.9, 126.8, 125.1, 123.9, 65.6, 56.6, 49.2, 42.4, 38.1, 37.3, 34.6, 26.7, 19.2, 15.8; HRMS (EI) calcd for C₂₃H₂₆ClN₃O₆ 469.1755, found 469.1725.

Example 46

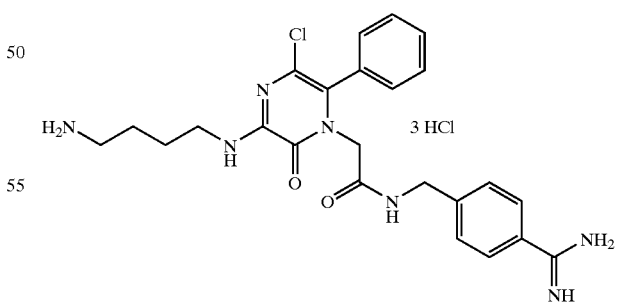

By following the method of Example 44 and substituting 2-[3-({4[(tert-butoxy)carbonylamino]butyl}amino)-5-chloro-2-oxo-6-phenylhydropyrazinyl]acetic acid for 2-[3-({2-[(tert-butoxy)carbonylamino]ethyl}amino)-5-chloro-2-oxo-6-phenylhydropyrazinyl]acetic acid, the product was prepared: $^1$H NMR (400 MHz, DMSO) d 9.49 (br s, 2H), 9.28 (s, 2H), 8.75 (s, 1H), 8.08 (s, 3H), 7.89–7.76 (m, 3H), 7.42 (s, 3H), 7.26–7.24 (m, 4H), 4.70 (br s, 4H), 4.23–4.21 (m, 3H), 2.73 (br s, 2H), 1.57 (br s, 3H), 1.03–0.96 (m, 2H); HRMS (EI) calcd for $C_{24}H_{29}ClN_7O_2$ 482.2071, found 482.2040.

Example 47

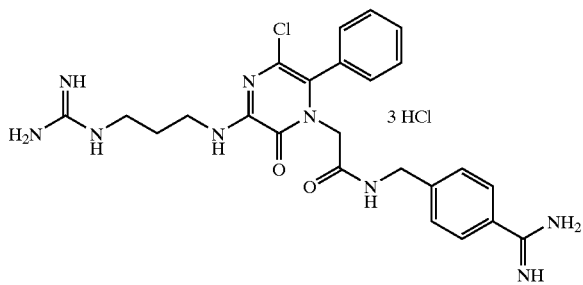

A solution of 1-(N-{4-[N-benzyloxycarbonylamidino] benzylamido}carbonylmethyl)-3-({3-[(tert-butoxy) carbonylamino]propyl}amino)-5-chloro-6-phenylpyrazinone hydrochloride (2.0075 g, 2.859 mmol), prepared as an intermediate in Example 45, in 28.0 mL ethanol/4 M HCl in dioxane (1:1, 0.1 M) was allowed to stir at room temperature for approximately 4 hours. The solvent was removed under reduced pressure. Purification by trituration with ethyl ether gave pure product EX-47A as a yellow solid: $^1$H NMR (400 MHz, DMSO) d 11.67 (br s, 1H), 10.53 (br s, 1H), 8.90–8.87 (m, 1H), 8.30–8.25 (m, 31H), 7.89–7.83 (m, 1H), 7.75–7.73 (m, 2H), 7.46–7.23 (m, 13H), 5.532 (s, 2H), 4.26–4.23 (m, 3H), 3.50 (s, 2H), 3.36–3.35 (m, 2H), 2.75 (br m, 2H); HRMS (EI) calcd for $C_{31}H_{32}ClN_7O_4$ 602.2283, found 602.2253.

To a solution of amino pyrazinone EX-47A (1.9093 g, 2.684 mmol) in 10.0 mL dimethyl formamide (0.25 M) was added triethylamine (1.90 mL, 13.63 mmol) To the resulting mixture was then added N,N'-di-BOC-N'-triflylguanidine (1.4021 g, 3.583 mmol, prepared according to Feichtinger, K., Zapf, C., Sings, H. L., and Goodman, M., *J. Org. Chem.*, 63, 3804–3805 (1998)) in one portion at room temperature. The resulting suspension was allowed to stir over night. The reaction mixture was diluted ethyl acetate (250 mL) and washed with saturated $NaHCO_3$ (2×100 mL) and brine (2×100 mL). The organic solution was dried ($MgSO_4$), filtered and concentrated. Purification by MPLC (75% ethyl acetate/hexanes) afforded EX-47B: $^1$H NMR (400 MHz, $CDCl_3$) d 11.53 (s, 1H), 8.55–8.48 (m, 2H), 7.97–7.93 (m, 4H), 7.49–7.24 (m, 13H), 5.13 (s, 2H), 4.30–4.25 (m, 4H), 3.90–3.33 (m, 4H), 1.84–1.79 (m, 2H), 1.49 (s, 9H), 1.41 (s, 9H); HRMS (EI) calcd for $C_{42}H_{51}ClN_9O_8$ 844.3549, found 844.3521.

A solution of pyrazinone EX-47B (1.5450 g, 1.8298 mmol) in 18.0 mL ethanol/4 M HCl in dioxane (3:1, 0.1 M) was flushed with hydrogen gas. To the solution was then added 157.2 mg 10% Pd/C (wet), and the resulting suspension was stirred at room temperature under an atmosphere of hydrogen (balloon pressure) for approximately 18 hours. The reaction mixture was filtered through a pad of Celite 545 and rinsed with ethanol. The solvent was removed under reduced pressure. The resulting oil was triturated with ethyl ether to provide the pure product in 63% yield: $^1$H NMR (400 MHz, DMSO) d 9.50 (s, 2H), 9.28 (s, 2H), 8.77 (s, 1H), 7.91 (s, 1H), 7.81–7.79 (m, 3H), 7.42 (br s, 4H), 7.26–7.24 (m, 5H), 6.28 (br s, 2H), 4.23–4.21 (m, 4H), 3.36–3.27 (m, 2H), 3.14–3.13 (br m, 2H), 1.77–1.74 (m, 2H); HRMS (ES) calcd for $C_{24}H_{29}ClN_9O_2$ 510.2133, found 510.2080.

Example 48

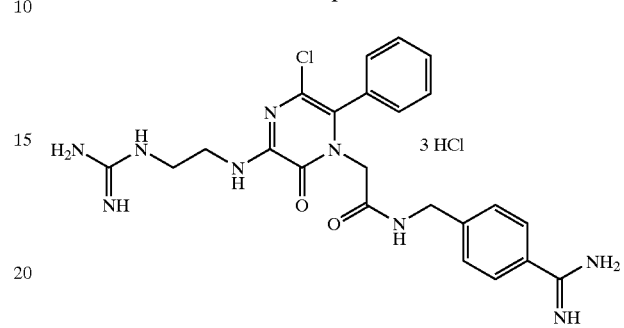

Using the method of Example 47 and substituting 1-(N-{4-[N-benzyloxycarbonylamidino] benzylamido}carbonylmethyl)-3-({2-[(tert-butoxy) carbonylamino]ethyl}amino)-5-chloro-6-phenylpyrazinone hydrochloride, prepared as an intermediate in Example 44, for the propyl analog used in Example 47, the product was prepared: $^1$H NMR (400 MHz, DMSO) d 9.51 (s, 2H), 9.29 (s, 2H), 8.80 (s, 1H), 7.90–7.78 (m, 5H), 7.43–7.37 (m, 5H), 7.35–7.23 (m, 5H), 4.23 (s, 4H), 4.03 (s, 2H), 3.40–3.34 (m, 4H); HRMS (EI) calcd for $C_{23}H_{27}ClN_9O_2$ 496.1976, found 496.1952.

Example 49

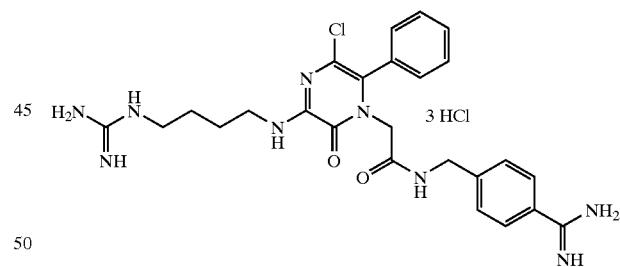

By following the method of Example 47 and substituting 1-(N-{4-[N-benzyloxycarbonylamidino] benzylamido}carbonylmethyl)-3-({4-[(tert-butoxy) carbonylamino]butyl}amino)-5-chloro-6-phenylpyrazinone hydrochloride (2.0075 g, 2.859 mmol), prepared as an intermediate in Example 46, for the propyl analog used in Example 47, the product was prepared: $^1$H NMR (400 MHz, DMSO) d 9.47 (s, 2H), 9.28 (s, 2H), 8.74–8.72 (m, 1H), 7.88 (br s, 1H), 7.80–7.73 (m, 3H), 7.43–7.31 (m, 4H), 7.27–7.20 (m, 5H), 5.36–5.32 (m, 3H), 4.25–4.21 (m, 4H), 3.28–3.27 (m, 2H), 3.10–3.08 (m, 2H), 1.58–1.53 (m, 2H), 1.48–1.43 (m, 2H); HRMS (EI) calcd for $C_{25}H_{31}ClN_9O_2$ 524.2289. found 524.2292.

Example 50

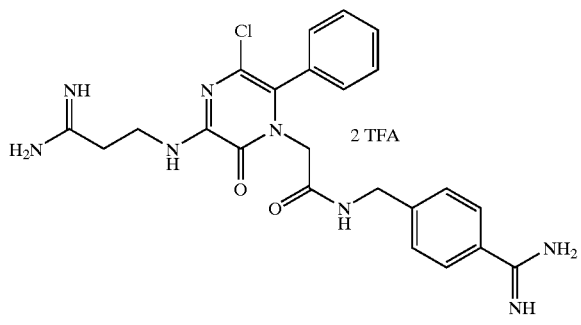

To a solution of 2-{5-chloro-3-[(2-cyanoethyl)amino]-2-oxo-6-phenylhydropyrazinyl}acetic acid (2.09 g, 6.28 mmol) in 31.0 mL dimethylformamide/tetrahydrofuran (1:1) was added N,N-diisopropylethylamine (5.50 mL, 31.57 mmol), N-hydroxybenzotriazole (1.02 g, 7.6 mmol), and 1-[3-(dimethylamino)propyl]-3-ethylcarbodiimide hydrochloride (1.45 g, 7.51 mmol). The resulting mixture was stirred for 30 minutes. To the reaction mixture was then added 4-cyanobenzylamine (1.28 g, 7.57 mmol) in one portion. The resulting mixture was allowed to stir over night. The reaction mixture was diluted with ethyl acetate (250 mL) and washed with 5% citric acid (1×50 mL), saturated NaHCO$_3$ (1×50 mL), and brine (1×50 mL). The organic solution was dried (MgSO$_4$), filtered and concentrated. The crude reaction was purified trituration with ethyl ether to give EX-50A: $^1$H NMR (300 MHz, DMSO) δ8.59 (t, J=5.6 Hz, 1H), 8.10 (t, J=5.6 Hz, 1H), 7.82 (d, J=8.1 Hz, 2H), 7.53–7.46 (m, 3H), 7.35–7.32 (m, 4H) 4.33–4.29 (m, 4H), 3.63–3.57 (m, 2H), 2.89 (t, J=6.3 Hz, 2H); $^{13}$C NMR (75 MHz, DMSO) δ166.7, 151.1, 149.6, 145.6, 132.93, 132.45, 131.16, 130.21, 129.55, 128.63, 124.97, 124.72, 120.0, 119.6, 110.4, 49.3, 42.6, 37.3, 17.3; HRMS (EI) calcd for C$_{23}$H$_{20}$ClN$_6$O$_2$ 447.1336, found 447.1330.

To a suspension of bis-nitrile pyrazinone EX-50A (2.26, 58.07 mmol) in 50 mL ethanol/H$_2$O (2.6:1, 0.1 M) was added hydroxyl amine hydrochloride (2.61 g, 37.6 mmol) followed by potassium carbonate (3.08 g, 22.3 mmol). The resulting white suspension was stirred and heated to 60° C. over night. The reaction mixture was cooled to room temperature and diluted with water (75.0 mL). The mixture was placed in an ice bath, and the pH was adjusted to approximately 7 using dilute acid. The precipitate that formed was collected by filtration, washed with cold water and dried under vacuum to afford pure EX-50B: $^1$H NMR (300 MHz, DMSO) δ9.63 (s, 1H), 8.95 (s, 1H), 8.47 (br s, 1H), 7.66–7.61 (m, 2H), 7.53–7.47 (m, 4H), 7.32 (d, J=5.2 Hz), 7.16–7.13 (m, 2H), 5.83 (s, 2H), 5.47 (s, 2H), 4.25 (s, 4H), 3.61–3.53 (m, 2H), 2.39–2.35 (m, 2H); 13C NMR (75 MHz, DMSO) δ166.5, 151.68, 151.35, 151.23, 149.6. 140.3. 132.70, 132.63, 131.3, 130.1, 129.5, 127.6, 126.0, 125.3, 49.2, 42.6, 38.4, 30.6; HRMS (EI) calcd for C$_{23}$H$_{26}$ClN$_8$O$_4$ 513.1766, found 513.1735.

To a solution of Bis-hydroxyamidine EX-50B (2.40 g, 4.67 mmol) in 19.0 mL acetic acid (0.25 M) was added acetic anhydride (1.80 mL, 19.1 mmol). The resulting mixture was stirred for 10 minutes and flushed with hydrogen gas. To the solution was then added Pd/C (wet) and the resulting mixture was allowed to stir under an atmosphere of hydrogen (balloon pressure) at room temperature, over night. The reaction mixture was filtered through a pad of Celite 545 and concentrated under vacuum. Purification by HPLC (1% acetonitrile to 60% acetonitrile/H$_2$O/0.1% trifluoroacetic acid) afford pure product: $^1$H NMR (400 MHz, DMSO) δ9.51 (s, 2H), 9.30 (s, 2H), 9.03 (s, 2H), 8.93 (s, 2H), 8.62–8.59 (m, 1H), 7.89–7.86 (m, 2H), 7.74 (d, J=8.3 Hz, 2H), 7.47–7.40 (m, 3H), 7.28–7.23 (m, 4H), 4.27–4.24 (m, 4H), 3.63–3.59 (m, 2H), 2.70–2.68 (m, 2H); HRMS (EI) calcd for C$_{23}$H$_{26}$ClN$_8$O$_2$ 481.1867, found 481.1836.

Example 51

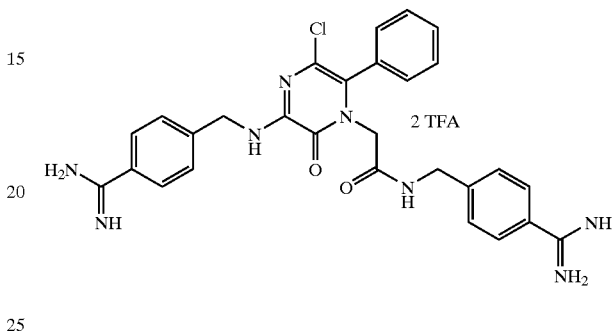

By following the method of Example 50 and substituting 2-{5-chloro-3-[(4-cyanobenzyl)amino]-2-oxo-6-phenylhydropyrazinyl}acetic acid for the 2-cyanoethylamino analog, the product was prepared: $^1$H NMR (400 MHz, DMSO) d 9.44 (d, J=16.9 Hz, 3H), 9.26 (d, J=17.2 Hz, 8.61 (br s, 1H), 8.47–8.44 (m, 1H), 7.74 (d, J=7.0 Hz, 4H), 7.52 (d, J=Hz, 2H), 7.43–7.42 (m, 3H), 7.28–7.22 (m, 4H), 4.56–4.55 (m, 2H), 4.25 (s, 4H); HRMS (EI) calcd for C$_{28}$H$_{28}$ClN$_8$O$_2$ 543.2024, found 543.1986.

Example 52

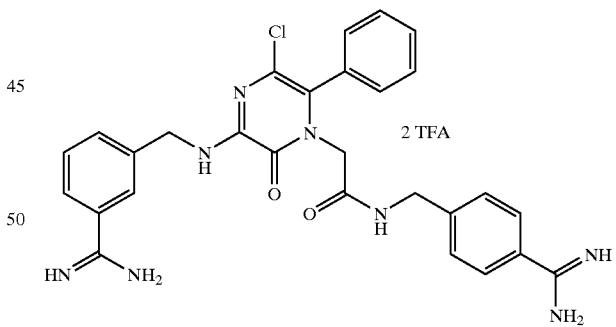

By following the method of Example 50 and substituting 2-{5-chloro-3-[(3-cyanobenzyl)amino]-2-oxo-6-phenylhydropyrazinyl}acetic acid for the 2-cyanoethylamino analog, the product was prepared: $^1$H NMR (400 MHz, DMSO) d 9.41 (s, 4H), 9.28 (d, J=11.0 Hz, 4H), 8.61–8.58 (m, 1H), 8.35–8.32 (m, 1H), 7.77–7.72 (m, 3H), 7.66–7.64 (m, 2H), 7.55–7.52 (m, 1H), 7.45–7.39 (m, 3H), 7.29–7.23 (m, 4H), 4.57–4.55 (m, 2H), 4.26–4.21 (m, 4H); $^{13}$C NMR (100 MHz, DMSO) δ166.7, 166.1, 159.8, 159.4, 151.2, 149.6, 145.9, 140.6, 133.3, 132.4, 131.1, 130.1, 129.6, 129.5, 129.1, 128.7, 127.93, 127.86, 127.3, 124.9, 124.5, 49.1, 44.0, 42.4; HRMS (EI) calcd for $C_{28}H_{28}ClN_8O_2$ 543.2024, found 543.2032.

Example 53

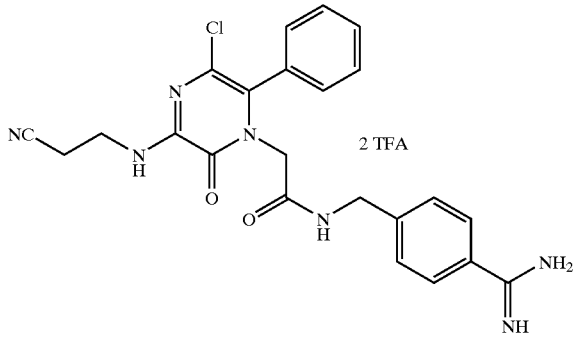

To a solution of 2-{5-chloro-3-[(2-cyanoethyl)amino]-2-oxo-6-phenylhydropyrazinyl}acetic acid (1.45 g, 3.25 mmol) in 17.0 mL dimethylformamide was added N,N-diisopropylethylamine (3.00 mL, 17.2 mmol), N-hydroxybenzotriazole (0.536 mg, 3.96 mmol), and 1-[3-(dimethylamino)propyl]-3-ethylcarbodiimide hydrochloride (0.752 mg, 3.923 mmol). The resulting mixture was allowed to stir for 30 minutes. The reaction mixture was then added the Cbz protected amidine (1.2631 g, 3.950 mmol) prepared and used in Example 44 in one portion. The resulting mixture was allowed to stir over night. The reaction mixture was diluted with ethyl acetate (250 mL) and washed with 5% citric acid (1×50 mL), saturated $NaHCO_3$ (1×50 mL), and brine (1×50 mL). The organic solution was dried ($MgSO_4$), filtered and concentrated. The crude reaction was purified by MPLC (100% ethyl acetate) to give pure EX-53A in 82% yield: $^1$H NMR (400 MHz, DMSO) δ9.06 (br s, 1H), 8.50–8.47 (m, 1H), 8.05–8.02 (m, 1H), 7.89 (d, J=8.2 Hz, 2H) 7.46–7.26 (m, 11H), 7.18 (d, J=8.2 Hz, 2H), 5.07 (s, 2H), 4.24–4.21 (m, 4H), 3.55–3.51 (m, 2H), 2.83–2.80 (m, 2H); HRMS (EI) calcd for $C_{31}H_{28}ClN_7O_4$ 598.1970, found 598.1970.

To a solution of pyrazinone EX-53A (1.497 g, 2.50 mmol) in 25.0 mL ethanol/4 M HCl in dioxane (3:1, 0.1 M) was flushed with hydrogen gas. To the solution was then added 10% Pd/C (wet) and the resulting suspension was allowed to stir at room temperature under an atmosphere of hydrogen (balloon pressure) for approximately 18 hours. The reaction mixture was filtered through a pad of Celite 545 and rinsed with ethanol. The solvent was removed under reduced pressure. Purification by HPLC (5% acetonitrile to 95% acetonitrile/$H_2O$/0.1% trifluoroacetic acid) provided pure product: $^1$H NMR (400 MHz, DMSO) d 9.51 (s, 2H), 9.29 (s, 2H), 8.63–8.60 (m, 1H), 8.03–8.00 (m, 1H), 7.74 (d, J=8.3 Hz, 2H), 7.44–7.40 (m, 3H), 7.29–7.27 (m, 4H), 4.27–4.24 (m, 4H), 3.55–3.51 (m, 3H), 2.83–2.80 (m, 3H); HRMS (ES) calcd for $C_{23}H_{23}ClN_7O_2$ 464.1602, found 464.1624.

Example 54

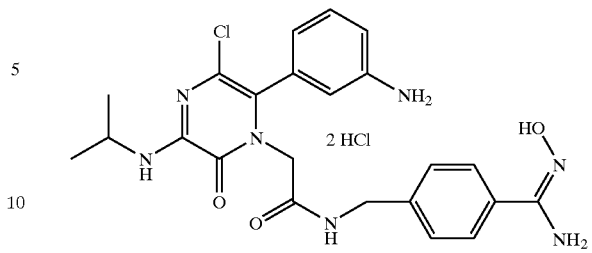

A solution of p-bromophenethylamine (40 g, 199.92 mmol) and phthalic anhydride (29.6 g, 199.84 mmol) in 250 mL of dioxane and 25 mL of dimethylformamide was heated at 120° C. for 24 hours. The flask was then cooled, and the resulting white precipitate was filtered and washed with methanol (200 mL) to give EX-54A in exceptional yield and purity: $^1$H NMR (400 MHz, CDCl$_3$) d 7.8 (m, 2H), 7.7 (m, 2H), 7.4 (d, 2H), 7.1 (d, 2H), 3.8 (t, 2H), 2.95 (t, 2H); MS (ES) calcd for $C_{16}H_{12}BrNO_2$ 330, found 331 (M+H).

A nitrogen purged solution of EX-54A (40 g, 121.15 mmol) and copper (I) cyanide (16.28 g, 181.72 mmol) in 500 mL of dimethylformamide was heated at 170° C. for 24 hours. The solvent was removed under vacuum, and the resulting material was taken up in ethyl acetate. The ethyl acetate suspension was flashed through celite and concentrated under vacuum. The resulting white precipitate EX-54B was of exceptional yield and purity: $^1$H NMR (300 MHz, CDCl$_3$) d 7.82 (m, 2H), 7.75 (m, 2H), 7.6 (d, 2H), 7.35 (d, 2H), 3.95 (t, 2H), 3.05 (t, 2H); MS (ES) calcd for $C_{17}H_{12}N_2O_2$ 276, found 277 (M+H).

A solution of p-cyanophenethylamine EX-54B (25 g, 90.48 mmol) and hydroxylamine hydrochloride (8 g, 115.12 mmol) in 1 L of ethanol and 20 mL (114.82 mmol) of diisopropylethylamine was heated at reflux for 16 hours. The flask was then cooled, and the resulting white precipitate was filtered and air dried to give EX-54C in an adequate yield and purity: $^1$H NMR (300 MHz, DMSO) d 7.75 (d, 2H), 7.55 (d, 2H), 7.25 (d, 2H), 7.2 (d, 2H), 3.8 (m, 2H), 2.95 (m, 2H); MS (ES) calcd for $C_{17}H_{15}N_3O_3$ 309, found 310 (M+H).

A solution of p-(N-hydroxy)amidinophenethyl phthalimide (EX-54C) (4.53 g, 14.64 mmol) in 200 mL of chloroform was treated with hydrazine monohydrate (1 mL, 20.62 mmol). The reaction was stirred vigorously at 50° C. for 24 hours. The flask was then cooled and the resulting white precipitate was filtered and washed with chloroform (200 mL). A 50:50 mixture of product EX-54D and phthalhydrazide was obtained and used as is: $^1$H NMR (300 MHz, DMSO) d 7.6 (d, 2H), 7.2 (d, 2H), 2.8 (t, 2H), 2.7 (m, 2H); MS (ES) calcd for $C_{17}H_{15}N_3O_3$ 179, found 180 (M+H).

Reacting EX-54D containing phthalhydrazide with 2-{5-chloro-6-(3-nitrophenyl)-3-[N-(1-methylethyl)amino]-2-oxohydropyrazinyl}acetic acid in place of 2-{5-chloro-6-(3-nitrophenyl)-3-cyclobutylamino-2-oxohydropyrazinyl}acetic acid and EX-27D and then hydrogenating the resulting intermediate according to the final two procedures described in Example 27 gave the product with an m/z+1 of 484.

Example 55

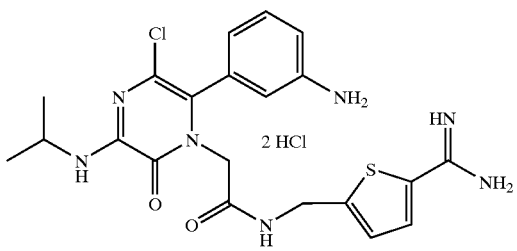

A solution of diisopropylamine (35.3 ml, 0.251 moles) in tetrahydrofuran (500 ml) was cooled to −78° C. under a nitrogen blanket. To this was added 1.6M n-butyllithium in hexanes (157 ml, 0.251 moles) and allowed to stir for 5 min. Then slowly added thiopene-2-carbonitrile (21.33 ml, 0.229 moles) in tetrahydrofuran (115 ml) and allowed to stir. After 45 min. was added NN-dimethylformamide (88.66 ml, 1.145 moles) at −78° C. Citric acid (40 g) was added after 2 h. followed by water (240 ml) and stirred for 18 h. The reaction was concentrated in vacuo, transferred to a separatory funnel, diluted with brine, and extracted twice with ether. The combined ether layers were washed with brine, dried over magnesium sulfate, filtered, and the solvent removed in vacuo. Chromatography yielded 15.8 g (50%) of 2-cyano-5-formylthiophene (EX-55A) as a brown solid: $^1$H NMR (300 MHZ, CDCl$_3$) d 10.02 (s, 1H), 7.79 (m, 1H), 7.30 (m, 1H).

2-Cyano-5-formylthiophene (EX-55A) (15.8 g, 0.229 moles) was stirred in ethanol (375 ml), and sodium borohydride (4.36 g, 0.115 moles) added in small portions. After 15 min., the solvent was removed in vacuo, and residue taken up in ethyl acetate. After the ethyl acetate was washed with 1 N potassium hydrogen sulfate and brine, the organic layer was dried over magnesium sulfate, filtered, and solvent removed in vacuo. The residue was dried on vacuum pump to yield 9.57 g (59%) of the alcohol EX-55B as a brown-orange oil: $^1$H NMR (300 MHz, CDCl$_3$) d 7.53 (m, 1H), 7.00 (m, 1H), 4.88 (s, 2H), 2.84 (br s, 1H).

To a stirring solution of EX-55B (9.57 g, 0.069 moles) in tetrahydrofuran (80 ml) was added triphenylphosphine (19.86 g, 0.075 moles) and carbon tetrabromide (25.11 g, 0.075 moles). After 18 h. the reaction was concentrated in vacuo, and the crude material chromatographed to yield EX-55C as a brown oil: $^1$H NMR (300 MHz, CDCl$_3$) d 7.52 (m, 1H), 7.14 (m, 1H), 4.69 (s,2H).

2-Aminomethyl-5-carbobenzyloxyamidinothiophene dihydrogen chloride salt (EX-55D) was prepared by the method outlined in Synthetic Communications, 28(23), 4419–4429 (1998) by substituting 5-bromomethyl-2-cyanothiophene (EX-55C) for 4-cyanobenzyl bromide to give after trituration with acetonitrile EX-55D: $^1$H NMR (300 MHz, DMSO) d 9.98 (br s, 1H), 8.83 (br s, 2H), 8.10 (s, 1H), 7.40–7.48 (m, 7H), 5.26 (s, 2H), 4.31 (s, 2H); HRMS calcd for C$_{14}$H$_{16}$N$_3$O$_2$S 290.0963, found 290.0949.

Reacting EX-55D with 2-{5-chloro-6-(3-nitrophenyl)-3-[N-(1-methylethyl)amino]-2-oxohydropyrazinyl}acetic acid in place of 2-{5-chloro-6-(3-nitrophenyl)-3-cyclobutylamino-2-oxohydropyrazinyl}acetic acid and EX-27D and then hydrogenating the resulting intermediate according to the final two procedures described in Example 27 gave the product with an m/z+1 of 474.

Example 56

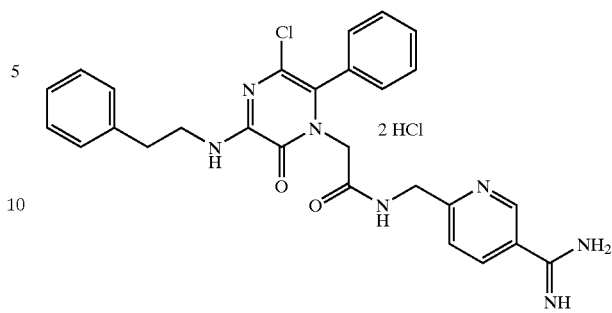

To a stirring solution of 3-cyano-6-methylpyridine (20 g, 0.169 moles) in carbon tetrachloride (850 ml) was added N-bromosuccinimde (30 g, 0.169 moles) and benzoyl peroxide (4.1 g, 0.0169 moles), and the solution was heated to reflux. After 18 h, the heat was discontinued, diluted with carbon tetrachloride (1 L) and washed twice with water (1 L). The solvent was removed in vacou and the crude material chromatographed to yield 12.05 g (36%) of dark brown solid EX-56A: $^1$H NMR (300 MHz, CDCl$_3$) d 8.86 (d, 1H), 7.00 (m, 1H), 7.62 (m, 1H), 4.60 (s, 2H); $^{13}$C NMR (300 MHz, CDCl$_3$) d 156.38, 147.70, 135.82, 118.98, 111.75, 104.66, 27.82; HRMS (EI) calcd for C$_7$H$_6$BrN$_2$ 196.9714, found 196.9661.

2-Aminomethyl-5-carbobenzyloxyamidinopyridine dihydrogen chloride salt (EX-56B) was prepared by the method outlined in Synthetic Commnunications, 28(23), 4419–4429 (1998) by substituting 5-bromomethyl-2-cyanopyridine (EX-55A) for 4-cyanobenzyl bromide to give EX-56B: HPLC/LRMS; 98%, (M+H)$^+$ 285.

Reacting EX-56B with 2-{5-chloro-6-phenyl-3-[N-(2-phenylethyl)amino]-2-oxohydropyrazinyl}acetic acid in place of 2-{5-chloro-6-(3-nitrophenyl)-3-cyclobutylamino-2-oxohydropyrazinyl}acetic acid and EX-27D and then hydrogenating the resulting intermediate according to the final two procedures described in Example 27 gave the product with an m/z+1 of 482.

Example 57

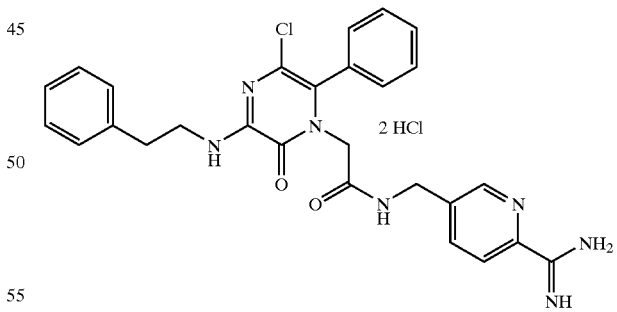

2-Cyano-5-methylpyridine (EX-57A) was prepared following the procedure outlined in Synthetic Communications, 19(13&14), 2371–2374(1989): HRMS (EI) calcd for C$_7$H$_7$N$_2$ 119.0609, found 119.0587.

By following the procedure of Example 56 and substituting 2-cyano-5-methylpyridine for 3-cyano-6-methylpyridine, the intermediate 5-bromomethyl-2-cyanopyridine (EX-57B) was prepared.

2-Aminomethyl-5carbobenzyloxyamidinopyridne dihydrogen chloride salt (EX-57C) was prepared by the method outlined in Example 56 substituting 5-bromomethyl-2-cyanopyridine for 6-bromomethyl-3-cyanopyridine: HPLC/LRMS; 95%, (M+H)+ 285.

Reacting 2-Aminomethyl-5carbohenzyloxyamidinopyridne dihydrogen chloride salt (EX-57C) with 2-{5-chlorophenyl-3-[N-(2-phenylethyl)amino]-2-oxohydropyrazinyl}acetic acid as described in Example 56 gave the product with an m/z+1 of 482.

Example 58

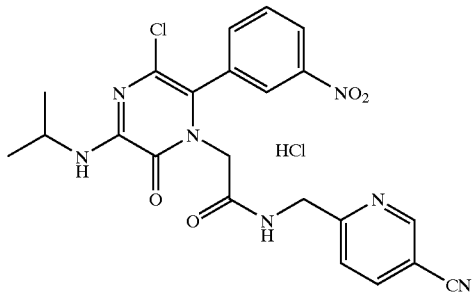

2-Aminomethyl-5-cyanopyridine hydrochloride (EX-58A) was prepared by the deprotection with 4N HCl Dioxane of the intermediate 2-{N,N-bis-(tert-butoxycarbonyl)aminomethyl}-5-cyanopyridine used to prepare 2-aminomethyl-5-carbobenzyloxyamidinopyridine dihydrogen chloride salt in Example 56: $^1$H NMR (400 MHz, DMSO) d 9.04 (s, 1H), 8.64 (br s, 2H), 8.34 (m, 1H), 7.69 (m, 1H), 4.25 (s, 2H); HRMS (EI) calcd for $C_7H_8N_3$ 134.0718, found 134.0699.

Using the procedure of Example 44 by substituting 2-[5-chloro-3-(N-{1-methylethyl}amino)-2-oxo-6-phenylhydropyrazinyl]acetic acid (EX-1D) for 2-[3-({2-[(tert-butoxy)carbonylamino]ethyl}amino)-5-chloro-2-oxo-6-phenylhydropyrazinyl]acetic acid, EX-58A was converted to the product which gave an m/z+1 of 482.

Example 59

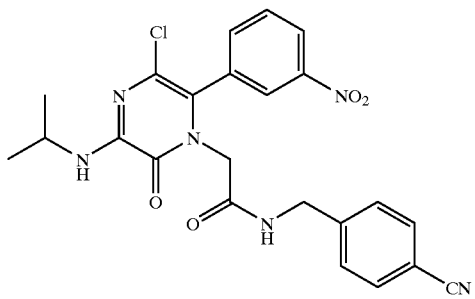

4-cyanobenzylamine hydrochloride (EX-59A) was prepared from 10 g (0.030 moles) of 4-{N,N-bis-(tert-butoxycarbonyl)aminomethyl}benzonitrile, prepared following Synthetic Communication, 28(23), 4419–4429 (1998), by stirring it in 4N HCl Dioxane (75 ml). After 3 h, the solution was concentraed in vacuo and triturated with ether. The solid was collected by filtration and vacuum dried to yield 5 g (98%) of EX-59A as a white solid: $^1$H NMR (DMSO) d 8.68 (br s, 2H) 7.84 (m, 2H), 7.67 (m, 2H), 4.06 (s, 2H); HRMS (EI) calcd for $C_8H_8N_2$ 133.0766, found 133.0807.

Using the procedure of Example 58, EX-59A was converted to the product which gave an m/z+1 of 481.

Using the procedures of Scheme 1, Scheme 2, and the Examples herein with suitable reagents, starting materials, and intermediates, additional pyrazinones of the present invention were prepared and these pryazinones are summarized in Table 3.

TABLE 3

Additional Substituted Pyrazinones of the Present Invention Prepared based on the Procedures of Scheme 1, Scheme 2, and Examples herein.

General Structure

| Ex. No. | R² | B-A- | Y⁰ | MW (m/z + 1) |
|---|---|---|---|---|
| 60 | Phenyl | 2-phenylethyl | 4-amidinobenzyl | 487 |
| 61 | 3-Nitrophenyl | isopropyl | 4-(N-hydroxyamidino)benzyl | 514 |
| 62 | 3-Aminophenyl | isopropyl | 2-(4-amidinophenyl)ethyl | 482 |
| 63 | Phenyl | 2-phenylethyl | 2-(4-amidinophenyl)ethyl | 495 |
| 64 | 3-Carbomethoxyphenyl | isopropyl | 4-amidinobenzyl | 511 |
| 65 | 3-Carboxyphenyl | isopropyl | 4-amidinobenzyl | 497 |
| 66 | 2-hydroxyphenyl | cyclobutyl | 4-amidinobenzyl | 481 |
| 67 | 3-hydroxyphenyl | cyclobutyl | 4-amidinobenzyl | 481 |
| 68 | 3-acetamidophenyl | isopropyl | 2-(4-amidinophenyl)ethyl | 524 |

Example 69

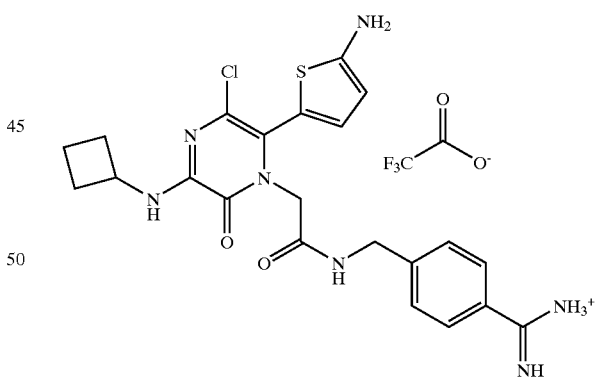

1-Benzyloxycarbonylmethyl-6-(5-bromothiophen-2yl)-3,5-dichloro pyrazinone (EX-69A) was synthesized as described in the general schemes of the patent and as described, for example, specifically for EX-1B substituting 5bromothiophenecarbaldehyde for benzaldehyde. EX-69A is a yellow crystalline solid: HPLC-MS (5 to 95% AcCN/6 min @ 1.0 mL/Min @ 254 nm @ 50° C.): retention time 4.38 min. M+Na+=494.9 for formula $C_{17}H_{11}BrCl_2N_2O_3SNa$; $^1$H NMR (400 MHz, CDCl$_3$): d 4.62 (s, 2H), 5.19 (s, 2H), 6.79 (d, J=4.0 Hz, 1H), 7.00 (d, J=4.0 Hz, 1H) 7.32 (m, 2H), 7.37 (m, 3H); $^{13}$C NMR (101 MHz, CDCl$_3$): d 49.0, 68.1, 117.8, 126.5, 128.6, 128.7, 128.8, 130.1, 130.7, 132.0, 134.5, 147.8, 151.9, 166.2.

EX-69A (12.15 g, 25.75 mmol) was treated with cyclobutylamine (3.80 g, 53.52 mmol) in 250 ml toluene at room temperature for 4 hours. The toluene solution was washed with saturated ammonium chloride solution and dried over anhydrous MgSO$_4$. After removing the toluene, the pure product EX-69B was obtained as a yellow solid (13.05 g, 99%): HPLC-MS (5 to 95% AcCN/6 min @ 1.0 mL/Min @ 254 nm @ 50° C.): retention time 4.90 min, M+H$^+$=508.0 for formula C$_{21}$H$_{20}$BrClN$_3$O$_3$S.

Potassium phthalimide (4.56 g, 24.6 mmol) and CuI (18.0 g, 94.7 mmol) were mixed in 200 ml dimethylacetamide. The mixture was stirred at room temperature for 10 minutes. To this mixture was added compound EX-69B (12.0 g, 23.7 mol). The resulting mixture was heated to 160° C. and stirred for 5 hours at an open air atmosphere. The reaction solution was filtered to remove all the insoluble solid and was concentrated via high vacuum distillation at a rotavapor. Aqueous work-up and silica gel flush chromatography yielded the pure product EX-69C as light yellow solid (6.8 g, 50%) with the des-bromo side product formation the reason for the low yield: HPLC-MS (5 to 95% AcCN/6 min @ 1.0 mL/Min @ 254 nm @ 50° C.): retention time 3.82 min, M+H$^+$=575.5 for formula C$_{29}$H$_{24}$ClN$_4$O$_5$S; $^1$H NMR (400 MHz, CDCl$_3$): d 1.69 (m, 2H), 1.92 (m, 2H), 2.36 (m, 2H), 4.45 (m, 1H), 4.49 (s, 2H), 5.07 (s, 2H), 6.54 (d, J=8.0 Hz, 1H), 6.75 (d, J=3.6 Hz, 1H), 7.17–7.25 (m, 7H), 7.50 (d, J=4.0 Hz, 1H), 7.71 (dd, J=2.8, 5.2 Hz, 2H), 7.85 (dd, J=2.8, 5.2 Hz, 2H); $^{13}$C NMR (101 MHz, CDCl$_3$): d 15.2, 30.9, 45.8, 47.4, 67.4, 114.7, 118.2, 123.9, 126.5, 128.28, 128.33, 128.36, 128.39, 128.42, 128.45, 129.5, 129.9, 131.1, 134.8, 134.9, 135.7, 148.5, 150.8, 165.2, 166.9.

EX-69C (0.55 g, 0.96 mmol) was treated with 1 ml hydrazine in 10 ml methanol and 5 ml dichloromethane for 4 hours. The reaction solution was acidified with 1N HCl and filtered to remove the solid by-product. Aqueous work-up yield the crude (90% pure) product EX-69D (0.49 g): HPLC-MS (5 to 95% AcCN/6 min @ 1.0 mL/Min @ 254 nm @ 50° C.): retention time 3.29 min, M+H$^+$=445.3 for formula C$_{21}$H$_{22}$ClN$_4$O$_3$S.

EX-69D (0.48 g, 1.08 mmol) was mixed with Boc anhydride (0.28 g, 1.30 mmol), triethylamine (0.22 g, 2.16 mmol) and DMAP (12 mg, 0.1 mmol). The reaction mixture was stirred for 4 hours at room temperature. After an aqueous work-up, the crude product in 2 ml CH$_3$CN and 2 ml THF was treated with 2 ml 1M LiOH for 3 hours. Aqueous work-up yield the crude carboxylic acid EX-69E: HPLC-MS (5 to 95% AcCN/6 min @ 1.0 mL/Min @ 254 nm @ 50° C.): retention time 3.18 min, M+H$^+$=455.4 for formula C$_{19}$H$_{24}$ClN$_4$O$_5$S.

EX-69E was coupled with the protected amidine, 4-(N-benzyloxycarbonylamidino)benzylamine hydrogen chloride salt, prepared using the procedure outlined Synthetic Communications, 28(23), 4419–4429 (1998) in the same way as described before using EDC, HOBt and DIEA in DMF to give the protected product EX-69F. EX-69F was purified by reverse phase HPLC using C18 column to give an off-white amorphous solid: HPLC-MS (5 to 95% AcCN/6 min @ 1.0 mL/Min @ 254 nm @ 50° C.): retention time 3.28 min, M+H$^+$=720.9 for formula C$_{35}$H$_{38}$ClN$_7$O$_6$S; $^1$H NMR (400 MHz, CDCl$_3$): d 1.49 (s, 9H), 1.80 (m, 2H), 2.03 (m, 2H), 2.45 (m, 2H), 4.3 (b, 2H), 4.49 (b, 3H), 5.07 (s, 2H), 6.66–6.78 (m, 2H), 7.0–7.18 (m, 2H), 7.33–7.47 (m, 5H).

EX-69F was converted to the product by hydrogenation as described before. After the hydrogenation, it was treated with HCl saturated methanol solution to remove the Boc group. The product was purified by reverse phase HPLC with a C18 column with amobile phase was 0.1% TFA in water and acetonitrile to give the product as a TFA salt and an off-white amorphous solid: HPLC-MS (5 to 95% AcCN/6 min @ 1.0 mL/Min @ 254 nm @ 50° C.): retention time 1.94 min, M+H$^+$=486.4 for formula C$_{22}$H$_{25}$ClN$_7$O$_2$S; $^1$H NMR (400 MHz, methanol-d$_4$): d 1.79 (m, 2H), 2.06 (m, 2H), 2.39 (m, 2H), 4.45 (s, 2H), 4.46 (m, 1H), 4.57 (s, 1H), 4.58 (s, 1H), 6.01 (d, J=4 Hz, 1H), 6.52 (m, 1H), 7.49 (d, J=8.4 Hz, 2H), 7.75 (m, 2H).

Sulfonyl analogs of pyrazinones wherein a sulfonyl is present as a replacement for the carbonyl of the acetamide at the N-1 position of the pyrazinone can be prepared using Scheme 3: Sulfonyl Pyrazinone detailed below along with the specific Example 70.

Scheme 3:
Sulfonyl Pyrazinones

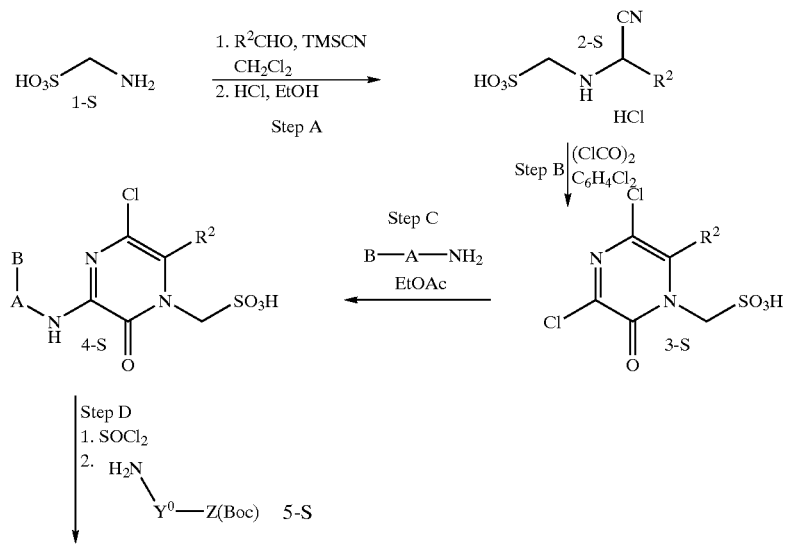

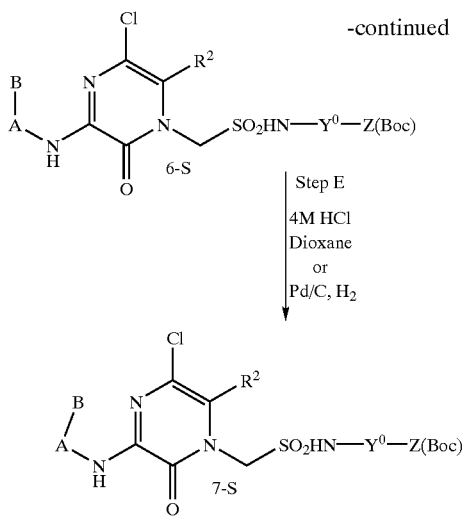

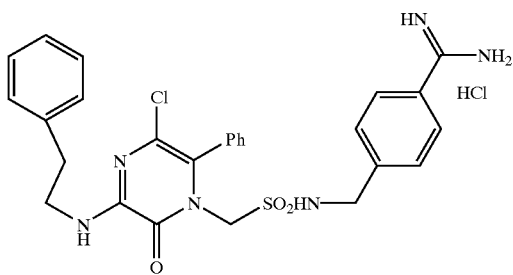

Example 70

Benzaldehyde (1 eq.) is added slowly by syringe to a solution of aminomethanesulfonic acid (1 eq.) in dichloromethane at room temperature. Trimethylsilyl cyanide (1 eq.) is added dropwise via syringe over a 10 minute period. The reaction is stirred for 4 hours at room temperature and then concentrated under reduced pressure. The residue is diluted with ethyl acetate, washed with brine, dried (MgSO$_4$), and concentrated. The residue is diluted with ethyl acetate (80 mL) and 9.9 M HCl (1.05 eq.) in ethanol is added (prepared by addition of 28.90 mL acetyl chloride to 41.0 mL cold ethanol), resulting in precipitation of the intermediate product EX-70A. The precipitate is collected by filtration, washed with ethyl ether, and dried to give pure product EX-70A.

To a suspension of 1 eq. of EX-70A in dry 1,2-dichlorobenzene (1.0 M) is added oxalyl chloride (4 eq.) with stirring at room temperature. The resulting suspension is heated at 100° C. for approximately 18 hours. The reaction is allowed to cool to room temperature and the volatiles are removed under reduced pressure. The remaining solution is passed through a silica gel column (hexane flush, followed by 50% ethyl acetate/hexanes). Concentration of the solution gives crude product EX-70B, which is purified by column chromatography.

Phenethylamine (3 eq.) is added to a solution of EX-70B (1 eq.) in ethyl acetate at room temperature. The resulting solution is heated at reflux for 18 hours. The solution is allowed to cool to room temperature, resulting in formation of a thick precipitate. The reaction mixture is diluted with ethyl acetate, washed with 0.5 N HCl, saturated NaHCO$_3$ and brine. The organic solution is dried (MgSO$_4$), filtered and concentrated to give the crude product. Recrystallization from ethyl acetate and hexanes affords pure product EX-70C.

A solution of 1 eq. of EX-70C in dichloromethane with several drops of dimethylformamide added is cooled to 0° C. Thionyl chloride (1.1 eq.) is added dropwise and the solution is slowly warmed to room temperature. After completion of the reaction, the volatile components are removed under reduced pressure and the product EX-70D is immediately used in the next step.

To the sulfonyl chloride EX-70D (1 eq.) in dichloromethane is added the amine, 4-(N-tert-butoxycarbonylamidino)benzylamine hydrochloride, in DMF with 5 eq. of N-methylmorpholine. After completion of the reaciton, polyaldehyde and/or polyamine resin (10 eq.) are added to remove any unreacted starting materials. The resins are filtered, rinsed with DMF/DCM (1:1) and the solvents are removed under reduced pressure to give pure product EX-70E.

To 1 eq. of EX-70E is added 40 eq. of 4 M HCl/dioxane. The resulting solution is stirred at room temperature overnight. The solution is concentrated and the crude product is triturated from solvent to afford pure product.

Methylene analogs of pyrazinones wherein a methylene is present as a replacement for the carbonyl of the acetamide at the N-1 position of the pyrazinone can be prepared using Scheme 4: Methylene Pyrazinone detailed below along with the specific Example 71.

Scheme 4
Methylene Pyrazinone

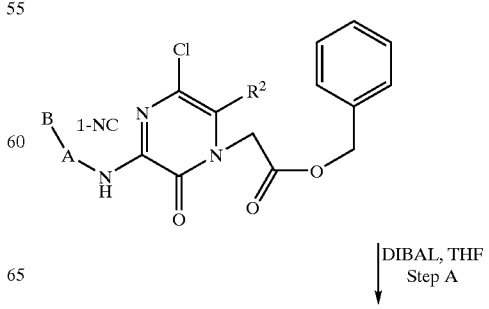

DIBAL, THF
Step A

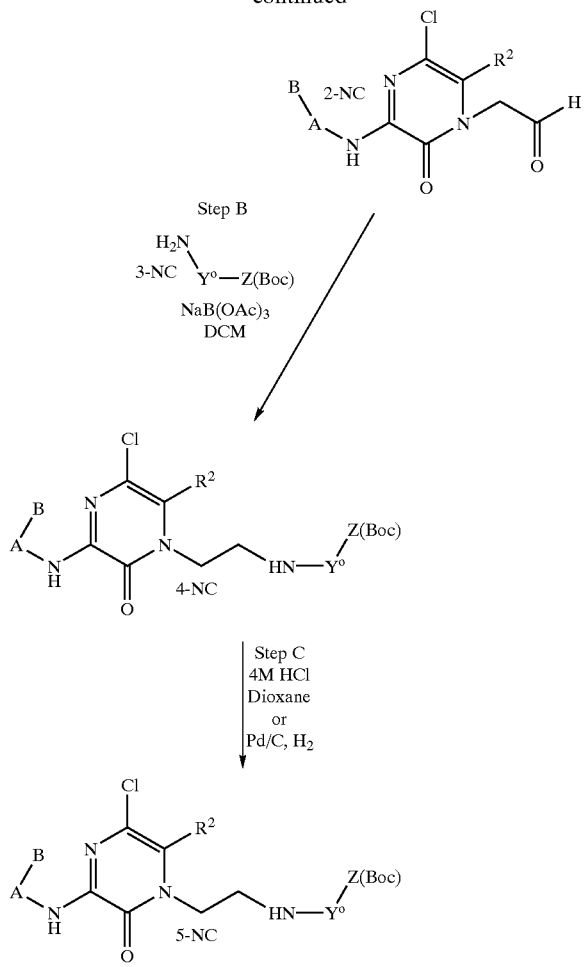

Example 71

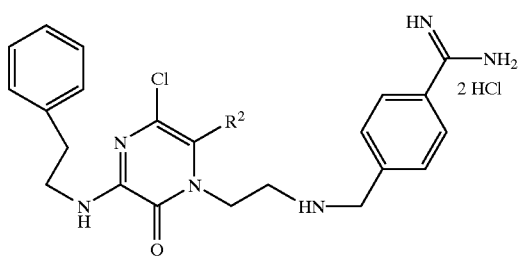

Diisobutylaluminum hydride (1.05 equiv.) is added over a period of 15 min to a cooled solution (−78° C.) of 1 eq. of 1-benzyloxycarbonylmethyl-chloro-6-phenyl-3-(2-phenylethylamino)pyrazinone in tetrahydrofuran. After stirring for 1 h at −78° C. the reaction is slowly quenched at −78° C. with cold methanol. The mixture is slowly poured into ice-cold 1N HCl and the aqueous mixture is extracted with ethyl acetate. The combined organic layers are washed with brine, dried with $MgSO_4$, filtered, and the solvents are removed under reduced pressure. The crude product is purified by column chromatography to afford purified product EX-71A.

Sodium triacetoxyborohydride (1.2 eq.) and a catalytic amount of acetic acid are added to a suspension of 1.0 eq. of EX-71A and 1.0 eq. of the amine, 4-(N-tert-butoxycarbonylamidino)benzylamine hydrochloride, in dichloromethane. The suspension quickly clears and becomes homogeneous. The reaction is stirred for several hours. The solution is cooled in an ice bath and basified with 1.0 N NaOH. The reaction mixture is diluted with dichloromethane and washed with brine. The organic solution is dried ($MgSO_4$), filtered and concentrated to give the crude product. The crude product is purified by silica gel chromatography to afford purified product EX-71B.

To 1 eq. of EX-71B is added 40 eq. of 4 M HCl/dioxane. The resulting solution is stirred at room temperature overnight. The solution is concentrated and the crude product is triturated from ethyl ether to afford pure product.

General Robotics and Experimental Procedure for the Robotic Parallel Synthesis of a Series of Amides E-i and Z-i from A-i Scheme 5 specifically illustrates the derivatization of the scaffold A-i to afford the desired product D-i in a parallel array synthesis format. In a parallel array synthesis reaction block, individual reaction products were prepared in each of multiple reaction block vessels in a spatially addressed format. A solution of the desired scaffold A-i (limiting amount) in acetonitrile (ACN) was added to the reaction vessels followed by a three-fold stoichiometric excess solution of the primary amine B-i in acetonitrile. Excess primary amine was used as a base and to effect complete conversion of scaffold A-i to product C-i. The reaction mixtures were incubated at 70° C. for 16–20 h. After cooling to ambient temperature, each reaction vessel was charged with one mL of methanol and an excess (3–4 fold stoichiometric excess) of aqueous potassium hydroxide. The reaction block was shaken vertically for 14–20 h on an orbital shaker at ambient temperature. The contents of each reaction vessel were then acidified with aqueous HCl. Each reaction vessel was then opened, and the solutions were evaporated to dryness under $N_2$ and/or a Savant apparatus. Polyamine resin R-1 (10–15 fold stoichiometric excess) was added to the solid carboxylic acid followed by dichloromethane and water (10:1). The mixture was shaken laterally for 14–20 h on an orbital shaker at ambient temperature (rotating the vials at least once so each side of the vial was agitated for a minimum of 2 h). The desired product D-i was sequestered away from the reaction by-products and excess reactants as the insoluble adduct D-x. Simple filtration of the insoluble resin-adduct D-x and rinsing of the resin cake with DMF, DCM, MeOH, and DCM afforded the desired resin-bound product. After drying the resin under vacuum for 2 h, an excess of HCl/dioxane (7–8 fold stoichiometric excess based on the loading of amine functionality) along with dichloromethane was added to each reaction vessel to cleave the desired product D-i from the resin. The reaction block was shaken laterally for 2–20 h on an orbital shaker at ambient temperature. Simple filtration of the solution, rinsing of the resin cake with dimethylformamide/dichloromethane, and evaporation of the solvents afforded the desired product D-i in purified form.

Scheme 6 and Scheme 7 illustrate the conversion of the carboxylic acid-containing scaffold D-i to the desired amide product E-i in a parallel synthesis format. A unique scaffold D-i was added as a solution in dichloromethane/dimethylformamide to each reaction vessel. A solution of hydroxybenzotriazole B-2 in dichloromethane/dimethylformamide was added to each reaction vessel, followed by the polymer-bound carbodiimide reagent R-2 (1.5 fold stoichiometric excess). The parallel reaction block was agitated vertically on an orbital shaker for 30 min to 1 h. A limiting amount of the same amine B-3 (0.8 equivalents) in DMF, along with a 3 fold stoichiometric excess of NMM if the amine B-3 was a salt, was added to the unique contents of each vessel. The parallel reaction block was then agitated vertically on an orbital shaker for 2–3 h at ambient temperature. An excess of the amine-functionalized resin R-1 and aldehyde resin R-3, along with dichloromethane solvent were added to each reaction vessel. The resin-charged reaction block was shaken vertically for 2 h on an orbital shaker at ambient temperature. The amine-containing resin R-1 sequestered B-2 and any remaining D-i as their resin-bound adducts, B-4 and D-2, respectively. The aldehyde-containing resin R-3 sequestered any unreacted B-3 as its resin-bound adduct R-5. Filtration of the insoluble resins and resin adducts R-1, R-2, R-3, R-4, R-5, B-4, and D-2 and subsequent rinsing of the vessel resin-bed with dichloromethane/dimethylformamide afforded filtrates containing the purified products E-i. Concentration of the filtrates afforded the purified products E-i, which were weighed and analyzed by LC/MS.

For those amines B-3 which contain a protecting group, a final deprotection step was required after the coupling reaction (Scheme 8). The residues E-i were dissolved in methanol, Pd/C was added, and the reaction mixtures were stirred under 10 psi of $H_2$ for 16–20 h. The mixtures were filtered through Celite, rinsed with methanol and concentrated to afford pure products Z-i, which were weighed and analyzed by LC/MS. If necessary, the products were purified by reverse-phase HPLC. Conversely, the deprotection step was done, as needed, in the presence of ammonium formate (5 fold stoichiometric excess) in place of the 10 psi of $H_2$.

A third method of deprotection uses TMSI generated in situ. The residues E-i were dissolved in acetonitrile. Sodium iodide and TMSCl (5 fold stoichiometric excess of each) were added, and the reaction mixtures were agitated vertically at 55° C. for 14–20 h. Methanol and (N,N-dimethyl)aminomethylpolystyrene resin were added to each vessel, and the mixtures were agitated for another 3 h. The mixtures were filtered through Celite, rinsed with acetonitrile and concentrated to afford products Z-i, which were weighed and analyzed by LC/MS. If necessary, the products were purified by reverse-phase HPLC.

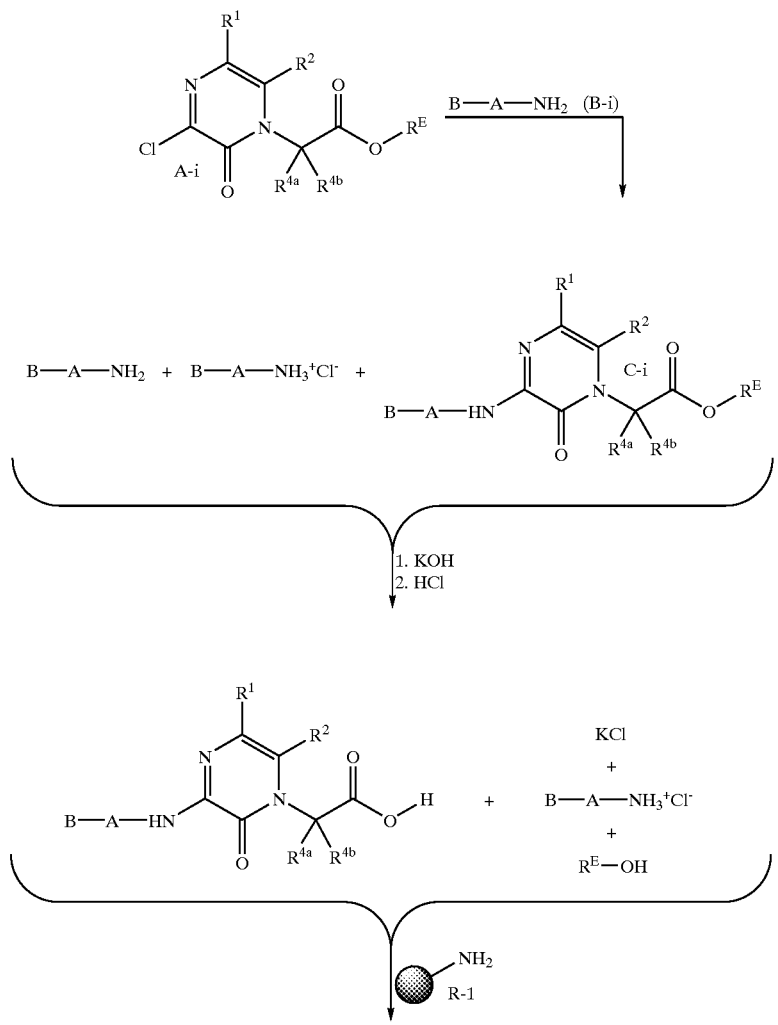

Scheme 5
General Robotic Synthesis

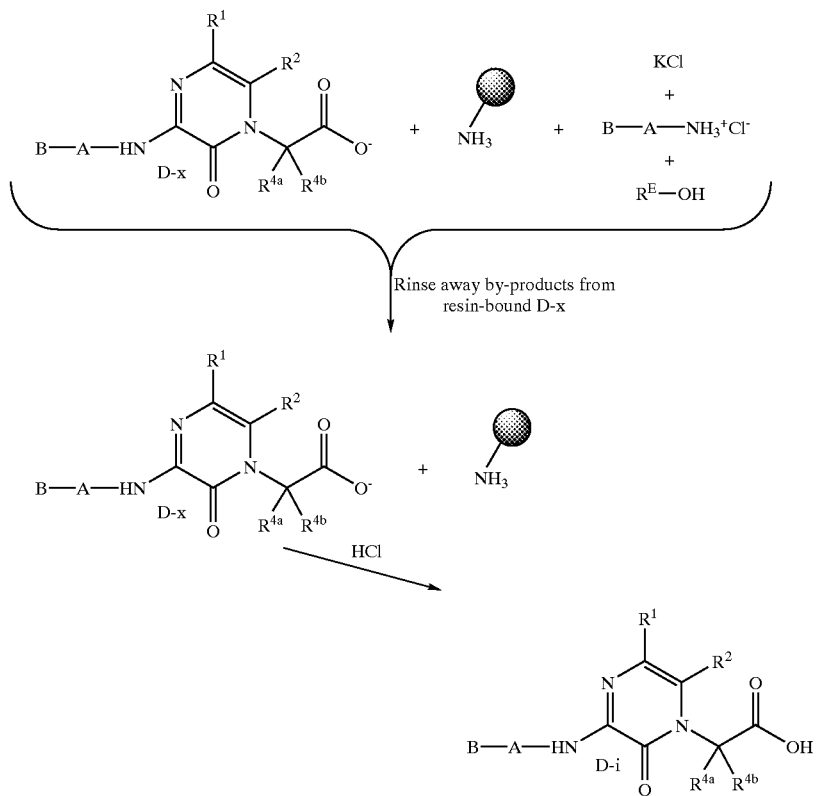
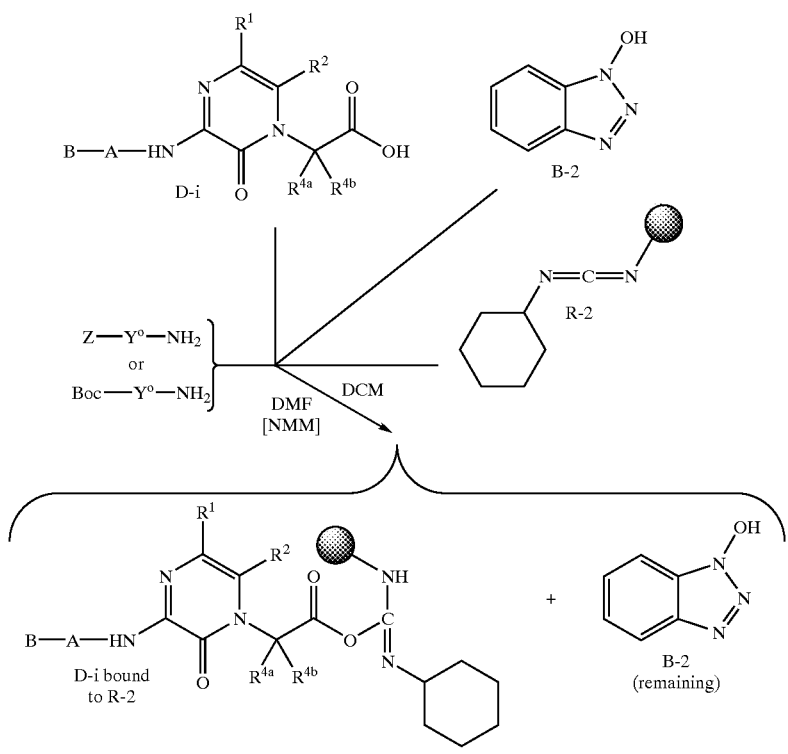
Scheme 6
General Robotic Synthesis (Continued)

-continued
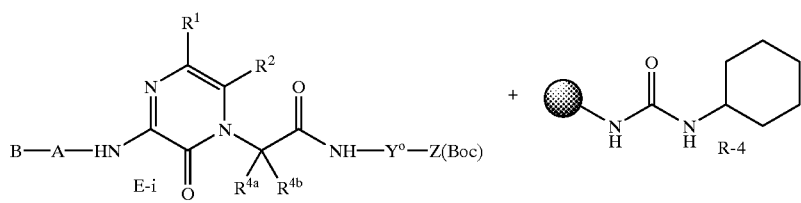
Scheme 7
General Robotic Synthesis (Continued)
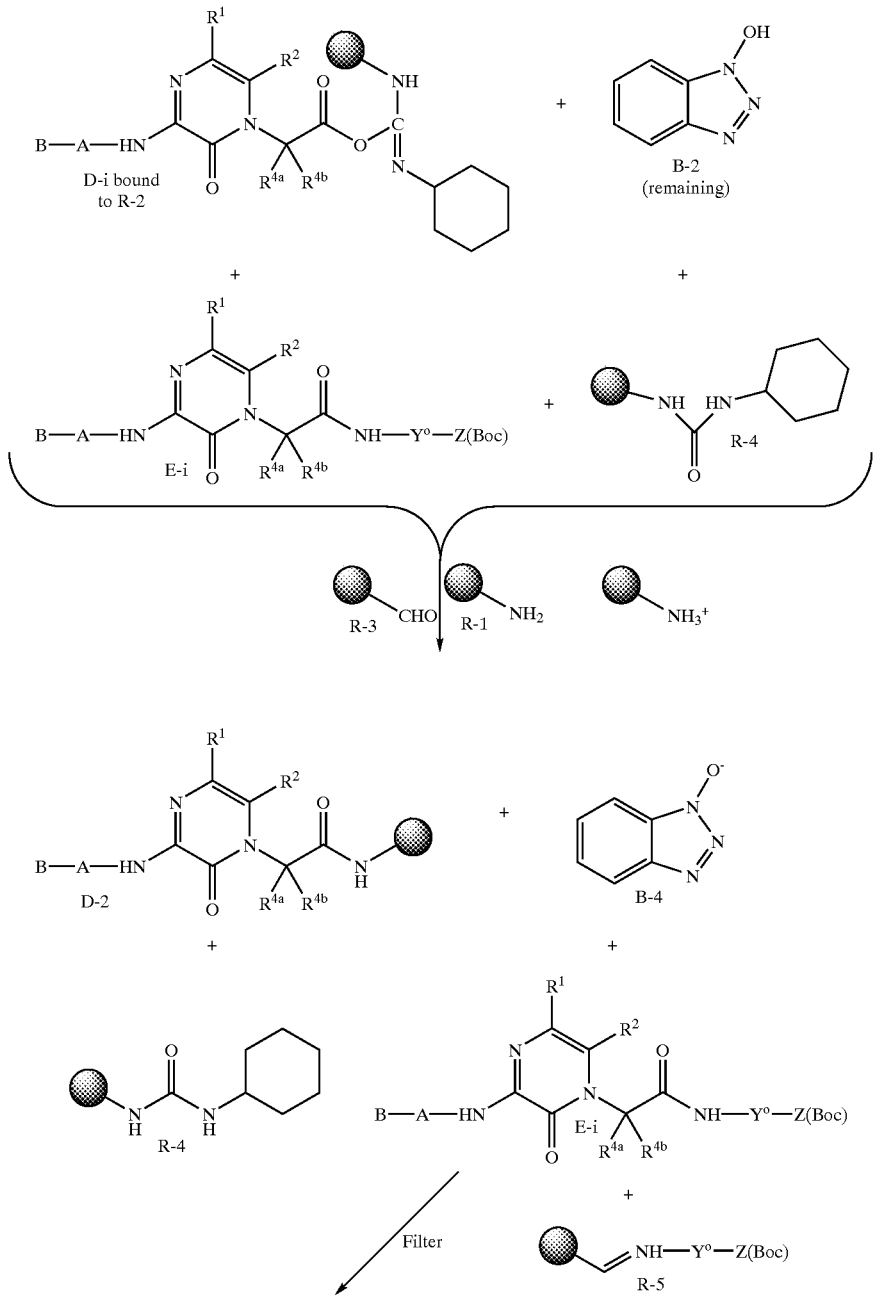

-continued

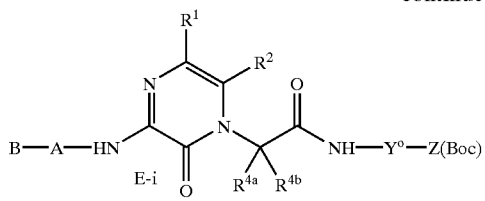

Scheme 8
General Robotic Synthesis (Concluded)

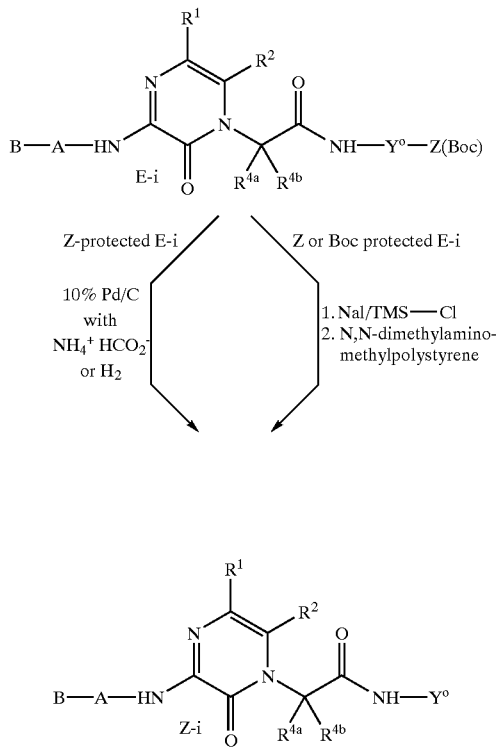

Although Schemes 5, 6, 7, and 8 describe the use of parallel array chemical library technology to prepare compounds of general formulae D-i, E-i and Z-i, it is noted that one with ordinary skill in the art of classical synthetic organic chemistry would be able to prepare D-i, E-i, and Z-i by conventional means (one compound prepared at a time in conventional glassware and purified by conventional means such as chromatography and/or crystallization).

The various functionalized resins utilized to prepare and purify parallel reaction mixtures, their source commercially or in the scientific literature, and the three representations (ie, the R number, an abbreviated functional structure, and the actual structural unit bound to the resin for each) are summarized below as follows:

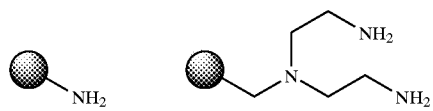

R-1

R-1 Reference: Prepared as reported in J. J. Parlow, D. A. Mischke, and S. S. Woodard, *J. Organic Chemistry*, 62, 5908–5919 (1997)

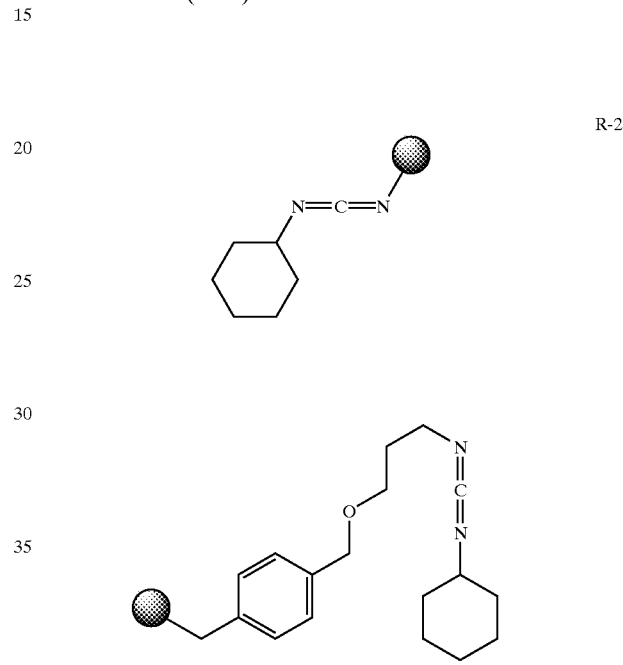

R-2 Reference: Polystyrene bound N-cyclohexylcarbodiimide (Argonaut Catalog Number 800371

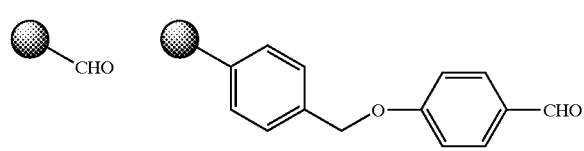

R-3 Reference: Polystyrene bound benzaldehyde Novabiochem Catalog Number 01-640182

The specific compounds prepared, by using the General Robotics and Experimental Procedure, Schemes 5 through 8, and general synthetic methods and processes disclosed herein, are listed below in Tables 4 through Table 7. Tables 4 through Table 7 further summarize the mass spectral characterization data that confirmed the indicated structure for each compound of the present invention disclosed in these tables.

TABLE 4

Structures of Pyrazinones Prepared by General Robotic and Experimental Procedures General Structure

| Ex. No. | R² | B-A- | Y⁰ | R¹ | MW (m/z + 1) |
|---|---|---|---|---|---|
| 73 | 5-amino-2-fluorophenyl | isopropyl | 4-amidino-2-fluorobenzyl | Cl | 504 |
| 74 | 2-chloro-5-pyridyl | isopropyl | 4-amidino-2-fluorobenzyl | Cl | 506 |
| 75 | 3-pyridyl | isopropyl | 4-amidinobenzyl | Cl | 454 |
| 76 | 5-amino-2-methyl-thiophenyl | isopropyl | 4-amidinobenzyl | Cl | 515 |
| 77 | 3-nitrophenyl | 2-phenylethyl | 4-amidinobenzyl | Cl | 560.2 |
| 78 | 2-methylphenyl | 2-phenylethyl | 4-amidinobenzyl | Cl | 529.4 |
| 79 | 4-methylphenyl | 2-phenylethyl | 4-amidinobenzyl | Cl | 529.3 |
| 80 | 1-naphthyl | 2-phenylethyl | 4-amidinobenzyl | Cl | 565.3 |
| 81 | 3-methylphenyl | 2-phenylethyl | 4-amidinobenzyl | Cl | 529.5 |
| 82 | 2-naphthyl | 2-phenylethyl | 4-amidinobenzyl | Cl | 564.9 |
| 83 | 3-methylphenyl | 2-phenylethyl | 4-amidinobenzyl | H | 495.8 |
| 84 | 3-methylphenyl | 2-phenylethyl | 4-amidinobenzyl | H | 495.5 |
| 85 | 3-methylphenyl | 2-phenylethyl | 4-amidinobenzyl | H | 495.4 |
| 86 | 3-aminophenyl | 2-phenylethyl | 4-amidinobenzyl | Cl | 530.3 |
| 87 | 3-aminophenyl | 2-(3-chlorophenyl)ethyl | 4-amidinobenzyl | Cl | 563.9 |
| 88 | 3-aminophenyl | benzyl | 4-amidinobenzyl | Cl | 516.2 |
| 89 | 3-aminophenyl | cyclobutyl | 2-phenylethyl | Cl | 452.3 |
| 90 | 3-aminophenyl | cyclobutyl | 4-amidinobenzyl | Cl | 480.5 |
| 91 | 3-aminophenyl | benzyl | 5-guanidino- | Cl | 608.4 |

TABLE 4-continued

Structures of Pyrazinones Prepared by General Robotic and Experimental Procedures

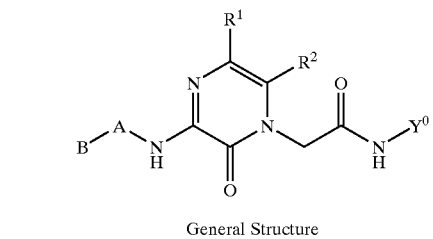

General Structure

| Ex. No. | R² | B-A- | Y⁰ | R¹ | MW (m/z + 1) |
|---|---|---|---|---|---|
| 92 | 3-aminophenyl | cyclobutyl | 1-oxo-1-(2-thiazolyl)-2-pentyl | H | 446.2 |
| 93 | 3-aminophenyl | t-butyl | 4-amidinobenzyl | Cl | 482 |
| 94 | 3-aminophenyl | N,N-dimethylamino | 4-amidinobenzyl | Cl | 469.2 |
| 95 | 3-(N-methylamino)-phenyl | 2-phenylethyl | 4-amidinobenzyl | Cl | 543.9 |
| 96 | 3-(N-methylamino)-phenyl | isopropyl | 4-amidinobenzyl | Cl | 481.6 |
| 97 | 2-methyl-3-aminophenyl | isopropyl | 4-amidinobenzyl | Cl | 482.2 |
| 98 | 2-methyl-3-aminophenyl | isopropyl | 4-amidinobenzyl | H | 448.8 |
| 99 | 3-aminophenyl | cyclobutyl | benzyl | Cl | 438.4 |

TABLE 5

Structures of Pyrazinones Prepared by General Robotic and Experimental Procedures

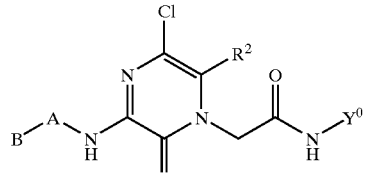

General Structure

| Ex. No. | R² | B—A— | Y⁰ | MW (m/z + 1) |
|---|---|---|---|---|
| E-0001 | methyl | benzyl | 2-(4-pyridyl)ethyl | 412 |
| E-0002 | methyl | 2-phenylethyl | 2-(4-pyridyl)ethyl | 426 |
| E-0003 | methyl | 2-(3-chlorophenyl)ethyl | 2-(4-pyridyl)ethyl | 460 |
| E-0004 | methyl | 2-(4-chlorophenyl)ethyl | 2-(4-pyridyl)ethyl | 460 |
| E-0005 | methyl | 2-(3-pyridyl)ethyl | 2-(4-pyridyl)ethyl | 427 |
| E-0006 | methyl | 2-(4-pyridyl)ethyl | 2-(4-pyridyl)ethyl | 427 |
| E-0007 | methyl | 2-(4-morpholinyl)ethyl | 2-(4-pyridyl)ethyl | 435 |

TABLE 5-continued

Structures of Pyrazinones Prepared by General Robotic and Experimental Procedures

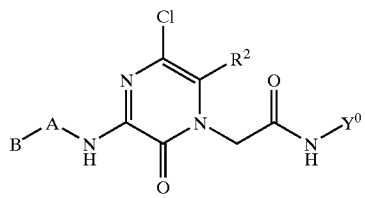

General Structure

| Ex. No. | R² | B—A— | Y⁰ | MW (m/z + 1) |
|---|---|---|---|---|
| E-0008 | methyl | 4-pyridylmethyl | 2-(4-pyridyl)ethyl | 413 |
| E-0009 | phenyl | benzyl | 2-(4-pyridyl)ethyl | 474 |
| E-0010 | phenyl | 2-phenylethyl | 2-(4-pyridyl)ethyl | 488 |
| E-0011 | phenyl | 2-(3-chlorophenyl)ethyl | 2-(4-pyridyl)ethyl | 522 |
| E-0012 | phenyl | 2-(4-chlorophenyl)ethyl | 2-(4-pyridyl)ethyl | 522 |
| E-0013 | phenyl | 2-(3-pyridyl)ethyl | 2-(4-pyridyl)ethyl | 489 |
| E-0014 | phenyl | 2-(4-pyridyl)ethyl | 2-(4-pyridyl)ethyl | 489 |
| E-0015 | phenyl | 2-(4-morpholinyl)ethyl | 2-(4-pyridyl)ethyl | 497 |
| E-0016 | phenyl | 4-pyridylmethyl | 2-(4-pyridyl)ethyl | 475 |
| E-0017 | 4-chlorophenyl | benzyl | 2-(4-pyridyl)ethyl | 508 |
| E-0018 | 4-chlorophenyl | 2-phenylethyl | 2-(4-pyridyl)ethyl | 522 |
| E-0019 | 4-chlorophenyl | 2-(3-chlorophenyl)ethyl | 2-(4-pyridyl)ethyl | 557 |
| E-0020 | 4-chlorophenyl | 2-(4-chlorophenyl)ethyl | 2-(4-pyridyl)ethyl | 557 |
| E-0021 | 4-chlorophenyl | 2-(3-pyridyl)ethyl | 2-(4-pyridyl)ethyl | 523 |
| E-0022 | 4-chlorophenyl | 2-(4-pyridyl)ethyl | 2-(4-pyridyl)ethyl | 523 |
| E-0023 | 4-chlorophenyl | 2-(4-morpholinyl)ethyl | 2-(4-pyridyl)ethyl | 531 |
| E-0024 | 4-chlorophenyl | 4-pyridylmethyl | 2-(4-pyridyl)ethyl | 509 |
| E-0025 | 4-chlorophenyl | benzyl | 2-(4-pyridyl)ethyl | 508 |
| E-0026 | 4-chlorophenyl | 2-phenylethyl | 2-(4-pyridyl)ethyl | 522 |
| E-0027 | 4-chlorophenyl | 2-(3-chlorophenyl)ethyl | 2-(4-pyridyl)ethyl | 557 |
| E-0028 | 4-chlorophenyl | 2-(4-chlorophenyl)ethyl | 2-(4-pyridyl)ethyl | 557 |
| E-0029 | 4-chlorophenyl | 2-(3-pyridyl)ethyl | 2-(4-pyridyl)ethyl | 523 |
| E-0030 | 4-chlorophenyl | 2-(4-pyridyl)ethyl | 2-(4-pyridyl)ethyl | 523 |
| E-0031 | 4-chlorophenyl | 2-(4-morpholinyl)ethyl | 2-(4-pyridyl)ethyl | 531 |
| E-0032 | 4-chlorophenyl | 4-pyridylmethyl | 2-(4-pyridyl)ethyl | 509 |
| E-0033 | 4-methoxyphenyl | benzyl | 2-(4-pyridyl)ethyl | 504 |
| E-0034 | 4-methoxyphenyl | 2-phenylethyl | 2-(4-pyridyl)ethyl | 518 |
| E-0035 | 4-methoxyphenyl | 2-(3-chlorophenyl)ethyl | 2-(4-pyridyl)ethyl | 552 |
| E-0036 | 4-methoxyphenyl | 2-(4-chlorophenyl)ethyl | 2-(4-pyridyl)ethyl | 552 |
| E-0037 | 4-methoxyphenyl | 2-(3-pyridyl)ethyl | 2-(4-pyridyl)ethyl | 519 |
| E-0038 | 4-methoxyphenyl | 2-(4-pyridyl)ethyl | 2-(4-pyridyl)ethyl | 519 |
| E-0039 | 4-methoxyphenyl | 2-(4-morpholinyl)ethyl | 2-(4-pyridyl)ethyl | 527 |
| E-0040 | 4-methoxyphenyl | 4-pyridylmethyl | 2-(4-pyridyl)ethyl | 505 |
| E-0041 | 3,4-methylene-dioxyphenyl | benzyl | 2-(4-pyridyl)ethyl | 518 |
| E-0042 | 3,4-methylene-dioxyphenyl | 2-phenylethyl | 2-(4-pyridyl)ethyl | 532 |
| E-0043 | 3,4-methylene-dioxyphenyl | 2-(3-chlorophenyl)ethyl | 2-(4-pyridyl)ethyl | 566 |
| E-0044 | 3,4-methylene-dioxyphenyl | 2-(4-chlorophenyl)ethyl | 2-(4-pyridyl)ethyl | 566 |
| E-0045 | 3,4-methylene-dioxyphenyl | 2-(3-pyridyl)ethyl | 2-(4-pyridyl)ethyl | 533 |
| E-0046 | 3,4-methylene-dioxyphenyl | 2-(4-pyridyl)ethyl | 2-(4-pyridyl)ethyl | 533 |
| E-0047 | 3,4-methylene-dioxyphenyl | 2-(4-morpholinyl)ethyl | 2-(4-pyridyl)ethyl | 541 |
| E-0048 | 3,4-methylene-dioxyphenyl | 4-pyridylmethyl | 2-(4-pyridyl)ethyl | 519 |
| E-0049 | 4-biphenyl | benzyl | 2-(4-pyridyl)ethyl | 550 |
| E-0050 | 4-biphenyl | 2-phenylethyl | 2-(4-pyridyl)ethyl | 564 |
| E-0051 | 4-biphenyl | 2-(3-chlorophenyl)ethyl | 2-(4-pyridyl)ethyl | 599 |
| E-0052 | 4-biphenyl | 2-(4-chlorophenyl)ethyl | 2-(4-pyridyl)ethyl | 599 |
| E-0053 | 4-biphenyl | 2-(3-pyridyl)ethyl | 2-(4-pyridyl)ethyl | 565 |
| E-0054 | 4-biphenyl | 2-(4-pyridyl)ethyl | 2-(4-pyridyl)ethyl | 565 |
| E-0055 | 4-biphenyl | 2-(4-morpholinyl)ethyl | 2-(4-pyridyl)ethyl | 573 |
| E-0056 | 4-biphenyl | 4-pyridylmethyl | 2-(4-pyridyl)ethyl | 551 |
| E-0057 | benzyl | benzyl | 2-(4-pyridyl)ethyl | 488 |
| E-0058 | benzyl | 2-phenylethyl | 2-(4-pyridyl)ethyl | 502 |
| E-0059 | benzyl | 2-(3-chlorophenyl)ethyl | 2-(4-pyridyl)ethyl | 536 |
| E-0060 | benzyl | 2-(4-chlorophenyl)ethyl | 2-(4-pyridyl)ethyl | 536 |
| E-0061 | benzyl | 2-(3-pyridyl)ethyl | 2-(4-pyridyl)ethyl | 503 |
| E-0062 | benzyl | 2-(4-pyridyl)ethyl | 2-(4-pyridyl)ethyl | 503 |

TABLE 5-continued

Structures of Pyrazinones Prepared by General Robotic and Experimental Procedures

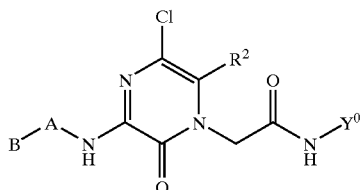

General Structure

| Ex. No. | R² | B—A— | Y⁰ | MW (m/z + 1) |
|---|---|---|---|---|
| E-0063 | benzyl | 2-(4-morpholinyl)ethyl | 2-(4-pyridyl)ethyl | 511 |
| E-0064 | benzyl | 4-pyridylmethyl | 2-(4-pyridyl)ethyl | 489 |
| E-0065 | 2-phenylethyl | benzyl | 2-(4-pyridyl)ethyl | 502 |
| E-0066 | 2-phenylethyl | 2-phenylethyl | 2-(4-pyridyl)ethyl | 516 |
| E-0067 | 2-phenylethyl | 2-(3-chlorophenyl)ethyl | 2-(4-pyridyl)ethyl | 550 |
| E-0068 | 2-phenylethyl | 2-(4-chlorophenyl)ethyl | 2-(4-pyridyl)ethyl | 550 |
| E-0069 | 2-phenylethyl | 2-(3-pyridyl)ethyl | 2-(4-pyridyl)ethyl | 517 |
| E-0070 | 2-phenylethyl | 2-(4-pyridyl)ethyl | 2-(4-pyridyl)ethyl | 517 |
| E-0071 | 2-phenylethyl | 2-(4-morpholinyl)ethyl | 2-(4-pyridyl)ethyl | 525 |
| E-0072 | 2-phenylethyl | 4-pyridylmethyl | 2-(4-pyridyl)ethyl | 503 |
| E-0073 | 3-chlorophenyl | benzyl | 2-(4-pyridyl)ethyl | 508 |
| E-0074 | 3-chlorophenyl | benzyl | 2-(3-pyridyl)ethyl | 508 |
| E-0075 | 3-chlorophenyl | benzyl | 4-piperidinylmethyl | 573 |
| E-0076 | 3-chlorophenyl | 2-phenylethyl | 2-(4-pyridyl)ethyl | 522 |
| E-0077 | 3-chlorophenyl | 2-phenylethyl | 2-(3-pyridyl)ethyl | 522 |
| E-0078 | 3-chlorophenyl | 2-phenylethyl | 4-piperidinylmethyl | 587 |
| E-0079 | 3-chlorophenyl | 2-(3-chlorophenyl)ethyl | 2-(4-pyridyl)ethyl | 557 |
| E-0080 | 3-chlorophenyl | 2-(3-chlorophenyl)ethyl | 2-(3-pyridyl)ethyl | 557 |
| E-0081 | 3-chlorophenyl | 2-(3-chlorophenyl)ethyl | 4-piperidinylmethyl | 622 |
| E-0082 | 3-chlorophenyl | 2-(4-chlorophenyl)ethyl | 2-(4-pyridyl)ethyl | 557 |
| E-0083 | 3-chlorophenyl | 2-(4-chlorophenyl)ethyl | 2-(3-pyridyl)ethyl | 557 |
| E-0084 | 3-chlorophenyl | 2-(4-chlorophenyl)ethyl | 4-piperidinylmethyl | 622 |
| E-0085 | 3-chlorophenyl | benzyl | 2-(4-pyridyl)ethyl | 508 |
| E-0086 | 3-chlorophenyl | benzyl | 2-(3-pyridyl)ethyl | 508 |
| E-0087 | 3-chlorophenyl | benzyl | 4-piperidinylmethyl | 573 |
| E-0088 | 3-chlorophenyl | 2-phenylethyl | 2-(4-pyridyl)ethyl | 522 |
| E-0089 | 3-chlorophenyl | 2-phenylethyl | 2-(3-pyridyl)ethyl | 522 |
| E-0090 | 3-chlorophenyl | 2-phenylethyl | 4-piperidinylmethyl | 587 |
| E-0091 | 3-chlorophenyl | 2-(3-chlorophenyl)ethyl | 2-(4-pyridyl)ethyl | 557 |
| E-0092 | 3-chlorophenyl | 2-(3-chlorophenyl)ethyl | 2-(3-pyridyl)ethyl | 557 |
| E-0093 | 3-chlorophenyl | 2-(3-chlorophenyl)ethyl | 4-piperidinylmethyl | 622 |
| E-0094 | 3-chlorophenyl | 2-(4-chlorophenyl)ethyl | 2-(4-pyridyl)ethyl | 557 |
| E-0095 | 3-chlorophenyl | 2-(4-chlorophenyl)ethyl | 2-(3-pyridyl)ethyl | 557 |
| E-0096 | 3-chlorophenyl | 2-(4-chlorophenyl)ethyl | 4-piperidinylmethyl | 622 |
| E-0097 | 4-methoxyphenyl | benzyl | 2-(4-pyridyl)ethyl | 504 |
| E-0098 | 4-methoxyphenyl | benzyl | 2-(3-pyridyl)ethyl | 504 |
| E-0099 | 4-methoxyphenyl | benzyl | 4-piperidinylmethyl | 569 |
| E-0100 | 4-methoxyphenyl | 2-phenylethyl | 2-(4-pyridyl)ethyl | 518 |
| E-0101 | 4-methoxyphenyl | 2-phenylethyl | 2-(3-pyridyl)ethyl | 518 |
| E-0102 | 4-methoxyphenyl | 2-phenylethyl | 4-piperidinylmethyl | 583 |
| E-0103 | 4-methoxyphenyl | 2-(3-chlorophenyl)ethyl | 2-(4-pyridyl)ethyl | 552 |
| E-0104 | 4-methoxyphenyl | 2-(3-chlorophenyl)ethyl | 2-(3-pyridyl)ethyl | 552 |
| E-0105 | 4-methoxyphenyl | 2-(3-chlorophenyl)ethyl | 4-piperidinylmethyl | 617 |
| E-0106 | 4-methoxyphenyl | 2-(4-chlorophenyl)ethyl | 2-(4-pyridyl)ethyl | 552 |
| E-0107 | 4-methoxyphenyl | 2-(4-chlorophenyl)ethyl | 2-(3-pyridyl)ethyl | 552 |
| E-0108 | 4-methoxyphenyl | 2-(4-chlorophenyl)ethyl | 4-piperidinylmethyl | 617 |
| E-0109 | 4-biphenyl | benzyl | 2-(4-pyridyl)ethyl | 550 |
| E-0110 | 4-biphenyl | benzyl | 2-(3-pyridyl)ethyl | 550 |
| E-0111 | 4-biphenyl | benzyl | 4-piperidinylmethyl | 615 |
| E-0112 | 4-biphenyl | 2-phenylethyl | 2-(4-pyridyl)ethyl | 564 |
| E-0113 | 4-biphenyl | 2-phenylethyl | 2-(3-pyridyl)ethyl | 564 |
| E-0114 | 4-biphenyl | 2-phenylethyl | 4-piperidinylmethyl | 629 |
| E-0115 | 4-biphenyl | 2-(3-chlorophenyl)ethyl | 2-(4-pyridyl)ethyl | 599 |
| E-0116 | 4-biphenyl | 2-(3-chlorophenyl)ethyl | 2-(3-pyridyl)ethyl | 599 |
| E-0117 | 4-biphenyl | 2-(3-chlorophenyl)ethyl | 4-piperidinylmethyl | 663 |
| E-0118 | 4-biphenyl | 2-(4-chlorophenyl)ethyl | 2-(4-pyridyl)ethyl | 599 |
| E-0119 | 4-biphenyl | 2-(4-chlorophenyl)ethyl | 2-(3-pyridyl)ethyl | 599 |
| E-0120 | 4-biphenyl | 2-(4-chlorophenyl)ethyl | 4-piperidinylmethyl | 663 |
| E-0121 | methyl | benzyl | 4-piperidinylmethyl | 477 |
| E-0122 | methyl | 2-phenylethyl | 4-piperidinylmethyl | 491 |
| E-0123 | methyl | 2-(3-chlorophenyl)ethyl | 4-piperidinylmethyl | 525 |
| E-0124 | methyl | 2-(4-chlorophenyl)ethyl | 4-piperidinylmethyl | 525 |
| E-0125 | methyl | 2-(3-pyridyl)ethyl | 4-piperidinylmethyl | 528 |

TABLE 5-continued

Structures of Pyrazinones Prepared by General Robotic and Experimental Procedures

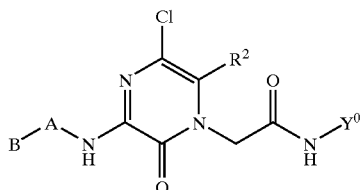

General Structure

| Ex. No. | R² | B—A— | Y⁰ | MW (m/z + 1) |
|---|---|---|---|---|
| E-0126 | methyl | 2-(4-pyridyl)ethyl | 4-piperidinylmethyl | 528 |
| E-0127 | methyl | 2-(4-morpholinyl)ethyl | 4-piperidinylmethyl | 536 |
| E-0128 | methyl | 2-(1-methylimidazol-4-yl)ethyl | 4-piperidinylmethyl | 531 |
| E-0129 | methyl | 2-(1-methylimidazol-5-yl)ethyl | 4-piperidinylmethyl | 531 |
| E-0130 | methyl | 4-pyridylmethyl | 4-piperidinylmethyl | 514 |
| E-0131 | phenyl | benzyl | 4-piperidinylmethyl | 539 |
| E-0132 | phenyl | 2-phenylethyl | 4-piperidinylmethyl | 553 |
| E-0133 | phenyl | 2-(3-chlorophenyl)ethyl | 4-piperidinylmethyl | 587 |
| E-0134 | phenyl | 2-(4-chlorophenyl)ethyl | 4-piperidinylmethyl | 587 |
| E-0135 | phenyl | 2-(3-pyridyl)ethyl | 4-piperidinylmethyl | 590 |
| E-0136 | phenyl | 2-(4-pyridyl)ethyl | 4-piperidinylmethyl | 590 |
| E-0137 | phenyl | 2-(4-morpholinyl)ethyl | 4-piperidinylmethyl | 598 |
| E-0138 | phenyl | 2-(1-methylimidazol-4-yl)ethyl | 4-piperidinylmethyl | 593 |
| E-0139 | phenyl | 2-(1-methylimidazol-5-yl)ethyl | 4-piperidinylmethyl | 593 |
| E-0140 | phenyl | 4-pyridylmethyl | 4-piperidinylmethyl | 576 |
| E-0141 | 4-chlorophenyl | benzyl | 4-piperidinylmethyl | 573 |
| E-0142 | 4-chlorophenyl | 2-phenylethyl | 4-piperidinylmethyl | 587 |
| E-0143 | 4-chlorophenyl | 2-(3-chlorophenyl)ethyl | 4-piperidinylmethyl | 622 |
| E-0144 | 4-chlorophenyl | 2-(4-chlorophenyl)ethyl | 4-piperidinylmethyl | 622 |
| E-0145 | 4-chlorophenyl | 2-(3-pyridyl)ethyl | 4-piperidinylmethyl | 625 |
| E-0146 | 4-chlorophenyl | 2-(4-pyridyl)ethyl | 4-piperidinylmethyl | 625 |
| E-0147 | 4-chlorophenyl | 2-(4-morpholinyl)ethyl | 4-piperidinylmethyl | 633 |
| E-0148 | 4-chlorophenyl | 2-(1-methylimidazol-4-yl)ethyl | 4-piperidinylmethyl | 628 |
| E-0149 | 4-chlorophenyl | 2-(1-methylimidazol-5-yl)ethyl | 4-piperidinylmethyl | 628 |
| E-0150 | 4-chlorophenyl | 4-pyridylmethyl | 4-piperidinylmethyl | 611 |
| E-0151 | 4-chlorophenyl | benzyl | 4-piperidinylmethyl | 573 |
| E-0152 | 4-chlorophenyl | 2-phenylethyl | 4-piperidinylmethyl | 587 |
| E-0153 | 4-chlorophenyl | 2-(3-chlorophenyl)ethyl | 4-piperidinylmethyl | 622 |
| E-0154 | 4-chlorophenyl | 2-(4-chlorophenyl)ethyl | 4-piperidinylmethyl | 622 |
| E-0155 | 4-chlorophenyl | 2-(3-pyridyl)ethyl | 4-piperidinylmethyl | 625 |
| E-0156 | 4-chlorophenyl | 2-(4-pyridyl)ethyl | 4-piperidinylmethyl | 625 |
| E-0157 | 4-chlorophenyl | 2-(4-morpholinyl)ethyl | 4-piperidinylmethyl | 633 |
| E-0158 | 4-chlorophenyl | 2-(1-methylimidazol-4-yl)ethyl | 4-piperidinylmethyl | 628 |
| E-0159 | 4-chlorophenyl | 2-(1-methylimidazol-5-yl)ethyl | 4-piperidinylmethyl | 628 |
| E-0160 | 4-chlorophenyl | 4-pyridylmethyl | 4-piperidinylmethyl | 611 |
| E-0161 | 4-methoxyphenyl | benzyl | 4-piperidinylmethyl | 569 |
| E-0162 | 4-methoxyphenyl | 2-phenylethyl | 4-piperidinylmethyl | 583 |
| E-0163 | 4-methoxyphenyl | 2-(3-chlorophenyl)ethyl | 4-piperidinylmethyl | 617 |
| E-0164 | 4-methoxyphenyl | 2-(4-chlorophenyl)ethyl | 4-piperidinylmethyl | 617 |
| E-0165 | 4-methoxyphenyl | 2-(3-pyridyl)ethyl | 4-piperidinylmethyl | 620 |
| E-0166 | 4-methoxyphenyl | 2-(4-pyridyl)ethyl | 4-piperidinylmethyl | 620 |
| E-0167 | 4-methoxyphenyl | 2-(4-morpholinyl)ethyl | 4-piperidinylmethyl | 628 |
| E-0168 | 4-methoxyphenyl | 2-(1-methylimidazol-4-yl)ethyl | 4-piperidinylmethyl | 623 |
| E-0169 | 4-methoxyphenyl | 2-(1-methylimidazol-5-yl)ethyl | 4-piperidinylmethyl | 623 |
| E-0170 | 4-methoxyphenyl | 4-pyridylmethyl | 4-piperidinylmethyl | 606 |
| E-0171 | 3,4-methylene-dioxyphenyl | benzyl | 4-piperidinylmethyl | 583 |
| E-0172 | 3,4-methylene-dioxyphenyl | 2-phenylethyl | 4-piperidinylmethyl | 597 |
| E-0173 | 3,4-methylene-dioxyphenyl | 2-(3-chlorophenyl)ethyl | 4-piperidinylmethyl | 631 |
| E-0174 | 3,4-methylene-dioxyphenyl | 2-(4-chlorophenyl)ethyl | 4-piperidinylmethyl | 631 |

TABLE 5-continued

Structures of Pyrazinones Prepared by General Robotic and Experimental Procedures

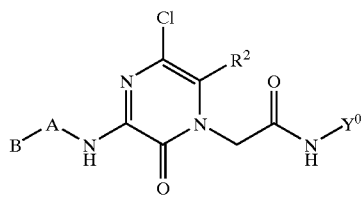

General Structure

| Ex. No. | R² | B—A— | Y⁰ | MW (m/z + 1) |
|---|---|---|---|---|
| E-0175 | 3,4-methylene-dioxyphenyl | 2-(3-pyridyl)ethyl | 4-piperidinylmethyl | 634 |
| E-0176 | 3,4-methylene dioxyphenyl | 2-(4-pyridyl)ethyl | 4-piperidinylmethyl | 634 |
| E-0177 | 3,4-methylene-dioxyphenyl | 2-(4-morpholinyl)ethyl | 4-piperidinylmethyl | 642 |
| E-0178 | 3,4-methylene-dioxyphenyl | 2-(1-methylimidazol-4-yl)ethyl | 4-piperidinylmethyl | 637 |
| E-0179 | 3,4-methylene-dioxyphenyl | 2-(1-methylimidazol-5-yl)ethyl | 4-piperidinylmethyl | 637 |
| E-0180 | 3,4-methylene-dioxyphenyl | 4-pyridylmethyl | 4-piperidinylmethyl | 620 |
| E-0181 | 4-biphenyl | benzyl | 4-piperidinylmethyl | 615 |
| E-0182 | 4-biphenyl | 2-phenylethyl | 4-piperidinylmethyl | 629 |
| E-0183 | 4-biphenyl | 2-(3-chlorophenyl)ethyl | 4-piperidinylmethyl | 663 |
| E-0184 | 4-biphenyl | 2-(4-chlorophenyl)ethyl | 4-piperidinylmethyl | 663 |
| E-0185 | 4-biphenyl | 2-(3-pyridyl)ethyl | 4-piperidinylmethyl | 666 |
| E-0186 | 4-biphenyl | 2-(4-pyridyl)ethyl | 4-piperidinylmethyl | 666 |
| E-0187 | 4-biphenyl | 2-(4-morpholinyl)ethyl | 4-piperidinylmethyl | 675 |
| E-0188 | 4-biphenyl | 2-(1-methylimidazol-4-yl)ethyl | 4-piperidinylmethyl | 669 |
| E-0189 | 4-biphenyl | 2-(1-methylimidazol-5-yl)ethyl | 4-piperidinylmethyl | 669 |
| E-0190 | 4-biphenyl | 4-pyridylmethyl | 4-piperidinylmethyl | 652 |
| E-0191 | benzyl | benzyl | 4-piperidinylmethyl | 553 |
| E-0192 | benzyl | 2-phenylethyl | 4-piperidinylmethyl | 567 |
| E-0193 | benzyl | 2-(3-chlorophenyl)ethyl | 4-piperidinylmethyl | 601 |
| E-0194 | benzyl | 2-(4-chlorophenyl)ethyl | 4-piperidinylmethyl | 601 |
| E-0195 | benzyl | 2-(3-pyridyl)ethyl | 4-piperidinylmethyl | 604 |
| E-0196 | benzyl | 2-(4-pyridyl)ethyl | 4-piperidinylmethyl | 604 |
| E-0197 | benzyl | 2-(4-morpholinyl)ethyl | 4-piperidinylmethyl | 612 |
| E-0198 | benzyl | 2-(1-methylimidazol-4-yl)ethyl | 4-piperidinylmethyl | 607 |
| E-0199 | benzyl | 2-(1-methylimidazol-5-yl)ethyl | 4-piperidinylmethyl | 607 |
| E-0200 | benzyl | 4-pyridylmethyl | 4-piperidinylmethyl | 590 |
| E-0201 | 2-phenylethyl | benzyl | 4-piperidinylmethyl | 567 |
| E-0202 | 2-phenylethyl | 2-phenylethyl | 4-piperidinylmethyl | 581 |
| E-0203 | 2-phenylethyl | 2-(3-chlorophenyl)ethyl | 4-piperidinylmethyl | 615 |
| E-0204 | 2-phenylethyl | 2-(4-chlorophenyl)ethyl | 4-piperidinylmethyl | 615 |
| E-0205 | 2-phenylethyl | 2-(3-pyridyl)ethyl | 4-piperidinylmethyl | 618 |
| E-0206 | 2-phenylethyl | 2-(4-pyridyl)ethyl | 4-piperidinylmethyl | 618 |
| E-0207 | 2-phenylethyl | 2-(4-morpholinyl)ethyl | 4-piperidinylmethyl | 626 |
| E-0208 | 2-phenylethyl | 2-(1-methylimidazol-4-yl)ethyl | 4-piperidinylmethyl | 621 |
| E-0209 | 2-phenylethyl | 2-(1-methylimidazol-5-yl)ethyl | 4-piperidinylmethyl | 621 |
| E-0210 | 2-phenylethyl | 4-pyridylmethyl | 4-piperidinylmethyl | 604 |

TABLE 6

Structures of Pyrazinones Prepared by General Robotic and Experiental Procedures

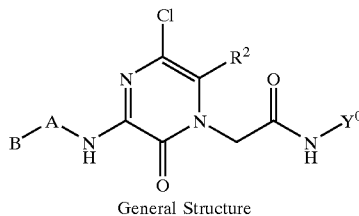

General Structure

| Ex. No. | R² | B—A— | Y⁰ | MW (m/z + 1) |
|---|---|---|---|---|
| 1471-1 | methyl | benzyl | 4-amidinobenzyl | 439 |
| 1471-2 | methyl | 2-(4-chlorophenyl)ethyl | 4-amidinobenzyl | 488 |
| 1471-3 | methyl | 4-pyridylmethyl | 4-amidinobenzyl | 440 |
| 1471-4 | methyl | 2-(4-morpholinyl)ethyl | 4-amidinobenzyl | 462 |
| 1471-5 | methyl | 2-(4-pyridyl)ethyl | 4-amidinobenzyl | 454 |
| 1471-6 | methyl | 2-(3-chlorophenyl)ethyl | 4-amidinobenzyl | 488 |
| 1471-7 | methyl | 2-phenylethyl | 4-amidinobenzyl | 453 |
| 1471-8 | methyl | 2-(3-pyridyl)ethyl | 4-amidinobenzyl | 454 |
| 1471-9 | phenyl | benzyl | 4-amidinobenzyl | 501 |
| 1471-10 | phenyl | 2-(4-chlorophenyl)ethyl | 4-amidinobenzyl | 550 |
| 1471-11 | phenyl | 4-pyridylmethyl | 4-amidinobenzyl | 502 |
| 1471-12 | phenyl | 2-(4-morpholinyl)ethyl | 4-amidinobenzyl | 525 |
| 1471-13 | phenyl | 2-(4-pyridyl)ethyl | 4-amidinobenzyl | 517 |
| 1471-14 | phenyl | 2-(3-chlorophenyl)ethyl | 4-amidinobenzyl | 550 |
| 1471-15 | phenyl | 2-phenylethyl | 4-amidinobenzyl | 516 |
| 1471-16 | phenyl | 2-(3-pyridyl)ethyl | 4-amidinobenzyl | 517 |
| 1471-17 | 4-Cl-phenyl | benzyl | 4-amidinobenzyl | 536 |
| 1471-18 | 4-Cl-phenyl | 2-(4-chlorophenyl)ethyl | 4-amidinobenzyl | 584 |
| 1471-19 | 4-Cl-phenyl | 4-pyridylmethyl | 4-amidinobenzyl | 537 |
| 1471-20 | 4-Cl-phenyl | 2-(4-morpholinyl)ethyl | 4-amidinobenzyl | 559 |
| 1471-21 | 4-Cl-phenyl | 2-(4-pyridyl)ethyl | 4-amidinobenzyl | 551 |
| 1471-22 | 4-Cl-phenyl | 2-(3-chlorophenyl)ethyl | 4-amidinobenzyl | 584 |
| 1471-23 | 4-Cl-phenyl | 2-phenylethyl | 4-amidinobenzyl | 550 |
| 1471-24 | 4-Cl-phenyl | 2-(3-pyridyl)ethyl | 4-amidinobenzyl | 551 |
| 1471-25 | 3-Cl-phenyl | benzyl | 4-amidinobenzyl | 536 |
| 1471-26 | 3-Cl-phenyl | 2-(4-chlorophenyl)ethyl | 4-amidinobenzyl | 584 |
| 1471-27 | 3-Cl-phenyl | 4-pyridylmethyl | 4-amidinobenzyl | 537 |
| 1471-28 | 3-Cl-phenyl | 2-(4-morpholinyl)ethyl | 4-amidinobenzyl | 559 |
| 1471-29 | 3-Cl-phenyl | 2-(4-pyridyl)ethyl | 4-amidinobenzyl | 551 |
| 1471-30 | 3-Cl-phenyl | 2-(3-chlorophenyl)ethyl | 4-amidinobenzyl | 584 |
| 1471-31 | 3-Cl-phenyl | 2-phenylethyl | 4-amidinobenzyl | 550 |
| 1471-32 | 3-Cl-phenyl | 2-(3-pyridyl)ethyl | 4-amidinobenzyl | 551 |
| 1471-33 | 4-methoxyphenyl | benzyl | 4-amidinobenzyl | 532 |
| 1471-34 | 4-methoxyphenyl | 2-(4-chlorophenyl)ethyl | 4-amidinobenzyl | 580 |
| 1471-35 | 4-methoxyphenyl | 4-pyridylmethyl | 4-amidinobenzyl | 533 |
| 1471-36 | 4-methoxyphenyl | 2-(4-morpholinyl)ethyl | 4-amidinobenzyl | 555 |
| 1471-37 | 4-methoxyphenyl | 2-(4-pyridyl)ethyl | 4-amidinobenzyl | 547 |
| 1471-38 | 4-methoxyphenyl | 2-(3-chlorophenyl)ethyl | 4-amidinobenzyl | 580 |
| 1471-39 | 4-methoxyphenyl | 2-phenylethyl | 4-amidinobenzyl | 546 |
| 1471-40 | 4-methoxyphenyl | 2-(3-pyridyl)ethyl | 4-amidinobenzyl | 547 |
| 1471-41 | 3,4-methylene-dioxyphenyl | benzyl | 4-amidinobenzyl | 545 |
| 1471-42 | 3,4-methylene-dioxyphenyl | 2-(4-chlorophenyl)ethyl | 4-amidinobenzyl | 594 |
| 1471-43 | 3,4-methylene-dioxyphenyl | 4-pyridylmethyl | 4-amidinobenzyl | 546 |
| 1471-44 | 3,4-methylene-dioxyphenyl | 2-(4-morpholinyl)ethyl | 4-amidinobenzyl | 569 |
| 1471-45 | 3,4-methylene-dioxyphenyl | 2-(4-pyridyl)ethyl | 4-amidinobenzyl | 561 |
| 1471-46 | 3,4-methylene-dioxyphenyl | 2-(3-chlorophenyl)ethyl | 4-amidinobenzyl | 594 |
| 1471-47 | 3,4-methylene-dioxyphenyl | 2-phenylethyl | 4-amidinobenzyl | 560 |
| 1471-48 | 3,4-methylene-dioxyphenyl | 2-(3-pyridyl)ethyl | 4-amidinobenzyl | 561 |
| 1471-57 | ethyl | benzyl | 4-amidinobenzyl | 553 |
| 1471-58 | ethyl | 2-(4-chlorophenyl)ethyl | 4-amidinobenzyl | 502 |
| 1471-59 | ethyl | 4-pyridylmethyl | 4-amidinobenzyl | 454 |
| 1471-60 | ethyl | 2-(4-morpholinyl)ethyl | 4-amidinobenzyl | 476 |
| 1471-61 | ethyl | 2-(4-pyridyl)ethyl | 4-amidinobenzyl | 468 |
| 1471-62 | ethyl | 2-(3-chlorophenyl)ethyl | 4-amidinobenzyl | 502 |

TABLE 6-continued

Structures of Pyrazinones Prepared by General Robotic and Experiental Procedures

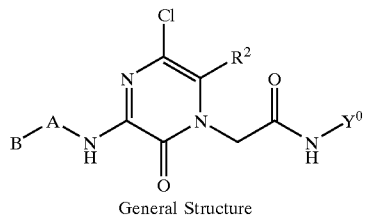

General Structure

| Ex. No. | R² | B—A— | Y⁰ | MW (m/z + 1) |
|---|---|---|---|---|
| 1471-63 | ethyl | 2-phenylethyl | 4-amidinobenzyl | 467 |
| 1471-64 | ethyl | 2-(3-pyridyl)ethyl | 4-amidinobenzyl | 468 |
| 1471-67 | 4-biphenyl | 4-pyridylmethyl | 4-amidinobenzyl | 579 |
| 1471-70 | 4-biphenyl | 2-(3-chlorophenyl)ethyl | 4-amidinobenzyl | 626 |
| 1471-71 | 4-biphenyl | 2-phenylethyl | 4-amidinobenzyl | 592 |
| 1471-72 | 4-biphenyl | 2-(3-pyridyl)ethyl | 4-amidinobenzyl | 593 |
| 1507-01 | phenyl | 3-trifluoromethylbenzyl | 4-amidinobenzyl | 569 |
| 1507-02 | phenyl | 1-indanyl | 4-amidinobenzyl | 528 |
| 1507-03 | phenyl | 2-Cl-benzyl | 4-amidinobenzyl | 536 |
| 1507-04 | phenyl | 4-trifluoromethoxy benzyl | 4-amidinobenzyl | 585 |
| 1507-05 | phenyl | 3-(1-imidazolyl)propyl | 4-amidinobenzyl | 520 |
| 1507-06 | phenyl | 2-(4-bromophenyl)ethyl | 4-amidinobenzyl | 594 |
| 1507-07 | phenyl | 1,2-(diphenyl)ethyl | 4-amidinobenzyl | 592 |
| 1507-08 | phenyl | 2-indanyl | 4-amidinobenzyl | 528 |
| 1507-09 | phenyl | 2,2-(diphenyl)ethyl | 4-amidinobenzyl | 592 |
| 1507-10 | phenyl | 3,3-(diphenyl)propyl | 4-amidinobenzyl | 606 |
| 1507-11 | phenyl | 2-(4-methoxyphenyl)ethyl | 4-amidinobenzyl | 546 |
| 1507-12 | phenyl | 2-(3-methoxyphenyl)ethyl | 4-amidinobenzyl | 546 |
| 1507-13 | phenyl | 4-methoxybenzyl | 4-amidinobenzyl | 532 |
| 1507-15 | phenyl | 2-trifluoromethylbenzyl | 4-amidinobenzyl | 569 |
| 1507-16 | phenyl | 1,2,3,4-tetrahydro-1-naphthyl | 4-amidinobenzyl | 542 |
| 1507-17 | phenyl | 2-(cyclohex-1-enyl)ethyl | 4-amidinobenzyl | 520 |
| 1507-18 | phenyl | 2-(2-thienyl)ethyl | 4-amidinobenzyl | 522 |
| 1507-19 | phenyl | 3-[1-(pyrrolidinyl-2-one)]propyl | 4-amidinobenzyl | 537 |
| 1507-20 | phenyl | 1-carboethoxy-piperidin-4-yl | 4-amidinobenzyl | 567 |
| 1507-21 | phenyl | cyclobutyl | 4-amidinobenzyl | 465 |
| 1507-22 | phenyl | 2,4-dichlorobenzyl | 4-amidinobenzyl | 570 |
| 1507-23 | phenyl | 2-(3-chlorophenyl)ethyl | 4-amidinobenzyl | 516 |
| 1507-24 | phenyl | 2-pyridylmethyl | 4-amidinobenzyl | 502 |
| 1507-25 | phenyl | cyclopentyl | 4-amidinobenzyl | 479 |
| 1507-26 | phenyl | 2,4-difluorobenzyl | 4-amidinobenzyl | 537 |
| 1507-28 | phenyl | 1-naphthylmethyl | 4-amidinobenzyl | 552 |
| 1507-29 | phenyl | cycloheptyl | 4-amidinobenzyl | 508 |
| 1507-30 | phenyl | 4-bromobenzyl | 4-amidinobenzyl | 580 |
| 1507-31 | phenyl | cyclopropyl | 4-amidinobenzyl | 451 |
| 1507-32 | phenyl | 2-methylpropyl | 4-amidinobenzyl | 467 |
| 1507-33 | phenyl | 2-methoxyethyl | 4-amidinobenzyl | 469 |
| 1507-34 | phenyl | (S)-α-methylbenzyl | 4-amidinobenzyl | 516 |
| 1507-35 | phenyl | 1,1-diphenylmethyl | 4-amidinobenzyl | 578 |
| 1507-36 | phenyl | 3-(2,3,4,5-tetrahydro-1,1-dioxothiophenyl) | 4-amidinobenzyl | 530 |
| 1507-38 | phenyl | 3-chlorobenzyl | 4-amidinobenzyl | 536 |
| 1507-40 | phenyl | 3,5-bis-trifluoromethylbenzyl | 4-amidinobenzyl | 637 |
| 1507-41 | phenyl | 2,2,2-trifluoromethyl | 4-amidinobenzyl | 493 |
| 1507-42 | phenyl | 3-fluorobenzyl | 4-amidinobenzyl | 519 |
| 1507-43 | phenyl | 4-phenylbutyl | 4-amidinobenzyl | 544 |
| 1507-44 | phenyl | 2-(3,4-dichloro-phenyl)ethyl | 4-amidinobenzyl | 584 |
| 1507-45 | phenyl | 2-(4-methylphenyl)ethyl | 4-amidinobenzyl | 530 |
| 1507-46 | phenyl | 4-chlorobenzyl | 4-amidinobenzyl | 536 |
| 1507-47 | phenyl | 3-(dimethylamino)propyl | 4-amidinobenzyl | 497 |
| 1507-48 | phenyl | 3,4-difluorobenzyl | 4-amidinobenzyl | 537 |
| 1512-01 | phenyl | 2H,3H-benzo[e]1,4-dioxan-2-ylmethyl | 4-amidinobenzyl | 560 |
| 1512-02 | phenyl | 2,3-dimethoxybenzyl | 4-amidinobenzyl | 562 |
| 1512-04 | phenyl | 3,4-methylenedioxyphenyl | 4-amidinobenzyl | 545 |
| 1512-05 | phenyl | 2-(3,4-dimethoxy-phenyl)ethyl | 4-amidinobenzyl | 576 |
| 1512-06 | phenyl | 3-(phenyl)propyl | 4-amidinobenzyl | 530 |

TABLE 6-continued

Structures of Pyrazinones Prepared by General Robotic and Experiental Procedures

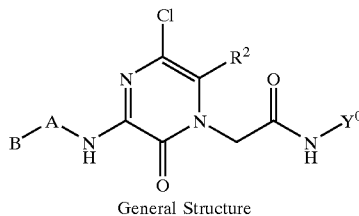

General Structure

| Ex. No. | R² | B—A— | Y⁰ | MW (m/z + 1) |
|---|---|---|---|---|
| 1512-07 | phenyl | 2-(3-methoxy)propyl | 4-amidinobenzyl | 483 |
| 1512-11 | phenyl | 2-ethoxybenzyl | 4-amidinobenzyl | 546 |
| 1512-12 | phenyl | 3-heptyl | 4-amidinobenzyl | 510 |
| 1512-14 | phenyl | butyl | 4-amidinobenzyl | 467 |
| 1512-15 | phenyl | 2-(dimethylamino)ethyl | 4-amidinobenzyl | 482 |
| 1512-16 | phenyl | cycloheptyl | 4-amidinobenzyl | 508 |
| 1512-17 | phenyl | 4-t-butylcyclohexyl | 4-amidinobenzyl | 550 |
| 1512-19 | phenyl | 3-(2,3,4,5-tetrahydro-1,1-dioxothiophenyl) | 4-amidinobenzyl | 530 |
| 1512-20 | phenyl | phenylamino | 4-amidinobenzyl | 487 |
| 1512-23 | phenyl | 2,3-dimethylcyclohexyl | 4-amidinobenzyl | 522 |
| 1512-26 | phenyl | 2-fluoro-4-trifluoro-methylbenzyl | 4-amidinobenzyl | 587 |
| 1512-27 | phenyl | 2-fluoro-5-trifluoro-methylbenzyl | 4-amidinobenzyl | 587 |
| 1512-29 | phenyl | 3-fluoro-5-trifluoro-methylbenzyl | 4-amidinobenzyl | 587 |
| 1512-31 | phenyl | 2-chloro-6-methylbenzyl | 4-amidinobenzyl | 550 |
| 1512-32 | phenyl | 3,4,5-trifluorobenzyl | 4-amidinobenzyl | 555 |
| 1512-35 | phenyl | 2,5-dichlorobenzyl | 4-amidinobenzyl | 570 |
| 1512-36 | phenyl | 2,5-difluorobenzyl | 4-amidinobenzyl | 537 |
| 1512-39 | phenyl | 3,5-difluorobenzyl | 4-amidinobenzyl | 537 |
| 1512-40 | phenyl | 3-trifluoromethoxybenzyl | 4-amidinobenzyl | 585 |
| 1512-41 | phenyl | 2-(3-trifluoromethyl-phenyl)ethyl | 4-amidinobenzyl | 584 |
| 1512-42 | phenyl | 2-trifluoromethoxybenzyl | 4-amidinobenzyl | 585 |
| 1512-43 | phenyl | 2,6-difluorobenzyl | 4-amidinobenzyl | 537 |
| 1512-44 | phenyl | 2-fluoro-6-trifluoro-methylbenzyl | 4-amidinobenzyl | 587 |
| 1512-45 | phenyl | 2,4-dichloro-6-methylbenzyl | 4-amidinobenzyl | 584 |
| 1512-46 | phenyl | 2-(1-methyl-pyrrolidin-2-yl)-ethyl | 4-amidinobenzyl | 523 |
| 1512-47 | phenyl | 2-(pyrid-2-yl)ethyl | 4-amidinobenzyl | 517 |
| 1515-01 | 3-trifluoromethyl-phenyl | benzyl | 4-amidinobenzyl | 569 |
| 1515-02 | 2-methoxyphenyl | benzyl | 4-amidinobenzyl | 532 |
| 1515-03 | 1-(2-bromo-thienyl) | benzyl | 4-amidinobenzyl | 586 |
| 1515-04 | 2-chlorophenyl | benzyl | 4-amidinobenzyl | 536 |
| 1515-05 | 3-methoxyphenyl | benzyl | 4-amidinobenzyl | 532 |
| 1515-06 | 2-thienyl | benzyl | 4-amidinobenzyl | 508 |
| 1515-07 | 4-fluorophenyl | benzyl | 4-amidinobenzyl | 519 |
| 1515-08 | 4-trifluoromethyl-phenyl | benzyl | 4-amidinobenzyl | 569 |
| 1515-09 | 3-fluorophenyl | benzyl | 4-amidinobenzyl | 519 |
| 1515-10 | 3-bromophenyl | benzyl | 4-amidinobenzyl | 580 |
| 1515-11 | 2-fluorophenyl | benzyl | 4-amidinobenzyl | 519 |
| 1515-12 | 2-trifluoromethyl-phenyl | benzyl | 4-amidinobenzyl | 569 |
| 1515-13 | 3-trifluoromethyl-phenyl | cyclobutyl | 4-amidinobenzyl | 533 |
| 1515-14 | 2-methoxyphenyl | cyclobutyl | 4-amidinobenzyl | 495 |
| 1515-15 | 1-(2-bromothienyl) | cyclobutyl | 4-amidinobenzyl | 550 |
| 1515-16 | 2-chlorophenyl | cyclobutyl | 4-amidinobenzyl | 500 |
| 1515-17 | 3-methoxyphenyl | cyclobutyl | 4-amidinobenzyl | 495 |
| 1515-18 | 2-thienyl | cyclobutyl | 4-amidinobenzyl | 471 |
| 1515-19 | 4-fluorophenyl | cyclobutyl | 4-amidinobenzyl | 483 |
| 1515-20 | 4-trifluoro-methylphenyl | cyclobutyl | 4-amidinobenzyl | 533 |
| 1515-22 | 3-bromophenyl | cyclobutyl | 4-amidinobenzyl | 544 |
| 1515-23 | 2-fluorophenyl | cyclobutyl | 4-amidinobenzyl | 483 |
| 1515-24 | 2-trifluoro-methylphenyl | cyclobutyl | 4-amidinobenzyl | 533 |

TABLE 6-continued

Structures of Pyrazinones Prepared by General Robotic and Experiental Procedures

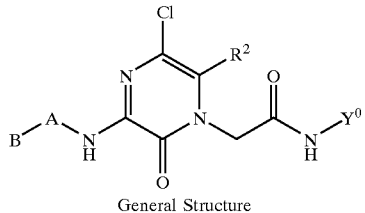

General Structure

| Ex. No. | R² | B—A— | Y⁰ | MW (m/z + 1) |
|---|---|---|---|---|
| 1515-25 | 3-trifluoro-methylphenyl | 2-phenylethyl | 4-amidinobenzyl | 584 |
| 1515-26 | 2-methoxyphenyl | 2-phenylethyl | 4-amidinobenzyl | 546 |
| 1515-27 | 3-bromo-2-thienyl) | 2-phenylethyl | 4-amidinobenzyl | 600 |
| 1515-28 | 2-chlorophenyl | 2-phenylethyl | 4-amidinobenzyl | 550 |
| 1515-29 | 3-methoxyphenyl | 2-phenylethyl | 4-amidinobenzyl | 546 |
| 1515-30 | 2-thienyl | 2-phenylethyl | 4-amidinobenzyl | 522 |
| 1515-31 | 4-fluorophenyl | 2-phenylethyl | 4-amidinobenzyl | 534 |
| 1515-32 | 4-trifluoro-methylphenyl | 2-phenylethyl | 4-amidinobenzyl | 584 |
| 1515-33 | 3-fluorophenyl | 2-phenylethyl | 4-amidinobenzyl | 534 |
| 1515-34 | 3-bromophenyl | 2-phenylethyl | 4-amidinobenzyl | 594 |
| 1515-35 | 2-fluorophenyl | 2-phenylethyl | 4-amidinobenzyl | 534 |
| 1515-36 | 2-trifluoro-methylphenyl | 2-phenylethyl | 4-amidinobenzyl | 584 |
| 1515-37 | 3-trifluoro-methylphenyl | 2-(3,4-dichloro-phenyl)ethyl | 4-amidinobenzyl | 618 |
| 1515-38 | 2-methoxyphenyl | 2-(3,4-dichloro-phenyl)ethyl | 4-amidinobenzyl | 580 |
| 1515-39 | 1-(2-bromothienyl) | 2-(3,4-dichlorophenyl)ethyl | 4-amidinobenzyl | 635 |
| 1515-40 | 2-chlorophenyl | 2-(3,4-dichlorophenyl)ethyl | 4-amidinobenzyl | 584 |
| 1515-41 | 3-methoxyphenyl | 2-(3,4-dichlorophenyl)ethyl | 4-amidinobenzyl | 580 |
| 1515-42 | 2-thienyl | 2-(3,4-dichlorophenyl)ethyl | 4-amidinobenzyl | 556 |
| 1515-43 | 4-fluorophenyl | 2-(3,4-dichlorophenyl)ethyl | 4-amidinobenzyl | 568 |
| 1515-44 | 4-trifluoro-methylphenyl | 2-(3,4-dichlorophenyl)ethyl | 4-amidinobenzyl | 618 |
| 1515-45 | 3-fluorophenyl | 2-(3,4-dichlorophenyl)ethyl | 4-amidinobenzyl | 568 |
| 1515-46 | 3-bromophenyl | 2-(3,4-dichlorophenyl)ethyl | 4-amidinobenzyl | 629 |
| 1515-47 | 2-fluorophenyl | 2-(3,4-dichlorophenyl)ethyl | 4-amidinobenzyl | 568 |
| 1515-48 | 2-trifluoromethylphenyl | 2-(3,4-dichlorophenyl)ethyl | 4-amidinobenzyl | 618 |
| 1522-02 | phenyl | 2-hydroxyethyl | 4-amidinobenzyl | 455 |
| 1522-05 | phenyl | 4-hydroxybutyl | 4-amidinobenzyl | 484 |
| 1522-06 | phenyl | (R)-2-butyl | 4-amidinobenzyl | 468 |
| 1522-07 | phenyl | 6-hydroxyhexyl | 4-amidinobenzyl | 512 |
| 1522-08 | phenyl | 2-(pyrrolidin-1-yl)-ethyl | 4-amidinobenzyl | 509 |
| 1522-09 | phenyl | (S)-2-butyl | 4-amidinobenzyl | 468 |
| 1522-11 | phenyl | 3-pentyl | 4-amidinobenzyl | 482 |
| 1522-12 | phenyl | (S)-2-methylbutyl | 4-amidinobenzyl | 482 |
| 1522-13 | phenyl | 2-methylbutyl | 4-amidinobenzyl | 482 |
| 1522-14 | phenyl | 3-methylbutyl | 4-amidinobenzyl | 482 |
| 1522-15 | phenyl | 2-(3-methyl)butyl | 4-amidinobenzyl | 482 |
| 1522-17 | phenyl | 2-(4-methyl)pentyl | 4-amidinobenzyl | 496 |
| 1522-18 | phenyl | 3,3-dimethylbutyl | 4-amidinobenzyl | 496 |
| 1522-19 | phenyl | tricyclo[5.3.1.1<3,9>]dodec-3-yl | 4-amidinobenzyl | 546 |
| 1522-20 | phenyl | tricyclo[5.3.1.1<3,9>]dodec-3-ylmethyl | 4-amidinobenzyl | 560 |
| 1522-21 | phenyl | 2-propynyl | 4-amidinobenzyl | 449 |
| 1522-23 | phenyl | 2-(dimethylamino)-propyl | 4-amidinobenzyl | 497 |
| 1522-27 | phenyl | N,N-butano | 4-amidinobenzyl | 465 |
| 1522-28 | phenyl | N,N-propano | 4-amidinobenzyl | 451 |
| 1522-31 | phenyl | benzylthio | 4-amidinobenzyl | 519 |
| 1522-33 | phenyl | 2-methoxyethyl | 4-amidinobenzyl | 469 |
| 1522-34 | phenyl | 2-methylpropyl | 4-amidinobenzyl | 468 |
| 1522-35 | phenyl | 1,2-diethyl-pyrazolidin-4-yl | 4-amidinobenzyl | 538 |
| 1522-36 | phenyl | cycloheptyl | 4-amidinobenzyl | 508 |
| 1522-37 | phenyl | N-(3-chloro-5-trifluoromethyl-pyrid-2-yl)-2-aminoethyl | 4-amidinobenzyl | 634 |
| 1522-38 | phenyl | N-(3-trifluoromethyl-pyrid-2-yl)-2-aminoethyl | 4-amidinobenzyl | 600 |

TABLE 6-continued

Structures of Pyrazinones Prepared by General Robotic and Experiental Procedures

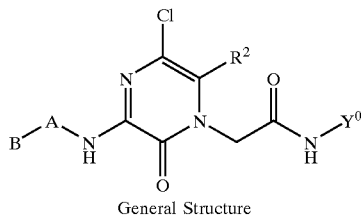

General Structure

| Ex. No. | R² | B—A— | Y⁰ | MW (m/z + 1) |
|---|---|---|---|---|
| 1522-40 | phenyl | 6-cyanohexyl | 4-amidinobenzyl | 507 |
| 1522-41 | phenyl | 3-hydroxypropyl | 4-amidinobenzyl | 469 |
| 1522-42 | phenyl | 4-(pyrrolidin-1-yl)-butyl | 4-amidinobenzyl | 537 |
| 1522-43 | phenyl | (S)-1-cyclohexylethyl | 4-amidinobenzyl | 522 |
| 1522-44 | phenyl | 2-(2R)-bicyclo-[2.2.1]heptyl | 4-amidinobenzyl | 506 |
| 1522-46 | phenyl | 3-(2,3,4,5-tetrahydro-1,1-dioxothiophenyl) | 4-amidinobenzyl | 530 |
| 1522-47 | phenyl | 4-t-butylcyclohexyl | 4-amidinobenzyl | 550 |
| 1526-01 | 3-aminophenyl | cyclopropyl | 4-amidinobenzyl | 466 |
| 1526-03 | 3-aminophenyl | cyclopentyl | 4-amidinobenzyl | 495 |
| 1526-04 | 3-aminophenyl | 2,2,2-trifluoroethyl | 4-amidinobenzyl | 508 |
| 1526-05 | 3-aminophenyl | 2-(3-methoxypropyl) | 4-amidinobenzyl | 499 |
| 1526-06 | 3-aminophenyl | 2-(2-methylbutyl) | 4-amidinobenzyl | 497 |
| 1526-07 | 3-aminophenyl | t-butyl | 4-amidinobenzyl | 483 |
| 1526-09 | 3-aminophenyl | (S)-2-butyl | 4-amidinobenzyl | 483 |
| 1526-11 | 3-aminophenyl | 3-pentyl | 4-amidinobenzyl | 497 |
| 1526-12 | 3-aminophenyl | ethyl | 4-amidinobenzyl | 454 |
| 1526-13 | 3-aminophenyl | propyl | 4-amidinobenzyl | 469 |
| 1526-14 | 3-aminophenyl | 2-butyl | 4-amidinobenzyl | 483 |
| 1526-15 | 3-aminophenyl | 2-(3-methylbutyl) | 4-amidinobenzyl | 497 |
| 1526-16 | 3-aminophenyl | (R)-2-butyl | 4-amidinobenzyl | 483 |
| 1526-17 | 3-aminophenyl | 2-(4-methylpentyl) | 4-amidinobenzyl | 511 |
| 1526-19 | 3-aminophenyl | 2-propenyl | 4-amidinobenzyl | 466 |
| 1526-21 | 3-aminophenyl | 2-propynyl | 4-amidinobenzyl | 464 |
| 1526-23 | 3-aminophenyl | cyclobutyl | 4-amidinobenzyl | 481 |
| 1526-24 | 3-aminophenyl | isopropyl | 4-amidinobenzyl | 469 |
| 1526-25 | 3-aminophenyl | 2-methoxyethyl | 4-amidinobenzyl | 485 |
| 1526-26 | 3-aminophenyl | 2-methylpropyl | 4-amidinobenzyl | 483 |
| 1526-29 | 3-aminophenyl | (1S)-1-cyclohexylethyl | 4-amidinobenzyl | 537 |
| 1526-30 | 3-aminophenyl | 2-(2R)bicyclo[2.2.1]-heptyl | 4-amidinobenzyl | 521 |
| 1526-33 | 3-aminophenyl | (2S)-oxalan-2-ylmethyl | 4-amidinobenzyl | 511 |
| 1526-40 | 3-aminophenyl | butyl | 4-amidinobenzyl | 483 |
| 1526-41 | 3-aminophenyl | cyclopropylmethyl | 4-amidinobenzyl | 481 |
| 1543-03 | 3-aminophenyl | 2-(pyrrolidin-1-yl)ethyl | 4-amidinobenzyl | 524 |
| 1543-05 | 3-aminophenyl | methyl | 4-amidinobenzyl | 440 |
| 1543-07 | 3-aminophenyl | 3-(1-imidazolyl)-propyl | 4-amidinobenzyl | 535 |
| 1543-09 | 3-aminophenyl | 2-dimethylaminoethyl | 4-amidinobenzyl | 498 |
| 1543-11 | 3-aminophenyl | 6-amidocarbonylhexyl | 4-amidinobenzyl | 540 |
| 1543-13 | 3-aminophenyl | 3-hydroxypropyl | 4-amidinobenzyl | 485 |
| 1543-15 | 3-aminophenyl | 2-(piperid-1-yl)ethyl | 4-amidinobenzyl | 538 |
| 1543-19 | 3-aminophenyl | 2-dimethylamino-propyl | 4-amidinobenzyl | 512 |
| 1543-21 | 3-aminophenyl | 4-(pyrrolidin-1-yl)butyl | 4-amidinobenzyl | 552 |
| 1543-25 | 3-aminophenyl | 2-(3-diethylamino)-propyl | 4-amidinobenzyl | 540 |
| 1543-27 | 3-aminophenyl | 3-(pyrrolidin-1-yl)propyl | 4-amidinobenzyl | 538 |
| 1543-31 | 3-aminophenyl | ethyl | 4-amidino-2-fluorobenzyl | 472 |
| 1543-33 | 3-aminophenyl | cyclopropyl | 4-amidino-2-fluorobenzyl | 484 |
| 1543-34 | 3-aminophenyl | cyclopentyl | 4-amidino-2-fluorobenzyl | 513 |
| 1543-35 | 3-aminophenyl | propyl | 4-amidino-2-fluorobenzyl | 486 |
| 1543-36 | 3-aminophenyl | butyl | 4-amidino-2- | 501 |

TABLE 6-continued

Structures of Pyrazinones Prepared by General Robotic and Experiental Procedures

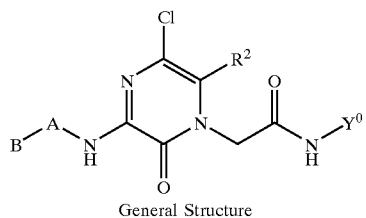

General Structure

| Ex. No. | R² | B—A— | Y⁰ | MW (m/z + 1) |
|---|---|---|---|---|
| 1543-37 | 3-aminophenyl | 2-(pyrrolidin-1-yl)ethyl | 4-amidino-2-fluorobenzyl | 542 |
| 1543-38 | 3-aminophenyl | 2-methylpropyl | 4-amidino-2-fluorobenzyl | 501 |
| 1543-39 | 3-aminophenyl | cyclobutyl | 4-amidino-2-fluorobenzyl | 499 |
| 1543-40 | 3-aminophenyl | isopropyl | 4-amidino-2-fluorobenzyl | 486 |
| 1543-41 | 3-aminophenyl | cyclobutyl | 8-aza-1,4-dioxa-spiro[4.5]decyl | 474 |
| 1543-45 | 3-aminophenyl | cyclobutyl | 3,3-diethyl-pyrrolidin-1-yl | 462 |
| 1543-46 | 3-aminophenyl | cyclobutyl | 4-(4-amino-phenyl)pyrazinyl | 497 |

TABLE 7

Structures of Pyrazinones Prepared by General Robotic and Experimental Procedures

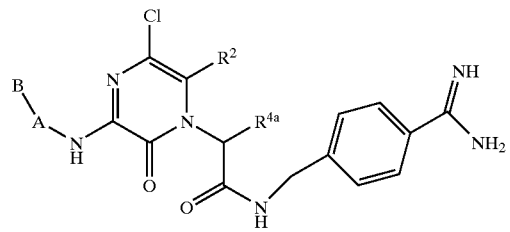

| Ex. No. | R² | B-A- | R⁴ᵃ | MW (m/z + 1) |
|---|---|---|---|---|
| 1517-01 | 3-thienyl | benzyl | H | 508 |
| 1517-03 | phenyl | benzyl | (S)-methyl | 516 |
| 1517-04 | phenyl | benzyl | methyl-thiomethyl | 562 |
| 1517-05 | phenyl | benzyl | (R)-methyl | 516 |
| 1517-06 | 2,6-dichlorophenyl | benzyl | H | 570 |
| 1517-07 | 3-thienyl | cyclobutyl | H | 472 |
| 1517-08 | phenyl | cyclobutyl | benzyl | 556 |
| 1517-09 | phenyl | cyclobutyl | (S)-methyl | 480 |
| 1517-10 | phenyl | cyclobutyl | methyl-thiomethyl | 526 |
| 1517-11 | phenyl | cyclobutyl | (R)-methyl | 480 |
| 1517-12 | 2,6-dichlorophenyl | cyclobutyl | H | 534 |
| 1517-13 | 3-thienyl | 2-phenylethyl | H | 522 |
| 1517-14 | phenyl | 2-phenylethyl | benzyl | 606 |
| 1517-15 | phenyl | 2-phenylethyl | (S)-methyl | 530 |
| 1517-16 | phenyl | 2-phenylethyl | methyl-thiomethyl | 576 |
| 1517-17 | phenyl | 2-phenylethyl | (R)-methyl | 530 |
| 1517-18 | 2,6-dichlorophenyl | 2-phenylethyl | H | 584 |

TABLE 7-continued

Structures of Pyrazinones Prepared by General Robotic and Experimental Procedures

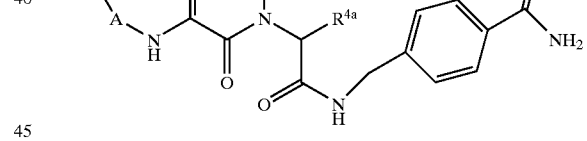

| Ex. No. | R² | B-A- | R⁴ᵃ | MW (m/z + 1) |
|---|---|---|---|---|
| 1517-19 | 3-thienyl | 2-(3-chlorophenyl)- | H | 556 |
| 1517-20 | phenyl | 2-(3-chlorophenyl)-ethyl | benzyl | 640 |
| 1517-23 | phenyl | 2-(3-chlorophenyl)-ethyl | (R)-methyl | 564 |
| 1517-24 | 2,6-dichlorophenyl | 2-(3-chlorophenyl)-ethyl | H | 619 |
| 1517-25 | phenyl | cyclohexyl | H | 494 |
| 1517-26 | phenyl | 4-heptyl | H | 510 |
| 1517-29 | phenyl | 2-hexyl | H | 496 |
| 1517-31 | phenyl | N-methyl N-(1-methylethyl) | H | 468 |
| 1517-33 | phenyl | propyl | H | 453 |
| 1517-35 | phenyl | butyl | H | 468 |
| 1517-36 | phenyl | trimethylsilylmethyl | H | 498 |
| 1517-37 | phenyl | 2-butyl | H | 468 |
| 1517-38 | phenyl | prop-2-enyl | H | 451 |
| 1517-39 | phenyl | methyl | H | 425 |
| 1517-40 | phenyl | 3-methylbutyl | H | 482 |
| 1517-41 | phenyl | 3,3-dimethylbutyl | H | 496 |
| 1517-43 | phenyl | cyclopropylmethyl | H | 465 |

TABLE 7-continued

Structures of Pyrazinones Prepared by General Robotic and Experimental Procedures

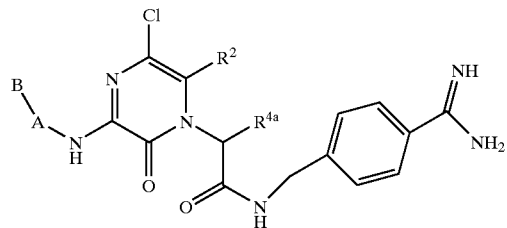

| Ex. No. | R² | B-A- | R⁴ᵃ | MW (m/z + 1) |
|---|---|---|---|---|
| 1517-44 | phenyl | isopropyl | H | 453 |
| 1517-46 | phenyl | ethyl | H | 439 |
| 1517-47 | phenyl | 3-heptyl | H | 524 |
| 1517-48 | phenyl | pentyl | H | 482 |

Formula (I) compounds of this invention possessing hydroxyl, thiol, and amine functional groups can be converted to a wide variety derivatives. Alternatively, derivatized Formula (I) compounds can be obtained by first derivatizing one or more intermediates in the processes of preparation before further transforming the derivatized intermediate to compounds of Formula (I). A hydroxyl group in the form of an alcohol or phenol can be readily converted to esters of carboxylic, sulfonic, carbamic, phosphonic, and phosphoric acids. Acylation to form a carboxylic acid ester is readily effected using a suitable acylating reagent such as an aliphatic acid anhydride or acid chloride. The corresponding aryl and heteroaryl acid anhydrides and acid chlorides can also be used. Such reactions are generally carried out using an amine catalyst such as pyridine in an inert solvent. Similarly, carbamic acid esters (urethanes) can be obtained by reacting a hydroxyl group with isocyanates and carbamoyl chlorides. Sulfonate, phosphonate, and phosphate esters can be prepared using the corresponding acid chloride and similar reagents. Compounds of Formula (I) that have at least one thiol group present can be converted to the corresponding thioesters derivatives analogous to those of alcohols and phenols using the same reagents and comparable reaction conditions. Compounds of Formula (I) that have at least one primary or secondary amine group present can be converted to the corresponding amide derivatives. Amides of carboxylic acids can be prepared using the appropriate acid chloride or anhydrides with reaction conditions analogous to those used with alcohols and phenols. Ureas of the corresponding primary or secondary amine can be prepared using isocyanates directly and carbamoyl chlorides in the presence of an acid scavenger such as triethylamine or pyridine. Sulfonamides can be prepared from the corresponding sulfonyl chloride in the presence of aqueous sodium hydroxide or a tertiary amine. Suitable procedures and methods for preparing these derivatives can be found in House's Modern Synthetic Reactions, W. A. Benjamin, Inc., Shriner, Fuson, and Curtin in The Systematic Identification of Organic Compounds, 5th Edition, John Wiley & Sons, and Fieser and Fieser in Reagents for Organic Synthesis, Volume 1, John Wiley & Sons. Reagents of a wide variety that can be used to derivatize hydroxyl, thiol, and amines of compounds of Formula (I) are available from commercial sources or the references cited above, which are incorporated herein by reference.

Formula (I) compounds of this invention possessing hydroxyl, thiol, and amine functional groups can be alkylated to a wide variety of derivatives. Alternatively, alkylated Formula (I) compounds can be obtained by first alkylating one or more intermediates in the processes of preparation before further transforming the alkylated intermediate to compounds of Formula (I). A hydroxyl group of compounds of Formula (I) can be readily converted to ethers. Alkylation to form an ether is readily effected using a suitable alkylating reagent such as an alkyl bromide, alkyl iodide or alkyl sulfonate. The corresponding aralkyl, heteroaralkyl, alkoxyalkyl, aralkyloxyalkyl, and heteroaralkyloxyalkyl bromides, iodides, and sulfonates can also be used. Such reactions are generally carried out using an alkoxide forming reagent such as sodium hydride, potassium t-butoxide, sodium amide, lithium amide, and n-butyl lithium using an inert polar solvent such as DMF, DMSO, THF, and similar, comparable solvents. amine catalyst such as pyridine in an inert solvent. Compounds of Formula (I) that have at least one thiol group present can be converted to the corresponding thioether derivatives analogous to those of alcohols and phenols using the same reagents and comparable reaction conditions. Compounds of Formula (I) that have at least one primary, secondary or tertiary amine group present can be converted to the corresponding secondary, tertiary or quaternary ammonium derivative. Quaternary ammonium derivatives can be prepared using the appropriate bromides, iodides, and sulfonates analogous to those used with alcohols and phenols. Conditions involve reaction of the amine by warming it with the alkylating reagent with a stoichiometric amount of the amine (i.e., one equivalent with a tertiary amine, two with a secondary; and three with a primary). With primary and secondary amines, two and one equivalents, respectively, of an acid scavenger are used concurrently. Secondary or tertiary amines can be prepared from the corresponding primary or secondary amine. A primary amine can be dialkylated by reductive amination using an aldehyde, such as formaldehyde, and sodium cyanoborohydride in the presence of glacial acetic acid. A primary amine can be monoalkylated by first monoprotecting the amine with a ready cleaved protecting group, such as trifluoroacetyl. An alkylating agent, such as dimethylsulfate, in the presence of a non-nucleophilic base, such as Barton's base (2-tert-butyl-1,1,3,3-tetramethylguanidine), gives the monomethylated protected amine. Removal of the protecting group using aqueous potassium hydroxide gives the desired monoalkylated amine. Additional suitable procedures and methods for preparing these derivatives can be found in House's Modem Synthetic Reactions, W. A. Benjamin, Inc., Shriner, Fuson, and Curtin in The Systematic Identification of Organic Compounds, 5th Edition, John Wiley & Sons, and Fieser and Fieser in Reagents for Organic Synthesis published by John Wiley & Sons. Perfluoroalkyl derivatives can be prepared as described by DesMarteau in J. Chem. Soc. Chem. Commun. 2241 (1998). Reagents of a wide variety that can be used to derivative hydroxyl, thiol, and amines of compounds of Formula (I) are available from commercial sources or the references cited above, which are incorporated herein by reference.

The examples of synthetic approaches to the preparation pyrazinones derivatized in a nucleophilic substituent such as may be present in B, R¹, R² and Y⁰ are shown in specific Examples 100 through 104 below. The specific examples recited below should be considered a being merely illustrative of the wide variety possible and not as limiting to one of ordinary skill in the art.

Example 100

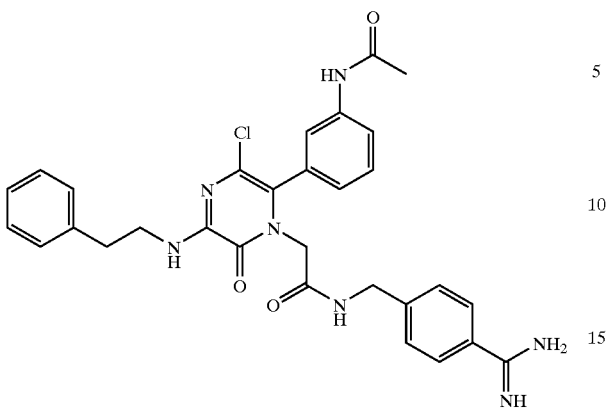

By following the method of Example 1 and substituting 3-nitrobenzaldehyde for benzaldehyde, 1-benzyloxycarbonylmethyl-3,5-dichloro-6-(3-nitrophenyl)pyrazinone (EX-100A) was obtained. The pyrazinone, 1-benzyl oxycarbonyl methyl-3,5-dichloro(3-nitrophenyl)pyrazinone (EX-100A), (15.01 g, 34.6 mmol) was taken up in 325 mL of 50% EtOH (w/w) and heated to 75° C. EtOAc was added until the solution was homogeneous (about 80 mL). Iron powder (9.4 g, 168 mmol) was added, followed by 0.57 mL of 12 M HCl (6.8 mmol) in about 0.6 mL of 50% EtOH. The reaction was monitored by TLC (80% EtOAc/hexanes) and was complete within 40 minutes. The reaction mixture was cooled to room temperature, and the iron was removed by filtration through Celite. The yellow solution was diluted with 600 mL of EtOAc and 300 mL of water. Saturated NaCl was added to help separate the layers. The organic phase was washed with saturated $NaHCO_3$ (2×250 mL), saturated NaCl (1×250 mL), dried over $MgSO_4$, filtered, and the solvents were removed under reduced pressure. The residue was taken up in 20–25 mL of 3.4 M HCl in EtOAc. Additional EtOAc (about 25 mL) was added, and the mixture was heated to dissolve all of the compound. The volatile components were removed under reduced pressure. The residue (crusty solid) was taken up in EtOAc and slowly dripped into hexanes. The pale yellow solid that precipitated was filtered and dried under vacuum at room temperature to yield 12.19 g (80% yield) of 1-benzyloxycarbonylmethyl-3,5-dichloro-6-(3-aminophenyl)pyrazinone hydrochloride (EX-100B) as a pale yellow solid: $^1$H NMR (300 MHz, $CD_3OD$) d 4.61 (AB q, 2 H, J=17 Hz), 5.20 (AB q, 2H, J=12 Hz), 7.31–7.51 (m, 7H), 7.63–7.67 (m, 2H); HPLC purity (retention time): 91% (3.0 min); LRMS m/z 404 ($M^+$+H).

The pyrazinone, 1-benzyloxycarbonylmethyl-3,5-dichloro-6-(3-aminophenyl)pyrazinone hydrochloride (EX-100B), (78.2 mg, 0.18 mmol) was taken up in 5 mL of dichloromethane. Pyridine (32 mL, 0.40 mmol) was added, followed by acetyl chloride (26 mL, 0.36 mmol) in 1 mL of dichloromethane. The reaction was stirred at ambient temperature until the reaction was complete by TLC and LC/MS after 24 hours. The reaction solution was then washed with saturated $NaHCO_3$ (4×5 mL), saturated NaCl (1×5 mL), dried over $MgSO_4$ and concentrated to give 68.9 mg (86% yield) of the product 1-benzyloxycarbonylmethyl-3,5-dichloro-6-(3-acetamidophenyl)pyrazinone (EX-100C): $^1$H NMR (300 MHz, $CDCl_3$) d 2.21 (s, 3H), 4.55 (AB q, 2H, J=16.6 Hz), 5.17 (s, 2H), 6.96 (d, 1H, J=7.7 Hz), 7.26–7.40 (m, 5H), 7.57 (s, 1H), 7.74–7.79 (m, 1H), 8.19–8.24 (br m, 1H), 8.65 (br s, 1H).

Following the necessary final steps of the procedure of Example 1, EX-100C was converted to the product: HPLC purity (retention time): 100% (2.9 min); LRMS m/z 572.5 ($M^+$+H).

Example 101

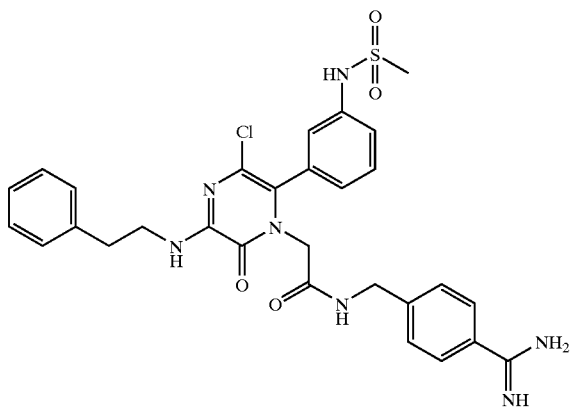

By following the method of Example 100 and substituting methanesulfonyl chloride for acetyl chloride the product was prepared: HPLC purity (retention time): 100% (2.9 min), LRMS m/z 608.2 ($M^+$+H).

Example 102

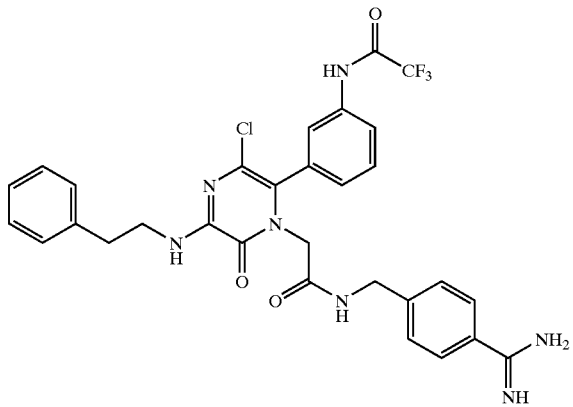

By following the method of Example 100 and substituting trifluoroacetic anhydride for acetyl chloride, the product was prepared: HPLC purity (retention time): 100% (3.3 min); LRMS m/z 626.3 ($M^+$+H).

Example 103

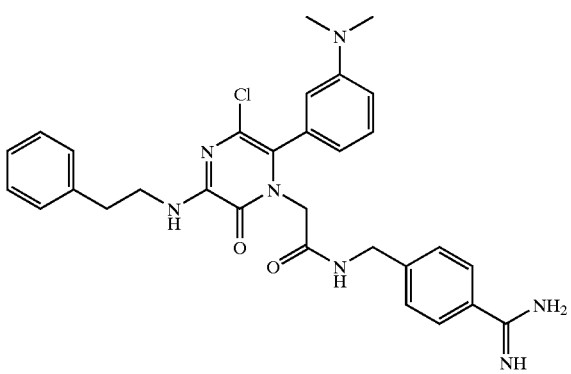

By following the method of Example 1 and substituting 3-nitrobenzaldehyde for benzaldehyde, 1-benzyloxycarbonylmethyl-3,5-dichloro-6-(3-aminophenyl)pyrazinone was obtained.

The 1-benzyloxycarbonylmethyl-3,5-dichloro-6-(3-aminophenyl)pyrazinone (210.6 mg, 0.48 mmol) was taken up in 9 mL of acetonitrile. Polyamine resin (1.05 g, 4.9 mmol) was added, along with about 10 mL of dichioromethane. After agitating about 10 mins the resin was filtered, rinsed with acetonitrile, and the solvents concentrated to about 10 mL. Formaldehyde (37%) (0.4 mL, 4.9 mmol) was added, followed by NaCNBH$_3$ (1.0 M in THF, 1.5 mL, 1.5 mmol) and the dropwise addition of two 50 mL portions of glacial acetic acid (17.4 M, 1.74 mmol). The reaction was monitored by LC/MS. A third 50 mL portion of glacial acetic acid was added after 3.5 h to force the reaction to completion. The solution was diluted with about 40 mL of diethyl ether and washed with 1.2 M NaOH (3×5 mL), saturated NaCl (1×5 mL), dried over MgSO$_4$, and the solvents were removed under reduced pressure to give 0.17 g (82% yield) of 1-benzyloxycarbonylmethyl-3,5-dichloro-6-(3-[N,N-dimethylamino]phenyl)pyrazinone (EX-103A): $^1$H NMR (300 MHz, CDCl$_3$): d 2.96 (s, 6H), 4.59 (s, 2H), 5.19 (s, 2H), 6.55 (m, 2H), 6.82 (d, 1H), 7.25–7.40 (m, 6H).

Following the necessary final steps of the procedure of Example 1, EX-103A was converted to the product: HPLC purity (retention time): 94% (2.6 min); LRMS m/z 558.4 (M$^+$+H).

Example 104

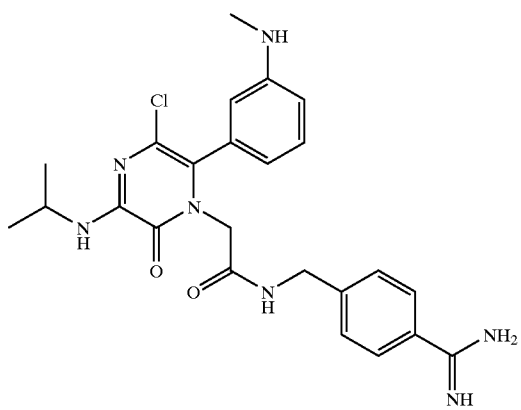

By following the method of Example 100 and replacing phenethylamine with isopropylamine, 1-benzyloxycarbonylmethyl-3-isopropylamino-5-chloro-6-(3-aminophenyl)pyrazinone was obtained.

The 1-benzyloxycarbonylmethyl-3-isopropylamino-5-chloro-6-(3-aminophenyl)pyrazinone (1.01 g, 2.4 mmol) was dissolved in 25 mL of THF. Pyridine (0.37 mL, 4.6 mmol) was added, followed by pentafluoropyridine trifluoroacetate (0.79 mL, 4.6 mmol). After 2 h, polyamine resin (3.1 g, 8.7 mmol) and 25 mL of dichloromethane was added, and the mixture was vigorously stirred for 1–2 h. The resin was filtered, rinsed with dichloromethane (3×5 mL), and the volatiles were removed under reduced presssure to give the desired product EX-104A in quantitative yield: $^1$H NMR (300 MHz, CDCl$_3$) d 1.30 (d, 3H, J=1.4 Hz), 1.32 (d, 3H, J=1.4 Hz), 4.24 (m, 1H), 4.47 (AB q, 2H, J=16.9 Hz), 5.15 (s, 2H), 6.22 (d, 1H, J=8.2Hz), 7.12 (d, 1H, J=7.7Hz), 7.25–7.42 (m, 5H), 7.54 (s, 1H), 7.73–7.81 (m, 1H), 8.62 (d, 1H, J=4.2 Hz), 9.10 (br s, 1H).

The 1-benzyloxycarbonylmethyl-3-isopropylamino-5-chloro-6-(3-[N-trifluoroacetamido]phenyl)pyrazinone (EX-104A) (0.63 g, 1.2 mmol) was dissolved in 20 mL of dichioromethane. Barton's base (2-tert-butyl-1,1,3,3-tetramethylguanidine) (0.5 mL, 2.5 mmol) and dimethylsulfate (0.66 mL, 7 mmol) wee added, and the reaction was stirred at ambient temperature overnight. The reaction was monitored by LC/MS, and after completion the solution was washed with aqueous NH$_4$OH (2×10 mL) and 5% HCl (1×10 mL). The combined aqueous washes were extracted with dichloromethane (1×10 mL). The combined organic phases were washed with saturated NaCl (1×10 mL), dried over MgSO$_4$, filtered, and the volatiles were removed under reduced pressure to give 0.51 g (80% yield) of the desired product (EX-104B): HPLC purity (retention time): 97% (4.4 min); LRMS m/z 537.5 (M$^+$+H).

Following the necessary final steps of the procedure of Example 1, EX-104B was converted to the product: $^1$H NMR (300 MHz, CD$_3$OD) d 1.31 (s, 3H), 1.33 (s, 3H), 2.94 (s, 3H), 4.22 (m, 1H), 4.40–4.52 (m, 4H), 7.01–7.05 (m, 2H), 7.17–7.19 (m, 1H), 7.42–7.45 (m, 1H), 7.49 (d, 2H, J=8.3 Hz) 7.80 (d, 2H, J=8.3 Hz); HPLC purity (retention time): 100% (2.1 min); LRMS m/z 481.6 (M$^+$+H).

Pyrazinones, wherein a B-A substituent is introduced by reaction of a 3-amino group of an intermediate pyrazinone with an electrophilic reagent, can be prepared using the general procedures and processes shown in Scheme 9 and Scheme 10 and as illustrated below in specific Examples 105–109.

Scheme 9
Introduction of B——A——N(R$^5$) into Pyrazidone Intermediates and the Resulting Products

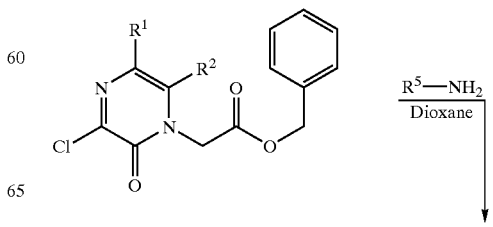

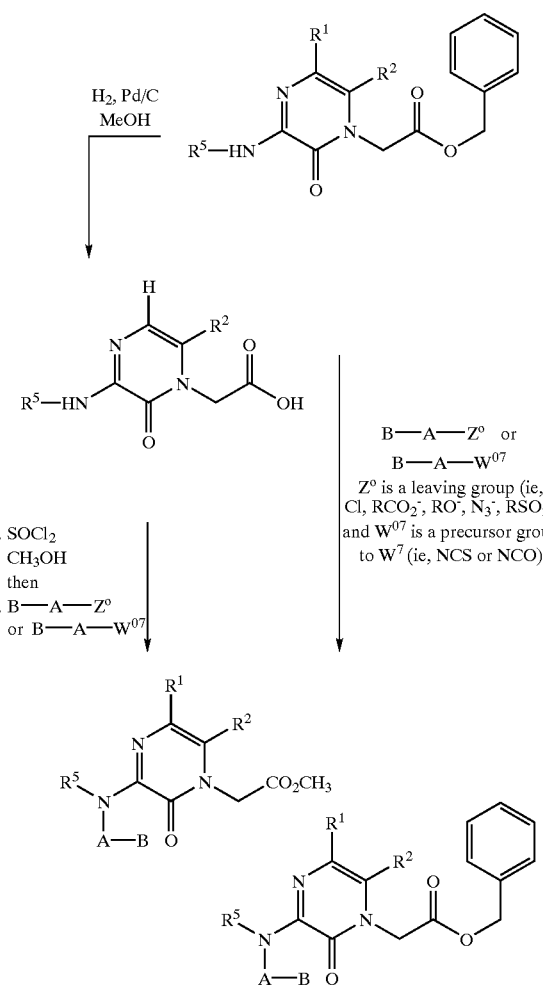
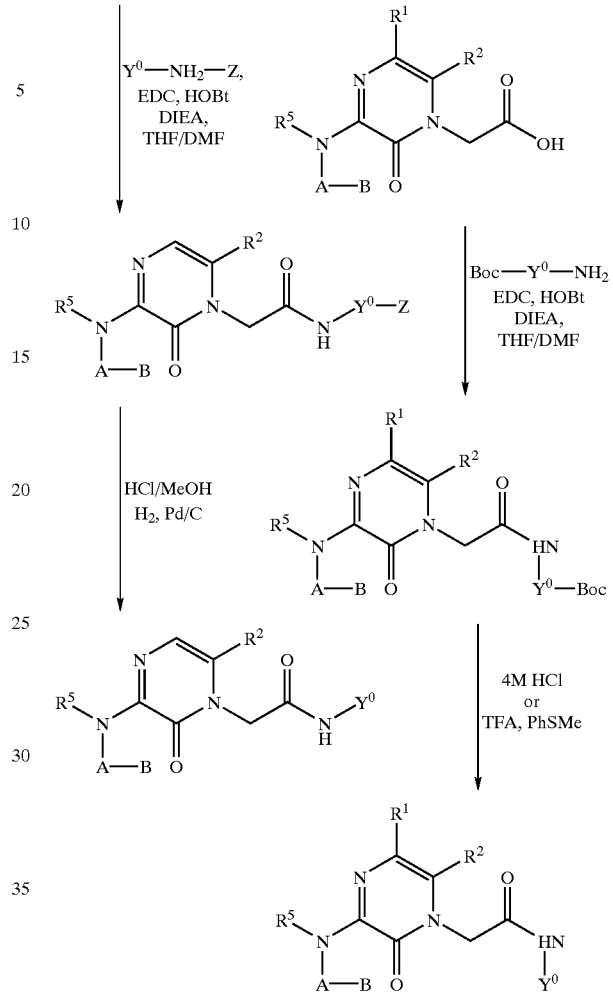

Scheme 10
Introduction of B—A—N(R⁵) into Pyrazidone Intermediates and the Resulting Products (Concluded)

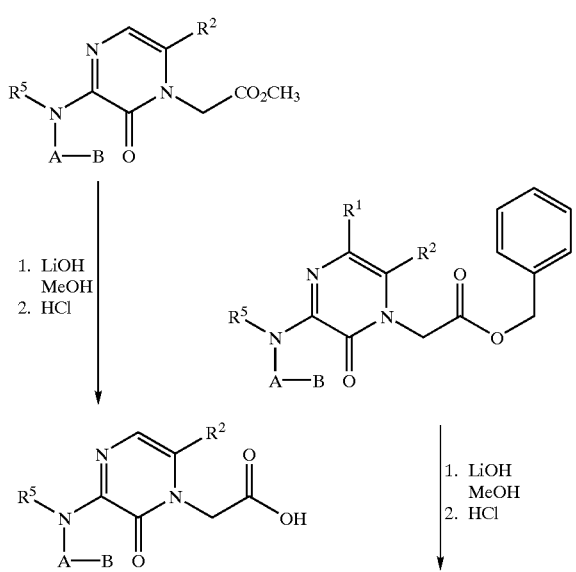

The examples of synthetic approaches to the preparation pyrazinones in which the substituents represented by B-A are introduced by reaction of a 3-amino group of the pyrazinone with an electrophilic reagent are shown in specific Examples 105 through 109 below. The specific examples recited below should be considered a being merely illustrative of the wide variety possible and not construed as limiting to one of ordinary skill in the art.

Example 105

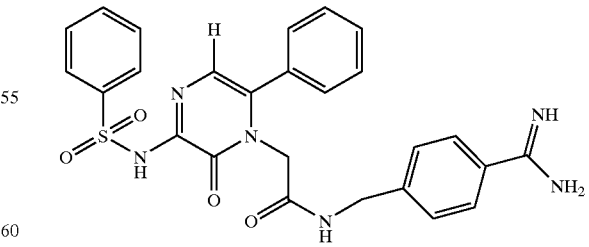

1-Benzyloxycarbonylmethyl-3,5-dichloro-6-phenylpyrazinone (EX-1B) (0.8 g, 2.06 mmol) was mixed with 20 ml 0.5 M ammonia in dioxane in a sealed tube. The tube was heated to 100° C. for 12 hours. After removing the dioxane under reduced pressure, the residue was dissolved in ethyl acetate. The ethyl acetate solution was washed with water and brine and dried over anhydrous $Na_2SO_4$. After removing the solvent, the product was recrystallized in acetone to yield the pure amino pyrazinone EX-105A as a white crystal solid (0.76 g, 99%): HPLC-MS (0 to 95% AcCN/6 min @ 1.0 mL/Min @ 254 nm @ 50° C.): retention time 3.75 min, M+H$^+$=370.0 for formula $C_{19}H_{17}ClN_3O_3$. $^1$H NMR (400 MHz, CDCl$_3$): d 4.43 (s, 2H), 5.13 (s, 2H), 5.78 (b, 2H), 7.21–7.27 (m, 5H), 7.35–7.39 (m, 5H).

EX-105A (4.7 g, 12.73 mmol) was mixed with 1.34 g 10% Pd/C in 100 ml methanol. The mixture was stirred under hydrogen atmosphere that was introduced via a balloon for 48 hours. After filtration and removing the solvent, a white crystal solid was obtained as the carboxylic acid product EX-105B (3.0 g, 97%): HPLC-MS (0 to 95% AcCN/6 min @ 1.0 mL/Min @ 254 nm @ 50° C.): retention time 1.45 min, M+H$^+$=246.0 for formula $C_{12}H_{12}N_3O_3$.

EX-105B (3.0 g, 12.2 mmol) in 100 ml methanol was cooled down to –50° C. SOCl$_2$ (1.4 ml, 19.1 mmol) was added to the solution. After stirring at room temperature for four hours, the mix was heated to reflux for three hours. After removing the solvent, the residue was subjected to a silica gel plug using ethyl acetate to elute. The pure product was obtained by recrystallization in methanol as a white crystal solid EX-105C (2.22 g, 68%): HPLC-MS (0 to 95% AcCN/6 min @ 1.0 mL/Min @ 254 nm @ 50° C.): retention time 1.94 min, M+H$^+$=260.0 for formula $C_{13}H_{14}N_3O_3$.

EX-105C (0.258 g, 1 mmol) was mixed with benzenesulfonyl chloride (0.353 g, 2 mmol) in 3 ml pyridine. The reaction mixture was heated at 90° C. for 2 hours. After removing the pyridine, the crude product was obtained by an aqueous work-up procedure. The crude product EX-105D was dissolved in 10 ml methanol and treated with 10 ml 1M LiOH solution for 15 minutes. After the solution was acidified with 2 N HCl to a pH of about 2 and the methanol removed under reduced pressure, a yellow precipitate was obtained via filtration and washing with water. The pure sulfonamide EX-105E is a yellow crystalline solid (0.267 g, 70%): HPLC-MS (0 to 95% AcCN/6 min @ 1.0 mL/Min @ 254 nm @ 50° C.): retention time 2.88 min, M+H$^+$=386.0 for formula $C_{18}H_{16}N_3O_5S$. $^1$H NMR (400 MHz, methanol-d$_4$): d 4.44 (s, 2H), 6.77 (s, 1H), 7.32 (dd, J=8.0, 1.6 Hz, 2H), 7.42–7.48 (m, 3H), 7.54 (t, J=8.0 Hz, 2H), 7.60–7.64 (m, 1H), 8.09 (d, J=8.0 Hz, 2H). $^{13}$C NMR (101 MHz, methanol-d$_4$): d 48.4, 129.2, 129.9, 130.0, 130.6, 131.0, 132.6, 134.4, 141.4, 146.1, 157.0, 159.0, 160.0, 170.3.

EX-105E (0.106 g, 0.275 mmol) was mixed with EDC (0.055 g, 0.289 mmol) and HOBt (0.044 g, 0.289 mmol) in 2 ml DMF. The mixture was stirred for 10 minutes. To this mixture was then added the protected amidine, 4-(N-benzyloxycarbonylamidino)benzylamine hydrogen chloride salt (0.289 mmol), and DIEA (0.144 ml, 0.825 mmol) in 1 ml DMF. The reaction solution was stirred for 2 hours at room temperature. The DMF was removed under reduced pressure. The remaining residue was triturated in 1 N HCl and washed with water to yield the product EX-105F as an off-white amorphous solid (0.152 g, 85%): HPLC-MS (0 to 95% AcCN/6 min @ 1.0 mL/Min @ 254 nm @ 50° C.): retention time 3.14 min, M+H$^+$=651.3 for formula $C_{34}H_{30}N_5O_7S$. $^1$H NMR (400 MHz, methanol-d$_4$): d 4.42 (s, 2H), 4.51 (s, 2H), 5.40 (s, 2H), 6.76 (s, 1H), 7.35–7.62 (m, 15H), 7.75 (d, J=8.0 Hz, 2H), 8.08 (d, J=8.0 Hz, 2H). $^{13}$C NMR (101 MHz, methanol-d$_4$): d 43.6, 49.7, 70.7, 111.6, 118.2, 119.7, 127.3, 128.7, 129.0, 129.1, 129.8, 129.9, 130.0, 130.8, 131.0, 132.6, 134.4, 135.8, 136.2, 141.5, 146.3, 147.6, 153.0, 154.5, 167.9, 169.0.

EX-105F (0.148 g, 0.228 mmol), p-toluenesulfonic acid mono hydrate (0.045 g, 0.24 mmol) and 10% Pd on activated carbon (0.012 g, 0.007 mmol) were mixed with 5 ml methanol. The mixture was stirred for 2 hours under an atmosphere of hydrogen that was introduced through a rubber balloon. After filtering off the catalyst and removing the methanol, the remaining residue was triturated in a solvent of 2:1 ether to methanol to yield a white amorphous solid as the product (0.105 g, 95%) as the mono-salt of p-toluenesulfonic acid: HPLC-MS (0 to 95% AcCN/6 min @ 1.0 mL/Min @ 254 nm @ 50° C.): retention time 2.64 min, M+H$^+$=517.5 for formula $C_{26}H_{25}N_6O_4S$. $^1$H NMR (400 MHz, methanol-d$_4$): d 2.35 (s, 3H), 4.40 (s, 2H), 4.52 (s, 2H), 6.77 (s, 1H), 7.21 (d, J=7.6 Hz, 2H), 7.34 (d, J=7.2 Hz, 2H), 7.41–7.51 (m, 3H), 7.55 (t, J=7.6 Hz, 2H), 7.64 (t, J=7.2 Hz, 1H), 7.79 (d, J=8.0 Hz, 2H), 7.74 (d, J=8.0 Hz, 2H). $^{13}$C NMR (101 MHz, methanol-d$_4$): d 21.2, 43.5, 70.7, 119.5, 126.8, 128.0, 128.7, 128.9, 129.0, 129.7, 129.8, 129.9, 130.6, 130.9, 132.4, 134.3, 136.0, 141.3, 141.6, 146.2, 146.4, 152.9, 167.9, 168.7.

Example 106

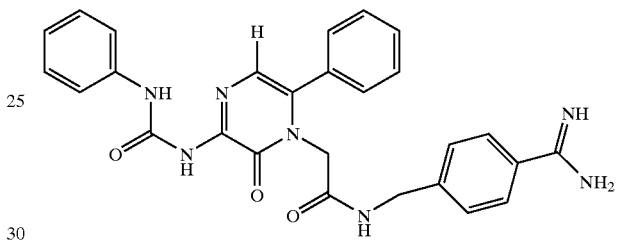

Following, the method of Example 105, EX-105C (0.0932 g, 0.36 mmol) was treated with phenyl isocyanate (0.128 g, 1.08 mmol) and 0.2 ml pyridine in 2 ml acetonitrile at 80° C. for 3 hours instead of benzenesulfonyl chloride. After the reaction mixture was kept in a freezer for two days, a nice crystal solid formed as the pure pyrazinone urea EX-106A (0.129 g, 95%): HPLC-MS (0 to 95% AcCN/6 min @ 1.0 mL/Min @ 254 nm @ 50° C.): retention time 3.73 min, M+H$^+$=379.3 for formula $C_{20}H_{19}N_4O_4$. $^1$H NMR (400 MHz, CDCl$_3$): d 3.75 (s, 3H), 4.55 (s, 2H), 6.97 (s, 1H), 7.10 (t, J=7.6 Hz, 1H), 7.32–7.38 (m, 4H), 7.46–7.52 (m, 3H) 7.58 (d, J=8.0 Hz, 2H), 8.28 (s, 1H), 11.1 (s, 1H). $^{13}$C NMR (101 MHz, CDCl$_3$): d 47.4, 52.8, 119.6, 120.2, 123.9, 128.9, 129.1, 129.4, 130.1, 130.9, 133.8, 137.8, 145.7, 150.8, 150.9, 167.3.

Saponification of compound EX-106A manner similar to the procedure as described in the synthesis of EX-105D yielded compound EX-106B. HPLC-MS (0 to 95% AcCN/6 min @ 1.0 mL/Min @ 254 nm @ 50° C.): retention time 3.34 min. M+H$^+$=365.1 for formula $C_{19}H_{16}N_4O_4$. Compound EX-106B was coupled with 4-(N-benzyloxycarbonylamidino)benzylamine hydrogen chloride salt using EDC, HOBt and DIEA as described before to yield the protected product EX-106C as an off-white solid: HPLC-MS (0 to 95% AcCN/6 min @ 1.0 mL/Min @ 254 nm @ 50° C.): retention time 3.58 min, M+H$^+$=630.0 for formula $C_{35}H_{32}N_7O_5$. $^1$H NMR (400 MHz, methanol-d$_4$): d 4.49 (s, 2H), 4.61 (s, 2H), 5.40 (s, 2H), 7.06 (s, 1H), 7.11 (t, J=7.2 Hz, 1H), 7.32–7.56 (m, 16H), 7.76 (d, J=8 Hz, 2H).

EX-106C was converted to the HCl salt of the product by hydrogenation in methanol in the presence of HCl with Pd/C as the catalyst. The product was an off-white amorphous solid: HPLC-MS (0 to 95% AcCN/6 min @ 1.0 mL/Min @ 254 nm @ 50° C.): retention time 3.01 min, M+H$^+$=496.4 for formula $C_{27}H_{26}N_7O_3$. $^1$H NMR (400 MHz, methanol-d4): d 4.47 (s, 2H), 4.65 (s, 2H), 6.97 (s, 1H), 7.15 (t, J=7.2 Hz, 1H), 7.27–7.54 (m, 9H), 7.57 (d, J=7.2 Hz, 2H) 7.78 (d, J=8.0 Hz, 2H), 8.76 (s, 1H), 9.26 (s, 1H). HRMS m/z MH+496.2036, calcd for $C_{27}H_{26}N_7O_3$ 496.2097.

Example 107

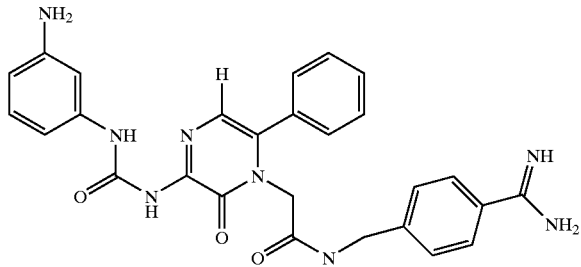

Using the procedure of Example 106 and substituting 3-(benzyloxycarbonylamido)phenyl isocyanate for phenyl isocyanate, the product was obtained as the HCl salt: HPLC-MS (0 to 95% AcCN/6 min @ 1.0 mL/Min @ 254 nm @ 50° C.): retention time 1.84 min, M+H+=511.6 for formula $C_{27}H_{27}N_8O_3$. 1H NMR (400 MHz, methanol-d4): d 4.46 (s, 2H), 4.65 (s, 2H), 6.97 (s, 1H), 7.17 (d, J=6.8 Hz, 1H), 7.45–7.60 (m, 8H), 7.78 (m, 3H) 7.94 (s, 1H), 8.77 (s, 1H), 9.26 (s, 1H). HRMS m/z MH+ 511.2251, calcd for $C_{27}H_{27}N_8O_3$ 511.2206.

Example 108

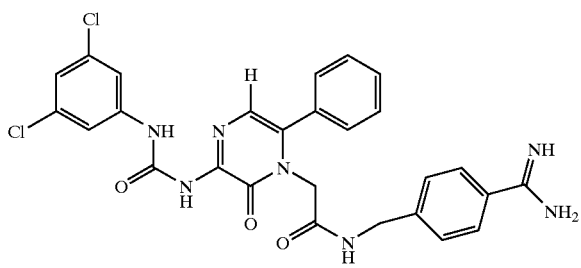

Using the procedure of Example 106 and substituting 3,5-dichlorophenyl isocyanate for phenyl isocyanate, the product was obtained as the HCl salt: HPLC-MS (0 to 95% AcCN/6 min @ 1.0 mL/Min @ 254 nm @ 50° C.): retention time 3.41 min, M+H+=564.4 for formula $C_{27}H_{24}Cl_2N_7O_3$. 1H NMR (400 MHz, methanol-d4): d 4.47 (s, 2H), 4.63 (s, 2H), 7.04 (s, 1H), 7.18 (t, J=1.6 Hz, 1H), 7.45–7.56 (m, 7H), 7.64 (d, J=2 Hz, 2H) 7.78 (d, J=8.0 Hz, 2H), 8.77 (s, 1H), 9.26 (s, 1H). HRMS m/z MH+ 564.1351, calcd for $C_{27}H_{24}Cl_2N_7O_3$ 564.1318.

Example 109

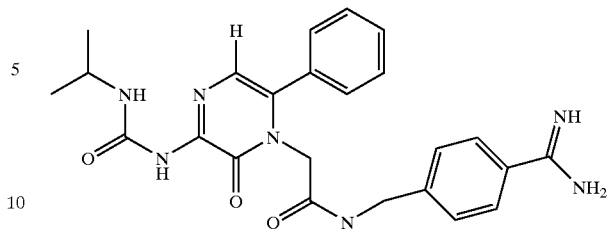

Using the procedure of Example 106 and substituting isopropyl isocyanate for phenyl isocyanate, the product was obtained as the HCl salt: HPLC-MS (0 to 95% AcCN/6 min @ 1.0 mL/Min @ 254 nm @ 50° C.): retention time 2.43 min, M+H+=462.4 for formula $C_{24}H_{28}N_7O_3$. 1H NMR (400 MHz, methanol-d4): d 1.25 (d, J=6.4 Hz, 6H), 3.99(m, 1 H), 4.45 (s, 2H), 4.64 (s, 2H), 6.82 (s, 1H), 7.43–7.53 (m, 5H), 7.60 (m, 1H) 7.67 (t, J=6.4 Hz, 1H), 7.78 (d, J=8.0 Hz, 2H), 8.77 (s, 1H), 9.26 (s, 1H). HRMS m/z MH+ 462.2230, calcd for $C_{24}H_{28}N_7O_3$ 462.2254.

Assays for Biological Activity

TF-VIIa Assay

In this assay 100 nM recombinant soluble tissue factor and 2 nM recombinant human factor VIIa are added to a 96-well assay plate containing 0.4 mM of the substrate, N-Methylsulfonyl-D-phe-gly-arg-p-nitroaniline and either inhibitor or buffer (5 mM $CaCl_2$, 50 mM Tris-HCl, pH 8.0, 100 mM NaCl, 0.1% BSA). The reaction, in a final volume of 100 ul is measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of TF-VIIa activity is calculated from $OD_{405\ nm}$ value from the experimental and control sample.

Xa Assay

Human factor Xa (0.3 nM) and 0.15 mM N-α-Benzyloxycarbonyl-D-arginyl-L-glycyl-L-arginine-p-nitroaniline-dihydrochloride (S-2765) are added to a 96-well assay plate containing either inhibitor or buffer (50 mM Tris-HCl, pH 8.0, 100 mM NaCl, 0.1% BSA). The reaction, in a final volume of 100 ul is measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of Xa activity is calculated from $OD_{405\ nm}$ value from the experimental and control sample.

Thrombin Assay

Human thrombin (0.28 nM) and 0.06 mM H-D-Phenylalanyl-L-pipecolyl-L-arginine-p-nitroaniline dihydrochloride are added to a 96-well assay plate containing either inhibitor or buffer (50 mM Tris-HCl, pH 8.0, 100 mM NaCl, 0.1% BSA). The reaction, in a final volume of 100 ul is measured immediately at 405 nm to determine background absorbance. The plate is incubated at room temperature for 60 min, at which time the rate of hydrolysis of the substrate is measured by monitoring the reaction at 405 nm for the release of p-nitroaniline.

Percent inhibition of thrombin activity is calculated from $OD_{405\ nm}$ value from the experimental and control sample.

Trypsin Assay

Trypsin (5 ug/ml; type IX from porcine pancreas) and 0.375 mM N-α-Benzoyl-L-arginine-p-nitroanilide (L-BAPNA) are added to a 96-well assay plate containing either inhibitor or buffer (50 mM Tris-HCl, pH 8.0, 100 mM NaCl, 0.1% BSA). The reactions, in a final volume of 100 ul are measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of trypsin activity is calculated from $OD_{405\ nm}$ value from the experimental and control sample.

Recombinant soluble TF, consisting of amino acids 1–219 of the mature protein sequence was expressed in *E. coli* and purified using a Mono Q Sepharose FPLC. Recombinant human VIIa was purchased from American Diagnostica, Greenwich Conn. and chromogenic substrate N-Methylsulfonyl-D-phe-gly-arg-p-nitroaniline was prepared by American Peptide Company, Inc., Sunnyvale, Calif. Factor Xa was obtained from Enzyme Research Laboratories, South Bend Ind., thrombin from Calbiochem, La Jolla, Calif., and trypsin and L-BAPNA from Sigma, St. Louis Mo. The chromogenic substrates S-2765 and S-2238 were purchased from Chromogenix, Sweden.

Using bioassay procedures described herein, the biological activity of the compounds of Examples 1 through Example 109 and Tables 1 through Table 7 are summarized in Table 8 and Table 9.

TABLE 8

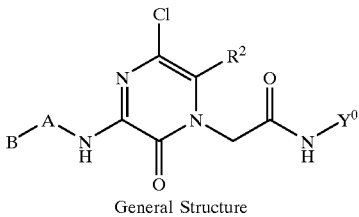

General Structure

Inhibitory Activity of Pyrazinones toward TF-VIIA, Thrombin II, Factor Xa, And Trypsin II.

| Ex. No. | IC50 or % Inhibition TF-VIIa (30 uM) | IC50 or % Inhibition Thrombin II (30 uM) | IC50 or % Inhibition Factor Xa (30 uM) | IC50 or % Inhibition Trpysin II (30 uM) |
|---|---|---|---|---|
| 1 | 1 | 1 | >100 | 0.2 |
| 2 | 5 | 0.4 | >100 | 1 |
| 3 | 0.2 | <0.04 | 1 | 0.4 |
| 4 | 0.3 | 0.1 | 3 | 0.5 |
| 5 | 7 | 1 | 4 | 1 |
| 6 | 0.1 | <0.04 | 1 | 0.4 |
| 7 | 0.2 | 0.1 | 3 | 0.4 |
| 8 | 3 | 0.2 | 1 | 0.4 |
| 9 | >30 | 30 | >0 | >30 |
| 10 | >30 | >0 | >0 | >30 |
| 11 | 91 | <0.1 | >100 | 1 |
| 12 | >100 | 7 | >100 | 1 |
| 13 | >100 | 48 | >100 | 14 |
| 14 | >100 | 29 | >100 | 0.3 |
| 15 | >100 | >100 | >100 | 1 |
| 16 | >100 | 13 | >100 | 1 |
| 17 | 0.71 | 15.32 | 41% | 0.24 |
| 18 | 47% | 20% | 0 | 1.13 |

TABLE 8-continued

General Structure

Inhibitory Activity of Pyrazinones toward TF-VIIA, Thrombin II, Factor Xa, And Trypsin II.

| Ex. No. | IC50 or % Inhibition TF-VIIa (30 uM) | IC50 or % Inhibition Thrombin II (30 uM) | IC50 or % Inhibition Factor Xa (30 uM) | IC50 or % Inhibition Trpysin II (30 uM) |
|---|---|---|---|---|
| 19 | 0.8 | 0.22 | 22% @ 30 | 0.27 |
| 20 | 41% @ 30 | 4 | 6% @ 30 | 7 |
| 21 | 8% @ 30 | 26.8 | 21% @ 30 | 2 |
| 22 | 0% @ 30 | 47% @ 30 | 13% @ 30 | 1.7 |
| 23 | 1.7 | 17 | 38% @ 30 | 0.32 |
| 24 | 0% @ 30 | 46% @ 30 | 22% @ 30 | 1.3 |
| 25 | 7% | 3% | 4% | 9% |
| 26 | 1% | 4% | 5% | 3% |
| 27 | 12.5 | >30 | >30 | 16 |
| 28 | 3 | >30 | >30 | 0.23 |
| 29 | pending | pending | pending | pending |
| 30 | pending | pending | pending | pending |
| 31 | 22% | 4% | 4% | 20% |
| 32 | 12 | 0 | 0 | 0 |
| 33 | 4% | 30 | 0 | 3.6 |
| 34 | 20% | 0.59 | 0 | 1.3 |
| 35 | 29% | 5% | 10% | 2.88 |
| 36 | 5% | 31% | 0 | 30% |
| 37 | 1.8 | 1.9 | 0 | 0.3 |
| 38 | 0.9 | 0.58 | 22% | 0.4 |
| 39 | 1.7 | 0.26 | 0 | 0.28 |
| 40 | 0.06 | 0 | 0 | 0.1 |
| 41 | 0.02 | 8 | 0 | 0.1 |
| 42 | 0.5 | 17% | 0 | 0.53 |
| 43 | 0.25 | 43% | 0 | 0.15 |
| 44 | 2.1 | 40% | 4% | 0.54 |
| 45 | 0.89 | 13 | 9% | 0.25 |
| 46 | 0.98 | 18.7 | 10% | 0.23 |
| 47 | 0.66 | 1.14 | 10.6 | 0.20 |
| 48 | 0.57 | 6.4 | 20% | 0.38 |
| 49 | 0.57 | 6.4 | 28.9 | 0.19 |
| 50 | 0.50 | 14.2 | 39% | 0.24 |
| 51 | 0.65 | 2.14 | 9.68 | 0.17 |
| 52 | 0.59 | 7.0 | 24.0 | 0.15 |
| 53 | 0.30 | 11.1 | 7% | 0.15 |
| 54 | 11.3 | 0% | 0% | 0% |
| 55 | 0.15 | 0.12 | 0% | 0.18 |
| 56 | 16.7 | 3.13 | 0% | 0.738 |
| 57 | 1.4 | 0.15 | 0% | 0.22 |
| 58 | 0% | 1% | 1% | 4% |
| 59 | 0% | 0% | 2% | 7% |
| 60 | 0.901 | <0.04 | 5.65 | 0.192 |
| 61 | 1% | 0% | 0% | 10% |
| 62 | 5.6 | 4% | 10% | 2.2 |
| 63 | 28% | 6% | 0 | 7 |
| 64 | 0.78 | 2 | 19% | 0.07 |
| 65 | 0.36 | 2.8 | 12% | 0.3 |
| 66 | 0.34 | 40% | 0 | 0.28 |
| 67 | 0.20 | 4.25 | 0 | 0.14 |
| 68 | 32% | 0% | 6% | 4.8 |
| 69 | 0.06 | 2.6 | 2.6 | 0.07 |
| 73 | 0.03 | 4.4 | 0 | 0.1 |
| 74 | 3.25 | 1.78 | 13% | 0.15 |
| 75 | 0.21 | 2 | 9% | 0.04 |
| 76 | 0.12 | 0 | 0 | 0.28 |
| 77 | 2.52 | 0.98 | >30 | 1.13 |
| 78 | 0.43 | 0.3 | 16% @ 30 | 0.23 |
| 79 | 4.14 | 0.3 | 30% @ 30 | 0.15 |
| 80 | 1.29 | 4.55 | 29% @ 30 | 0.16 |

TABLE 8-continued

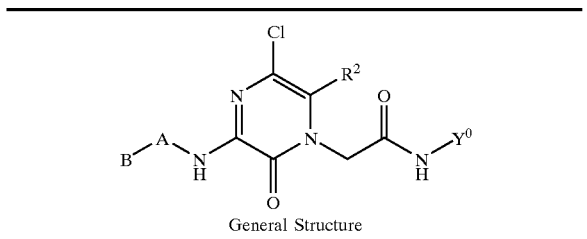

General Structure

Inhibitory Activity of Pyrazinones toward TF-VIIA, Thrombin II, Factor Xa, And Trypsin II.

| Ex. No. | IC50 or % Inhibition TF-VIIa (30 uM) | IC50 or % Inhibition Thrombin II (30 uM) | IC50 or % Inhibition Factor Xa (30 uM) | IC50 or % Inhibition Trpysin II (30 uM) |
|---|---|---|---|---|
| 81 | 1 | 0.89 | 33% @ 30 | 0.22 |
| 82 | 20 | 4.67 | 32% @ 30 | 0.17 |
| 83 | 0.75 | 0.84 | >30 | 0.36 |
| 84 | 3.03 | 0.5 | >30 | 0.2 |
| 85 | 0.88 | 0.92 | 42% @ 30 | 0.19 |
| 86 | 0.07 | 0.9 | 26% @ 30 | 78% @ 1 |
| 87 | 0.07 | 1.5 | >30 | 0.26 |
| 88 | 0.1 | 15 | >30 | 0.27 |
| 89 | 5% @ 30 | 3% @ 30 | 5% @ 30 | 9% @ 30 |
| 90 | 0.02 | 8 | 16% @ 30 | 0.1 |
| 91 | 0.07 | 0.4 | 7 | 0.5 |
| 92 | 0.053 | 17.7 | 18% @ 30 | 0.25 |
| 93 | 0.07 | 15.4 | >30 | 0.16 |
| 94 | 0.04 | 48% @ 30 | >30 | 0.24 |
| 95 | 0.6 | 0.58 | >30 | 0.21 |
| 96 | 0.26 | 6.39 | >30 | 0.12 |
| 97 | 0.04 | 29% @ 30 | >30 | 0.24 |
| 98 | 0.09 | 20% @ 30 | 10% @ 30 | 0.07 |
| 99 | 6% @ 30 | 0% @ 30 | 8% @ 30 | 7% @ 30 |
| 100 | 1.6 | 0.1 | >30 | 62% @ 1 |
| 101 | 0.6 | 0.1 | >30 | 83% @ 1 |
| 102 | 1.2 | 1 | 43% @ 30 | 0.39 |
| 103 | 0.3 | 1.3 | 11% @ 30 | 0.45 |
| 104 | 1.2 | 19 | >30 | 0.7 |
| 105 | 0 | 17% | 5% | 0.49 |
| 106 | 1.11 | 28.8 | 30% | 0.25 |
| 107 | 0.57 | 48% | 35% | 0.24 |
| 108 | 4.13 | 16% | 20% | 0.5 |
| 109 | 6.17 | 46% | 10% | 0.22 |
| 1471-1 | 8.17 | 2.57 | 10% | 0.79 |
| 1471-2 | 3.62 | 86% @ .04 | 10% | 0 |
| 1471-3 | 13.59 | 6.31 | 0 | 1.29 |
| 1471-4 | 29.4 | 18.3 | 0 | 3.1 |
| 1471-5 | 8.69 | 0.09 | 12% | 1.79 |
| 1471-6 | 2.85 | 63% @ .04 | 14% | 0.68 |
| 1471-7 | 4.28 | 0.06 | 4% | 0.87 |
| 1471-8 | 3.86 | 70% @ .04 | 27% | 0.65 |
| 1471-9 | 0.77 | 7.63 | 29% | 0.24 |
| 1471-10 | 0.6 | 69% @ .04 | 45% | 0.18 |
| 1471-11 | 1.69 | 12.03 | 9% | 0.93 |
| 1471-12 | 7.97 | 37% @ 30 | 9% | 0.93 |
| 1471-13 | 1.47 | 0.33 | 0% | 0.53 |
| 1471-14 | 0.18 | 62% @ .04 | 23 | 0.05 |
| 1471-15 | 0.63 | 0.16 | 10% | 0.24 |
| 1471-16 | 0.82 | 0.1 | 23% | 0.28 |
| 1471-17 | 11.01 | 3.76 | 16 | 0.24 |
| 1471-18 | 11.21 | 0.15 | 26% | 0.8 |
| 1471-19 | 33% | 16.86 | 26% | 1.6 |
| 1471-20 | 42% | 9.46 | 34% | 0.57 |
| 1471-21 | 8.18 | 0.08 | 30 | 0.24 |
| 1471-22 | 14.56 | 0.32 | 28% | 0.5 |
| 1471-23 | 8.88 | 0.2 | 36% | 0.28 |
| 1471-24 | 10.05 | 0.05 | 23 | 0.27 |
| 1471-25 | 2.45 | 24.47 | 31% | 0.36 |
| 1471-27 | 4.19 | 40% | 16% | 0.59 |
| 1471-28 | 7.22 | 26.99 | 8% | 0.39 |
| 1471-29 | 2.18 | 0.67 | 21% | 0.47 |
| 1471-30 | 0.83 | 0.13 | 41% | 0.08 |
| 1471-31 | 1.98 | 0.72 | 17% | 0.47 |
| 1471-32 | 1.19 | 0.17 | 25% | 0.23 |
| 1471-33 | 31% | 34% | 22% | 0.36 |
| 1471-34 | 17.47 | 0.74 | 24% | 0.25 |
| 1471-35 | 37% | 40% | 22% | 0.27 |
| 1471-36 | 11% | 15% | 6% | 0.74 |
| 1471-37 | 39% | 6.02 | 7% | 0.43 |
| 1471-38 | 24.38 | 3.92 | 18% | 0.34 |
| 1471-39 | 23.45 | 4.06 | 11% | 0.29 |
| 1471-40 | 40% | 4.03 | 11% | 0.47 |
| 1471-41 | 18.33 | 25.8 | 34% | 0.33 |
| 1471-42 | 10.45 | 0.55 | 15% | 0.45 |
| 1471-43 | 25.26 | 34% | 18% | 0.44 |
| 1471-44 | 34% | 25% | 13% | 0.53 |
| 1471-45 | 13.22 | 1.19 | 24% | 0.27 |
| 1471-46 | 13.02 | 1.76 | 21% | 0.37 |
| 1471-47 | 12.59 | 2.24 | 22% | 0.41 |
| 1471-48 | 15.7 | 0.92 | 17% | 0.42 |
| 1471-57 | 4.73 | 0.9 | 11% | 0.67 |
| 1471-58 | 12.44 | 76% @ .04 | 0% | 4.03 |
| 1471-59 | 7.52 | 1.95 | 0% | 1.03 |
| 1471-60 | 13.01 | 2.97 | 0% | 1.52 |
| 1471-61 | 5 | 0.04 | 0% | 1.2 |
| 1471-62 | 4% | 24% | 0% | >30 |
| 1471-63 | 3.45 | 56% @ .04 | 2% | 0.84 |
| 1471-64 | 3.02 | 78% @ .04 | 2% | 0.61 |
| 1471-67 | 12% | 27% | 16% | 0.82 |
| 1471-70 | 10% | 33% | 12% | 1.01 |
| 1471-71 | 6% | 24% | 0% | 2.58 |
| 1471-72 | 15% | 12.2 | 22% | 0.72 |
| 1507-01 | 6.3 | 18.9 | 16% | 0.9 |
| 1507-02 | 9.4 | 36% | 9% | 1.1 |
| 1507-03 | 3.6 | 21 | 21% | 0.8 |
| 1507-04 | 29.5 | 9.5% | >30 | 9% @ 1 |
| 1507-05 | 4.7 | 22 | 10% | |
| 1507-06 | 20 | 0.5 | >30 | 8% @ 1 |
| 1507-07 | 25% | 27 | >30 | 7% @ 1 |
| 1507-08 | 7% | 10% | 1% | |
| 1507-09 | 22.6 | 0.97 | 13% | 0.7 |
| 1507-10 | 24% | 39.5% | >30 | 7% @ 1 |
| 1507-11 | 3 | <0.04 | >30 | 27% @ 1 |
| 1507-12 | 6.7 | 0.6 | >30 | 12% @ 1 |
| 1507-13 | 26.7 | 6% | >30 | 8% @ 1 |
| 1507-15 | 12 | 25% | >30 | 11% @ 1 |
| 1507-16 | 5.8 | 21.3 | 18% | 1 |
| 1507-17 | 27.4 | 0.9 | 16% | 2.8 |
| 1507-18 | 10.6 | 10.6 | >30 | 6% @ 1 |
| 1507-19 | 12.9 | 45% | 4% | |
| 1507-20 | 20.9 | 10.5% | >30 | 11% @ 1 |
| 1507-21 | 0.4 | 4.6 | 23% | 0.36 |
| 1507-22 | 45% | 1.5% | >30 | 8% @ 1 |
| 1507-23 | 28.9 | 11% | >30 | 11% @ 1 |
| 1507-24 | 0% | 7.5% | 15% | 25% @ 30 |
| 1507-25 | 1.6 | 22.4 | >30 | 60% @ 1 |
| 1507-26 | 20.5 | 11.5% | >30 | 11% @ 1 |
| 1507-28 | 38% | 1.5 | >30 | 1% @ 1 |
| 1507-29 | 5.8 | 27% | 4% | |
| 1507-30 | 13.4 | 18.5 | >30 | 0% @ 1 |
| 1507-31 | 3.7 | 21.5% | >30 | 2% @ 1 |
| 1507-32 | 21.3 | 16.5% | >30 | 0% @ 1 |

TABLE 8-continued

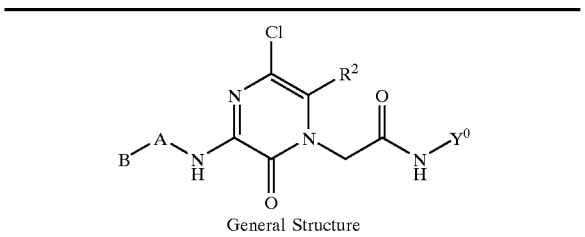

General Structure

Inhibitory Activity of Pyrazinones toward TF-VIIA, Thrombin II, Factor Xa, And Trypsin II.

| Ex. No. | IC50 or % Inhibition TF-VIIa (30 uM) | IC50 or % Inhibition Thrombin II (30 uM) | IC50 or % Inhibition Factor Xa (30 uM) | IC50 or % Inhibition Trpysin II (30 uM) |
|---|---|---|---|---|
| 1507-33 | 28.4 | 8.5% | >30 | 2% @ 1 |
| 1507-34 | 8.5 | 20% | >30 | 0% @ 1 |
| 1507-35 | 19.9 | 15.9 | 28% | 0.49 |
| 1507-36 | 13.8 | 18% | 0% | |
| 1507-38 | 16 | 34.5% | >30 | 0% @ 1 |
| 1507-40 | 5.7 | 30 | 11% | |
| 1507-41 | 48% | 10.5% | 17% | 13.9 |
| 1507-42 | 11.6 | 23.5% | >30 | 0% @ 1 |
| 1507-43 | 4.1 | 7.1 | 21% | 0.97 |
| 1507-44 | 6 | 0.5 | 9% | |
| 1507-45 | 7.3 | 1 | >30 | 0% @ 1 |
| 1507-46 | 4.3 | 36% | 8% | |
| 1507-47 | 17.6 | 37% | 19% | 1.6 |
| 1507-48 | 18.3 | 14% | >30 | 11% @ 1 |
| 1512-01 | 18 | 18% | 4% | |
| 1512-02 | 19.2 | 19% | 3% | |
| 1512-04 | 10.8 | 17% | 8% | |
| 1512-05 | 16.7 | 1.7 | 10% | |
| 1512-06 | 12.6 | 23.6 | 4% | |
| 1512-07 | 3.6 | 30 | 4% | |
| 1512-11 | 30 | 22% | 5% | |
| 1512-12 | 11.3 | 10.5 | 5% | |
| 1512-14 | 3.2 | 27.9 | 7% | |
| 1512-15 | 20.9 | 23% | 6% | |
| 1512-16 | 6.5 | 34% | 10% | |
| 1512-17 | 39% | 6% | 4% | |
| 1512-19 | 14.3 | 17% | 3% | |
| 1512-20 | 11.2 | 9% | 8% | |
| 1512-23 | 14.6 | 34% | 6% | |
| 1512-26 | 26.9 | 7% | 5% | |
| 1512-27 | 16.5 | 13% | 3% | |
| 1512-29 | 47% | 8% | 4% | |
| 1512-31 | 43% | 9% | 14% | |
| 1512-32 | 21.9 | 10% | 5% | |
| 1512-35 | 22.5 | 23% | 4% | |
| 1512-36 | 3.8 | 48% | 9% | |
| 1512-39 | 6 | 47% | 4% | |
| 1512-40 | 40% | 9% | 3% | |
| 1512-41 | 30 | 4.4 | 4% | |
| 1512-42 | 25 | 15% | 1% | |
| 1512-43 | 11 | 27% | 9% | |
| 1512-44 | 43% | 20% | 6% | |
| 1512-45 | 27% | 16% | 11% | |
| 1512-46 | 11.7 | 27.2 | 10% | |
| 1512-47 | 3.5 | 0.3 | 13% | |
| 1515-01 | 7 | 25% | >30 | 2.3 |
| 1515-02 | 3.8 | 26% | >30 | 1.5 |
| 1515-03 | 1.9 | 40% | >30 | 2.9 |
| 1515-04 | 5.2 | 43% | >30 | 2.8 |
| 1515-05 | 4 | 9.8 | >30 | 0.9 |
| 1515-06 | 1.7 | 6.2 | >30 | 1.1 |
| 1515-07 | 14.2 | 3.8 | >30 | 1.2 |
| 1515-08 | 11% | 9% | >30 | 2 |
| 1515-09 | 4.1 | 44% | >30 | 1.1 |
| 1515-10 | 5.7 | 38% | >30 | 1.1 |
| 1515-11 | 4.3 | 44% | >30 | 1.9 |
| 1515-12 | 6.3 | 9% | >30 | 8.2 |
| 1515-13 | 1.4 | 37% | >30 | 1.3 |
| 1515-14 | 2.9 | 7% | >30 | 4 |

TABLE 8-continued

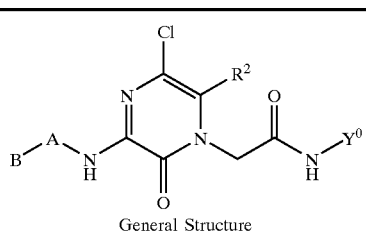

General Structure

Inhibitory Activity of Pyrazinones toward TF-VIIA, Thrombin II, Factor Xa, And Trypsin II.

| Ex. No. | IC50 or % Inhibition TF-VIIa (30 uM) | IC50 or % Inhibition Thrombin II (30 uM) | IC50 or % Inhibition Factor Xa (30 uM) | IC50 or % Inhibition Trpysin II (30 uM) |
|---|---|---|---|---|
| 1515-15 | 2.6 | 1% | >30 | 11.7 |
| 1515-16 | 8.8 | 3% | >30 | 17.3 |
| 1515-17 | 4.4 | 43% | >30 | 3.2 |
| 1515-18 | 0.6 | 4.4 | >30 | 1.1 |
| 1515-19 | 24.2 | 9.4 | >30 | 8.4 |
| 1515-20 | 32% | 36% | >30 | 1.2 |
| 1515-22 | 4.2 | 25% | >30 | 2.7 |
| 1515-23 | 6.2 | 18% | >30 | 8.5 |
| 1515-24 | 1.6 | 22% | >30 | 6.7 |
| 1515-25 | 2.9 | 3.5 | >30 | 1.4 |
| 1515-26 | 1.6 | 3.3 | >30 | 1.3 |
| 1515-27 | 1.1 | 2 | >30 | 2 |
| 1515-28 | 3 | 2.1 | >30 | 2.4 |
| 1515-29 | 5.2 | 1 | >30 | 2.2 |
| 1515-30 | 1.2 | 0.4 | >30 | 1.2 |
| 1515-31 | 8.1 | 0.1 | >30 | 1.2 |
| 1515-32 | 25% | 6.3 | >30 | 1.4 |
| 1515-33 | 2.3 | 1.1 | >30 | 1 |
| 1515-34 | 4.4 | 2.4 | >30 | 1.3 |
| 1515-35 | 1.8 | 1.2 | >30 | 1.1 |
| 1515-36 | 2.7 | 8.6 | >30 | 5.4 |
| 1515-37 | 3.6 | 4 | >30 | 1.6 |
| 1515-38 | 1.8 | 2.5 | >30 | 1.4 |
| 1515-39 | 1.6 | 1.7 | >30 | 2.3 |
| 1515-40 | 4.4 | 1.7 | >30 | 2.4 |
| 1515-41 | 2.6 | 0.4 | >30 | 1 |
| 1515-42 | 1.8 | 0.5 | >30 | 1.4 |
| 1515-43 | 6.8 | 0.1 | >30 | 1.1 |
| 1515-44 | 30% | 7.7 | >30 | 1.4 |
| 1515-45 | 2.9 | 1 | >30 | 1.2 |
| 1515-46 | 4.8 | 2 | >30 | 1.3 |
| 1515-47 | 3.1 | 1.6 | >30 | 1.8 |
| 1515-48 | 4.1 | 6.2 | >30 | 4.1 |
| 1517-01 | 1.2 | 1.8 | 0 | 0.38 |
| 1517-03 | 9 | 36% | 0 | 2 |
| 1517-04 | 5.7 | 14.5 | 0 | 4.5 |
| 1517-05 | 4.6 | 29.8 | 0 | 1.2 |
| 1517-06 | 2.5 | 11.9 | 0 | 1.6 |
| 1517-07 | 0.4 | 1.1 | 0 | 0.32 |
| 1517-08 | 43% | 30% | 0 | 3.8 |
| 1517-09 | 2.6 | 30% | 0 | 1.5 |
| 1517-10 | 2 | 38% | 0 | 2.1 |
| 1517-11 | 3 | 22% | 0 | 1.9 |
| 1517-12 | 0.8 | 18.1 | 0 | 2.1 |
| 1517-13 | 0.6 | 0.1 | 0 | 0.28 |
| 1517-14 | 30% | 20% | 0 | 8.4 |
| 1517-15 | 3.1 | 5.3 | 0 | 1.5 |
| 1517-16 | 3.4 | 26.1 | 0 | 5.1 |
| 1517-17 | 1.8 | 4.1 | 0 | 0.85 |
| 1517-18 | 1.3 | 1 | 0 | 0.98 |
| 1517-19 | 0.9 | 0.1 | 0 | 0.4 |
| 1517-20 | 22% | 25% | 0 | 7.3 |
| 1517-23 | 2.3 | 4.3 | 0 | 1.4 |
| 1517-24 | 1.8 | 1 | 0 | 0.84 |
| 1517-25 | 1.4 | 16.5 | 0 | 0.72 |
| 1517-26 | 1.8 | 2.1 | 0 | 0.32 |
| 1517-29 | 0.9 | 1.2 | 0 | 0.3 |
| 1517-31 | 9.1 | 19.9 | 0 | 0.69 |
| 1517-33 | 0.4 | 5.2 | 0 | 0.21 |

TABLE 8-continued

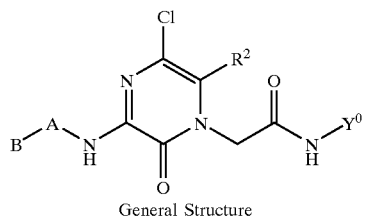

General Structure

Inhibitory Activity of Pyrazinones toward TF-VIIA, Thrombin II, Factor Xa, And Trypsin II.

| Ex. No. | IC50 or % Inhibition TF-VIIa (30 μM) | IC50 or % Inhibition Thrombin II (30 μM) | IC50 or % Inhibition Factor Xa (30 μM) | IC50 or % Inhibition Trpysin II (30 μM) |
|---|---|---|---|---|
| 1517-35 | 33% | 9% | 0 | 23.6 |
| 1517-36 | 3 | 28.1 | 0 | 0.61 |
| 1517-37 | 0.4 | 3.7 | 0 | 0.28 |
| 1517-38 | 0.7 | 8.7 | 0 | 0.33 |
| 1517-39 | 0.7 | 20.4 | 0 | 0.43 |
| 1517-40 | 1.2 | 6.4 | 0 | 0.37 |
| 1517-41 | 2.2 | 16.6 | 0 | 0.59 |
| 1517-43 | 25% | 4% | 0 | 43% |
| 1517-44 | 0.2 | 4 | 0 | 0.22 |
| 1517-46 | 0.4 | 11.3 | 0 | 0.36 |
| 1517-47 | 9.8 | 5.2 | 0 | 0.65 |
| 1517-48 | 1.2 | 2.4 | 0 | 0.29 |
| 1522-02 | 0.5 | 20 | >30 | 0.2 |
| 1522-05 | 0.6 | 10 | >30 | 0.2 |
| 1522-06 | 5.5 | 20 | >30 | 0.3 |
| 1522-07 | 0.47 | 1 | >30 | 0.15 |
| 1522-08 | 0.27 | 1 | >30 | 0.1 |
| 1522-09 | 0.2 | 3 | >30 | 0.2 |
| 1522-11 | 0.43 | 1 | >30 | 0.2 |
| 1522-12 | 0.81 | 8 | >30 | 0.3 |
| 1522-13 | 0.75 | 8 | >30 | 0.2 |
| 1522-14 | 0.84 | 8 | >30 | 0.2 |
| 1522-15 | 0.54 | 4 | >30 | 0.2 |
| 1522-17 | 0.62 | 1 | >30 | 0.35 |
| 1522-18 | 1.7 | 20 | >30 | 0.2 |
| 1522-19 | 13 | >30 | >30 | 0.3 |
| 1522-20 | 5 | >30 | >30 | 0.2 |
| 1522-21 | 0.72 | 3 | >30 | 0.2 |
| 1522-23 | 2.2 | 20 | >30 | 0.3 |
| 1522-27 | 6.3 | 20 | >30 | 0.35 |
| 1522-28 | >30 | >30 | >30 | 2 |
| 1522-31 | 6.4 | 8 | >30 | 0.35 |
| 1522-33 | 0.88 | 10 | >30 | 0.2 |
| 1522-34 | 0.5 | 8 | >30 | 0.2 |
| 1522-35 | 4 | 10 | >30 | 0.35 |
| 1522-36 | 1 | 10 | >30 | 0.3 |
| 1522-37 | 2 | 0.08 | >30 | 0.3 |
| 1522-38 | 1 | 0.1 | >30 | 0.3 |
| 1522-40 | 0.5 | 0.8 | >30 | 0.2 |
| 1522-41 | 0.5 | 10 | >30 | 0.2 |
| 1522-42 | 1 | 2 | >30 | 0.15 |
| 1522-43 | 0.8 | 20 | >30 | 0.3 |
| 1522-44 | 0.8 | 10 | >30 | 0.2 |
| 1522-46 | 1 | 10 | >30 | 0.2 |
| 1522-47 | 3 | 15 | >30 | 2 |
| 1526-01 | 0.02 | 13.13 | >30 | 0.15 |
| 1526-03 | 0.06 | 17.3 | >30 | 0.15 |
| 1526-04 | 0.03 | 18.08 | >30 | 0.16 |
| 1526-05 | 0.1 | 15 | >30 | 0.19 |
| 1526-06 | 0.17 | 12.04 | >30 | 0.21 |
| 1526-07 | 0.08 | 20.91 | >30 | 0.19 |
| 1526-09 | 0.03 | 11.23 | >30 | 0.14 |
| 1526-11 | 0.05 | 3.21 | >30 | 0.15 |
| 1526-12 | 0.04 | 28.41 | >30 | 0.2 |
| 1526-13 | 0.06 | 22.42 | >30 | 0.2 |
| 1526-14 | 0.04 | 7.63 | >30 | 0.14 |
| 1526-15 | 0.06 | 6.88 | >30 | 0.15 |
| 1526-16 | 0.04 | 5.6 | >30 | 0.13 |
| 1526-17 | 0.08 | 2.21 | >30 | 0.17 |
| 1526-19 | 0.04 | 16.97 | >30 | 0.15 |
| 1526-21 | 0.05 | 20.03 | >30 | 0.18 |
| 1526-23 | 0.03 | 9.45 | >30 | 0.15 |
| 1526-24 | 0.04 | 11.06 | >30 | 0.17 |
| 1526-25 | 0.14 | 40% | >30 | 0.19 |
| 1526-26 | 0.06 | 14.27 | >30 | 0.16 |
| 1526-29 | 0.12 | 50% | >30 | 0.22 |
| 1526-30 | 0.08 | 21.42 | >30 | 0.2 |
| 1526-33 | 0.26 | 29% | >30 | 0.24 |
| 1526-40 | 0.1 | 17.85 | >30 | 0.22 |
| 1526-41 | 0.07 | 24.04 | >30 | 0.16 |
| 1543-03 | 0.64 | 26% | 34% | 0.06 |
| 1543-05 | 0.06 | 27% | 14% | 0.07 |
| 1543-07 | 0.21 | 24.56 | 19% | 0.09 |
| 1543-09 | 0.69 | 14% | 12% | 0.18 |
| 1543-11 | 0.07 | 16.56 | 24% | 0.04 |
| 1543-13 | 0.09 | 41% | 12% | 0.06 |
| 1543-15 | 0.95 | 45% | 41% | 0.14 |
| 1543-19 | 0.22 | 37% | 11% | 0.08 |
| 1543-21 | 0.29 | 17.12 | 27% | 0.06 |
| 1543-25 | 0.28 | 8.12 | 26% | 0.05 |
| 1543-27 | 0.38 | 24.6 | 27% | 0.06 |
| 1543-31 | 0.04 | 24.26 | 8% | 0.06 |
| 1543-33 | 0.03 | 19.34 | 14% | 0.05 |
| 1543-34 | 0.08 | 17.32 | 20% | 0.06 |
| 1543-35 | 0.07 | 23.61 | 8% | 0.07 |
| 1543-36 | 0.08 | 12.57 | 15% | 0.05 |
| 1543-37 | 1.23 | 16% | 16% | 0.12 |
| 1543-38 | 0.09 | 18.26 | 14% | 0.06 |
| 1543-39 | 0.04 | 12.77 | 14% | 0.05 |
| 1543-40 | 0.04 | 11.45 | 10% | 0.04 |
| 1543-41 | 3% | 0% | 9% | 6% |
| 1543-45 | 1% | 0% | 5% | 8% |
| 1543-46 | 22% | 0% | 11% | 18% |

TABLE 9

Inhibitory Activity of Pyrazinones toward Factor Xa, TF-VIIA, Thrombin II, and Trypsin II.

| Example Number | % Inhibition TF-VIIa (100 vM) | % Inhibition Thrombin II (100 vM) | % Inhibition Factor Xa (100 vM) | % Inhibition Trpysin II (100 vM) |
|---|---|---|---|---|
| E-0001 | 0 | 0 | 1 | 0 |
| E-0002 | 0 | 0 | 0 | 0 |
| E-0003 | 0 | 10 | 0 | 0 |
| E-0004 | 0 | 6 | 0 | 0 |
| E-0005 | 0 | 0 | 0 | 0 |
| E-0006 | 2 | 0 | 0 | 1 |
| E-0007 | 0 | 0 | 0 | 0 |
| E-0008 | 0 | -0.2 | 0 | 0 |
| E-0009 | 0 | 8 | 1 | 1 |
| E-0010 | 0 | 5 | 0 | 0 |
| E-0011 | 0 | 0 | 0 | 0 |

TABLE 9-continued

Inhibitory Activity of Pyrazinones toward Factor Xa, TF-VIIA, Thrombin II, and Trypsin II.

| Example Number | % Inhibition TF-VIIa (100 vM) | % Inhibition Thrombin II (100 vM) | % Inhibition Factor Xa (100 vM) | % Inhibition Trpysin II (100 vM) |
|---|---|---|---|---|
| E-0012 | 0 | 0 | 0 | 0 |
| E-0013 | 0 | 2 | 0 | 1 |
| E-0014 | 0 | 6 | 0 | 0 |
| E-0015 | 0 | 3 | 0 | 3 |
| E-0016 | 0 | 10 | 0 | 4 |
| E-0017 | 0 | 10 | 0 | 1 |
| E-0018 | 1 | 10 | 0 | 4 |
| E-0019 | 0 | 9 | 0 | 2 |
| E-0020 | 0 | 13 | 1 | 4 |
| E-0021 | 0 | 9 | 1 | 5 |
| E-0022 | 0 | 12 | 0 | 2 |
| E-0023 | 0 | 5 | 0 | 1 |
| E-0024 | 0 | 0 | 0 | 1 |
| E-0025 | 0 | 13 | 0 | 3 |
| E-0026 | 0 | 13 | 0 | 3 |
| E-0027 | 0 | 10 | 0 | 2 |
| E-0028 | 0 | 8 | 0 | 3 |
| E-0029 | 0 | 8 | 0 | 2 |
| E-0030 | 0 | 8 | 0 | 4 |
| E-0031 | 0 | 4 | 0 | 1 |
| E-0032 | 0 | 6 | 0 | 3 |
| E-0033 | 0 | 6 | 0 | 5 |
| E-0034 | 0 | 7 | 6 | 3 |
| E-0035 | 4 | 12 | 0 | 2 |
| E-0036 | 0 | 1 | 0 | 0 |
| E-0037 | 0 | 5 | 0 | 2 |
| E-0038 | 0 | 9 | 0 | 3 |
| E-0039 | 0 | 9 | 1 | 2 |
| E-0040 | 0 | 7 | 0 | 4 |
| E-0041 | 0 | 8 | 0 | 2 |
| E-0042 | 0 | 8 | 0 | 5 |
| E-0043 | 0 | 12 | 0 | 3 |
| E-0044 | 0 | 9 | 0 | 3 |
| E-0045 | 0 | 7 | 0 | 4 |
| E-0046 | 0 | 7 | 0 | 4 |
| E-0047 | 0 | 9 | 0 | 2 |
| E-0048 | 0 | 1 | 0 | 0 |
| E-0049 | 2 | 0 | 0 | 0 |
| E-0050 | 0 | 0 | 0 | 0 |
| E-0051 | 0 | 0 | 0 | 0 |
| E-0052 | 0 | 0 | 0 | 0 |
| E-0053 | 0 | 0 | 0 | 0 |
| E-0054 | 0 | 0 | 0 | 0 |
| E-0055 | 0 | 0 | 0 | 0 |
| E-0056 | 0 | 0 | 0 | 0 |
| E-0057 | 0 | 0 | 6 | 0 |
| E-0058 | 0 | 0 | 0 | 0 |
| E-0059 | 0 | 0 | 0 | 0 |
| E-0060 | 0 | 0 | 0 | 0 |
| E-0061 | 0 | 0 | 0 | 0 |
| E-0062 | 0 | 0 | 0 | 0 |
| E-0063 | 0 | 0 | 0 | 0 |
| E-0064 | 0 | 0 | 0 | 0 |
| E-0065 | 0 | 0 | 0 | 0 |
| E-0066 | 0 | −0.2 | 0 | 0 |
| E-0067 | 0 | 1 | 0 | 0 |
| E-0068 | 0 | 3 | 0 | 0 |
| E-0069 | 0 | 0 | 0 | 0 |
| E-0070 | 0 | 0 | 0 | 0 |
| E-0071 | 0 | 0 | 0 | 0 |
| E-0072 | 0 | 0 | 0 | 0 |
| E-0073 | 0 | 0 | 2 | 6 |
| E-0074 | 0 | 0 | 0 | 8 |
| E-0075 | 0 | 0 | 0 | 7 |
| E-0076 | 0 | 0 | 1 | 10 |
| E-0077 | 0 | 0 | 3 | 7 |
| E-0078 | 0 | 3 | 1 | 10 |
| E-0079 | 0 | 0 | 4 | 11 |
| E-0080 | 1 | 0 | 4 | 5 |
| E-0081 | 0 | 24 | 5 | 8 |
| E-0082 | 4 | 0 | 4 | 3 |
| E-0083 | 2 | 53 | 3 | 6 |
| E-0084 | 0 | 0 | 0 | 8 |
| E-0085 | 0 | 5 | 0 | 9 |
| E-0086 | 0 | 0 | 4 | 11 |
| E-0087 | 0 | 0 | 0 | 10 |
| E-0088 | 0 | 0 | 3 | 9 |
| E-0089 | 3 | 0 | 4 | 8 |
| E-0090 | 0 | 0 | 2 | 11 |
| E-0091 | 1 | 0 | 4 | 8 |
| E-0092 | 1 | 0 | 3 | 9 |
| E-0093 | 0 | 14 | 0 | 10 |
| E-0094 | 2 | 0 | 2 | 7 |
| E-0095 | 2 | 0 | 4 | 9 |
| E-0096 | 0 | 5 | 0 | 10 |
| E-0097 | 0 | 0 | 3 | 11 |
| E-0098 | 0 | 0 | 2 | 8 |
| E-0099 | 0 | 0 | 1 | 10 |
| E-0100 | 7 | 0 | 6 | 12 |
| E-0101 | 11 | 2 | 10 | 11 |
| E-0102 | 0.4 | 0 | 3 | 13 |
| E-0103 | 2 | 0 | 3 | 11 |
| E-0104 | 3 | 0 | 5 | 9 |
| E-0105 | 0 | 0 | 3 | 12 |
| E-0106 | 5 | 0 | 3 | 9 |
| E-0107 | 4 | 0 | 6 | 12 |
| E-0108 | 0 | 0 | 4 | 12 |
| E-0109 | 2 | 0 | 3 | 12 |
| E-0110 | 0 | 0 | 3 | 14 |
| E-0111 | 4 | 0 | 1 | 14 |
| E-0112 | 11 | 0 | 1 | 13 |
| E-0113 | 14 | 0 | 3 | 11 |
| E-0114 | 10 | 0 | 3 | 14 |
| E-0115 | 15 | 0 | 3 | 11 |
| E-0116 | 13 | 0 | 4 | 10 |
| E-0117 | 9 | 0 | 1 | 9 |
| E-0118 | 12 | 0 | 3 | 9 |
| E-0119 | 13 | 0 | 5 | 10 |
| E-0120 | 8 | 0 | 1 | 9 |
| E-0121 | 0 | 8 | 0.1 | 0 |
| E-0122 | 0 | 8 | 0.1 | 0 |
| E-0123 | 0 | 6 | 0.1 | 1 |
| E-0124 | 0 | 6 | 0.1 | 0 |
| E-0125 | 0 | 4 | 0.1 | 0 |
| E-0126 | 0 | 4 | 0.1 | 0 |
| E-0127 | 0 | 5 | 0.1 | 0 |
| E-0128 | 0 | 7 | 0.1 | 0 |
| E-0129 | 0 | 5 | 0.1 | 0 |
| E-0130 | 0 | 2 | 0.1 | 0 |
| E-0131 | 0 | 0 | 0.1 | 1 |
| E-0132 | 0 | 0 | 0.1 | 0 |
| E-0133 | 0 | 5 | 0.1 | 0 |
| E-0134 | 0 | 5 | 0.1 | 1 |
| E-0135 | 0 | 3 | 0.1 | 2 |
| E-0136 | 0 | 3 | 0.1 | 1 |
| E-0137 | 2 | 3 | 0.1 | 0 |
| E-0138 | 1 | 4 | 0.1 | 3 |
| E-0139 | 0 | 4 | 0.1 | 3 |
| E-0140 | 0 | 4 | 0.1 | 2 |
| E-0141 | 0 | 4 | 0.1 | 2 |
| E-0142 | 1 | 5 | 0.1 | 3 |
| E-0143 | 1 | 2 | 0.1 | 1 |
| E-0144 | 0 | 0 | 0.1 | 1 |
| E-0145 | 0 | 5 | 0.1 | 0 |
| E-0146 | 0 | 8 | 0.1 | 0 |
| E-0147 | 0 | 3 | 0.1 | 1 |
| E-0148 | 0 | 5 | 0.1 | 3 |
| E-0149 | 0 | 4 | 0.1 | 0 |
| E-0150 | 0 | 6 | 0.1 | 2 |
| E-0151 | 0 | 6 | 0.1 | 3 |

TABLE 9-continued

Inhibitory Activity of Pyrazinones toward Factor Xa, TF-VIIA, Thrombin II, and Trypsin II.

| Example Number | % Inhibition TF-VIIa (100 vM) | % Inhibition Thrombin II (100 vM) | % Inhibition Factor Xa (100 vM) | % Inhibition Trpysin II (100 vM) |
|---|---|---|---|---|
| E-0152 | 0 | 6 | 0.1 | 4 |
| E-0153 | 0 | 3 | 0.1 | 1 |
| E-0154 | 0 | 5 | 0.1 | 3 |
| E-0155 | 2 | 6 | 0.1 | 4 |
| E-0156 | 0 | -0.4 | 0.1 | 1 |
| E-0157 | 0 | 5 | 0.1 | 0 |
| E-0158 | 0 | 3 | 0.1 | 6 |
| E-0159 | 0 | 4 | 0.1 | 1 |
| E-0160 | 0 | 6 | 0.1 | 2 |
| E-0161 | 0 | 6 | 0.1 | 1 |
| E-0162 | 0 | 7 | 0.1 | 4 |
| E-0163 | 0 | 5 | 0.1 | 0 |
| E-0164 | 0 | 5 | 0.1 | 0 |
| E-0165 | 0 | 7 | 0.1 | 0 |
| E-0166 | 0 | 6 | 0.1 | 1 |
| E-0167 | 0 | 4 | 0.1 | 1 |
| E-0168 | 7 | 5 | 0.1 | 0 |
| E-0169 | 0 | 2 | 0.1 | 1 |
| E-0170 | 0 | 7 | 0.1 | 0 |
| E-0171 | 0 | 9 | 0.1 | 2 |
| E-0172 | 0 | 6 | 0.1 | 0 |
| E-0173 | 0 | 5 | 0.1 | 1 |
| E-0174 | 0 | 5 | 0.1 | 1 |
| E-0175 | 0 | 6 | 0.1 | 2 |
| E-0176 | 0 | 7 | 0.1 | 0 |
| E-0177 | 0 | 6 | 0.1 | 0 |
| E-0178 | 0 | 3 | 0.1 | 2 |
| E-0179 | 0 | 10 | 0.1 | 0 |
| E-0180 | 0 | 3 | 0.1 | 0 |
| E-0181 | 0 | 5 | 0.1 | 3 |
| E-0182 | 0 | 5 | 0.1 | 0 |
| E-0183 | 0 | 5 | 0.1 | 2 |
| E-0184 | 0 | 2 | 0.1 | 0 |
| E-0185 | 0 | 3 | 0.1 | 2 |
| E-0186 | 0 | 5 | 0.1 | 0 |
| E-0187 | 0 | 8 | 0.1 | 1 |
| E-0188 | 0 | 2 | 0.1 | 8 |
| E-0189 | 0 | 6 | 0.1 | 1 |
| E-0190 | 0 | 4 | 0.1 | 3 |
| E-0191 | 0 | 6 | 0.1 | 0 |
| E-0192 | 0 | 0 | 0.1 | 0 |
| E-0193 | 0 | 5 | 0.1 | 0 |
| E-0194 | 0 | 14 | 0.2 | 0 |
| E-0195 | 0 | 1 | 0.1 | 0 |
| E-0196 | 0 | 1 | 0.1 | 0 |
| E-0197 | 0 | 3 | 0.1 | 1 |
| E-0198 | 0 | 0 | 0.1 | 3 |
| E-0199 | 0 | 1 | 0.1 | 2 |
| E-0200 | 0 | 33 | 0.2 | 2 |
| E-0201 | 0 | 1 | 0.1 | 1 |
| E-0202 | 0 | 1 | 0.1 | 1 |
| E-0203 | 0 | 5 | 0.1 | 2 |
| E-0204 | 0 | 1 | 0.1 | 1 |
| E-0205 | 0 | 1 | 0.1 | 2 |
| E-0206 | 0 | 2 | 0.1 | 1 |
| E-0207 | 0 | 2 | 0.1 | 1 |
| E-0208 | 0 | 4 | 0.1 | 1 |
| E-0209 | 1 | 3 | 0.1 | 3 |
| E-0210 | 0 | 6 | 0.1 | 2 |

What we claim is:
1. A compound having the Formula:

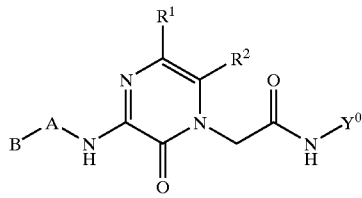

or a pharmaceutically acceptable salt thereof, wherein;
B is selected from the group consisting of hydrido, trialkylsilyl, C2–C4 alkyl, C3–C5 alkylenyl, C3–C4 alkenyl, C3–C4 alkynyl, and C2–C4 haloalkyl, wherein each member of group B is optionally substituted at any carbon up to and including 3 atoms from the point of attachment of B to A with one or more of the group consisting of $R^{32}$, $R^{33}$, and $R^{34}$;

$R^{32}$, $R^{33}$, and $R^{34}$ are independently selected from the group consisting of hydrido, acetamido, haloacetamido, amidino, guanidino, alkoxy, hydroxy, amino, alkoxyamino, lower alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, and cyano;

A is $(CH(R^{15}))_{pa}$—$N(R^7)$ wherein pa is an integer selected from 1 through 2 and $R^7$ is selected from the group consisting of hydrido and alkyl;

$R^{15}$ is selected from the group consisting of hydrido, halo, alkyl, and haloalkyl;

$R^1$ is selected from the group consisting of hydrido, alkyl, cyano, halo, and haloalkyl;

$R^2$ is $Z^0$—Q;

$Z^0$ is a covalent single bond;

Q is selected from the group consisting of aryl and heteroaryl, wherein (a) a ring carbon in a first alpha position relative to the ring carbon at the point of attachment is optionally substituted by $R^9$, (b) a ring carbon in a second alpha position relative to the ring carbon at the point of attachment is optionally substituted by $R^{13}$, (c) a ring carbon, in a first beta position relative to the ring carbon at the point of attachment and in an alpha position relative to the ring atom optionally substituted by $R^9$, is optionally substituted by $R^{10}$, (d) a ring carbon, in a second beta position relative to the ring carbon at the point of attachment and in an alpha position relative to the ring atom optionally substituted by $R^{13}$, is optionally substituted by $R^{12}$, and (e) a ring carbon, if present, in the gamma position relative to the ring carbon at the point of attachment and in an alpha position relative to each of the ring atoms optionally substituted by $R^{10}$ and $R^{12}$, respectively, is optionally substituted by $R^{11}$;

$R^9$, $R^{11}$, and $R^{13}$ are independently selected from the group consisting of hydrido, hydroxy, amino, amidino, guanidino, lower alkylamino, alkylthio, alkylsulfonamido, alkylsulfinyl, alkylsulfonyl, amidosulfonyl, monoalkyl amidosulfonyl, alkyl, alkoxy, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, hydroxy, amino, alkoxyamino, lower alkylamino, alkylsulfonamido, amidosulfonyl, monoalkyl amidosulfonyl, dialkyl amidosulfonyl, hydroxyalkyl, aminoalkyl, carboalkoxy, carboxy, carboxyalkyl, amidocarbonyl, halo, haloalkyl, and cyano;

$Y^0$ is formula (IV):

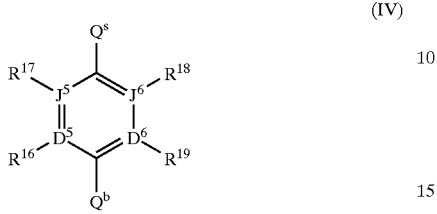

wherein $D^5$, $D^6$, $J^5$, and $J^6$ are independently selected from the group consisting of C, N, O, S and a covalent bond with the provisos that no more than one is a covalent bond, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N, with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$, $R^{17}$, $R^{18}$, and $R^{19}$ are independently selected from the group consisting of hydrido, amidino, guanidino, carboxy, haloalkylthio, alkoxy, hydroxy, amino, lower alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$Q^b$ is selected from the group consisting of $NR^{20}R^{21}$, hydrido, $C(NR^{25})NR^{23}R^{24}$, and $N(R^{26})C(NR^{25})N(R^{23})(R^{24})$, with the provisos that no more than one of $R^{20}$ and $R^{21}$ is hydroxy and that no more than one of $R^{23}$ and $R^{24}$ is hydroxy;

$R^{20}$, $R^{21}$, $R^{23}$, $R^{24}$, $R^{25}$, and $R^{26}$ are independently selected from the group consisting of hydrido, alkyl, and hydroxy; and $Q^s$ is selected from the group consisting of a single covalent bond, $CH_2$, and $CH_2CH_2$.

2. The compound as recited in claim 1 or a pharmaceutically acceptable salt thereof, wherein;

B is selected from the group consisting of ethyl, 2-propenyl, 2-propynyl, propyl, isopropyl, trimethylene, tetramethylene, butyl, 2-butenyl, 3-butenyl, 2-butynyl, sec-butyl, tert-butyl, isobutyl, 2-methylpropenyl, 2,2,2-trifluoroethyl, 3,3,3-trifluoropropyl, and 2,2-difluoropropyl, wherein each member of group B is optionally substituted at any carbon up to and including 3 atoms from the point of attachment of B to A with one or more of the group consisting of $R^{32}$, $R^{33}$, and $R^{34}$;

$R^{32}$, $R^{33}$, and $R^{34}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, and cyano;

A is $CH_2N(CH_3)$, $CH_2N(CH_2CH_3)$, $CH_2CH_2N(CH_3)$, or $CH_2CH_2N(CH_2CH_3)$;

$R^1$ is selected from the group consisting of hydrido, methyl, ethyl, propyl, trifluoromethyl, pentafluoroethyl, 2,2,2-trifluoroethyl, 2,2,3,3,3-pentafluoropropyl, fluoro, chloro, and bromo;

$R^2$ is $Z^0$—Q;

$Z^0$ is a covalent single bond;

Q is selected from the group consisting of phenyl and 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl heteroaryl rings, wherein (a) a ring carbon in a first alpha position relative to the ring carbon at the point of attachment is optionally substituted by $R^9$, (b) a ring carbon in a second alpha position relative to the ring carbon at the point of attachment is optionally substituted by $R^{13}$, (c) a ring carbon, in a first beta position relative to the ring carbon at the point of attachment and in an alpha position relative to the ring atom optionally substituted by $R^9$, is optionally substituted by $R^{10}$, (d) a ring carbon, in a second beta position relative to the ring carbon at the point of attachment and in an alpha position relative to the ring atom optionally substituted by $R^{13}$, is optionally substituted by $R^{12}$, and (e) a ring carbon, if present, in the gamma position relative to the ring carbon at the point of attachment and in an alpha position relative to each of the ring atoms optionally substituted by $R^{10}$ and $R^{12}$, respectively, is optionally substituted by $R^{11}$;

$R^9$, $R^{11}$, and $R^{13}$ are independently selected from the group consisting of hydrido, amidino, guanidino, carboxy, methyl, ethyl, propyl, isopropyl, methoxy, ethoxy, isopropoxy, propoxy, hydroxy, amino, N-methylamino, N,N-dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, amidocarbonyl, N-methylamidocarbonyl, N,N-dimethylamidocarbonyl, and cyano;

$R^{10}$ and $R^{12}$ are independently selected from the group consisting of hydrido, amidino, guanidino, carboxy, carboxymethyl, methyl, ethyl, propyl, isopropyl, methoxy, ethoxy, isopropoxy, propoxy, hydroxy, amino, methoxyamino, ethoxyamino, acetamido, trifluoroacetamido, aminomethyl, 1-aminoethyl, 2-aminoethyl, N-methylamino, dimethylamino, N-ethylamino, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, fluoro, chloro, bromo, and cyano;

$Y^0$ is selected from the group consisting of:

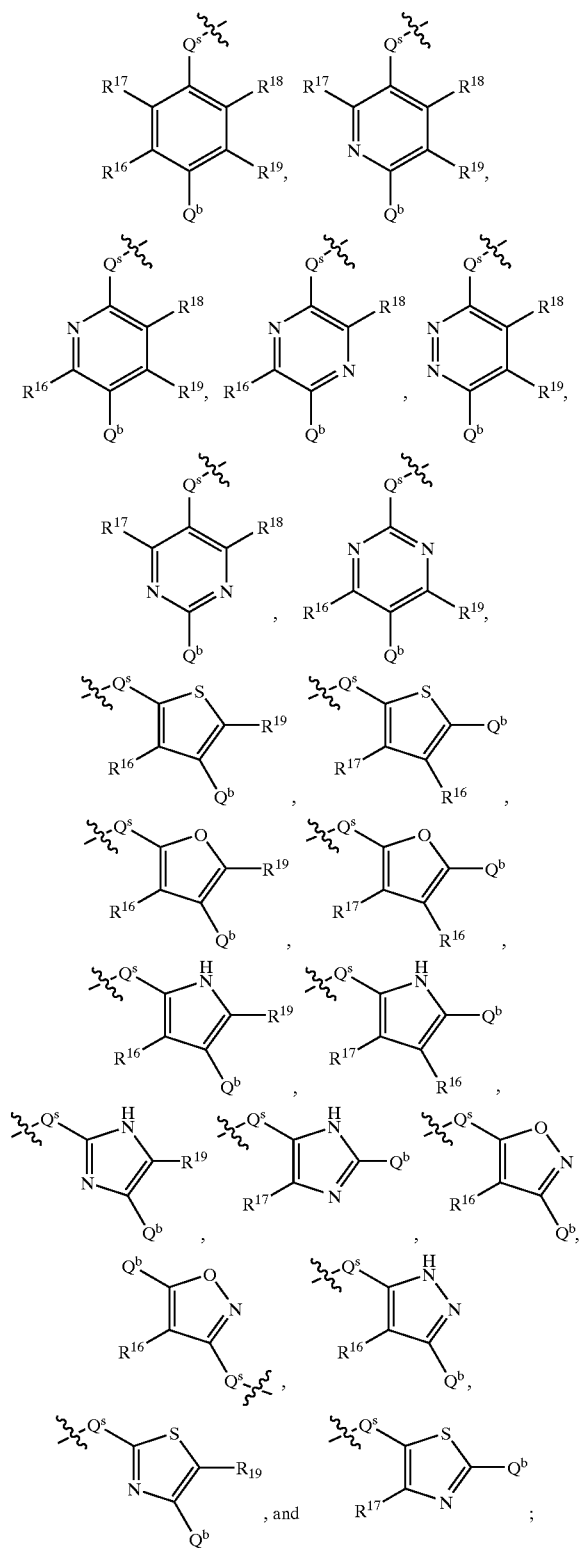

$R^{16}$, $R^{17}$, $R^{18}$, and $R^{19}$ are independently selected from the group consisting of hydrido, methyl, ethyl, isopropyl, propyl, carboxy, amidino, guanidino, methoxy, ethoxy, isopropoxy, propoxy, hydroxy, amino, aminomethyl, 1-aminoethyl, 2-aminoethyl, N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, and cyano;

$Q^b$ is selected from the group consisting of $NR^{20}R^{21}$, hydrido, $C(NR^{25})NR^{23}R^{24}$, and $N(R^{26})C(NR^{25})N(R^{23})(R^{24})$, with the provisos that no more than one of $R^{20}$, $R^{21}$, $R^{23}$, and $R^{24}$ can be hydroxy, when any two of the group consisting of $R^{20}$, $R^{21}$, $R^{23}$, and $R^{24}$ are bonded to the same atom;

$R^{20}$, $R^{21}$, $R^{23}$, $R^{24}$, $R^{25}$, and $R^{25}$ are independently selected from the group consisting of hydrido, methyl, ethyl, propyl, butyl, isopropyl, and hydroxy; and $Q^s$ is selected from the group consisting of a single covalent bond, $CH_2$, and $CH_2CH_2$.

3. The compound as recited in claim 1, or a pharmaceutically acceptable salt thereof, wherein;

A is selected from the group consisting of $CH_2N(CH_3)$, $CH_2N(CH_2CH_3)$, $CH_2CH_2N(CH_3)$, and $CH_2CH_2N(CH_2CH_3)$;

$R^1$ is selected from the group consisting of hydrido, methyl, ethyl, trifluoromethyl, pentafluoroethyl, 2,2,2-trifluoroethyl, fluoro, chloro, and bromo;

$R^2$ is $Z^0$—Q;

$Z^0$ is a covalent single bond;

Q is selected from the group consisting of phenyl and 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl heteroaryl rings, wherein (a) a ring carbon in a first alpha position relative to the ring carbon at the point of attachment is optionally substituted by $R^9$, (b) a ring carbon in a second alpha position relative to the ring carbon at the point of attachment is optionally substituted by $R^{13}$, (c) a ring carbon, in a first beta position relative to the ring carbon at the point of attachment and in an alpha position relative to the ring atom optionally substituted by $R^9$, is optionally substituted by $R^{10}$, (d) a ring carbon, in a second beta position relative to the ring carbon at the point of attachment and in an alpha position relative to the ring atom optionally substituted by $R^{13}$, is optionally substituted by $R^{12}$, and (e) a ring carbon, if present, in the gamma position relative to the ring carbon at the point of attachment and in an alpha position relative to each of the ring atoms optionally substituted by $R^{10}$ and $R^{12}$, respectively, is optionally substituted by $R^{11}$;

$R^9$, $R^{11}$, and $R^{13}$ are independently selected from the group consisting of hydrido, amidino, guanidino, carboxy, methyl, ethyl, propyl, isopropyl, methoxy, ethoxy, isopropoxy, propoxy, hydroxy, amino, N-methylamino, N,N-dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, amidocarbonyl, N-methylamidocarbonyl, N,N-dimethylamidocarbonyl, and cyano;

$R^{10}$ and $R^{12}$ are independently selected from the group consisting of hydrido, amidino, guanidino, carboxy, carboxymethyl, methyl, ethyl, propyl, isopropyl, methoxy, ethoxy, isopropoxy, propoxy, hydroxy, amino, methoxyamino, ethoxyamino, acetamido, trifluoroacetamido, aminomethyl, 1-aminoethyl, 2-aminoethyl, N-methylamino, dimethylamino, N-ethylamino, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, fluoro, chloro, bromo, and cyano;

$Y^0$ is selected from the group consisting of:

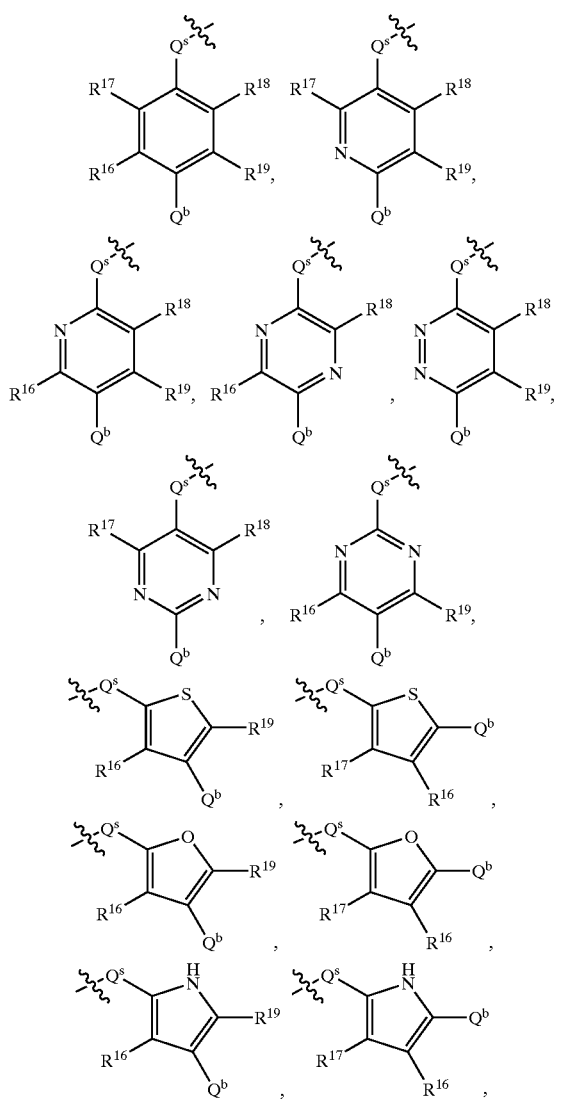

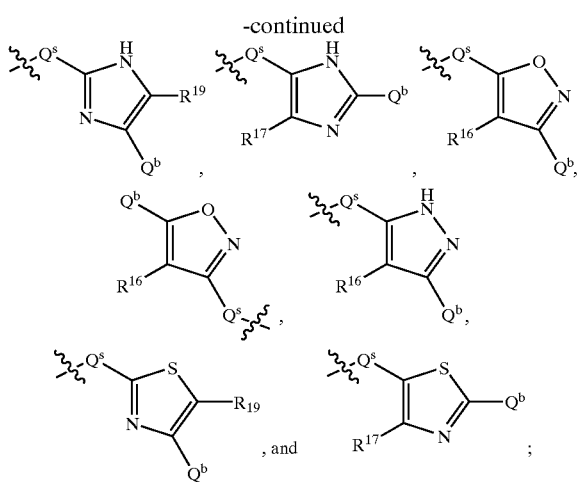

$R^{16}, R^{17}, R^{18,}$ and $R^{19}$ are independently selected from the group consisting of hydrido, methyl, ethyl, isopropyl, propyl, amidino, guanidino, methoxy, ethoxy, isopropoxy, propoxy, hydroxy, amino, aminomethyl, 1-aminoethyl, 2-aminoethyl, N-N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, and cyano;

$Q^b$ is selected from the group consisting of $NR^{20}R^{21}$, $C(NR^{25})NR^{23}R^{24}$, and $N(R^{26})C(NR^{25})N(R^{23})(R^{24})$, with the provisos that no more than one of $R^{20}$, $R^{21}$, $R^{23}$, and $R^{24}$ can be hydroxy when any two of the group consisting of $R^{20}$, $R^{21}$, $R^{23}$, and $R^{24}$ are bonded to the same atom;

$R^{20}$, $R^{21}$, $R^{23}$, $R^{24}$, $R^{25}$, and $R^{26}$ are independently selected from the group consisting of hydrido, methyl, ethyl, propyl, butyl, isopropyl, and hydroxy; and $Q^s$ is selected from the group consisting of a single covalent bond, $CH_2$, and $CH_2CH_2$.

4. The compound as-recited in claim 3 or a pharmaceutically acceptable salt thereof, wherein;

A is selected from the group consisting of $CH_2N(CH_3)$, $CH_2N(CH_2CH_3)$, $CH_2CH_2N(CH_3)$, and $CH_2CH_2N(CH_2CH_3)$;

$R^1$ is selected from the group consisting of hydrido, methyl, ethyl, propyl, trifluoromethyl, pentafluoroethyl, 2,2,2-trifluoroethyl, fluoro, chloro, and bromo;

$R^2$ is $Z^0$—Q;

$Z^0$ is a covalent single bond;

Q is selected from the group consisting of 5-amino-3-amidocarbonylphenyl, 5-amino-2-fluorophenyl, 3-amino-5-hydroxymethylphenyl, 5-amino-3-methoxycarbonylphenyl, 3-amidinophenyl, 3-amino-2-methylphenyl, 5-amino-2-methylthiophenyl, 3-aminophenyl, benzyl, 3-carboxyphenyl, 3-carboxy-5-hydroxyphenyl, 3-carboxy-5-aminophenyl, 3-chlorophenyl, 2-chlorophenyl, 3-cyanophenyl, 3-dimethylaminophenyl, 2-fluorophenyl, 3-fluorophenyl, 2-hydroxyphenyl, 3-hydroxyphenyl, 3-methanesulfonylaminophenyl, 2-methoxyphenyl, 3-methoxyphenyl, 3-methoxyaminophenyl, 3-methoxycarbonylphenyl, 2-methylaminophenyl, 3-methylaminophenyl, 2-methylphenyl, 3-methylphenyl, 4-methylphenyl, phenyl, 3-trifluoroacetamidophenyl, 3-trifluoromethylphenyl, 2-trifluoromethylphenyl, 5-amino-2-thienyl, 5-amino-3-thienyl, 3-bromo-2-thienyl, 3-pyridyl, 4-pyridyl, 2-thienyl, and 3-thienyl;

$Y^0$ is selected from the group consisting of:

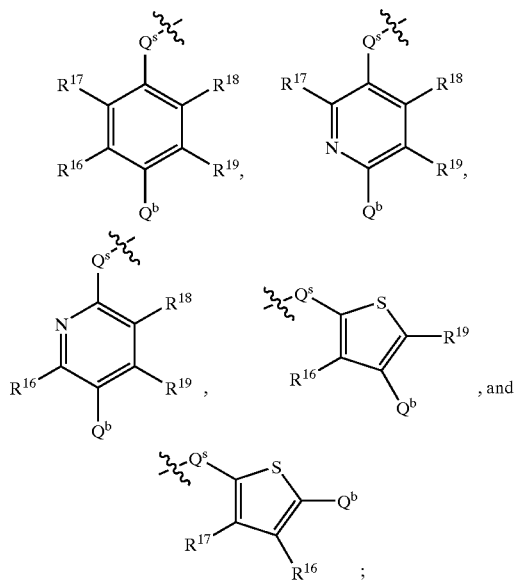

$R^{16}$ and $R^{19}$ are independently selected from the group consisting of: hydrido, amidino, amino, aminomethyl, methoxy, methylamino, hydroxy, hydroxymethyl, fluoro, chloro, and cyano;

$R^{17}$ and $R^{18}$ are independently selected from the group consisting of hydrido, fluoro, chloro, hydroxy, hydroxymethyl, amino, carboxy, and cyano;

$Q^b$ is selected from the group consisting of hydrido and $C(NR^{25})NR^{23}R^{24}$;

$R^{23}$, $R^{24}$, and $R^{25}$ are independently selected from the group consisting of hydrido and methyl; and $Q^s$ is $CH_2$.

5. A compound, or a pharmaceutically acceptable salt thereof, where said compound is selected from the group consisting of:

6-[3-aminophenyl]-5-chloro-N-[[4-iminomethylphenyl]methyl]-3-[N,N-dimethylhydrazino]-2-oxo-1(2H)-pyrazineacetamide;

6-[3-aminophenyl]-5-chloro-3-[N-ethyl-N-methylhydrazino]-N-[[4-iminomethylphenyl]methyl]-2-oxo-1(2H)-pyrazineacetamide;

6-[3-aminophenyl]-5-chloro-3-[N,N-diethylhydrazino]-N-[[4-iminomethylphenyl]methyl]-2-oxo-1(2H)-pyrazineacetamide; and 6-[3-aminophenyl]-3-[N-(azetidin-1-yl)amino]-5-chloro-N-[[4-iminomethylphenyl]methyl]-2-oxo-1(2H)-pyrazineacetamide.

6. A compound having the Formula:

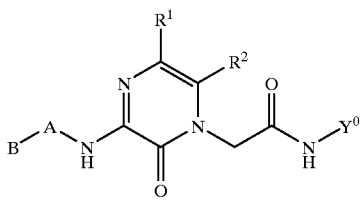

or a pharmaceutically acceptable salt thereof, wherein;

B is selected from the group consisting of hydrido C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, lower alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and $Q^b$;

$Q^b$ is selected from the group consisting of $NR^{20}R^{21}$, hydrido, $C(NR^{25})NR^{23}R^{24}$, and $N(R^{26})C(NR^{25})N(R^{23})(R^{24})$, with the provisos that no more than one of $R^{20}$ and $R^{21}$ is hydroxy and that no more than one of $R^{23}$ and $R^{24}$ is hydroxy;

$R^{20}$, $R^{21}$, $R^{23}$, $R^{24}$, $R^{25}$, and $R^{26}$ are independently selected from the group consisting of hydrido, alkyl, and hydroxy;

A is selected from the group consisting of single covalent bond and $(CH(R^{15}))_{pa}$—$(W^7)_{rr}$ wherein rr is an integer selected from 0 through 1, pa is an integer selected from 0 through 3, and $W^7$ is selected from the group consisting of $(R^7)NC(O)$ and $N(R^7)$;

$R^7$ is selected from the group consisting of hydrido, hydroxy and alkyl;

$R^{15}$ is selected from the group consisting of hydrido, halo, alkyl, and haloalkyl;

$R^1$ is selected from the group consisting of hydrido, alkyl, cyano, haloalkyl, and halo;

$R^2$ is $Z^0$—Q;

$Z^0$ is a covalent single bond;

Q is selected from the group consisting of aryl and heteroaryl wherein (a) a ring carbon in a first alpha position relative to the ring carbon at the point of attachment is optionally substituted by $R^9$, (b) a ring carbon in a second alpha position relative to the ring carbon at the point of attachment is optionally substituted by $R^{13}$, (c) a ring carbon, in a first beta position relative to the ring carbon at the point of attachment and in an alpha position relative to the ring atom optionally substituted by $R^9$, is optionally substituted by $R^{10}$, (d) a ring carbon, in a second beta position relative to the ring carbon at the point of attachment and in an alpha position relative to the ring atom optionally substituted by $R^{13}$, is optionally substituted by $R^{12}$, and (e) a ring carbon, if present, in the gamma position relative to the ring carbon at the point of attachment and in an alpha position relative to each of the ring atoms optionally substituted by $R^{10}$ and $R^{12}$, respectively, is optionally substituted by $R^{11}$;

$R^9$, $R^{11}$, and $R^{13}$ are independently selected from the group consisting of hydrido, hydroxy, amino, amidino, guanidino, lower alkylamino, alkylthio, alkylsulfonamido, alkylsulfinyl, alkylsulfonyl, amidosulfonyl, monoalkyl amidosulfonyl, alkyl, alkoxy, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, hydroxy, amino, alkoxyamino, lower alkylamino, alkylsulfonamido, amidosulfonyl, monoalkyl amidosulfonyl, dialkyl amidosulfonyl, hydroxyalkyl, aminoalkyl, carboalkoxy, carboxy, carboxyalkyl, amidocarbonyl, halo, haloalkyl, and cyano;

$Y^0$ is formula (IV):

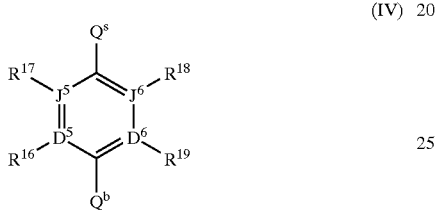

(IV)

wherein $D^5$, $D^6$, $J^5$, and $J^6$ are independently selected from the group consisting of C, N, O, S and a covalent bond with the provisos that no more than one is a covalent bond, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N;

$R^{16}$, $R^{17}$, $R^{18}$, and $R^{19}$ are independently selected from the group consisting of hydrido, amidino, guanidino, carboxy, haloalkylthio, alkoxy, hydroxy, amino, lower alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano; and $Q^s$ is selected from the group consisting of a single covalent bond, $CH_2$, and $CH_2CH_2$.

7. The compound as recited in claim 6 or a pharmaceutically acceptable salt thereof, wherein;

B is selected from the group consisting of hydrido, ethyl, 2-propynyl, 2-propenyl, propyl, isopropyl, butyl, 2-butenyl, 3-butenyl, 2-butynyl, sec-butyl, tert-butyl, isobutyl, 2-methylpropenyl, 1-pentyl, 2-pentenyl, 3-pentenyl, 4-pentenyl, 2-pentynyl, 3-pentynyl, 2-pentyl, 1-methyl-2-butenyl, 1-methyl-3-butenyl, 1-methyl-2-butynyl, 3-pentyl, 1-ethyl-2-propenyl, 2-methylbutyl, 2-methyl-2-butenyl, 2-methyl-3-butenyl, 2-methyl-3-butynyl, 3-methylbutyl, 3-methyl-2-butenyl, 3-methyl-3-butenyl, 1-hexyl, 2-hexenyl, 3-hexenyl, 4-hexenyl, 5-hexenyl, 2-hexynyl, 3-hexynyl, 4-hexynyl, 2-hexyl, 1-methyl-2-pentenyl, 1-methyl-3-pentenyl, 1-methyl-4-pentenyl, 1-methyl-2-pentynyl, 1-methyl-3-pentynyl, 3-hexyl, 1-ethyl-2-butenyl, 1-ethyl-3-butenyl, 1-propyl-2-propenyl, 1-ethyl-2-butynyl, 1-heptyl, 2-heptenyl, 3-heptenyl, 4-heptenyl, 5-heptenyl, 6-heptenyl, 2-heptynyl, 3-heptynyl, 4-heptynyl, 5-heptynyl, 2-heptyl, 1-methyl-2-hexenyl, 1-methyl-3-hexenyl, 1-methyl-4-hexenyl, 1-methyl-5-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-4-pentenyl, 1-butyl-2-propenyl, 1-ethyl-2-pentynyl, 1-ethyl-3-pentynyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, cyano, and $Q^b$;

$Q^b$ is selected from the group consisting of $NR^{20}R^{21}$, hydrido, $C(NR^{25})NR^{23}R^{24}$, and $N(R^{26})C(NR^{25})N(R^{23})(R^{24})$, with the provisos that no more than one of $R^{20}$ and $R^{21}$ is hydroxy and that no more than one of $R^{23}$ and $R^{24}$ is hydroxy;

$R^{20}$, $R^{21}$, $R^{23}$, $R^{24}$, $R^{25}$, and $R^{26}$ are independently selected from the group consisting of hydrido, methyl, ethyl, propyl, butyl, isopropyl, and hydroxy;

A is selected from the group consisting of single covalent bond, NH, $N(CH_3)$, N(OH), $CH_2$, $CH_3CH$, $CF_3CH$, NHC(O), $N(CH_3)C(O)$, C(O)NH, $C(O)N(CH_3)$, $CH_2CH_2$, $CH_2CH_2CH_2$, $CH_3CHCH_2$, and $CF_3CHCH_2$;

$R^1$ is selected from the group consisting of hydrido, methyl, ethyl, propyl, trifluoromethyl, pentafluoroethyl, 2,2,2-trifluoroethyl, 2,2,3,3,3-pentafluoropropyl, fluoro, chloro, and bromo;

$R^2$ is $Z^0$—Q;

$Z^0$ is a covalent single bond;

Q is selected from the group consisting of phenyl and 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2pyrimidinyl, 4-pyrimidinyl, 5-pyrimidinyl, 3-pyridazinyl, 4-pyridazinyl, and 1,3,5-triazin-2-yl heteroaryl rings, wherein (a) a ring carbon in a first alpha position relative to the ring carbon at the point of attachment is optionally substituted by $R^9$, (b) a ring carbon in a second alpha position relative to the ring carbon at the point of attachment is optionally substituted by $R^{13}$, (c) a ring carbon, in a first beta position relative to the ring carbon at the point of attachment and in an alpha position relative to the ring atom optionally substituted by $R^9$, is optionally substituted by $R^{10}$, (d) a ring carbon, in a second beta position relative to the ring carbon at the point of attachment and in an alpha position relative to the ring atom optionally substituted by $R^{13}$, is optionally substituted by $R^{12}$, and (e) a ring carbon, if present, in the gamma position relative to the ring carbon at the point of attachment and in an alpha position relative to each of the ring atoms optionally substituted by $R^{10}$ and $R^{12}$, respectively, is optionally substituted by $R^{11}$;

$R^9$, $R^{11}$, and $R^{13}$ are independently selected from the group consisting of hydrido, amidino, guanidino, carboxy, methyl, ethyl, propyl, isopropyl, methoxy, ethoxy, isopropoxy, propoxy, hydroxy, amino, N-methylamino, N,N-dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, amidocarbonyl, N-methylamidocarbonyl, N,N-dimethylamidocarbonyl, and cyano;

$R^{10}$ and $R^{12}$ are independently selected from the group consisting of hydrido, amidino, guanidino, carboxy, carboxymethyl, methyl, ethyl, propyl, isopropyl, methoxy, ethoxy, isopropoxy, propoxy, hydroxy, amino, methoxyamino, ethoxyamino, acetamido, trifluoroacetamido, aminomethyl, 1-aminoethyl, 2-aminoethyl, N-methylamino, dimethylamino, N-ethylamino, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, fluoro, chloro, bromo, and cyano;

$Y^0$ is selected from the group consisting of:

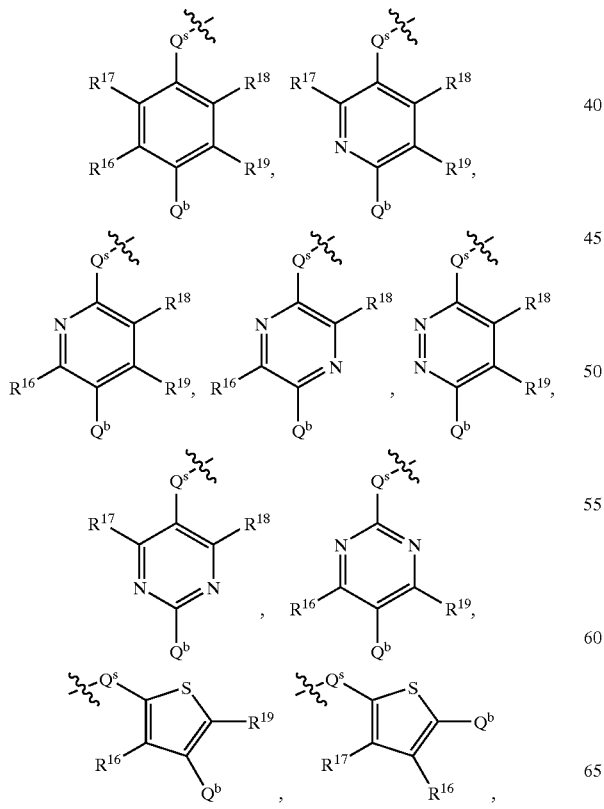

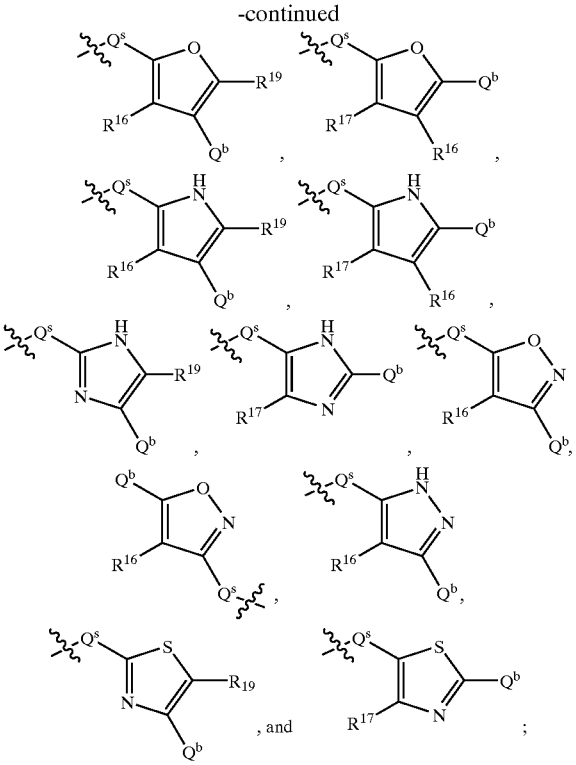

$R^{16}$, $R^{17}$, $R^{18}$, $R^{19}$ are independently selected from the group consisting of hydrido, methyl, ethyl, isopropyl, propyl, carboxy, amidino, guanidino, methoxy, ethoxy, isopropoxy, propoxy, hydroxy, amino, aminomethyl, 1-aminoethyl, 2-aminoethyl, N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, and cyano; and $Q^s$ is selected from the group consisting of a single covalent bond, $CH_2$, and $CH_2CH_2$.

8. The compound as recited in claim 7 or a pharmaceutically acceptable salt thereof, wherein;

B is selected from the group consisting of hydrido, ethyl, 2-propenyl, 2-propynyl, propyl, isopropyl, butyl, 2-butyl, (R)-2-butyl,(S)-2-butyl, tert-butyl, isobutyl, 1-pentyl, 3-pentyl, 2-methylbutyl, 2,2,2-trifluoroethyl, 6-amidocarbonylhexyl, 4-methyl-2-pentyl, 3-hydroxypropyl, 3-methoxy-2-propyl, 2-methoxyethyl, 2-methyl-2-butyl, 3-methyl-2-butyl, 2-dimethylaminopropyl, 2-cyanoethyl, 6-hydroxyhexyl, 2-hydroxyethyl, 2-amidinoethyl, 2-guanidinoethyl, 3-guanidinopropyl, 4-guanidinobutyl, 3-hydroxypropyl, 4-hydroxybutyl, 6-cyanohexyl, 2-dimethylaminoethyl, 3-methylbutyl, 2-methylbutyl, (S)-2-methylbutyl, 3-aminopropyl, 2-hexyl, and 4-aminobutyl;

A is selected from the group consisting of single covalent bond, $CH_2$, $NHC(O)$, $CH_2CH_2$, $CH_2CH_2CH_2$, and $CH_3CHCH_2$;

R¹ is selected from the group consisting of hydrido, methyl, ethyl, propyl, trifluoromethyl, pentafluoroethyl, 2,2,2-trifluoroethyl, fluoro, chloro, and bromo;

R² is Z⁰—Q;

Z⁰ is a covalent single bond;

Q is selected from the group consisting of 5-amino-3-amidocarbonylphenyl, 5-amino-2-fluorophenyl, 3-amino-5-hydroxymethylphenyl, 5-amino-3-methoxycarbonylphenyl, 3-amidinophenyl, 3-amino-2-methylphenyl, 5-amino-2-methylthiophenyl, 3-aminophenyl, benzyl, 3-carboxyphenyl, 3-carboxy-5-aminophenyl, 3-carboxy-5-hydroxyphenyl, 3-carboxymethyl-5-aminophenyl, 3-carboxymethyl-5-hydroxyphenyl, 3-carboxymethylphenyl, 3-chlorophenyl, 2-chlorophenyl, 2,6-dichlorophenyl, 3-cyanophenyl, 3-dimethylaminophenyl, 2-fluorophenyl, 3-fluorophenyl, 2,5-difluorophenyl, 2-hydroxyphenyl, 3-hydroxyphenyl, 3-methanesulfonylaminophenyl, 2-methoxyphenyl, 3-methoxyphenyl, 3-methoxyaminophenyl, 3-methoxycarbonylphenyl, 2-methylaminophenyl, 3-methylaminophenyl, 2-methylphenyl, 3-methylphenyl, 4-methylphenyl, phenyl, 3-trifluoroacetamidophenyl, 3-trifluoromethylphenyl, 2-trifluoromethylphenyl, 5-amino-2-thienyl, 5-amino-3-thienyl, 3-bromo-2-thienyl, 3-pyridyl, 4-pyridyl, 2-thienyl, and 3-thienyl;

Y⁰ is selected from the group consisting of:

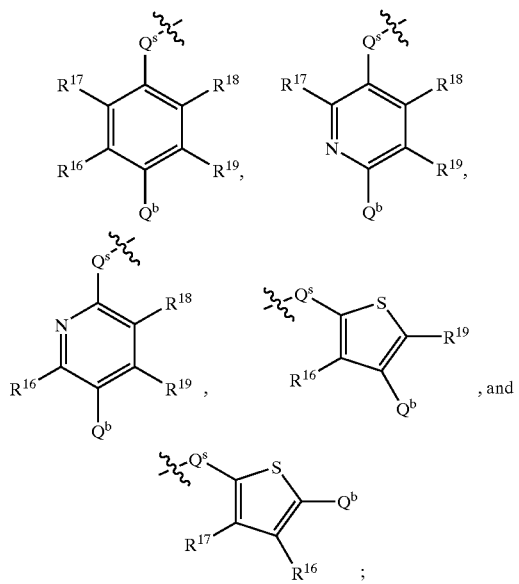

R¹⁶ and R¹⁹ are independently selected from the group consisting of: hydrido, amidino, amino, aminomethyl, methoxy, methylamino, hydroxy, hydroxymethyl, fluoro, chloro, and cyano;

R¹⁷ and R¹⁸ are independently selected from the group consisting of hydrido, fluoro, chloro, hydroxy, hydroxymethyl, amino, carboxy, and cyano;

Qᵇ is selected from the group consisting of hydrido and C(NR²⁵)NR²³R²⁴;

R²³, R²⁴, and R²⁵ are independently selected from the group consisting of hydrido and methyl; and Qˢ is CH₂.

9. The compound as recited in claim 6, or a pharmaceutically acceptable salt thereof, wherein;

B is selected from the group consisting of hydrido, C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of R³², R³³, R³⁴, R³⁵, and R³⁶;

R³², R³³, R³⁴, R³⁵, and R³⁶ are independently selected from the group consisting of hydrido, acetamido, haloacetamido, amidino, guanidino, alkoxy, hydroxy, amino, alkoxyamino, lower alkylamino, alkylthio, amidosulfonyl, monoalkyl amidosulfonyl, dialkyl amidosulfonyl, alkyl, halo, haloalkyl, haloalkoxy, hydroxyalkyl, carboalkoxy, carboxy, carboxamido, cyano, and Qᵇ;

Qᵇ is selected from the group consisting of NR²⁰R²¹, hydrido, N(R²⁶)C(NR²⁵)N(R²³)(R²⁴), and C(NR²⁵)NR²³R²⁴;

R²⁰, R²¹, R²³, R²⁴, R²⁵, and R²⁶ are independently selected from the group consisting of hydrido and alkyl;

A is selected from the group consisting of single covalent bond and (CH(R¹⁵))ₚₐ—(W⁷)ᵣᵣ wherein rr is an integer selected from 0 through 1, pa is an integer selected from 0 through 3, and W⁷ is N(R⁷);

R⁷ is selected from the group consisting of hydrido and alkyl;

R¹⁵ is selected from the group consisting of hydrido, halo, alkyl, and haloalkyl;

R¹ is selected from the group consisting of hydrido, cyano, haloalkyl, and halo;

R² is Z⁰—Q;

Z⁰ is a covalent single bond;

Q is selected from the group consisting of aryl and heteroaryl wherein (a) a ring carbon in a first alpha position relative to the ring carbon at the point of attachment is optionally substituted by R⁹, (b) a ring carbon in a second alpha position relative to the ring carbon at the point of attachment is optionally substituted by R¹³, (c) a ring carbon, in a first beta position relative to the ring carbon at the point of attachment and in an alpha position relative to the ring atom optionally substituted by R⁹, is optionally substituted by R¹⁰, (d) a ring carbon, in a second beta position relative to the ring carbon at the point of attachment and in an alpha position relative to the ring atom optionally substituted by R¹³, is optionally substituted by R¹², and (e) a ring carbon, if present, in the gamma position relative to the ring carbon at the point of attachment and in an alpha position relative to each of the ring atoms optionally substituted by R¹⁰ and R¹², respectively, is optionally substituted by R¹¹;

R⁹, R¹¹, and R¹³ are independently selected from the group consisting of hydrido, hydroxy, amino, amidino, guanidino, lower alkylamino, alkylthio, alkoxy, alkylsulfinyl, alkylsulfonyl, amidosulfonyl, monoalkylamidosulfonyl, alkyl, halo, haloalkyl, haloalkoxy, hydroxyalkyl, carboxy, carboxamido, and cyano;

R¹⁰ and R¹² are independently selected from the group consisting of hydrido, acetamido, haloacetamido, amidino, guanidino, alkyl, alkoxy, alkoxyamino, aminoalkyl, hydroxy, amino, lower alkylamino, alkylsulfonamido, amidosulfonyl, monoalkyl amidosulfonyl, dialkyl amidosulfonyl, hydroxyalkyl, aminoalkyl, halo, haloalkyl, carboalkoxy, carboxy, carboxyamido, carboxyalkyl, and cyano;

$Y^0$ is formula (IV):

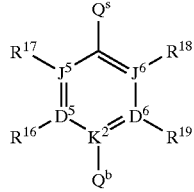

(IV)

wherein $D^5$, $D^6$, $J^5$, and $J^6$ are independently selected from the group consisting of C, N, O, S and a covalent bond with the provisos that no more than one is a covalent bond, no more than one of $D^5$, $D^6$, $J^5$, and $J^6$ is O, no more than one of $D^5$, $D^6$, $J^5$, and $J^6$ is S, one of $D^5$, $D^6$, $J^5$, and $J^6$ must be a covalent bond when two of $D^5$, $D^6$, $J^5$, and $J^6$ are O and S, and no more than four of $D^5$, $D^6$, $J^5$, and $J^6$ are N;

$R^{16}$, $R^{17}$, $R^{18}$, and $R^{19}$ are independently selected from the group consisting of hydrido, amidino, guanidino, carboxy, haloalkylthio, alkoxy, hydroxy, amino, lower alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano; and $Q^s$ is $CH_2$.

10. The compound as recited in claim 6 or a pharmaceutically acceptable salt thereof, wherein;

B is selected from the group consisting of hydrido, ethyl, 2-propenyl, 2-propynyl, propyl, isopropyl, butyl, 2-butenyl, 2-butynyl, sec-butyl, tert-butyl, isobutyl, 2-methylpropenyl, 1-pentyl, 2-pentenyl, 3-pentenyl, 2-pentynyl, 3-pentynyl, 2-pentyl, 3-pentyl, 2-methylbutyl, 2-methyl-2-butenyl, 3-methylbutyl, 3-methyl-2-butenyl, 1-hexyl, 2-hexenyl, 3-hexenyl, 4-hexenyl, 2-hexynyl, 3-hexynyl, 4-hexynyl, 2-hexyl, 1-methyl-2-pentenyl, 1-methyl-3-pentenyl, 1-methyl-2-pentenyl, 1-methyl-3-pentynyl, 3-hexyl, 1-ethyl-2-butenyl, 1-heptyl, 2-heptenyl, 3-heptenyl, 4-heptenyl, 5-heptenyl, 2-heptynyl, 3-heptynyl, 4-heptynyl, 5-heptynyl, 2-heptyl, 1-methyl-2-hexenyl, 1-methyl-3-hexenyl, 1-methyl4-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-2-pentynyl, 1-ethyl-3-pentynyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, amidino, guanidino, methyl, ethyl, methoxy, ethoxy, hydroxy, amino, N-methylamino, dimethylamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, carboxy, cyano, and $Q^b$;

$R^{20}$, $R^{21}$, $R^{23}$, $R^{24}$, $R^{25}$, and $R^{26}$ are independently selected from the group consisting of hydrido, methyl, and ethyl;

A is selected from the group consisting of:
(i) a single covalent bond, NH, $N(CH_3)$, $CH_2$, $CH_3CH$, and $CH_2CH_2$; and
(ii) $CH_2N(CH_3)$, $CH_2N(CH_2CH_3)$, $CH_2CH_2N(CH_3)$, and $CH_2CH_2N(CH_2CH_3)$ with the proviso that B is hydrido;

$R^1$ is selected from the group consisting of hydrido, trifluoromethyl, pentafluoroethyl, fluoro, and chloro;

$R^2$ is selected from the group consisting of phenyl and 2-thienyl, 2-furyl, 2-pyrrolyl, 2-imidazolyl, 2-thiazolyl, 3-isoxazolyl, 2-pyridyl, and 3-pyridyl heteroaryl rings, wherein (a) a ring carbon in a first alpha position relative to the ring carbon at the point of attachment is optionally substituted by $R^9$, (b) a ring carbon in a second alpha position relative to the ring carbon at the point of attachment is optionally substituted by $R^{13}$, (c) a ring carbon, in a first beta position relative to the ring carbon at the point of attachment and in an alpha position relative to the ring atom optionally substituted by $R^9$, is optionally substituted by $R^{10}$, (d) a ring carbon, in a second beta position relative to the ring carbon at the point of attachment and in an alpha position relative to the ring atom optionally substituted by $R^{13}$, is optionally substituted by $R^{12}$, and (e) a ring carbon, if present, in the gamma position relative to the ring carbon at the point of attachment and in an alpha position relative to each of the ring atoms optionally substituted by $R^{10}$ and $R^{12}$, respectively, is optionally substituted by $R^{11}$;

$R^9$, $R^{11}$, and $R^{13}$ are independently selected from the group consisting of hydrido, methyl, ethyl, methoxy, ethoxy, hydroxy, amino, N-methylamino, N,N-dimethylamino, methylthio, trifluoromethyl, pentafluoroethyl, 2,2,2-trifluoroethyl, fluoro, chloro, bromo, amidosulfonyl, N-methylamidosulfonyl, N,N-dimethylamidosulfonyl, hydroxymethyl, 1-hydroxyethyl, amidocarbonyl, N-methylamidocarbonyl, carboxy, and cyano;

$R^{10}$ and $R^{12}$ are independently selected from the group consisting of hydrido, amidino, amidocarbonyl, N-methylamidocarbonyl, guanidino, methyl, ethyl, methoxy, ethoxy, hydroxy, hydroxymethyl, 1-hydroxyethyl, 2-hydroxyethyl, carboxy, carboxymethyl, amino, acetamido, trifluoromethyl, pentafluoroethyl, 2,2,2-trifluoroethyl, trifluoroacetamido, aminomethyl, N-methylamino, dimethylamino, amidosulfonyl, N-methylamidosulfonyl, N,N-dimethylamidosulfonyl, methoxycarbonyl, fluoro, chloro, bromo, and cyano;

$Y^0$ is selected from the group consisting of:

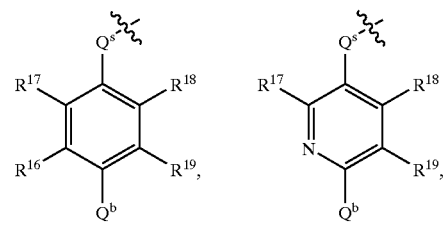

-continued $R^{16}$, $R^{17}$, $R^{18}$, and $R^{19}$ are independently selected from the group consisting of hydrido, methyl, ethyl, amidino, guanidino, methoxy, hydroxy, amino, aminomethyl, 1-aminoethyl, 2-aminoethyl, N-methylamino, dimethylamino, methylthio, ethylthio, trifluoromethylthio, methylsulfinyl, methylsulfonyl, trifluoromethyl, pentafluoroethyl, 2,2,2-trifluoroethyl, trifluoromethoxy, fluoro, chloro, amidosulfonyl, N-methylamidosulfonyl, hydroxymethyl, carboxy, and cyano.

$Q^b$ is selected from the group consisting of $NR^{20}R^{21}$, $C(NR^{25})NR^{23}R^{24}$, and $N(R^{26})C(NR^{25})N(R^{23})(R^{24})$;

$R^{20}$, $R^{21}$, $R^{23}$, $R^{24}$, $R^{25}$, and $R^{26}$ are independently selected from the group consisting of hydrido, methyl, and ethyl; and $Q^s$ is $CH_2$.

11. The compound as recited in claim 10 or a pharmaceutically acceptable salt thereof, wherein;

B is selected from the group consisting of hydrido,ethyl, 2-propenyl, 2-propynyl, propyl, isopropyl, butyl, 2-butyl, (R)-2-butyl,(S)-2-butyl, tert-butyl, isobutyl, 1-pentyl, 3-pentyl, 2-methylbutyl, 2,2,2-trifluoroethyl, 6-amidocarbonylhexyl, 4-methyl-2-pentyl, 3-hydroxypropyl, 3-methoxy-2-propyl, 2-methoxyethyl, 2-methyl-2-butyl, 3-methyl-2-butyl, 2-dimethylaminopropyl, 2-cyanoethyl, 6-hydroxyhexyl, 2-hydroxyethyl, 2-amidinoethyl, 2-guanidinoethyl, 3-guanidinopropyl, 4-guanidinobutyl, 3-hydroxypropyl, 4-hydroxybutyl, 6-cyanohexyl, 2-dimethylaminoethyl, 3-methylbutyl, 2-methylbutyl, (S)-2-methylbutyl, 3-aminopropyl, 2-hexyl, and 4-aminobutyl;

A is selected from the group consisting of single covalent bond, $CH_2$, $CH_3CH$, and $CH_2CH_2$;

$R^1$ is selected from the group consisting of hydrido, trifluoromethyl, fluoro, and chloro;

$R^2$ is selected from the group consisting of 5-amino-3-amidocarbonylphenyl, 5-amino-2-fluorophenyl, 3-amino-5-hydroxymethylphenyl, 5-amino-3-methoxycarbonylphenyl, 3-amidinophenyl, 3-amino-2-methylphenyl, 5-amino-2-methylthiophenyl, 3-aminophenyl, benzyl, 3-carboxyphenyl, 3-carboxy-5-aminophenyl, 3-carboxy-5-hydroxyphenyl, 3-carboxymethyl-5-aminophenyl, 3-carboxymethyl-5-hydroxyphenyl, 3-carboxymethylphenyl, 3-chlorophenyl, 2-chlorophenyl, 2,6-dichlorophenyl, 3-cyanophenyl, 3-dimethylaminophenyl, 2-fluorophenyl, 3-fluorophenyl, 2,5-difluorophenyl, 2-hydroxyphenyl, 3-hydroxyphenyl, 3-methanesulfonylaminophenyl, 2-methoxyphenyl, 3-methoxyphenyl, 3-methoxyaminophenyl, 3-methoxycarbonylphenyl, 2-methylaminophenyl, 3-methylaminophenyl, 2-methylphenyl, 3-methylphenyl, 4-methylphenyl, phenyl, 3-trifluoroacetamidophenyl, 3-trifluoromethylphenyl, 2-trifluoromethylphenyl, 5-amino-2-thienyl, 5-amino-3-thienyl, 3-bromo-2-thienyl, 3-pyridyl, 4-pyridyl, 2-thienyl, and 3-thienyl;

$Y^o$ is selected from the group consisting of:

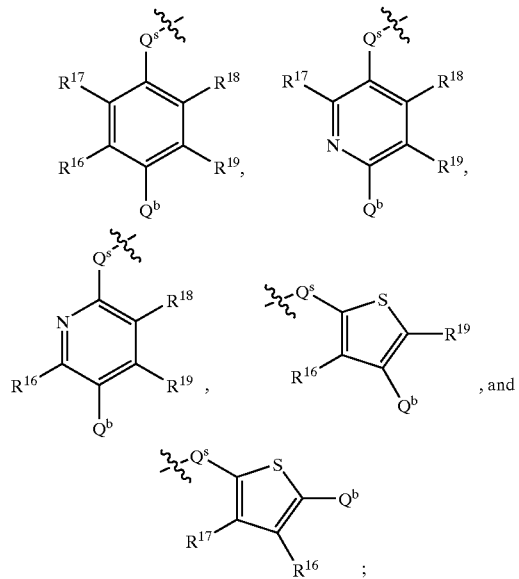

$R^{16}$ and $R^{19}$ are independently selected from the group consisting of: hydrido, amidino, amino, aminomethyl, methoxy, methylamino, hydroxy, hydroxymethyl, fluoro, chloro, and cyano;

$R^{17}$ and $R^{18}$ are independently selected from the group consisting of hydrido, fluoro, chloro, hydroxy, hydroxymethyl, amino, carboxy, and cyano;

$Q^b$ is selected from the group consisting of hydrido and $C(NR^{25})NR^{23}R^{24}$;

$R^{23}$, $R^{24}$, and $R^{25}$ are independently selected from the group consisting of hydrido and methyl; and $Q^s$ is $CH_2$.

12. The compound as recited in claim 11 or a pharmaceutically acceptable salt thereof, wherein;

B is selected from the group consisting of hydrido,ethyl, 2-propenyl, 2-propynyl, propyl, isopropyl, butyl, 2-butyl, (R)-2-butyl,(S)-2-butyl, tert-butyl, isobutyl, 1-pentyl, 3-pentyl, 2-methylbutyl, 2,2,2-trifluoroethyl, 6-amidocarbonylhexyl, 4-methyl-2-pentyl, 3-hydroxypropyl, 3-methoxy-2-propyl, 2-methoxyethyl, 2-methyl-2-butyl, 3-methyl-2-butyl, 2-dimethylaminopropyl, 2-cyanoethyl, 6-hydroxyhexyl, 2-hydroxyethyl, 2-amidinoethyl, 2-guanidinoethyl, 3-guanidinopropyl, 4-guanidinobutyl, 3-hydroxypropyl, 4-hydroxybutyl, 6-cyanohexyl, 2-dimethylaminoethyl, 3-methylbutyl, 2-methylbutyl, (S)-2-methylbutyl, 3-aminopropyl, 2-hexyl, and 4-aminobutyl;

A is selected from the group consisting of single covalent bond, $CH_2$, $CH_3CH$, and $CH_2CH_2$;

$R^1$ is selected from the group consisting of hydrido and chloro;

$R^2$ is selected from the group consisting of 5-amino-2-fluorophenyl, 3-amino-2-methylphenyl, 5-amino-2-methylthiophenyl, 3-aminophenyl, 3-carboxyphenyl, 3-cyanophenyl, 3-methoxycarbonylphenyl, phenyl, and 3-pyridyl;

$Y^0$ is selected from the group consisting of 5-amidino-2-thienylmethyl, 4-amidinobenzyl, 2-fluoro-4-amidinobenzyl, and 3-fluoro-4-amidinobenzyl.

13. A compound as recited in claim 6, or a pharmaceutically acceptable salt thereof, wherein:

$R^2$ is 3-aminophenyl, B is 2,2,2-trifluoroethyl, A is single bond, $Y^0$ is 4-amidinobenzyl, and $R^1$ is chloro;

$R^2$ is 3-aminophenyl, B is (S)-2-butyl, A is single bond, $Y^0$ is 4-amidinobenzyl, and $R^1$ is chloro;

$R^2$ is 5-amino-2-fluorophenyl, B is isopropyl, A is single bond, $Y^0$ is 4-amidinobenzyl, and $R^1$ is chloro;

$R^2$ is 2-methyl-3-aminophenyl, B is isopropyl, A is single bond, $Y^0$ is 4-amidinobenzyl, and $R^1$ is chloro;

$R^2$ is 3-aminophenyl, B is ethyl, A is single bond, $Y^0$ is 4-amidinobenzyl, and $R^1$ is chloro;

$R^2$ is 3-aminophenyl, B is ethyl, A is single bond, $Y^0$ is 4-amidino-2-fluorobenzyl, and $R^1$ is chloro;

$R^2$ is 3-aminophenyl, B is 2-propenyl, A is single bond, $Y^0$ is 4-amidinobenzyl, and $R^1$ is chloro;

$R^2$ is 3-aminophenyl, B is isopropyl, A is single bond, $Y^0$ is 4-amidino-2-fluorobenzyl, and $R^1$ is chloro;

$R^2$ is 3-aminophenyl, B is isopropyl, A is single bond, $Y^0$ is 4-amidinobenzyl, and $R^1$ is chloro;

$R^2$ is 3-aminophenyl, B is 2-butyl, A is single bond, $Y^0$ is 4-amidinobenzyl, and $R^1$ is chloro;

$R^2$ is 3-aminophenyl, B is (R)-2-butyl, A is single bond, $Y^0$ is 4-amidinobenzyl, and $R^1$ is chloro;

$R^2$ is 3-aminophenyl, B is 2-propynyl, A is single bond, $Y^0$ is 4-amidinobenzyl, and $R^1$ is chloro;

$R^2$ is 3-aminophenyl, B is 3-pentyl, A is single bond, $Y^0$ is 4-amidinobenzyl, and $R^1$ is hydrido;

$R^2$ is 3-aminophenyl, B is hydrido, A is $CH_2$, $Y^0$ is 4-amidinobenzyl, and $R^1$ is chloro;

$R^2$ is 3-aminophenyl, B is ethyl, A is $CH_2$, $Y^0$ is 4-amidinobenzyl, and $R^1$ is chloro;

$R^2$ is 3-aminophenyl, B is 2-methypropyl, A is single bond, $Y^0$ is 4-amidinobenzyl, and $R^1$ is chloro;

$R^2$ is 3-aminophenyl, B is 2-propyl, A is $CH_3CH$, $Y^0$ is 4-amidinobenzyl, and $R^1$ is chloro;

$R^2$ is 3-aminophenyl, B is propyl, A is single bond, $Y^0$ is 4-amidino-2-fluorobenzyl, and $R^1$ is chloro;

$R^2$ is 3-aminophenyl, B is 6-amidocarbonylhexyl, A is single bond, $Y^0$ is 4-amidinobenzyl, and $R^1$ is chloro;

$R^2$ is 3-aminophenyl, B is tert-butyl, A is single bond, $Y^0$ is 4-amidinobenzyl, and $R^1$ is hydrido;

$R^2$ is 3-aminophenyl, B is tert-butyl, A is single bond, $Y^0$ is 4-amidinobenzyl, and $R^1$ is chloro;

$R^2$ is 3-aminophenyl, B is 3-hydroxypropyl, A is single bond, $Y^0$ is 4-amidinobenzyl, and $R^1$ is chloro;

$R^2$ is 3-aminophenyl, B is 2-methylpropyl, A is single bond, $Y^0$ is 4-amidino-2-fluorobenzyl, and $R^1$ is chloro;

$R^2$ is 3-aminophenyl, B is butyl, A is single bond, $Y^0$ is 4-amidinobenzyl, and $R^1$ is chloro;

$R^2$ is 3-aminophenyl, B is 3-methoxy-2-propyl, A is single bond, $Y^0$ is 4-amidinobenzyl, and $R^1$ is chloro;

$R^2$ is 3-aminophenyl, B is 3-methoxy-2-propyl, A is single bond, $Y^0$ is 4-amidinobenzyl, and $R^1$ is chloro;

$R^2$ is 3-aminophenyl, B is 2-methoxy-2-ethyl, A is single bond, $Y^0$ is 4-amidinobenzyl, and $R^1$ is chloro;

$R^2$ is 3-aminophenyl, B is 2-propyl, A is single bond, $Y^0$ is 5-amidino-2-thienylmethyl, and $R^1$ is chloro;

$R^2$ is 3-aminophenyl, B is 2-propyl, A is single bond, $Y^0$ is 4-amidino-3-fluorobenzyl, and $R^1$ is hydrido;

$R^2$ is 3-carboxyphenyl, B is 2-propyl, A is single bond, $Y^0$ is 4-amidinobenzyl, and $R^1$ is hydrido; or $R^2$ is 3-aminophenyl, B is 2-propyl, A is single bond, $Y^0$ is 4-amidino-3-fluorobenzyl, and $R^1$ is chloro.

14. A composition for inhibiting thrombotic conditions in blood comprising a compound of any one of claim 5 or 13 and a pharmaceutically acceptable carrier.

15. A composition for inhibiting thrombotic conditions in blood comprising a compound of any one of claims 1–4 or 6–13 and a pharmaceutically acceptable carrier.

16. A method for inhibiting thrombotic conditions in blood comprising adding to blood a therapeutically effective amount of a composition of any one of claims 1–5 or 6–13.

17. A method for inhibiting formation of blood platelet aggregates in blood comprising adding to blood a therapeutically effective amount of a composition of any one of claims 1–5 or 6–13.

18. A method for inhibiting thrombus formation in blood comprising adding to blood a therapeutically effective amount of a composition of any one of claims 1–5 or 6–13.

19. A method for treating venuous thromboembolism and pulmonary embolism in a mammal comprising administering to the mammal a therapeutically effective amount of a composition of any one of claims 1–5 or 6–13.

20. A method for treating deep vein thrombosis in a mammal comprising administering to the mammal a therapeutically effective amount of a composition of any one of claims 1–5 or 6–13.

21. A method for treating cardiogenic thromboembolism in a mammal comprising administering to the mammal a therapeutically effective amount of a composition of any one of claims 1–5 or 6–13.

22. A method for treating thromboembolic stroke in humans and other mammals comprising administering to the mammal a therapeutically effective amount of a composition of any one of claims 1–5 or 6–13.

23. A method for treating thrombosis associated with cancer and cancer chemotherapy in humans and other mammals comprising administering to the mammal a therapeutically effective amount of a composition of any one of claims 1–5 or 6–13.

24. A method for treating unstable angina in humans and other mammals comprising administering to the mammal a therapeutically effective amount of a composition of any one of claims 1–5 or 6–13.

25. A method for inhibiting thrombus formation in blood comprising adding to blood a therapeutically effective amount of a compound of any one of claims 1–5 or 6–13 with a therapeutically effective amount of fibrinogen receptor antagonist.

26. A compound having the Formula:

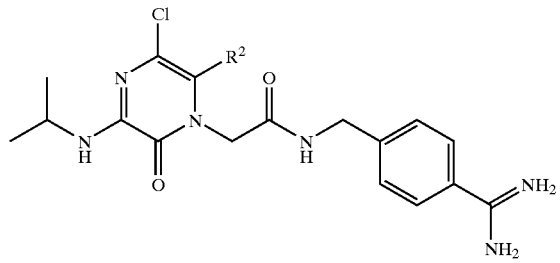

wherein $R^2$ is selected from the group consisting of 3-pyridyl, 5-amino-2-methylthiophenyl, 3-(N-methylamino)phenyl, 2-methyl-3-aminophenyl and 3-aminophenyl.

27. A compound having the Formula:

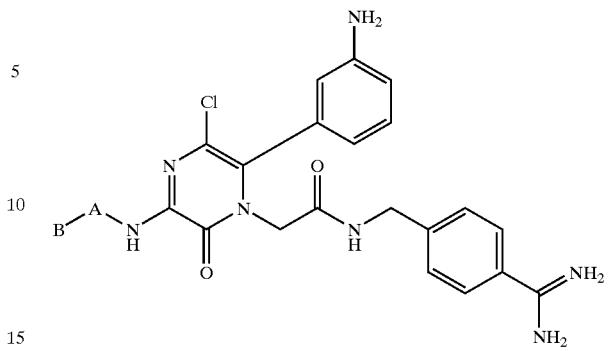

wherein
A is a bond; and
B is selected from the group consisting of t-butyl, 3-pentyl, ethyl, propyl, 2-butyl, 2-(3-methylbutyl), (R)-2-butyl, 2-(4-methylpentyl), 2-propenyl, and 2-propynyl.

* * * * *

UNITED STATES PATENT AND TRADEMARK OFFICE
CERTIFICATE OF CORRECTION

PATENT NO.      : 6,664,255 B1                                    Page 1 of 3
DATED           : December 16, 2003
INVENTOR(S)     : Michael S. South et al.

It is certified that error appears in the above-identified patent and that said Letters Patent is hereby corrected as shown below:

Column 181,
Lines 7-12, chemical structure (IV) should read:

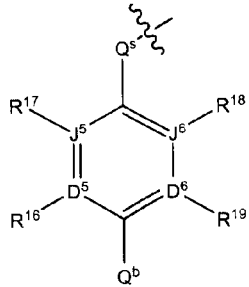

Column 184,
Line 15, "hydroxy, when" should read -- hydroxy when --.
Line 18, "and $R^{25}$ are" should read -- and $R^{26}$ are --.

Column 185,
Line 2, "N-methylamidosulfonyi," should read -- N-methylamidosulfonyl, --.

Column 186,
Line 47, "as-recited" should read -- as recited --.

Column 187,
Line 38, "of: hydrido" should read -- of hydrido --.

Column 189,
Lines 20-27, chemical structute (IV) should read:

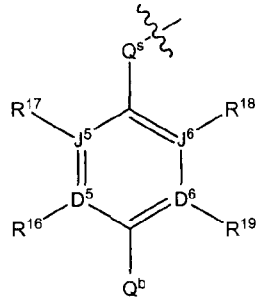

UNITED STATES PATENT AND TRADEMARK OFFICE
CERTIFICATE OF CORRECTION

PATENT NO. : 6,664,255 B1
DATED : December 16, 2003
INVENTOR(S) : Michael S. South et al.

It is certified that error appears in the above-identified patent and that said Letters Patent is hereby corrected as shown below:

Column 192,
Line 51, "hydrido,ethyl," should read -- hydrido, ethyl, --.
Line 66, "bond,CH$_2$," should read -- bond, CH$_2$, --.

Column 193,
Line 57, "of: hydrido" should read -- of hydrido --.

Column 195,
Lines 6-14, chemical structure (IV) should read:

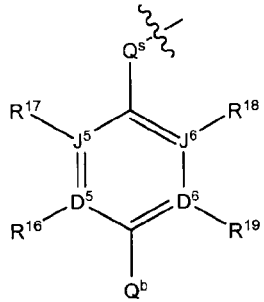

Line 46, "1-methyl4-hexenyl," should read -- 1-methyl-4-hexenyl, --.

Column 198,
Line 50, "of: hydrido" should read -- of hydrido --.

Column 199,
Line 19, "3-pyridyl;" should read -- 3-pyridyl; and --.

Column 200,
Line 26, "claim 5" should read -- claims 5 --.
Line 30, "6-13" should read -- 6-12 --.

UNITED STATES PATENT AND TRADEMARK OFFICE
CERTIFICATE OF CORRECTION

PATENT NO. : 6,664,255 B1
DATED : December 16, 2003
INVENTOR(S) : Michael S. South et al.

It is certified that error appears in the above-identified patent and that said Letters Patent is hereby corrected as shown below:

Column 201,
Lines 6-15, the chemical structure should read:

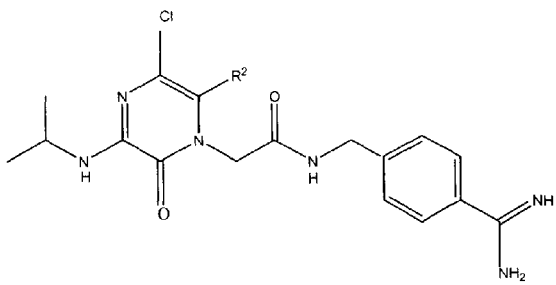

Column 202,
Lines 3-15, the chemical structure should read:

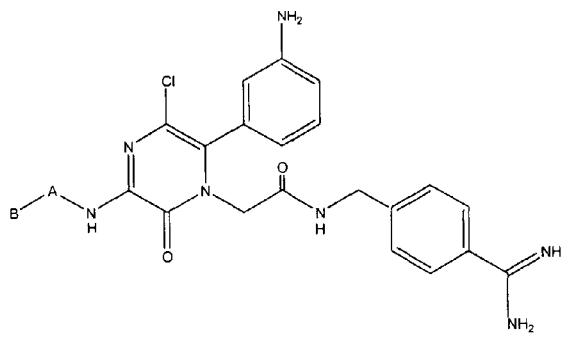

Signed and Sealed this

Thirtieth Day of August, 2005

JON W. DUDAS
*Director of the United States Patent and Trademark Office*